US008841437B2

(12) United States Patent
Chen et al.

(10) Patent No.: US 8,841,437 B2
(45) Date of Patent: Sep. 23, 2014

(54) PRECURSOR MIRNA LOOP-MODULATED TARGET REGULATION

(75) Inventors: Chang-Zheng Chen, Stanford, CA (US); Robin Trujillo, Mountain View, CA (US); Sibiao Yue, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 270 days.

(21) Appl. No.: 12/802,084

(22) Filed: May 28, 2010

(65) Prior Publication Data

US 2011/0020816 A1     Jan. 27, 2011

Related U.S. Application Data

(63) Continuation-in-part of application No. 12/214,793, filed on Jun. 20, 2008, now abandoned.

(60) Provisional application No. 61/271,615, filed on Jul. 23, 2009.

(51) Int. Cl.
| *C07H 21/04* | (2006.01) |
| *C12Q 1/68* | (2006.01) |
| *C12N 5/0783* | (2010.01) |
| *C12N 15/11* | (2006.01) |

(52) U.S. Cl.
CPC .......... *C12N 5/0636* (2013.01); *C12Q 1/6811* (2013.01); *C12N 2506/11* (2013.01); *C12N 15/111* (2013.01); *C12N 2310/141* (2013.01); *C12N 2510/00* (2013.01); *C12N 2501/42* (2013.01); *C12N 2501/515* (2013.01)
USPC ........................................ 536/24.5; 514/44 A

(58) Field of Classification Search
None
See application file for complete search history.

(56) References Cited

U.S. PATENT DOCUMENTS

| 2003/0198627 A1* | 10/2003 | Arts et al. .................... 424/93.21 |
| 2005/0075492 A1* | 4/2005 | Chen et al. .................... 536/23.1 |
| 2006/0015264 A1 | 1/2006 | McShae et al. |
| 2007/0111227 A1 | 5/2007 | Green et al. |
| 2007/0118918 A1 | 5/2007 | Huang et al. |
| 2010/0256222 A1* | 10/2010 | Kelley et al. ................. 514/44 R |

OTHER PUBLICATIONS

Miyagishi et al., Optimization of an siRNA-expression system with an improved hairpin and its significant suppressive effects in mammalian cells, 2004, The Journal of Gene Medicine, vol. 6, pp. 715-723.*
TargetScan 5.2: predicted miRNA targets of miR-181, Releae date: Jun. 2011, accessed and retrieved from www.targetscan.org on Nov. 7, 2013.*

Brennecke, J., et al., "Principles of microRNA-target recognition," *PLoS Biol* (2005) 3(3)e85:0404-0418.
Brunel, C., et al., "RNA loop-loop interactions as dynamic functional motifs," *Biochimie* (2002) 84:925-944.
Cullen, B., "Transcription and processing of human microRNA precursors," *Mol Cell* (2004) 16:861-865.
Didiano, D. & Hobert, O., "Perfect seed pairing is not a generally reliable predictor for miRNA-target interactions," *Nat Structural & Mol Biol* (2006) 13(9):849-851.
Han, J., et al., "Molecular basis for the recognition of primary microRNAs by the drosha-DGCR8 complex," *Cell* (2006) 125:887-901.
Jain, K.K., "Commercial potential of RNAi," *Mol BioSyst* (2006) 2:523-526.
Lewis, B., et al., "Conserved seed pairing, often flanked by adenosines, indicates that thousands of human genes are microRNA targets," *Cell* (2005) 120:15-20.
miRNA Entry forMI0000270, "has-mir-181b-1," accessed http://microrna.sanger.ac.uk/cgi-bin/sequences/mirna_entry.pl?acc=MI0000270 on Mar. 16, 2009, 3 print-out pages are enclosed.
miRNA Entry forMI0000289, "has-mir-181a-1," accessed http://microrna.sanger.ac.uk/cgi-bin/sequences/mirna_entry.pl?acc=MI0000289 on Mar. 16, 2009, 3 print-out pages are enclosed.
miRNA Entry forMI0000458, "has-mir-142," accessed http://microrna.sanger.ac.uk/cgi-bin/sequences/mirna_entry.pl?acc=MI0000458 on Mar. 20, 2009, 3 print-out pages are enclosed.
Neilson, J.R., et al., "Dynamic regulation of miRNA expression in ordered stages of cellular development," *Genes & Develop* (2007) 21:578-589.
Nelson, K.M., et al., "MicroRNAs and cancer: past, present, and potential future," *Mol Cancer Ther* (2008) 7(12):3655-3660.
Newman, M., et al., "Lin-28 interactive with the Let-7 precursor loop indicates regulated microRNA processing," *RNA* (2008) 14:1-11.
Nucleotide—*Homo sapiens* GATA binding protein 3 (GATA3), transcript variant 1, mRNA, GenBank Accession No. NM_001002295, accessed http://www.ncbi.nlm.nih.gov/nuccore/50541958 on Mar. 20, 2009, 7 print-out pages are enclosed.
Osada, H. & Takahashi, T., "MicroRNAs in biological processes and carcinogenesis," *Carcinogenesis* (2007) 28(1):2-12.
Pasquinelli, A.E., et al., "MicroRNAs: a developing story," *Curr Opin in Genet & Dev* (2005) 15:200-205.
Pekarik, V., "Design of shRNAs for RNAi—A lesson from pre-miRNA processing: Possible clinical applications," *Brain Res Bull* (2005) 68:115-120.
Piskounova, E., et al., "Determinants of MicroRNA Processing Inhibition by the Developmentally Regulated RNA-binding Protein Lin28," *J Biol Chem* (2008) 283(31):21310-21314.

(Continued)

*Primary Examiner* — Dana Shin
(74) *Attorney, Agent, or Firm* — Casimir Jones, S.C.

(57) ABSTRACT

Modulation of mRNA activity is achieved with precursor miRNAs (ta-RNAs). ta-RNAs, primarily pre-miRNAs and pri-miRNAs, including truncated and mutated ta-RNAs, are employed for modulation of mRNA expression where it is found that pri- and pre-miRNA have activity independently of the presence of functional mature miRNAs. Modification of at least one of the stem and loop of the ta-RNAs to enhance binding of the ta-RNA to the target mRNA is employed. The modification may be enhanced complementarity between the ta-RNA and the target mRNA and/or improved thermodynamic efficiency in binding of the ta-RNA to the target.

5 Claims, 59 Drawing Sheets

(56) References Cited

OTHER PUBLICATIONS

Schmidt, C., "Negotiating the RNAi patent thicket," *Nat Biotech* (2007) 25(3):273-275.

Ying, S.-Y., et al., "The microRNA (miRNA): overview of the RNA genes that modulate gene function," *Mol Biotechnol* (2008) 38:257-268.

Zeng, Y., et al., "Both natural and designed micro RNAs can inhibit the expression of cognate mRNAs when expressed in human cells," *Mol Cell* (2002) 9:1327-1333.

Office Action mailed Mar. 30, 2009 in U.S. Appl. No. 12/214,793.
Office Action mailed Aug. 25, 2009 in U.S. Appl. No. 12/214,793.
Office Action mailed Apr. 28, 2010 in U.S. Appl. No. 12/214,793.

* cited by examiner miR-181a AACAUUCAACGCUGUCGGUGAGU SEQ ID NO. 60
miR-181c AACAUUCAAC-CUGUCGGUGAGU SEQ ID NO. 61

Fig. 2A

| | | | | |
|---|---|---|---|---|
| Wild-Type miRNA genes | mir-181a-1 | | AACAUUCAACG CU GUCGGUG A GU... | SEQ ID NO. 62 |
| | mir-181c | | A ACAUUCAAC CU GUCGGUG A GUUG GCA / GUGAGUUG C CAGCUAC CAAAC AGAC | SEQ ID NO. 63 |
| Mature chimeric miRNA genes | 181a (c stem) | | A ACAUUCAAC CU GUCGGUG A GUUG G GCA / GUGAGUUG C CAGCUAC CAAA AUA | SEQ ID NO. 64 |
| | 181c (a stem 1) | | A ACA U UCAACG CU GUCGGUG A GUUG GCA / UGU AGUUGC--CAGCUAC-CAAAC AGAC | SEQ ID NO. 65 |
| | 181c (a stem 2) G←↕←C | | A ACAUUCAACG CU GUCGGUG A UUUG GCA / GUGAGUUGC C CAGCUAC- AAAC AGAC | SEQ ID NO. 66 |
| | 181c (a stem 3) T←↕←C | | A ACAUUCAACG CU GUCGGUG A GU UG GCA / GUGAGUUGC C CAGCUAC-CA AC AGAC | SEQ ID NO. 67 |
| Pre-chimeric miRNA genes | 181a (Pre-181c) | | A ACAUUCAAC CU GUCGGUG A GUUU G GCA / GUGAGUUG C CAGCUAC CAAAC AGAC | SEQ ID NO. 63 |
| | 181c (Pre-181a) | | A ACA U UCAACG CU GUCGGUG A GU... | SEQ ID NO. 62 |
| Loop-chimeric miRNA genes | 181a (c-loop) | | A ACA U UCAACG CU GUCGGUG A GUUG GCA / UGU U AGUUGC CAGCUAC AGAC | SEQ ID NO. 65 |
| | 181c (a-loop) | | A ACAUUCAAC CU GUCGGUG A GUUU G GAAU / GUGAGUUG C CAGCUAC CAAA AUA | SEQ ID NO. 64 |

Fig. 2B

| | | | |
|---|---|---|---|
| miR-181a | 5' | AACAUUCAACGCUGUCGGUGAGU 3' | SEQ ID NO. 74 |

| | | | | |
|---|---|---|---|---|
| 2-nt mutants | M1 | 5' | AUAAUUCAACGCUGUCGGUGAGU 3' | SEQ ID NO. 76 |
| | M2 | 5' | AACUAUCAACGCUGUCGGUGAGU 3' | SEQ ID NO. 77 |
| | M3 | 5' | AACAUAAACGCUGUCGGUGAGU 3' | SEQ ID NO. 78 |
| | M4 | 5' | AACAUUCUUCGCUGUCGGUGAGU 3' | SEQ ID NO. 79 |
| | M5 | 5' | AACAUUCAAACCUGUCGGUGAGU 3' | SEQ ID NO. 80 |
| | M6 | 5' | AACAUUCAACGAAGUCGGUGAGU 3' | SEQ ID NO. 81 |
| | M7 | 5' | AACAUUCAACGCUCACGGUGAGU 3' | SEQ ID NO. 82 |
| | M8 | 5' | AACAUUCAACGCUGUACGUGAGU 3' | SEQ ID NO. 83 |
| | M9 | 5' | AACAUUCAACGCUGUCGCAGAGU 3' | SEQ ID NO. 84 |
| | M10 | 5' | AACAUUCAACGCUGUCGGUCUGU 3' | SEQ ID NO. 85 |
| | M11 | 5' | AACAUUCAACGCUGUCGGUGACA 3' | SEQ ID NO. 86 |

| | | | | |
|---|---|---|---|---|
| segment mutants | SM1 | 5' | AUAUAAAACGCUGUCGGUGAGU 3' | SEQ ID NO. 87 |
| | SM2 | 5' | AACAUUCUUACAACACGGUGAGU 3' | SEQ ID NO. 88 |
| | SM3 | 5' | AACAUUCAACGCUGUAACACUCA 3' | SEQ ID NO. 89 |
| | SM4 | 5' | AACAUUCUUACAACAACCACUCA 3' | SEQ ID NO. 90 |

Fig. 7A

| | SEQ ID NO. 62 | | SEQ ID NO. 102 |
|---|---|---|---|
| mir-181a-1 | $^A$ACA$^U$UCAACG$^{CU}$GUCGGUG$^A$G$^U$uu$^{GGAAUU}$C<br>$_A$UGU$_U$AGUUGC—CAGCUAC-CAaa$_{AAUAAA}$ | SM1 | $^A$uau$^a$aaAACG$^{CU}$GUCGGUG$^A$G$^U$uu$^{GGAAUU}$C<br>$_A$aua$_u$uuUUGC—CAGCUAC-CAaa$_{AAUAAA}$ |
| SEQ ID NO. 91<br>M1 | $^A$t$_a$A$^U$UCAACG$^{CU}$GUCGGUG$^A$G$^U$uu$^{GGAAUU}$C<br>$_A$at$_U$AGUUGC—CAGCUAC-CAaa$_{AAUAAA}$ | SEQ ID NO. 103<br>SM2 | $^A$ACA$^U$UCuuac$^{aa}$caCGGUG$^A$G$^U$uu$^{GGAAUU}$C<br>$_A$UGU$_U$AGaaug—guGCUAC-CAaa$_{AAUAAA}$ |
| SEQ ID NO. 92<br>M2 | $^A$AC$^a$t$^U$UCAACG$^{CU}$GUCGGUG$^A$G$^U$uu$^{GGAAUU}$C<br>$_A$UGa$_a$AGUUGC—CAGCUAC-CAaa$_{AAUAAA}$ | SEQ ID NO. 104<br>SM3 | $^A$ACA$^U$UCAACG$^{CU}$GU accac$^u$cauu$^{GGAAUU}$C<br>$_A$UGU$_U$AGUUGC—CAuggug-guaa$_{AAUAAA}$ |
| SEQ ID NO. 93<br>M3 | $^A$ACA$^U$aaAACG$^{CU}$GUCGGUG$^A$G$^U$uu$^{GGAAUU}$C<br>$_A$UGU$_U$uuUUGC—CAGCUAC-CAaa$_{AAUAAA}$ | SEQ ID NO. 105<br>SM4 | $^A$ACA$^U$UCuuac$^{aa}$caaccac$^u$cauu$^{GGAAUU}$C<br>$_A$UGU$_U$AGaaug—guuggug-guaa$_{AAUAAA}$ |
| SEQ ID NO. 94<br>M4 | $^A$ACA$^U$UCttCG$^{CU}$GUCGGUG$^A$G$^U$uu$^{GGAAUU}$C<br>$_A$UGU$_U$AGaaGC—CAGCUAC-CAaa$_{AAUAAA}$ | | |
| SEQ ID NO. 95<br>M5 | $^A$ACA$^U$UCAAac$^{CU}$GUCGGUG$^A$G$^U$uu$^{GGAAUU}$C<br>$_A$UGU$_U$AGUUug—CAGCUAC-CAaa$_{AAUAAA}$ | | |
| SEQ ID NO. 96<br>M6 | $^A$ACA$^U$UCAACG$^{aa}$GUCGGUG$^A$G$^U$uu$^{GGAAUU}$C<br>$_A$UGU$_U$AGUUGC—CAGCUAC-CAaa$_{AAUAAA}$ | | |
| SEQ ID NO. 97<br>M7 | $^A$ACA$^U$UCAACG$^{CU}$caCGGUG$^A$G$^U$uu$^{GGAAUU}$C<br>$_A$UGU$_U$AGUUGC—guGCUAC-CAaa$_{AAUAAA}$ | | |
| SEQ ID NO. 98<br>M8 | $^A$ACA$^U$UCAACG$^{CU}$GUacGUG$^A$G$^U$uu$^{GGAAUU}$C<br>$_A$UGU$_U$AGUUGC—CAugUAC-CAaa$_{AAUAAA}$ | | |
| SEQ ID NO. 99<br>M9 | $^A$ACA$^U$UCAACG$^{CU}$GUCGcaG$^A$G$^U$uu$^{GGAAUU}$C<br>$_A$UGU$_U$AGUUGC—CAGCguC-CAaa$_{AAUAAA}$ | | |
| SEQ ID NO. 100<br>M10 | $^A$ACA$^U$UCAACG$^{CU}$GUCGGU$c^u$G$^U$uu$^{GGAAUU}$C<br>$_A$UGU$_U$AGUUGC—CAGCUAg-CAaa$_{AAUAAA}$ | | |
| SEQ ID NO. 101<br>M11 | $^A$ACA$^U$UCAACG$^{CU}$GUCGGUG$^A$cauu$^{GGAAUU}$C<br>$_A$UGU$_U$AGUUGC—CAGCUAC-guaa$_{AAUAAA}$ | | |

Fig. 8 mir-181a-1  5' AACAUUCAACGCUGUCGGUGAGU 3' SEQ ID NO. 74
M1          5' AUAAUUCAACGCUGUCGGUGAGU 3' SEQ ID NO. 76 miR-181a AACAUUCAACGCUGUCGGUGAGU SEQ ID NO. 106
miR-181b AACAUUCAUUGCUGUCGGUGGG SEQ ID NO. 107
miR-181c AACAUUCAAC-CUGUCGGUGAGU SEQ ID NO. 108
miR-181d AACAUUCAUUGUUGUCGGUGGGUU SEQ ID NO. 109

Fig. 10A

Mouse | Human

SEQ ID NO. 110 mir-181a-1
SEQ ID NO. 116

SEQ ID NO. 111 mir-181a-2
SEQ ID NO. 117

SEQ ID NO. 112 mir-181b-1
SEQ ID NO. 118

SEQ ID NO. 113 mir-181b-2
SEQ ID NO. 119

SEQ ID NO. 114 mir-181c
SEQ ID NO. 120

SEQ ID NO. 115 mir-181d
SEQ ID NO. 121

Fig. 10B

| miRNA Vector | p (Compared to vector) | p (Compared to *mir-181a-1*) |
|---|---|---|
| Vector | - | <0.0001 |
| *mir-181a-1* | <0.0001 | - |
| M1 | 0.2366 | <0.0001 |
| M2 | 0.0351 | <0.0001 |
| M3 | 0.0304 | <0.0001 |
| M4 | <0.0001 | 0.1261 |
| M5 | <0.0001 | 0.0304 |
| M6 | <0.0001 | 0.977 |
| M7 | <0.0001 | 0.1573 |
| M8 | <0.0001 | 0.0532 |
| M9 | <0.0001 | 0.5068 |
| M10 | 0.0073 | 0.0142 |
| M11 | <0.0001 | 0.931 |
| SM1 | 0.1749 | <0.0001 |
| SM2 | <0.0001 | 0.6236 |
| SM3 | 0.0783 | 0.0002 |
| SM4 | 0.002 | 0.0011 |

Fig. 12C

| miRNA Vector | p (Compared to vector) | p (Compared to mir-181a-1) |
|---|---|---|
| Vector | - | < 0.0001 |
| mir-181a-1 | < 0.0001 | - |
| mir-181c | 0.4095 | < 0.0001 |
| mir-181a (c stem) | 0.0005 | 0.0496 |
| mir-181c (a stem 1) | 1 | < 0.0001 |
| mir-181c (a stem 2) | 0.7553 | < 0.0001 |
| mir-181c (a stem 3) | 0.4095 | < 0.0001 |
| mir-181a(Pre-181c) | 0.0530 | < 0.0001 |
| mir-181c (Pre-181a) | 0.0007 | 0.00086 |
| mir-181a(c loop) | 0.0121 | < 0.0001 |
| mir-181c(a loop) | < 0.0001 | 0.05186 |

Fig. 13B

| miRNA Vector | p (Compared to vector) | p (Compared to mir-181a-1) |
|---|---|---|
| Vector | - | <0.0001 |
| mir-181a-1 | 0.0001 | - |
| 181a-LP1 | 0.2366 | 0.0001 |
| 181a-LP2 | <0.0001 | 0.977 |
| 181a-LP3 | 0.0003 | 0.0304 |
| 181a-LP4 | 0.0073 | 0.0007 |
| 181a-LP5 | <0.0001 | 0.3408 |
| 181a-LP6 | 0.0007 | 0.4705 |

| Name | Sequence | SEQ ID |
|---|---|---|
| ppy-mir-181a-1 | uugg- -AAUAAAAUCAAA- - | SEQ ID NO. 122 |
| ptr-mir-181a-1 | uugg- -AAUAAAAUCAAA- - | SEQ ID NO. 123 |
| ppa-mir-181a-1 | uugg- -AAUAAAAUCAAA- - | SEQ ID NO. 124 |
| mne-mir-181a-1 | uugg- -AAUAAAAUCAAA- - | SEQ ID NO. 125 |
| mml-mir-181a-1 | uugg- -AAUAAAAUCAAA- - | SEQ ID NO. 126 |
| lla-mir-181a-1 | uugg- -AAUAAAAUCAAA- - | SEQ ID NO. 127 |
| hsa-mir-181a-1 | uugg- -AAUAAAAUCAAA- - | SEQ ID NO. 128 |
| ggo-mir-181a-1 | uugg- -AAUAAAAUCAAA- - | SEQ ID NO. 129 |
| mmu-mir-181a-1 | uugg- -AAUCAAALAAA- - | SEQ ID NO. 130 |
| mo-mir-181a-1 | uugg- -AAUUCAALAAA- - | SEQ ID NO. 131 |
| gga-mir-181a-1 | uugg- -AAUUAAGAGAAA- - | SEQ ID NO. 132 |
| fru-mir-181a-1 | uugg- -ABCUAAAUUGAAAA- | SEQ ID NO. 133 |
| tni-mir-181a-1 | uugg- -ABCCAAAUUGAAAA | SEQ ID NO. 134 |
| dre-mir-181a-1 | uugg- -ABCUAAAUUGAAAA | SEQ ID NO. 135 |
| ggo-mir-181c | uugcgcCAGCUCAGGCAA- - | SEQ ID NO. 136 |
| hsa-mir-181c | uugcgcCAGCUCAGGCAA- - | SEQ ID NO. 137 |
| mml-mir-181c | uugcgcCAGCUCAGGCAA- - | SEQ ID NO. 138 |
| ppa-mir-181c | uugcgcCAGCUCAGGCAA- - | SEQ ID NO. 139 |
| ptr-mir-181c | uugcgcCAGCUCAGGCAA- - | SEQ ID NO. 140 |
| ssc-mir-181c | uugcgcCAGCUCAGGCAA- - | SEQ ID NO. 141 |
| mmu-mir-181c | uugcgcCAGCUCAGACAA- - | SEQ ID NO. 142 |
| mo-mir-181c | uugcgcCAGCUCAGACAA- - | SEQ ID NO. 143 |

Fig. 17

MXW-PGK-IRES-GFP

MDH1-PGK-GFP 2.0

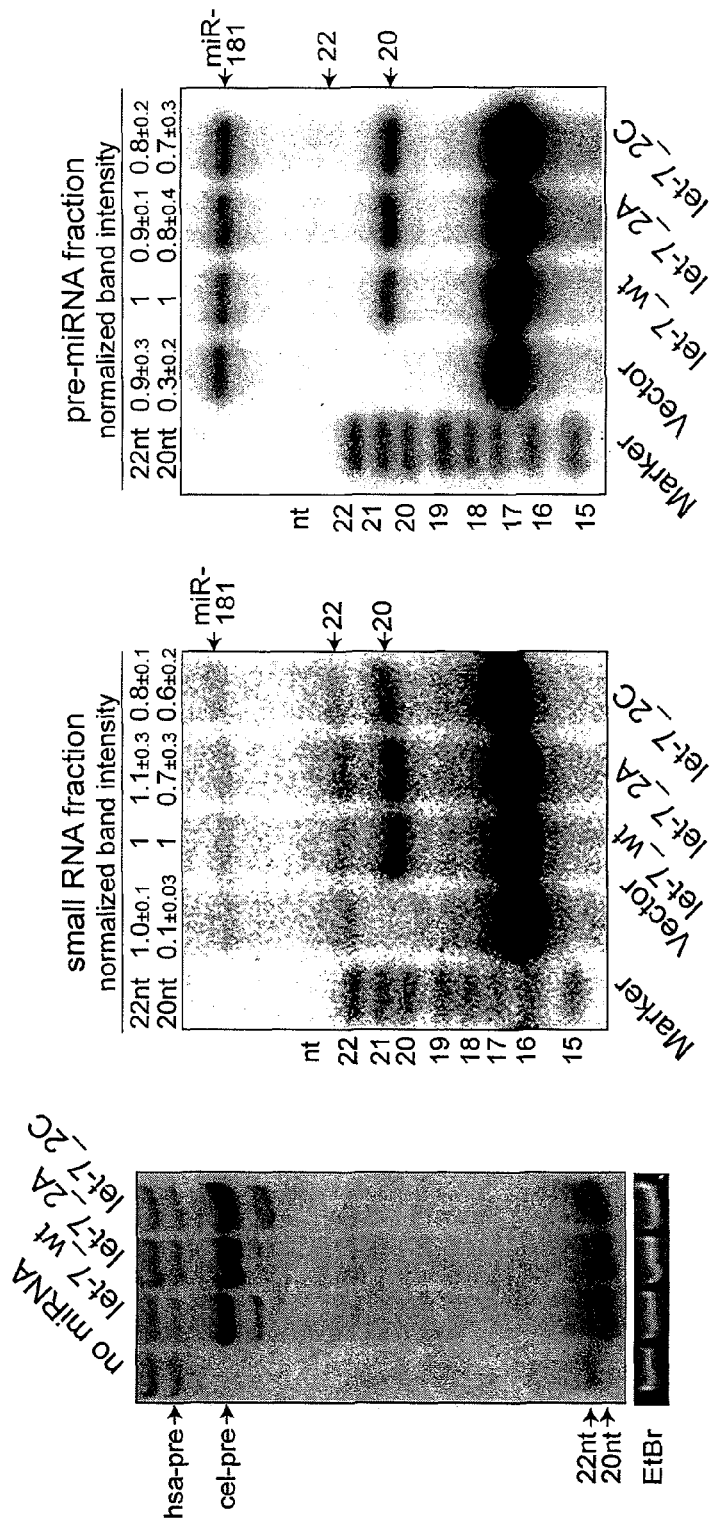

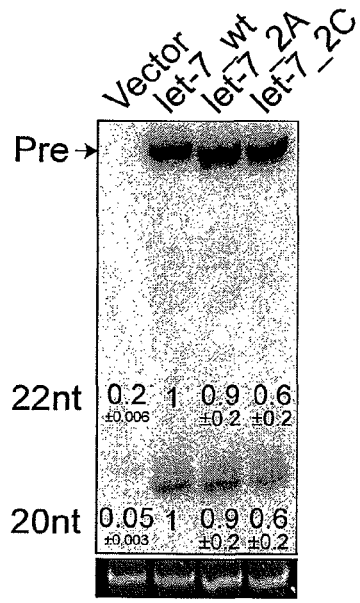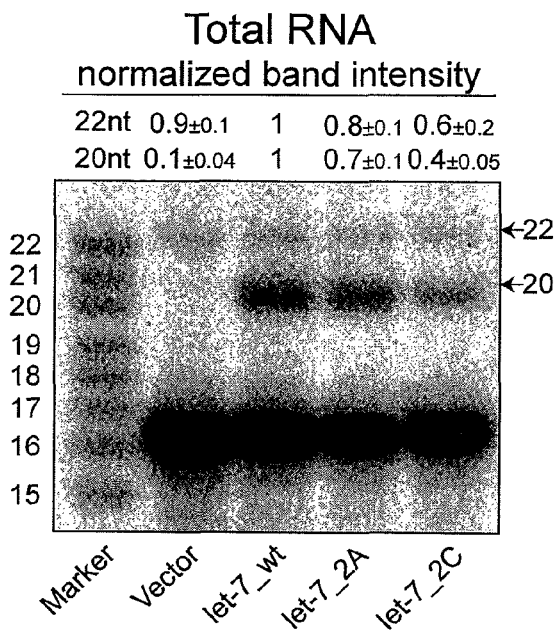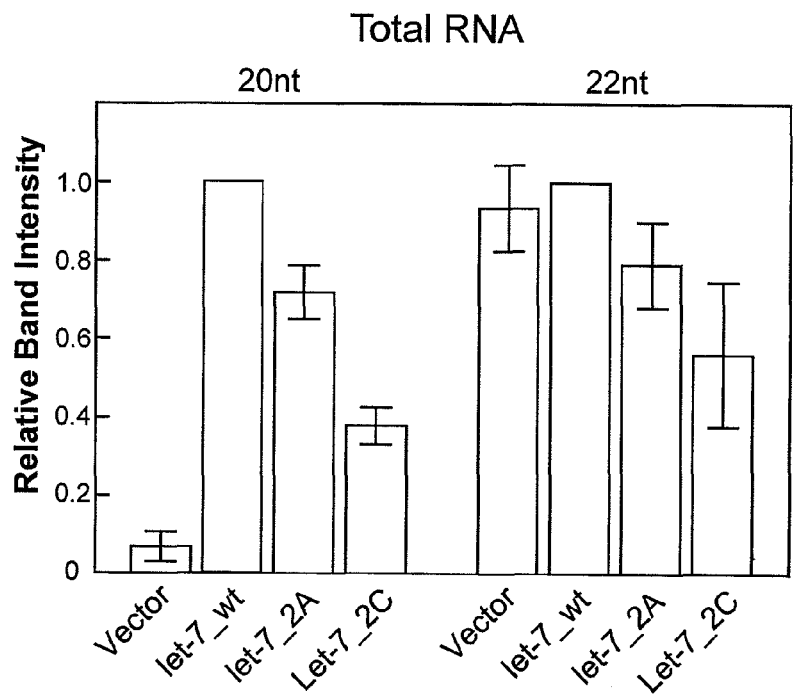
Fig. 22A Fig. 22B
Fig. 22C

Fig. 26

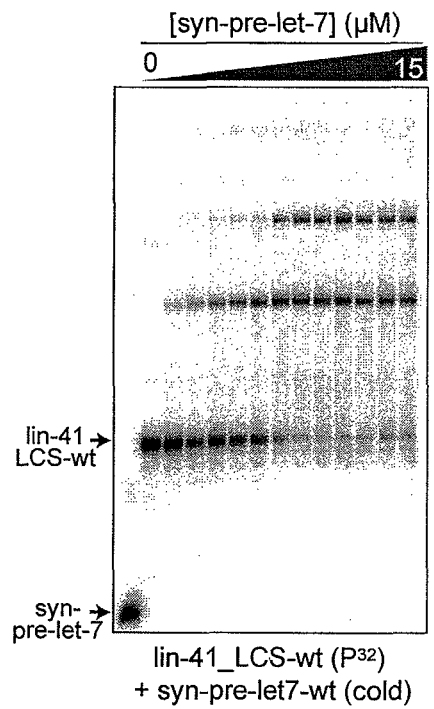
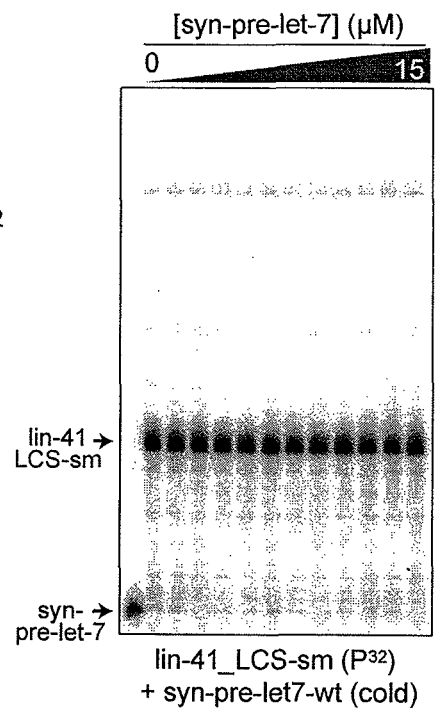
Fig. 27A
Fig. 27B
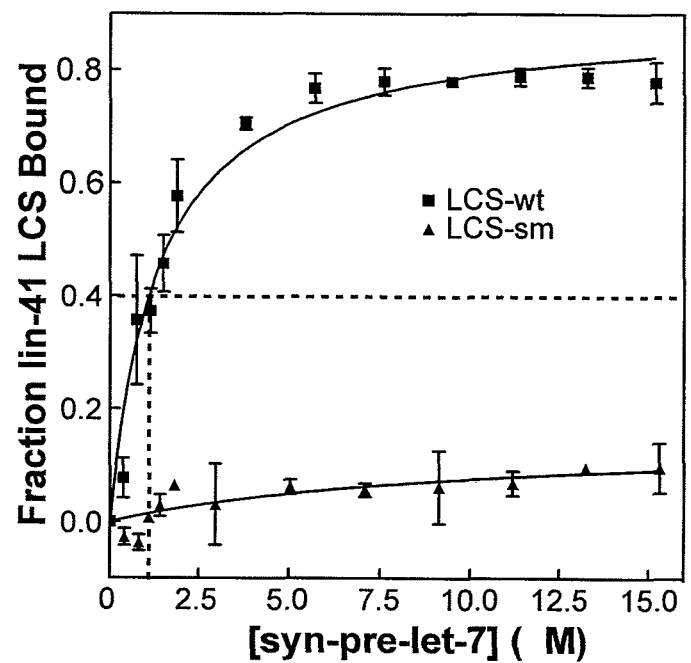
Fig. 27C

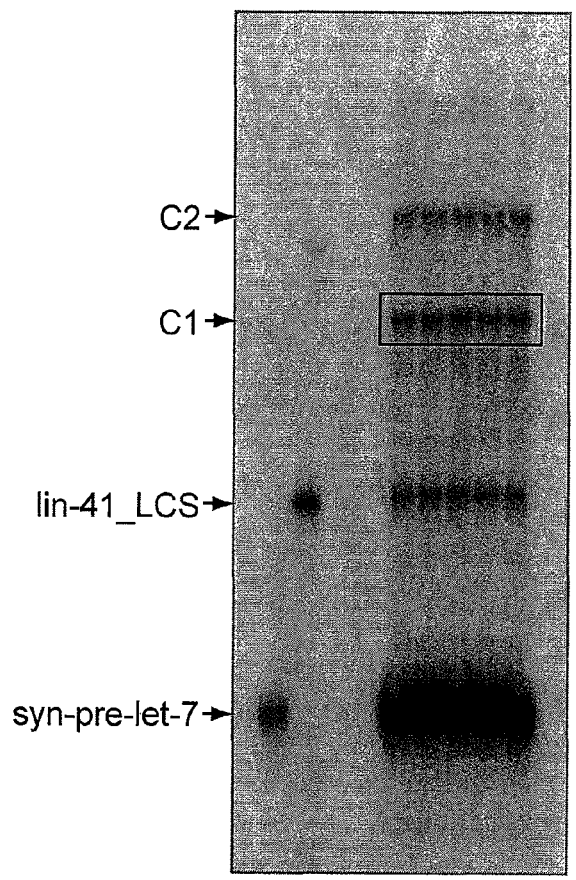
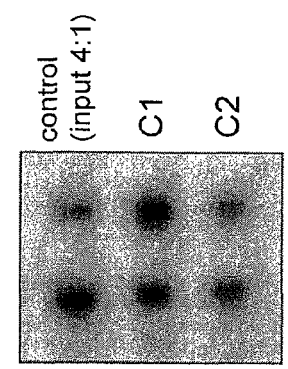
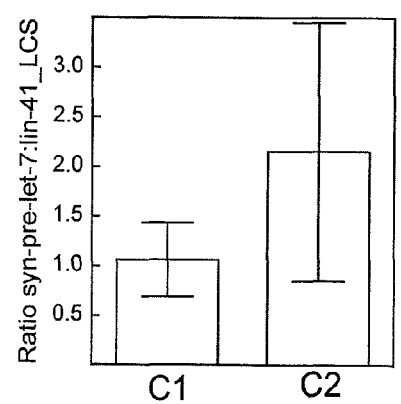
Fig. 29A
Fig. 29B
Fig. 29C let-7_mut2   5'-UGAGCAUCUAGGUUGUAUAGUU-3' SEQ ID NO. 203
let-7_mut3   5'-UGAGGUAGAUCCAACUAUAGUU-3' SEQ ID NO. 204
let-7_mut4   5'-UGAGGUAGUAGGUUGAUAUCAA-3' SEQ ID NO. 205 mature let-7 + lin-41_LCS

SEQ ID NO. 220

SEQ ID NO. 237

SEQUENCE LISTING

```
<160> NUMBER OF SEQ ID NOS: 239

<210> SEQ ID NO 1
<211> LENGTH: 6075
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3000)
<223> OTHER INFORMATION: at least 1000 and up to 3000 N's are present or
      absent; if present, N is a, g, c, or t
<220> FEATURE:
<221> NAME/KEY: misc_feature
<222> LOCATION: (3001)..(3010)
<223> OTHER INFORMATION: at least 6 and up to 10 N's are present or
      absent; if present, N is a, g, c, or t
<220> FEATURE:
<221> NAME/KEY: misc_feature
<222> LOCATION: (3011)..(3020)
<223> OTHER INFORMATION: at least 6 and up to 10 N's are present or
      absent; if present, N is a, g, c, or t
<220> FEATURE:
<221> NAME/KEY: misc_feature
<222> LOCATION: (3021)..(3030)
<223> OTHER INFORMATION: at least 2 and up to 10 N's are present or
      absent; if present, N is a, g, c, or t
<220> FEATURE:
<221> NAME/KEY: misc_feature
<222> LOCATION: (3031)..(3045)
```

```
<223> OTHER INFORMATION: at least 10 and up to 15 N's are present or
      absent; if present, N is a, g, c, or t
<220> FEATURE:
<221> NAME/KEY: misc_feature
<222> LOCATION: (3046)..(3055)
<223> OTHER INFORMATION: at least 2 and up to 10 N's are present or
      absent; if present, N is a, g, c, or t
<220> FEATURE:
<221> NAME/KEY: misc_feature
<222> LOCATION: (3056)..(3065)
<223> OTHER INFORMATION: at least 6 and up to 10 N's are present or
      absent; if present, N is a, g, c, or t
<220> FEATURE:
<221> NAME/KEY: misc_feature
<222> LOCATION: (3066)..(3075)
<223> OTHER INFORMATION: at least 6 and up to 10 N's are present or
      absent; if present, N is a, g, c, or t
<220> FEATURE:
<221> NAME/KEY: misc_feature
<222> LOCATION: (3076)..(6075)
<223> OTHER INFORMATION: at least 1000 and up to 3000 N's are present or
      absent; if present, N is a, g, c, or t

<400> SEQUENCE: 1
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
```

-continued

| | |
|---|---|
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |

| | |
|---|---|
| nnnnnnnnnn nnnnnnnnnn nnnnnnnnnn nnnnnnnnnn nnnnnnnnnn nnnnnnnnnn | 4080 |
| nnnnnnnnnn nnnnnnnnnn nnnnnnnnnn nnnnnnnnnn nnnnnnnnnn nnnnnnnnnn | 4140 |
| nnnnnnnnnn nnnnnnnnnn nnnnnnnnnn nnnnnnnnnn nnnnnnnnnn nnnnnnnnnn | 4200 |
| nnnnnnnnnn nnnnnnnnnn nnnnnnnnnn nnnnnnnnnn nnnnnnnnnn nnnnnnnnnn | 4260 |
| nnnnnnnnnn nnnnnnnnnn nnnnnnnnnn nnnnnnnnnn nnnnnnnnnn nnnnnnnnnn | 4320 |
| nnnnnnnnnn nnnnnnnnnn nnnnnnnnnn nnnnnnnnnn nnnnnnnnnn nnnnnnnnnn | 4380 |
| nnnnnnnnnn nnnnnnnnnn nnnnnnnnnn nnnnnnnnnn nnnnnnnnnn nnnnnnnnnn | 4440 |
| nnnnnnnnnn nnnnnnnnnn nnnnnnnnnn nnnnnnnnnn nnnnnnnnnn nnnnnnnnnn | 4500 |
| nnnnnnnnnn nnnnnnnnnn nnnnnnnnnn nnnnnnnnnn nnnnnnnnnn nnnnnnnnnn | 4560 |
| nnnnnnnnnn nnnnnnnnnn nnnnnnnnnn nnnnnnnnnn nnnnnnnnnn nnnnnnnnnn | 4620 |
| nnnnnnnnnn nnnnnnnnnn nnnnnnnnnn nnnnnnnnnn nnnnnnnnnn nnnnnnnnnn | 4680 |
| nnnnnnnnnn nnnnnnnnnn nnnnnnnnnn nnnnnnnnnn nnnnnnnnnn nnnnnnnnnn | 4740 |
| nnnnnnnnnn nnnnnnnnnn nnnnnnnnnn nnnnnnnnnn nnnnnnnnnn nnnnnnnnnn | 4800 |
| nnnnnnnnnn nnnnnnnnnn nnnnnnnnnn nnnnnnnnnn nnnnnnnnnn nnnnnnnnnn | 4860 |
| nnnnnnnnnn nnnnnnnnnn nnnnnnnnnn nnnnnnnnnn nnnnnnnnnn nnnnnnnnnn | 4920 |
| nnnnnnnnnn nnnnnnnnnn nnnnnnnnnn nnnnnnnnnn nnnnnnnnnn nnnnnnnnnn | 4980 |
| nnnnnnnnnn nnnnnnnnnn nnnnnnnnnn nnnnnnnnnn nnnnnnnnnn nnnnnnnnnn | 5040 |
| nnnnnnnnnn nnnnnnnnnn nnnnnnnnnn nnnnnnnnnn nnnnnnnnnn nnnnnnnnnn | 5100 |
| nnnnnnnnnn nnnnnnnnnn nnnnnnnnnn nnnnnnnnnn nnnnnnnnnn nnnnnnnnnn | 5160 |
| nnnnnnnnnn nnnnnnnnnn nnnnnnnnnn nnnnnnnnnn nnnnnnnnnn nnnnnnnnnn | 5220 |
| nnnnnnnnnn nnnnnnnnnn nnnnnnnnnn nnnnnnnnnn nnnnnnnnnn nnnnnnnnnn | 5280 |
| nnnnnnnnnn nnnnnnnnnn nnnnnnnnnn nnnnnnnnnn nnnnnnnnnn nnnnnnnnnn | 5340 |
| nnnnnnnnnn nnnnnnnnnn nnnnnnnnnn nnnnnnnnnn nnnnnnnnnn nnnnnnnnnn | 5400 |
| nnnnnnnnnn nnnnnnnnnn nnnnnnnnnn nnnnnnnnnn nnnnnnnnnn nnnnnnnnnn | 5460 |
| nnnnnnnnnn nnnnnnnnnn nnnnnnnnnn nnnnnnnnnn nnnnnnnnnn nnnnnnnnnn | 5520 |
| nnnnnnnnnn nnnnnnnnnn nnnnnnnnnn nnnnnnnnnn nnnnnnnnnn nnnnnnnnnn | 5580 |
| nnnnnnnnnn nnnnnnnnnn nnnnnnnnnn nnnnnnnnnn nnnnnnnnnn nnnnnnnnnn | 5640 |
| nnnnnnnnnn nnnnnnnnnn nnnnnnnnnn nnnnnnnnnn nnnnnnnnnn nnnnnnnnnn | 5700 |
| nnnnnnnnnn nnnnnnnnnn nnnnnnnnnn nnnnnnnnnn nnnnnnnnnn nnnnnnnnnn | 5760 |
| nnnnnnnnnn nnnnnnnnnn nnnnnnnnnn nnnnnnnnnn nnnnnnnnnn nnnnnnnnnn | 5820 |
| nnnnnnnnnn nnnnnnnnnn nnnnnnnnnn nnnnnnnnnn nnnnnnnnnn nnnnnnnnnn | 5880 |
| nnnnnnnnnn nnnnnnnnnn nnnnnnnnnn nnnnnnnnnn nnnnnnnnnn nnnnnnnnnn | 5940 |
| nnnnnnnnnn nnnnnnnnnn nnnnnnnnnn nnnnnnnnnn nnnnnnnnnn nnnnnnnnnn | 6000 |
| nnnnnnnnnn nnnnnnnnnn nnnnnnnnnn nnnnnnnnnn nnnnnnnnnn nnnnnnnnnn | 6060 |
| nnnnnnnnnn nnnnn | 6075 |

<210> SEQ ID NO 2
<211> LENGTH: 388
<212> TYPE: DNA
<213> ORGANISM: Unknown
<220> FEATURE:
<223> OTHER INFORMATION: Wild-type mir-181a-1 gene

```
<400> SEQUENCE: 2
ctcgagtgtg acaggtttgg ttaaaggatt gggctttcct ctgcctccct cctgctccag    60
actcccacag atactgttta atcagcaca tctctgcctc acaggttgct tcagtgaaca    120
ttcaacgctg tcggtgagtt tggaattcaa ataaaaacca tcgaccgttg attgtaccct    180
atagctaacc atcatctact ccatggccct ctgcgtttgc tgaagacaga accgcaaagc    240
aggacccgac aggattcttt tttaattaag aattcctagg aattcttgcc aaacctacag    300
gtggggtctt tcattccccc cttttctgg agactaaata aaatcttta ttttatcgat     360 aagcttggct gcaggtcgac gcggccgc                                       388

<210> SEQ ID NO 3
<211> LENGTH: 60
<212> TYPE: DNA
<213> ORGANISM: Unknown
<220> FEATURE:
<223> OTHER INFORMATION: Wild-type pre-miR-181a-1 precursor

<400> SEQUENCE: 3
aacattcaac gctgtcggtg agtttggaat tcaaataaaa accatcgacc gttgattgta    60

<210> SEQ ID NO 4
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 4
ataattcaac gctgtcggtg agtttggaat tcaaataaaa accatcgacc gttgatttaa    60

<210> SEQ ID NO 5
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 5
aactatcaac gctgtcggtg agtttggaat tcaaataaaa accatcgacc gttgaaagta    60

<210> SEQ ID NO 6
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 6
aacataaaac gctgtcggtg agtttggaat tcaaataaaa accatcgacc gttttttgta    60

<210> SEQ ID NO 7
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 7
aacattcttc gctgtcggtg agtttggaat tcaaataaaa accatcgacc gaagattgta    60
```

<210> SEQ ID NO 8
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 8
aacattcaaa cctgtcggtg agtttggaat tcaaataaaa accatcgacg tttgattgta      60

<210> SEQ ID NO 9
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 9
aacattcaac gaagtcggtg agtttggaat tcaaataaaa accatcgacc gttgattgta      60

<210> SEQ ID NO 10
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 10
aacattcaac gctcacggtg agtttggaat tcaaataaaa accatcgtgc gttgattgta      60

<210> SEQ ID NO 11
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 11
aacattcaac gctgtacgtg agtttggaat tcaaataaaa accatgtacc gttgattgta      60

<210> SEQ ID NO 12
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 12
aacattcaac gctgtcgcag agtttggaat tcaaataaaa acctgcgacc gttgattgta      60

<210> SEQ ID NO 13
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 13
aacattcaac gctgtcggtc tgtttggaat tcaaataaaa acgatcgacc gttgattgta      60

```
<210> SEQ ID NO 14
<211> LENGTH: 60
<212> TYPE: DNA
<213> ORGANISM: Artificial Sequence
<220> FEATURE:
<223> OTHER INFORMATION: Chemically synthesized 2-nt mature miR-181a-1
      mutant

<400> SEQUENCE: 14
aacattcaac gctgtcggtg acattggaat tcaaataaaa tgcatcgacc gttgattgta    60

<210> SEQ ID NO 15
<211> LENGTH: 60
<212> TYPE: DNA
<213> ORGANISM: Artificial Sequence
<220> FEATURE:
<223> OTHER INFORMATION: Chemically synthesized segment mature miR-181a-
      1 mutant

<400> SEQUENCE: 15
atataaaaac gctgtcggtg agtttggaat tcaaataaaa accatcgacc gtttttataa    60

<210> SEQ ID NO 16
<211> LENGTH: 60
<212> TYPE: DNA
<213> ORGANISM: Artificial Sequence
<220> FEATURE:
<223> OTHER INFORMATION: Chemically synthesized segment mature miR-181a-
      1 mutant

<400> SEQUENCE: 16
aacattctta caacacggtg agtttggaat tcaaataaaa accatcgtgg taagattgta    60

<210> SEQ ID NO 17
<211> LENGTH: 60
<212> TYPE: DNA
<213> ORGANISM: Artificial Sequence
<220> FEATURE:
<223> OTHER INFORMATION: Chemically synthesized segment mature miR-181a-
      1 mutant

<400> SEQUENCE: 17
aacattcaac gctgtaccac tcattggaat tcaaataaaa tggtggtacc gttgattgta    60

<210> SEQ ID NO 18
<211> LENGTH: 60
<212> TYPE: DNA
<213> ORGANISM: Artificial Sequence
<220> FEATURE:
<223> OTHER INFORMATION: Chemically synthesized segment mature miR-181a-
      1 mutant

<400> SEQUENCE: 18
aacattctta caacaaccac tcattggaat tcaaataaaa tggtggttgg taagattgta    60

<210> SEQ ID NO 19
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 19
aacattcaac gctgtcggtg agtttccaat tcaaataaaa accatcgacc gttgattgta    60

<210> SEQ ID NO 20
```

```
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 20
aacattcaac gctgtcggtg agtttggttt tcaaataaaa accatcgacc gttgattgta      60

<210> SEQ ID NO 21
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 21
aacattcaac gctgtcggtg agtttggaaa acaaataaaa accatcgacc gttgattgta      60

<210> SEQ ID NO 22
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 22
aacattcaac gctgtcggtg agtttggaat tgtaataaaa accatcgacc gttgattgta      60

<210> SEQ ID NO 23
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 23
aacattcaac gctgtcggtg agtttggaat tcacgtaaaa accatcgacc gttgattgta      60

<210> SEQ ID NO 24
<211> LENGTH: 60
<212> TYPE: DNA
<213> ORGANISM: Artificial Sequence
<220> FEATURE:
<223> OTHER INFORMATION: Chemically synthesized miR-181a-1 Loop Mutant

<400> SEQUENCE: 24
aacattcaac gctgtcggtg agtttggaat tcaaaataaa accatcgacc gttgattgta      60

<210> SEQ ID NO 25
<211> LENGTH: 290
<212> TYPE: DNA
<213> ORGANISM: Unknown
<220> FEATURE:
<223> OTHER INFORMATION: Wild-type mir-181c gene

<400> SEQUENCE: 25
gatcctcgag gtgagtcaaa ggggaccctg gtttctctct cgtcccacat gctctctgcc      60
ttgctggcct actctcccaa ctccagttat ccaagaactt gccaagggtt tgggggaaca     120
ttcaacctgt cggtgagttt ggcagctca gacaaaccat cgaccgttga gtggaccccg      180
aggcctggaa ctgccacccg tctaccccat ccccaccctg tagacccggg agagccccag     240
gcagcatccc ctgcctcagg ccacagcaaa ggtcacaatt gaattcgatc                 290
```

```
<210> SEQ ID NO 26
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 26
actcaccgac agcgttgaat gtt                                              23

<210> SEQ ID NO 27
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 27
actcaccgac aggttgaatg tt                                               22

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized Northern Probe sequence

<400> SEQUENCE: 28
tcaccgacag cgttgaatta t                                                21

<210> SEQ ID NO 29
<211> LENGTH: 21
<212> TYPE: DNA
<213> ORGANISM: Artificial Sequence
<220> FEATURE:
<223> OTHER INFORMATION: Chemically synthesized Northern Probe sequence

<400> SEQUENCE: 29
tcaccgacag cgttgatagt t                                                21

<210> SEQ ID NO 30
<211> LENGTH: 21
<212> TYPE: DNA
<213> ORGANISM: Artificial Sequence
<220> FEATURE:
<223> OTHER INFORMATION: Chemically synthesized Northern Probe sequence

<400> SEQUENCE: 30
tcaccgacag cgttttatgt t                                                21

<210> SEQ ID NO 31
<211> LENGTH: 21
<212> TYPE: DNA
<213> ORGANISM: Artificial Sequence
<220> FEATURE:
<223> OTHER INFORMATION: Chemically synthesized Northern Probe sequence

<400> SEQUENCE: 31
tcaccgacag cgaagaatgt t                                                21

<210> SEQ ID NO 32
<211> LENGTH: 23
<212> TYPE: DNA
<213> ORGANISM: Artificial Sequence
<220> FEATURE:
<223> OTHER INFORMATION: Chemically synthesized Northern Probe sequence
```

```
<400> SEQUENCE: 32
actcaccgac aggtttgaat gtt                                           23

<210> SEQ ID NO 33
<211> LENGTH: 21
<212> TYPE: DNA
<213> ORGANISM: Artificial Sequence
<220> FEATURE:
<223> OTHER INFORMATION: Chemically synthesized Northern Probe sequence

<400> SEQUENCE: 33
tcaccgactt cgttgaatgt t                                             21

<210> SEQ ID NO 34
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 34
actcaccgtg agcgttgaat gtt                                           23

<210> SEQ ID NO 35
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 35
actcacgtac agcgttgaat gtt                                           23

<210> SEQ ID NO 36
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 36
actctgcgac agcgttgaat gtt                                           23

<210> SEQ ID NO 37
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 37
acagaccgac agcgttgaat gtt                                           23

<210> SEQ ID NO 38
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 38
tgtcaccgac agcgttgaat gtt                                           23

<210> SEQ ID NO 39
<211> LENGTH: 23
```

```
<212> TYPE: DNA
<213> ORGANISM: Artificial Sequence
<220> FEATURE:
<223> OTHER INFORMATION: Chemically synthesized Northern Probe sequence

<400> SEQUENCE: 39
actcaccgac agcgttttta tat                                              23

<210> SEQ ID NO 40
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 40
tgagtggtac agcgttgaat gtt                                              23

<210> SEQ ID NO 41
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 41
actcaccgtg ttgtaagaat gtt                                              23

<210> SEQ ID NO 42
<211> LENGTH: 23
<212> TYPE: DNA
<213> ORGANISM: Artificial Sequence
<220> FEATURE:
<223> OTHER INFORMATION: Chemically synthesized Northern Probe sequence

<400> SEQUENCE: 42
tgagtggttg ttgtaagaat gtt                                              23

<210> SEQ ID NO 43
<211> LENGTH: 15
<212> TYPE: DNA
<213> ORGANISM: Artificial Sequence
<220> FEATURE:
<223> OTHER INFORMATION: Chemically synthesized 15-nt miR-181a primer

<400> SEQUENCE: 43
actcaccgac agcgt                                                       15

<210> SEQ ID NO 44
<211> LENGTH: 15
<212> TYPE: DNA
<213> ORGANISM: Artificial Sequence
<220> FEATURE:
<223> OTHER INFORMATION: Chemically synthesized 15nt miR-181c primer

<400> SEQUENCE: 44
actcaccgac agcgt                                                       15

<210> SEQ ID NO 45
<211> LENGTH: 16
<212> TYPE: DNA
<213> ORGANISM: Artificial Sequence
<220> FEATURE:
<223> OTHER INFORMATION: Chemically synthesized miR-181a ladder oligo

<400> SEQUENCE: 45
```

-continued actcaccgac agcgtt                                        16

<210> SEQ ID NO 46
<211> LENGTH: 17
<212> TYPE: DNA
<213> ORGANISM: Artificial Sequence
<220> FEATURE:
<223> OTHER INFORMATION: Chemically synthesized miR-181a ladder oligo

<400> SEQUENCE: 46
actcaccgac agcgttg                                       17

<210> SEQ ID NO 47
<211> LENGTH: 18
<212> TYPE: DNA
<213> ORGANISM: Artificial Sequence
<220> FEATURE:
<223> OTHER INFORMATION: Chemically synthesized miR-181a ladder oligo

<400> SEQUENCE: 47
actcaccgac agcgttga                                      18

<210> SEQ ID NO 48
<211> LENGTH: 19
<212> TYPE: DNA
<213> ORGANISM: Artificial Sequence
<220> FEATURE:
<223> OTHER INFORMATION: Chemically synthesized miR-181a ladder oligo

<400> SEQUENCE: 48
actcaccgac agcgttgaa                                     19

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized miR-181a ladder oligo

<400> SEQUENCE: 49
actcaccgac agcgttgaat                                    20

<210> SEQ ID NO 50
<211> LENGTH: 21
<212> TYPE: DNA
<213> ORGANISM: Artificial Sequence
<220> FEATURE:
<223> OTHER INFORMATION: Chemically synthesized miR-181a ladder oligo

<400> SEQUENCE: 50
actcaccgac agcgttgaat g                                  21

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized miR-181a ladder oligo

<400> SEQUENCE: 51
actcaccgac agcgttgaat gt                                 22

<210> SEQ ID NO 52
<211> LENGTH: 23
<212> TYPE: DNA
<213> ORGANISM: Artificial Sequence

```
<220> FEATURE:
<223> OTHER INFORMATION: Chemically synthesized miR-181a ladder oligo

<400> SEQUENCE: 52
actcaccgac agcgttgaat gtt                                              23

<210> SEQ ID NO 53
<211> LENGTH: 16
<212> TYPE: DNA
<213> ORGANISM: Artificial Sequence
<220> FEATURE:
<223> OTHER INFORMATION: Chemically synthesized miR-181c ladder oligo

<400> SEQUENCE: 53
actcaccgac aggttg                                                      16

<210> SEQ ID NO 54
<211> LENGTH: 17
<212> TYPE: DNA
<213> ORGANISM: Artificial Sequence
<220> FEATURE:
<223> OTHER INFORMATION: Chemically synthesized miR-181c ladder oligo

<400> SEQUENCE: 54
actcaccgac aggttga                                                     17

<210> SEQ ID NO 55
<211> LENGTH: 18
<212> TYPE: DNA
<213> ORGANISM: Artificial Sequence
<220> FEATURE:
<223> OTHER INFORMATION: Chemically synthesized miR-181c ladder oligo

<400> SEQUENCE: 55
actcaccgac aggttgaa                                                    18

<210> SEQ ID NO 56
<211> LENGTH: 19
<212> TYPE: DNA
<213> ORGANISM: Artificial Sequence
<220> FEATURE:
<223> OTHER INFORMATION: Chemically synthesized miR-181c ladder oligo

<400> SEQUENCE: 56
actcaccgac aggttgaat                                                   19

<210> SEQ ID NO 57
<211> LENGTH: 20
<212> TYPE: DNA
<213> ORGANISM: Artificial Sequence
<220> FEATURE:
<223> OTHER INFORMATION: Chemically synthesized miR-181c ladder oligo

<400> SEQUENCE: 57
actcaccgac aggttgaatg                                                  20

<210> SEQ ID NO 58
<211> LENGTH: 21
<212> TYPE: DNA
<213> ORGANISM: Artificial Sequence
<220> FEATURE:
<223> OTHER INFORMATION: Chemically synthesized miR-181c ladder oligo

<400> SEQUENCE: 58
actcaccgac aggttgaatg t                                                21
```

```
<210> SEQ ID NO 59
<211> LENGTH: 22
<212> TYPE: DNA
<213> ORGANISM: Artificial Sequence
<220> FEATURE:
<223> OTHER INFORMATION: Chemically synthesized miR-181c ladder oligo

<400> SEQUENCE: 59
actcaccgac aggttgaatg tt                                              22

<210> SEQ ID NO 60
<211> LENGTH: 23
<212> TYPE: RNA
<213> ORGANISM: Artificial Sequence
<220> FEATURE:
<223> OTHER INFORMATION: Chemically synthesized mature miRNA: miR-181a

<400> SEQUENCE: 60
aacauucaac gcugucggug agu                                             23

<210> SEQ ID NO 61
<211> LENGTH: 22
<212> TYPE: RNA
<213> ORGANISM: Artificial Sequence
<220> FEATURE:
<223> OTHER INFORMATION: Chemically synthesized mature miRNA: miR-181c

<400> SEQUENCE: 61
aacauucaac cugucgguga gu                                              22

<210> SEQ ID NO 62
<211> LENGTH: 60
<212> TYPE: RNA
<213> ORGANISM: Unknown
<220> FEATURE:
<223> OTHER INFORMATION: Wild-type mir-181a-1 gene

<400> SEQUENCE: 62
aacauucaac gcugucggug aguuuggaau ucaaauaaaa accaucgacc guugauugua     60

<210> SEQ ID NO 63
<211> LENGTH: 59
<212> TYPE: RNA
<213> ORGANISM: Unknown
<220> FEATURE:
<223> OTHER INFORMATION: Wild-type miR-181c

<400> SEQUENCE: 63
aacauucaac cugucgguga guuugggcag cucagacaaa ccaucgaccg uugagugga      59

<210> SEQ ID NO 64
<211> LENGTH: 59
<212> TYPE: RNA
<213> ORGANISM: Artificial Sequence
<220> FEATURE:
<223> OTHER INFORMATION: Chemically synthesized mature miRNA: 181a (c
      stem)

<400> SEQUENCE: 64
aacauucaac cugucgguga guuuggaauu caaauaaaaa ccaucgaccg uugagugga      59

<210> SEQ ID NO 65
<211> LENGTH: 60
<212> TYPE: RNA
<213> ORGANISM: Artificial Sequence
<220> FEATURE:
```

```
<223> OTHER INFORMATION: Chemically synthesized mature miRNA: 181c (a
      stem 1)

<400> SEQUENCE: 65
aacauucaac gcugucggug aguuugggca gcucagacaa accaucgacc guugauugua      60

<210> SEQ ID NO 66
<211> LENGTH: 59
<212> TYPE: RNA
<213> ORGANISM: Artificial Sequence
<220> FEATURE:
<223> OTHER INFORMATION: Chemically synthesized mature miRNA: 181c (a
      stem 2)

<400> SEQUENCE: 66
aacauucaac gcugucggug auuugggcag cucagacaaa caucgacccg uugagugga       59

<210> SEQ ID NO 67
<211> LENGTH: 59
<212> TYPE: RNA
<213> ORGANISM: Artificial Sequence
<220> FEATURE:
<223> OTHER INFORMATION: Chemically synthesized mature miRNA: 181c (a
      stem 3)

<400> SEQUENCE: 67
aacauucaac gcugucggug aguugggcag cucagacaac caucgacccg uugagugga       59

<210> SEQ ID NO 68
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
      mutant: LP1

<400> SEQUENCE: 68
aacauucaac gcugucggug aguuccaau ucaaauaaaa accaucgacc guugauugua       60

<210> SEQ ID NO 69
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
      mutant: LP2

<400> SEQUENCE: 69
aacauucaac gcugucggug aguuuggauu ucaaauaaaa accaucgacc guugauugua      60

<210> SEQ ID NO 70
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
      mutant: LP3

<400> SEQUENCE: 70
aacauucaac gcugucggug aguuggaaa acaaauaaaa accaucgacc guugauugua       60

<210> SEQ ID NO 71
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
```

-continued mutant: LP4

<400> SEQUENCE: 71
aacauucaac gcugucggug aguuuggaau uguaauaaaa accaucgacc guugauugua    60

<210> SEQ ID NO 72
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
      mutant: LP5

<400> SEQUENCE: 72
aacauucaac gcugucggug aguuuggaau ucacguaaaa accaucgacc guugauugua    60

<210> SEQ ID NO 73
<211> LENGTH: 60
<212> TYPE: RNA
<213> ORGANISM: Artificial Sequence
<220> FEATURE:
<223> OTHER INFORMATION: Chemically synthesized pre-miR-181a-1 loop
      mutant: LP6

<400> SEQUENCE: 73
aacauucaac gcugucggug aguuuggaau ucaaauaaaa accaucgacc guugauugua    60

<210> SEQ ID NO 74
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 74
aacauucaac gcugucggug agu                                            23

<210> SEQ ID NO 75
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 75
uuggaauuca aauaaaa                                                   17

<210> SEQ ID NO 76
<211> LENGTH: 23
<212> TYPE: RNA
<213> ORGANISM: Artificial Sequence
<220> FEATURE:
<223> OTHER INFORMATION: Chemically synthesized mir-181a-1mutant: M1

<400> SEQUENCE: 76
auaauucaac gcugucggug agu                                            23

<210> SEQ ID NO 77
<211> LENGTH: 23
<212> TYPE: RNA
<213> ORGANISM: Artificial Sequence
<220> FEATURE:
<223> OTHER INFORMATION: Chemically synthesized mir-181a-1mutant: M2

<400> SEQUENCE: 77
aacuaucaac gcugucggug agu                                            23

<210> SEQ ID NO 78
<211> LENGTH: 23
<212> TYPE: RNA
<213> ORGANISM: Artificial Sequence
<220> FEATURE:
<223> OTHER INFORMATION: Chemically synthesized mir-181a-1mutant: M3

<400> SEQUENCE: 78
aacauaaaac gcugucggug agu                                           23

<210> SEQ ID NO 79
<211> LENGTH: 23
<212> TYPE: RNA
<213> ORGANISM: Artificial Sequence
<220> FEATURE:
<223> OTHER INFORMATION: Chemically synthesized mir-181a-1mutant: M4

<400> SEQUENCE: 79
aacauucuuc gcugucggug agu                                           23

<210> SEQ ID NO 80
<211> LENGTH: 23
<212> TYPE: RNA
<213> ORGANISM: Artificial Sequence
<220> FEATURE:
<223> OTHER INFORMATION: Chemically synthesized mir-181a-1mutant: M5

<400> SEQUENCE: 80
aacauucaaa ccugucggug agu                                           23

<210> SEQ ID NO 81
<211> LENGTH: 23
<212> TYPE: RNA
<213> ORGANISM: Artificial Sequence
<220> FEATURE:
<223> OTHER INFORMATION: Chemically synthesized mir-181a-1mutant: M6

<400> SEQUENCE: 81
aacauucaac gaagucggug agu                                           23

<210> SEQ ID NO 82
<211> LENGTH: 23
<212> TYPE: RNA
<213> ORGANISM: Artificial Sequence
<220> FEATURE:
<223> OTHER INFORMATION: Chemically synthesized mir-181a-1mutant: M7

<400> SEQUENCE: 82
aacauucaac gcucacggug agu                                           23

<210> SEQ ID NO 83
<211> LENGTH: 23
<212> TYPE: RNA
<213> ORGANISM: Artificial Sequence
<220> FEATURE:
<223> OTHER INFORMATION: Chemically synthesized mir-181a-1mutant: M8

<400> SEQUENCE: 83
aacauucaac gcuguacgug agu                                           23

<210> SEQ ID NO 84
<211> LENGTH: 23
<212> TYPE: RNA
<213> ORGANISM: Artificial Sequence
<220> FEATURE:

<223> OTHER INFORMATION: Chemically synthesized mir-181a-1mutant: M9

<400> SEQUENCE: 84
aacauucaac gcugucgcag agu                                        23

<210> SEQ ID NO 85
<211> LENGTH: 23
<212> TYPE: RNA
<213> ORGANISM: Artificial Sequence
<220> FEATURE:
<223> OTHER INFORMATION: Chemically synthesized mir-181a-1mutant: M10

<400> SEQUENCE: 85
aacauucaac gcugucgguc ugu                                        23

<210> SEQ ID NO 86
<211> LENGTH: 23
<212> TYPE: RNA
<213> ORGANISM: Artificial Sequence
<220> FEATURE:
<223> OTHER INFORMATION: Chemically synthesized mir-181a-1mutant: M11

<400> SEQUENCE: 86
aacauucaac gcugucggug aca                                        23

<210> SEQ ID NO 87
<211> LENGTH: 23
<212> TYPE: RNA
<213> ORGANISM: Artificial Sequence
<220> FEATURE:
<223> OTHER INFORMATION: Chemically synthesized mir-181a-1mutant: SM1

<400> SEQUENCE: 87
auauaaaaac gcugucggug agu                                        23

<210> SEQ ID NO 88
<211> LENGTH: 23
<212> TYPE: RNA
<213> ORGANISM: Artificial Sequence
<220> FEATURE:
<223> OTHER INFORMATION: Chemically synthesized mir-181a-1mutant: SM2

<400> SEQUENCE: 88
aacauucuua caacacggug agu                                        23

<210> SEQ ID NO 89
<211> LENGTH: 23
<212> TYPE: RNA
<213> ORGANISM: Artificial Sequence
<220> FEATURE:
<223> OTHER INFORMATION: Chemically synthesized mir-181a-1mutant: SM3

<400> SEQUENCE: 89
aacauucaac gcuguaacac uca                                        23

<210> SEQ ID NO 90
<211> LENGTH: 23
<212> TYPE: RNA
<213> ORGANISM: Artificial Sequence
<220> FEATURE:
<223> OTHER INFORMATION: Chemically synthesized mir-181a-1mutant: SM4

<400> SEQUENCE: 90
aacauucuua caacaaccac uca                                        23

```
<210> SEQ ID NO 91
<211> LENGTH: 60
<212> TYPE: DNA
<213> ORGANISM: Artificial Sequence
<220> FEATURE:
<223> OTHER INFORMATION: Chemically synthesized mir-181a-1mutant: M1

<400> SEQUENCE: 91
ataauucaac gcugucggug aguuuggaau ucaauaaaa accaucgacc guugauutaa    60

<210> SEQ ID NO 92
<211> LENGTH: 60
<212> TYPE: DNA
<213> ORGANISM: Artificial Sequence
<220> FEATURE:
<223> OTHER INFORMATION: Chemically synthesized mir-181a-1mutant: M2

<400> SEQUENCE: 92
aactaucaac gcugucggug aguuuggaau ucaauaaaa accaucgacc guugaaagua    60

<210> SEQ ID NO 93
<211> LENGTH: 60
<212> TYPE: RNA
<213> ORGANISM: Artificial Sequence
<220> FEATURE:
<223> OTHER INFORMATION: Chemically synthesized mir-181a-1mutant: M3

<400> SEQUENCE: 93
aacauaaaac gcugucggug aguuuggaau ucaauaaaa accaucgacc guuuuugua    60

<210> SEQ ID NO 94
<211> LENGTH: 60
<212> TYPE: RNA
<213> ORGANISM: Artificial Sequence
<220> FEATURE:
<223> OTHER INFORMATION: Chemically synthesized mir-181a-1mutant: M4

<400> SEQUENCE: 94
aacauucuuc gcugucggug aguuuggaau ucaauaaaa accaucgacc gaagauugua    60

<210> SEQ ID NO 95
<211> LENGTH: 60
<212> TYPE: RNA
<213> ORGANISM: Artificial Sequence
<220> FEATURE:
<223> OTHER INFORMATION: Chemically synthesized mir-181a-1mutant: M5

<400> SEQUENCE: 95
aacauucaaa ccgucggug aguuuggaau ucaauaaaa accaucgacg uuugauugua    60

<210> SEQ ID NO 96
<211> LENGTH: 60
<212> TYPE: RNA
<213> ORGANISM: Artificial Sequence
<220> FEATURE:
<223> OTHER INFORMATION: Chemically synthesized mir-181a-1mutant: M6

<400> SEQUENCE: 96
aacauucaac gaagucggug aguuuggaau ucaauaaaa accaucgacc guugauugua    60

<210> SEQ ID NO 97
<211> LENGTH: 60
<212> TYPE: RNA
<213> ORGANISM: Artificial Sequence
<220> FEATURE:
<223> OTHER INFORMATION: Chemically synthesized mir-181a-1mutant: M7
```

-continued

<400> SEQUENCE: 97
aacauucaac gcucacggug aguuuggaau ucaaauaaaa accaucgugc guugauugua     60

<210> SEQ ID NO 98
<211> LENGTH: 60
<212> TYPE: RNA
<213> ORGANISM: Artificial Sequence
<220> FEATURE:
<223> OTHER INFORMATION: Chemically synthesized mir-181a-1mutant: M8

<400> SEQUENCE: 98
aacauucaac gcguacgug aguuuggaau ucaaauaaaa accauguacc guugauugua     60

<210> SEQ ID NO 99
<211> LENGTH: 60
<212> TYPE: RNA
<213> ORGANISM: Artificial Sequence
<220> FEATURE:
<223> OTHER INFORMATION: Chemically synthesized mir-181a-1mutant: M9

<400> SEQUENCE: 99
aacauucaac gcgucgcag aguuuggaau ucaaauaaaa accgcgacc guugauugua     60

<210> SEQ ID NO 100
<211> LENGTH: 60
<212> TYPE: RNA
<213> ORGANISM: Artificial Sequence
<220> FEATURE:
<223> OTHER INFORMATION: Chemically synthesized mir-181a-1mutant: M10

<400> SEQUENCE: 100
aacauucaac gcgucgguc uguuuggaau ucaaauaaaa acgaucgacc guugauugua     60

<210> SEQ ID NO 101
<211> LENGTH: 60
<212> TYPE: RNA
<213> ORGANISM: Artificial Sequence
<220> FEATURE:
<223> OTHER INFORMATION: Chemically synthesized mir-181a-1mutant: M11

<400> SEQUENCE: 101
aacauucaac gcgucggug acauuggaau ucaaauaaaa ugcaucgacc guugauugua     60

<210> SEQ ID NO 102
<211> LENGTH: 60
<212> TYPE: RNA
<213> ORGANISM: Artificial Sequence
<220> FEATURE:
<223> OTHER INFORMATION: Chemically synthesized mir-181a-1mutant: SM1

<400> SEQUENCE: 102
auauaaaaac gcgucggug aguuuggaau ucaaauaaaa accaucgacc guuuuauaa     60

<210> SEQ ID NO 103
<211> LENGTH: 60
<212> TYPE: RNA
<213> ORGANISM: Artificial Sequence
<220> FEATURE:
<223> OTHER INFORMATION: Chemically synthesized mir-181a-1mutant: SM2

<400> SEQUENCE: 103
aacauucuua caacacggug aguuuggaau ucaaauaaaa accaucgugg uaagauugua     60

<210> SEQ ID NO 104
<211> LENGTH: 60

```
<212> TYPE: RNA
<213> ORGANISM: Artificial Sequence
<220> FEATURE:
<223> OTHER INFORMATION: Chemically synthesized mir-181a-1mutant: SM3

<400> SEQUENCE: 104
aacauucaac gcuguaccac ucauuggaau ucaaauaaaa ugguggacc guugauugua    60

<210> SEQ ID NO 105
<211> LENGTH: 60
<212> TYPE: RNA
<213> ORGANISM: Artificial Sequence
<220> FEATURE:
<223> OTHER INFORMATION: Chemically synthesized mir-181a-1mutant: SM4

<400> SEQUENCE: 105
aacauucuua caacaaccac ucauuggaau ucaaauaaaa uggugguugg uaagauugua    60

<210> SEQ ID NO 106
<211> LENGTH: 23
<212> TYPE: RNA
<213> ORGANISM: Artificial Sequence
<220> FEATURE:
<223> OTHER INFORMATION: Chemically synthesized sequence derived from
      Mouse miR-181a

<400> SEQUENCE: 106
aacauucaac gcugucggug agu                                           23

<210> SEQ ID NO 107
<211> LENGTH: 22
<212> TYPE: RNA
<213> ORGANISM: Artificial Sequence
<220> FEATURE:
<223> OTHER INFORMATION: Chemically synthesized sequence derived from
      Mouse miR-181b

<400> SEQUENCE: 107
aacauucauu gcugucggug gg                                            22

<210> SEQ ID NO 108
<211> LENGTH: 22
<212> TYPE: RNA
<213> ORGANISM: Artificial Sequence
<220> FEATURE:
<223> OTHER INFORMATION: Chemically synthesized sequence derived from
      Mouse miR-181c

<400> SEQUENCE: 108
aacauucaac cugucgguga gu                                            22

<210> SEQ ID NO 109
<211> LENGTH: 24
<212> TYPE: RNA
<213> ORGANISM: Artificial Sequence
<220> FEATURE:
<223> OTHER INFORMATION: Chemically synthesized sequence derived from
      Mouse miR-181d

<400> SEQUENCE: 109
aacauucauu guguucggug gguu                                          24

<210> SEQ ID NO 110
<211> LENGTH: 60
<212> TYPE: RNA
<213> ORGANISM: Artificial Sequence
<220> FEATURE:
```

```
<223> OTHER INFORMATION: Chemically synthesized sequence derived from
      Mouse pre-mir-181a-1

<400> SEQUENCE: 110
aacauucaac gcugucggug aguuuggaau ucaaauaaaa accaucgacc guugauugua      60

<210> SEQ ID NO 111
<211> LENGTH: 64
<212> TYPE: RNA
<213> ORGANISM: Artificial Sequence
<220> FEATURE:
<223> OTHER INFORMATION: Chemically synthesized sequence derived from
      Mouse pre-mir-181a-2

<400> SEQUENCE: 111
aacauucaac gcugucggug aguuuggaau ucaaaaacaa aaaaccauc gaccguugau       60 ugua                                                                  64

<210> SEQ ID NO 112
<211> LENGTH: 60
<212> TYPE: RNA
<213> ORGANISM: Artificial Sequence
<220> FEATURE:
<223> OTHER INFORMATION: Chemically synthesized sequence derived from
      Mouse pre-mir-181b-1

<400> SEQUENCE: 112
aacauucauu gcugucggug gguugaacug uguagaaaag cucacugaac aaugaaugca      60

<210> SEQ ID NO 113
<211> LENGTH: 58
<212> TYPE: RNA
<213> ORGANISM: Artificial Sequence
<220> FEATURE:
<223> OTHER INFORMATION: Chemically synthesized sequence derived from
      Mouse pre-mir-181b-2

<400> SEQUENCE: 113
aacauucauu gcugucggug gguuugaaug ucaaccaacu cacugaucaa ugaaugca        58

<210> SEQ ID NO 114
<211> LENGTH: 59
<212> TYPE: RNA
<213> ORGANISM: Artificial Sequence
<220> FEATURE:
<223> OTHER INFORMATION: Chemically synthesized sequence derived from
      Mouse pre-mir-181c

<400> SEQUENCE: 114
aacauucaac cugucgguga guuugggcag cucagacaaa ccaucgaccg uugagugga       59

<210> SEQ ID NO 115
<211> LENGTH: 62
<212> TYPE: RNA
<213> ORGANISM: Artificial Sequence
<220> FEATURE:
<223> OTHER INFORMATION: Chemically synthesized sequence derived from
      Mouse pre-mir-181d

<400> SEQUENCE: 115
aacauucauu guugucggug gguugugagg aggcagccag acccaccggg ggaugaaugu      60
ca                                                                    62

<210> SEQ ID NO 116
<211> LENGTH: 60
```

```
<212> TYPE: RNA
<213> ORGANISM: Artificial Sequence
<220> FEATURE:
<223> OTHER INFORMATION: Chemically synthesized sequence derived from
      Human pre-mir-181a-1

<400> SEQUENCE: 116
aacauucaac gcugucggug aguuuggaau uaaaaucaaa accaucgacc guugauugua      60

<210> SEQ ID NO 117
<211> LENGTH: 58
<212> TYPE: RNA
<213> ORGANISM: Artificial Sequence
<220> FEATURE:
<223> OTHER INFORMATION: Chemically synthesized sequence derived from
      Human pre-mir-181a-2

<400> SEQUENCE: 117
aacauucaac gcugucggug aguuugggau uugaaaaaac caucgaccgu ugauugua        58

<210> SEQ ID NO 118
<211> LENGTH: 60
<212> TYPE: RNA
<213> ORGANISM: Artificial Sequence
<220> FEATURE:
<223> OTHER INFORMATION: Chemically synthesized sequence derived from
      Human pre-mir-181b-1

<400> SEQUENCE: 118
aacauucauu gcugucggug gguugaacug ugggacaag cucacugaac aaugaaugca       60

<210> SEQ ID NO 119
<211> LENGTH: 58
<212> TYPE: RNA
<213> ORGANISM: Artificial Sequence
<220> FEATURE:
<223> OTHER INFORMATION: Chemically synthesized sequence derived from
      Human pre-mir-181b-2

<400> SEQUENCE: 119
aacauucauu gcugucggug gguuugaguc ugaaucaacu cacugaucaa ugaaugca        58

<210> SEQ ID NO 120
<211> LENGTH: 59
<212> TYPE: RNA
<213> ORGANISM: Artificial Sequence
<220> FEATURE:
<223> OTHER INFORMATION: Chemically synthesized sequence derived from
      Human pre-mir-181c

<400> SEQUENCE: 120
aacauucaac cugucgguga guuugggcag cucaggcaaa ccaucgaccg uugagugga       59

<210> SEQ ID NO 121
<211> LENGTH: 63
<212> TYPE: RNA
<213> ORGANISM: Artificial Sequence
<220> FEATURE:
<223> OTHER INFORMATION: Chemically synthesized sequence derived from
      Human pre-mir-181d

<400> SEQUENCE: 121
aacauucauu guugucggug gguugugagg acugaggcca gacccaccgg gggaugaaug      60
uca                                                                   63

<210> SEQ ID NO 122
```

```
<211> LENGTH: 17
<212> TYPE: RNA
<213> ORGANISM: Artificial Sequence
<220> FEATURE:
<223> OTHER INFORMATION: Chemically synthesized sequence, ppy-mir-181a-
      1, derived from Pongo pygmaeus

<400> SEQUENCE: 122
uuggaauuaa aaucaaa                                                   17

<210> SEQ ID NO 123
<211> LENGTH: 17
<212> TYPE: RNA
<213> ORGANISM: Artificial Sequence
<220> FEATURE:
<223> OTHER INFORMATION: Chemically synthesized sequence, ptr-mir-181a-
      1, derived from Pan troglodytes

<400> SEQUENCE: 123
uuggaauuaa aaucaaa                                                   17

<210> SEQ ID NO 124
<211> LENGTH: 17
<212> TYPE: RNA
<213> ORGANISM: Artificial Sequence
<220> FEATURE:
<223> OTHER INFORMATION: Chemically synthesized sequence, ppa-mir-181a-
      1, derived from Pan paniscus

<400> SEQUENCE: 124
uuggaauuaa aaucaaa                                                   17

<210> SEQ ID NO 125
<211> LENGTH: 17
<212> TYPE: RNA
<213> ORGANISM: Artificial Sequence
<220> FEATURE:
<223> OTHER INFORMATION: Chemically synthesized sequence, mne-mir-181a-
      1, derived from Macaca nemestrina

<400> SEQUENCE: 125
uuggaauuaa aaucaaa                                                   17

<210> SEQ ID NO 126
<211> LENGTH: 17
<212> TYPE: RNA
<213> ORGANISM: Artificial Sequence
<220> FEATURE:
<223> OTHER INFORMATION: Chemically synthesized sequence, mml-mir-181a-
      1, derived from Macaca mulatta

<400> SEQUENCE: 126
uuggaauuaa aaucaaa                                                   17

<210> SEQ ID NO 127
<211> LENGTH: 17
<212> TYPE: RNA
<213> ORGANISM: Artificial Sequence
<220> FEATURE:
<223> OTHER INFORMATION: Chemically synthesized sequence, lla-mir-181a-
      1, derived from Lagothrix lagotricha

<400> SEQUENCE: 127
uuggaauuaa aaucaaa                                                   17

<210> SEQ ID NO 128
<211> LENGTH: 17
```

```
<212> TYPE: RNA
<213> ORGANISM: Artificial Sequence
<220> FEATURE:
<223> OTHER INFORMATION: Chemically synthesized sequence, hsa-mir-181a-
      1, derived from Homo sapiens

<400> SEQUENCE: 128
uuggaauuaa aaucaaa                                                    17

<210> SEQ ID NO 129
<211> LENGTH: 17
<212> TYPE: RNA
<213> ORGANISM: Artificial Sequence
<220> FEATURE:
<223> OTHER INFORMATION: Chemically synthesized sequence, ggo-mir-181a-
      1, derived from Gorilla gorilla

<400> SEQUENCE: 129
uuggaauuaa aaucaaa                                                    17

<210> SEQ ID NO 130
<211> LENGTH: 17
<212> TYPE: RNA
<213> ORGANISM: Artificial Sequence
<220> FEATURE:
<223> OTHER INFORMATION: Chemically synthesized sequence, mmu-mir-181a-
      1, derived from Mus musculus

<400> SEQUENCE: 130
uuggaauuca aauaaaa                                                    17

<210> SEQ ID NO 131
<211> LENGTH: 18
<212> TYPE: RNA
<213> ORGANISM: Artificial Sequence
<220> FEATURE:
<223> OTHER INFORMATION: Chemically synthesized sequence, rno-mir-181a-
      1, derived from Rattus norvegicus

<400> SEQUENCE: 131
uuggaauuca aauaaaaa                                                   18

<210> SEQ ID NO 132
<211> LENGTH: 17
<212> TYPE: RNA
<213> ORGANISM: Artificial Sequence
<220> FEATURE:
<223> OTHER INFORMATION: Chemically synthesized sequence, gga-mir-181a-
      1, derived from Gallus gallus

<400> SEQUENCE: 132
uuggaauuua agugaaa                                                    17

<210> SEQ ID NO 133
<211> LENGTH: 18
<212> TYPE: RNA
<213> ORGANISM: Artificial Sequence
<220> FEATURE:
<223> OTHER INFORMATION: Chemically synthesized sequence, fru-mir-181a-
      1, derived from Fugu rubripes

<400> SEQUENCE: 133
uugagcuaaa uuggaaaa                                                   18

<210> SEQ ID NO 134
<211> LENGTH: 18
<212> TYPE: RNA
```

```
<213> ORGANISM: Artificial Sequence
<220> FEATURE:
<223> OTHER INFORMATION: Chemically synthesized sequence, tni-mir-181a-
      1, derived from Tetraodon nigroviridis

<400> SEQUENCE: 134
uugagccaaa uuggaaaa                                                   18

<210> SEQ ID NO 135
<211> LENGTH: 18
<212> TYPE: RNA
<213> ORGANISM: Artificial Sequence
<220> FEATURE:
<223> OTHER INFORMATION: Chemically synthesized sequence, dre-mir-181a-
      1, derived from Danio rerio

<400> SEQUENCE: 135
uugagcuaaa uggaaaaa                                                   18

<210> SEQ ID NO 136
<211> LENGTH: 17
<212> TYPE: RNA
<213> ORGANISM: Artificial Sequence
<220> FEATURE:
<223> OTHER INFORMATION: Chemically synthesized sequence, ggo-mir-181c,
      derived from Gorilla gorilla

<400> SEQUENCE: 136
uugggcagcu caggcaa                                                    17

<210> SEQ ID NO 137
<211> LENGTH: 17
<212> TYPE: RNA
<213> ORGANISM: Artificial Sequence
<220> FEATURE:
<223> OTHER INFORMATION: Chemically synthesized sequence, hsa-mir-181c,
      derived from Homo sapiens

<400> SEQUENCE: 137
uugggcagcu caggcaa                                                    17

<210> SEQ ID NO 138
<211> LENGTH: 17
<212> TYPE: RNA
<213> ORGANISM: Artificial Sequence
<220> FEATURE:
<223> OTHER INFORMATION: Chemically synthesized sequence, mml-mir-181c,
      derived from Macaca mulatta

<400> SEQUENCE: 138
uugggcagcu caggcaa                                                    17

<210> SEQ ID NO 139
<211> LENGTH: 17
<212> TYPE: RNA
<213> ORGANISM: Artificial Sequence
<220> FEATURE:
<223> OTHER INFORMATION: Chemically synthesized sequence, ppa-mir-181c,
      derived from Pan paniscus

<400> SEQUENCE: 139
uugggcagcu caggcaa                                                    17

<210> SEQ ID NO 140
<211> LENGTH: 17
<212> TYPE: RNA
<213> ORGANISM: Artificial Sequence
```

```
<220> FEATURE:
<223> OTHER INFORMATION: Chemically synthesized sequence, ptr-mir-181c,
      derived from Pan troglodytes

<400> SEQUENCE: 140
uugggcagcu caggcaa                                                   17

<210> SEQ ID NO 141
<211> LENGTH: 17
<212> TYPE: RNA
<213> ORGANISM: Artificial Sequence
<220> FEATURE:
<223> OTHER INFORMATION: Chemically synthesized sequence, ssc-mir-181c,
      derived from Sus scrofa

<400> SEQUENCE: 141
uugggcagcu caggcaa                                                   17

<210> SEQ ID NO 142
<211> LENGTH: 17
<212> TYPE: RNA
<213> ORGANISM: Artificial Sequence
<220> FEATURE:
<223> OTHER INFORMATION: Chemically synthesized sequence, mmu-mir-181c,
      derived from Mus musculus

<400> SEQUENCE: 142
uugggcagcu cagacaa                                                   17

<210> SEQ ID NO 143
<211> LENGTH: 17
<212> TYPE: RNA
<213> ORGANISM: Artificial Sequence
<220> FEATURE:
<223> OTHER INFORMATION: Chemically synthesized sequence, rno-mir-181c,
      derived from Rattus norvegicus

<400> SEQUENCE: 143
uugggcagcu cagacaa                                                   17

<210> SEQ ID NO 144
<211> LENGTH: 65
<212> TYPE: DNA
<213> ORGANISM: C. elegans
<220> FEATURE:
<221> NAME/KEY: misc_feature
<223> OTHER INFORMATION: Wild-type c-let-7 sequence

<400> SEQUENCE: 144
tgaggtagta ggttgtatag tttggaatat taccaccggt gaactatgca attttctacc    60
ttacc                                                                65

<210> SEQ ID NO 145
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_2G->A

<400> SEQUENCE: 145
taaggtagta ggttgtatag tttggaatat taccaccggt gaactatgca attttctacc    60
ttacc                                                                65

<210> SEQ ID NO 146
```

```
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_2G->C

<400> SEQUENCE: 146
tcaggtagta ggttgtatag tttggaatat taccaccggt gaactatgca attttctacc    60
ttacc                                                                65

<210> SEQ ID NO 147
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_LPA

<400> SEQUENCE: 147
tgaggtagta ggttgtatag tttccaatat taccaccggt gaactatgca attttctacc    60
ttacc                                                                65

<210> SEQ ID NO 148
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_LPB

<400> SEQUENCE: 148
tgaggtagta ggttgtatag tttccaatat taccaggcct gaactatgca attttctacc    60
ttacc                                                                65

<210> SEQ ID NO 149
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_LPC

<400> SEQUENCE: 149
tgaggtagta ggttgtatag tttggaatat taccacccct gaactatgca attttctacc    60
ttacc                                                                65

<210> SEQ ID NO 150
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_LPD

<400> SEQUENCE: 150
tgaggtagta ggttgtatag tttccaatat taccacccct gaactatgca attttctacc    60
ttacc                                                                65

<210> SEQ ID NO 151
<211> LENGTH: 65
<212> TYPE: DNA
<213> ORGANISM: Artificial Sequence
<220> FEATURE:
```

```
<223> OTHER INFORMATION: Chemically synthesized mutant c-let-7 sequence:
      Let-7_stem1

<400> SEQUENCE: 151
actcgtagta ggttgtatag tttggaatat taccaccggt gaactatgca attttctacg    60
agtcc                                                                65

<210> SEQ ID NO 152
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_stem2

<400> SEQUENCE: 152
tgagcatcta ggttgtatag tttggaatat taccaccggt gaactatgca attttgatgc    60
ttacc                                                                65

<210> SEQ ID NO 153
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_stem3

<400> SEQUENCE: 153
tgaggtagat ccaactatag tttggaatat taccaccggt gaactatggt tggaactacc    60
ttacc                                                                65

<210> SEQ ID NO 154
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_stem4

<400> SEQUENCE: 154
tgaggtagta ggttgatatc aatggaatat taccaccggt gttgatatca attttctacc    60
ttacc                                                                65

<210> SEQ ID NO 155
<211> LENGTH: 65
<212> TYPE: DNA
<213> ORGANISM: Artificial Sequence
<220> FEATURE:
<223> OTHER INFORMATION: Chemically synthesized mutant c-let-7 sequence:
      Let-7_PS

<400> SEQUENCE: 155
tgaggtagta ggttgtatag tttggaatat taccaccggt gaactataca acctactacc    60
tcacc                                                                65

<210> SEQ ID NO 156
<211> LENGTH: 85
<212> TYPE: DNA
<213> ORGANISM: Artificial Sequence
<220> FEATURE:
<223> OTHER INFORMATION: Chemically synthesized pre-let-7 sequence

<400> SEQUENCE: 156
```

```
tcgagccctg aggtagtagg ttgtatagtt tggaatatta ccaccggtga actatgcaat    60
tttctacctt acctttttaa ttaag                                          85
```

<210> SEQ ID NO 157
<211> LENGTH: 85
<212> TYPE: DNA
<213> ORGANISM: Artificial Sequence
<220> FEATURE:
<223> OTHER INFORMATION: Chemically synthesized sh-let-7 sequence

<400> SEQUENCE: 157

```
tcgagccctg aggtagtagg ttgtatagtt tggaatatta ccaccggtga actatacaac    60
ctactacctc acctttttaa ttaag                                          85
```

<210> SEQ ID NO 158
<211> LENGTH: 102
<212> TYPE: DNA
<213> ORGANISM: Renilla reniformis
<220> FEATURE:
<221> NAME/KEY: misc_feature
<223> OTHER INFORMATION: Lin-41_LCS-wt

<400> SEQUENCE: 158

```
aactcaagta tacctttat acaaccgttc tacactcaac gcgatgtaaa tatcgcaatc     60 ccttttata caaccattct gcctctgaac cattgaaacc tt                        102
```

<210> SEQ ID NO 159
<211> LENGTH: 102
<212> TYPE: DNA
<213> ORGANISM: Artificial Sequence
<220> FEATURE:
<223> OTHER INFORMATION: Chemically synthesized mutant Lin-41-LCS
      sequence: Lin-41_LCS-sm

<400> SEQUENCE: 159

```
aactcaagta tacctttat acaaccgttc ttgtgagaac gcgatgtaaa tatcgcaatc     60 ccttttata caaccattga cggactgaac cattgaaacc tt                        102
```

<210> SEQ ID NO 160
<211> LENGTH: 102
<212> TYPE: DNA
<213> ORGANISM: Artificial Sequence
<220> FEATURE:
<223> OTHER INFORMATION: Chemically synthesized mutant Lin-41-LCS
      sequence: Lin-41_LCS-2U

<400> SEQUENCE: 160

```
aactcaagta tacctttat acaaccgttc tacacttaac gcgatgtaaa tatcgcaatc     60 ccttttata caaccattct gcctttgaac cattgaaacc tt                        102
```

<210> SEQ ID NO 161
<211> LENGTH: 102
<212> TYPE: DNA
<213> ORGANISM: Artificial Sequence
<220> FEATURE:
<223> OTHER INFORMATION: Chemically synthesized mutant Lin-41-LCS
      sequence: Lin-41_LCS-2G

<400> SEQUENCE: 161

```
aactcaagta tacctttat acaaccgttc tacactgaac gcgatgtaaa tatcgcaatc     60 ccttttata caaccattct gcctgtgaac cattgaaacc tt                        102
```

```
<210> SEQ ID NO 162
<211> LENGTH: 103
<212> TYPE: DNA
<213> ORGANISM: Renilla reniformis
<220> FEATURE:
<221> NAME/KEY: misc_feature
<223> OTHER INFORMATION: Lin-41_T1T2P-wt

<400> SEQUENCE: 162
aactcaagta taccttaact atacaaccta ctacctcaac gcgatgtaaa tatcgcaatc      60
ccttaactat acaacctact acctcatgaa ccattgaaac ctt                      103

<210> SEQ ID NO 163
<211> LENGTH: 103
<212> TYPE: DNA
<213> ORGANISM: Artificial Sequence
<220> FEATURE:
<223> OTHER INFORMATION: Chemically synthesized mutant Lin-41_T1T2P
      sequence:
      Lin-41_T1T2P-sm

<400> SEQUENCE: 163
aactcaagta taccttaact atacaaccta ctgtgagaac gcgatgtaaa tatcgcaatc      60
ccttaactat acaacctacg acggaatgaa ccattgaaac ctt                      103

<210> SEQ ID NO 164
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 164
aactatacaa cctactacct ca                                              22

<210> SEQ ID NO 165
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 165
aactatacaa cctactacct ca                                              22

<210> SEQ ID NO 166
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 166
aactatacaa cctactacga gt                                              22

<210> SEQ ID NO 167
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 167
aactatacaa cctagatgct ca                                              22
```

-continued

```
<210> SEQ ID NO 168
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 168
aactatagtt ggatctacct ca                                              22

<210> SEQ ID NO 169
<211> LENGTH: 22
<212> TYPE: DNA
<213> ORGANISM: Artificial Sequence
<220> FEATURE:
<223> OTHER INFORMATION: Chemically synthesized Northern Probe sequence

<400> SEQUENCE: 169
ttgatatcaa cctactacct ca                                              22

<210> SEQ ID NO 170
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 170
aactatacaa cctact                                                     16

<210> SEQ ID NO 171
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 171
ugagguagua gguuguauag uu                                              22

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
aactatacaa cctactacct                                                 20

<210> SEQ ID NO 173
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 173
aactatacaa cctact                                                     16

<210> SEQ ID NO 174
<211> LENGTH: 16
<212> TYPE: DNA
<213> ORGANISM: Artificial Sequence
<220> FEATURE:
<223> OTHER INFORMATION: Synthetic oligonucleotide
```

```
<400> SEQUENCE: 174
agtactcacc gacagc                                                      16

<210> SEQ ID NO 175
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 175
agtactcacc gacagc                                                      16

<210> SEQ ID NO 176
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 176
aacauucaac gcugucggug agu                                              23

<210> SEQ ID NO 177
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 177
agtactcacc gacagcgttg aatgtt                                           26

<210> SEQ ID NO 178
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 178
agtactcacc gacagc                                                      16

<210> SEQ ID NO 179
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 179
aactatacaa cctact                                                      16

<210> SEQ ID NO 180
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 180
aactatacaa cctacta                                                     17

<210> SEQ ID NO 181
<211> LENGTH: 18
```

```
<212> TYPE: DNA
<213> ORGANISM: Artificial Sequence
<220> FEATURE:
<223> OTHER INFORMATION: Synthetic oligonucleotide

<400> SEQUENCE: 181
aactatacaa cctactac                                                      18

<210> SEQ ID NO 182
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 182
aactatacaa cctactacc                                                     19

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 183
aactatacaa cctactacct                                                    20

<210> SEQ ID NO 184
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 184
aactatacaa cctactacct c                                                  21

<210> SEQ ID NO 185
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 185
aactatacaa cctactacct ca                                                 22

<210> SEQ ID NO 186
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 186
aactatacaa cctactacct ca                                                 22

<210> SEQ ID NO 187

<400> SEQUENCE: 187

000

<210> SEQ ID NO 188
```

```
<400> SEQUENCE: 188

000

<210> SEQ ID NO 189

<400> SEQUENCE: 189

000

<210> SEQ ID NO 190
<211> LENGTH: 15
<212> TYPE: RNA
<213> ORGANISM: Artificial Sequence
<220> FEATURE:
<223> OTHER INFORMATION: Synthetic oligonucleotide

<400> SEQUENCE: 190
gggagaagag aauuc                                                    15

<210> SEQ ID NO 191
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 191
gggagaagag aauuccucga g                                             21

<210> SEQ ID NO 192
<211> LENGTH: 81
<212> TYPE: RNA
<213> ORGANISM: Artificial Sequence
<220> FEATURE:
<223> OTHER INFORMATION: Chemically synthesized syn-pre-let-7 RNA

<400> SEQUENCE: 192
gggagaagag aauucugagg uaguagguug uauaguuugg aauauuacca ccgugaacu    60 augcaauuuu cuaccuuacc a                                             81

<210> SEQ ID NO 193
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: LPA

<400> SEQUENCE: 193
gggagaagag aauucugagg uaguagguug uauaguuucc aauauuacca ccgugaacu    60 augcaauuuu cuaccuuacc a                                             81

<210> SEQ ID NO 194
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: LPB

<400> SEQUENCE: 194
gggagaagag aauucugagg uaguagguug uauaguuucc aauauuacca ggccugaacu   60
augcaauuuu cuaccuuacc a                                             81

<210> SEQ ID NO 195
```

```
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: LPC

<400> SEQUENCE: 195
gggagaagag aauucugagg uaguagguug uauaguuugg aauauuacca ccccugaacu      60
augcaauuuu cuaccuuacc a                                               81

<210> SEQ ID NO 196
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: LPD

<400> SEQUENCE: 196
gggagaagag aauucugagg uaguagguug uauaguuucc aauauuacca ccccugaacu      60
augcaauuuu cuaccuuacc a                                               81

<210> SEQ ID NO 197
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: Stem1

<400> SEQUENCE: 197
gggagaagag aaucacucg uaguagguug uauaguuugg aauauuacca ccggugaacu       60
augcaauuuu cuacgagucc a                                               81

<210> SEQ ID NO 198
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: Stem2

<400> SEQUENCE: 198
gggagaagag aaucugagc aucuagguug uauaguuugg aauauuacca ccggugaacu       60
augcaauuuu gaugcuuacc a                                               81

<210> SEQ ID NO 199
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: Stem3

<400> SEQUENCE: 199
gggagaagag aaucugagg uagauccaac uauaguuugg aauauuacca ccggugaacu       60
augguuggaa cuaccuuacc a                                               81

<210> SEQ ID NO 200
<211> LENGTH: 81
<212> TYPE: RNA
<213> ORGANISM: Artificial Sequence
<220> FEATURE:
<223> OTHER INFORMATION: Chemically synthesized syn-pre-let-7 RNA: Stem4

<400> SEQUENCE: 200
gggagaagag aaucugagg uaguagguug auaucaaugg aauauuacca ccgguguuga      60
```

```
uaucaauuuu cuaccuuacc a                                              81
```

<210> SEQ ID NO 201
<211> LENGTH: 22
<212> TYPE: RNA
<213> ORGANISM: Artificial Sequence
<220> FEATURE:
<223> OTHER INFORMATION: Chemically synthesized mature let-7 RNA oligo:
      Let-7_wt

<400> SEQUENCE: 201

```
ugagguagua gguuguauag uu                                             22
```

<210> SEQ ID NO 202
<211> LENGTH: 22
<212> TYPE: RNA
<213> ORGANISM: Artificial Sequence
<220> FEATURE:
<223> OTHER INFORMATION: Chemically synthesized mature let-7 RNA oligo:
      Let-7_mut1

<400> SEQUENCE: 202

```
acucguagua gguuguauag uu                                             22
```

<210> SEQ ID NO 203
<211> LENGTH: 22
<212> TYPE: RNA
<213> ORGANISM: Artificial Sequence
<220> FEATURE:
<223> OTHER INFORMATION: Chemically synthesized mature let-7 RNA oligo:
      Let-7_mut2

<400> SEQUENCE: 203

```
ugagcaucua gguuguauag uu                                             22
```

<210> SEQ ID NO 204
<211> LENGTH: 22
<212> TYPE: RNA
<213> ORGANISM: Artificial Sequence
<220> FEATURE:
<223> OTHER INFORMATION: Chemically synthesized mature let-7 RNA oligo:
      Let-7_mut3

<400> SEQUENCE: 204

```
ugagguagau ccaacuauag uu                                             22
```

<210> SEQ ID NO 205
<211> LENGTH: 22
<212> TYPE: RNA
<213> ORGANISM: Artificial Sequence
<220> FEATURE:
<223> OTHER INFORMATION: Chemically synthesized mature let-7 RNA oligo:
      Let-7_mut4

<400> SEQUENCE: 205

```
ugagguagua gguugauauc aa                                             22
```

<210> SEQ ID NO 206
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 206

```
uuauacaacc guucuacacu ca                                             22
```

<210> SEQ ID NO 207
<211> LENGTH: 21
<212> TYPE: RNA
<213> ORGANISM: Artificial Sequence
<220> FEATURE:
<223> OTHER INFORMATION: Chemically synthesized sequence

<400> SEQUENCE: 207
uuuauacaac cauucugccu c                                              21

<210> SEQ ID NO 208
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 208
uuauacaacc guucuuguga ga                                             22

<210> SEQ ID NO 209
<211> LENGTH: 21
<212> TYPE: RNA
<213> ORGANISM: Artificial Sequence
<220> FEATURE:
<223> OTHER INFORMATION: Chemically synthesized sequence

<400> SEQUENCE: 209
uuuauacaac cauugacgga c                                              21

<210> SEQ ID NO 210
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 210
uaagguagua gguuguauag uu                                             22

<210> SEQ ID NO 211
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 211
ucagguagua gguuguauag uu                                             22

<210> SEQ ID NO 212
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 212
uuauacaacc guucuacacu ua                                             22

<210> SEQ ID NO 213
<211> LENGTH: 21
<212> TYPE: RNA
<213> ORGANISM: Artificial Sequence
<220> FEATURE:

-continued

<223> OTHER INFORMATION: Chemically synthesized sequence

<400> SEQUENCE: 213
uuuauacaac cauucugccu u                                       21

<210> SEQ ID NO 214
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 214
uuauacaacc guucuacacu ga                                      22

<210> SEQ ID NO 215
<211> LENGTH: 21
<212> TYPE: RNA
<213> ORGANISM: Artificial Sequence
<220> FEATURE:
<223> OTHER INFORMATION: Chemically synthesized sequence

<400> SEQUENCE: 215
uuuauacaac cauucugccu g                                       21

<210> SEQ ID NO 216
<211> LENGTH: 102
<212> TYPE: RNA
<213> ORGANISM: Artificial Sequence
<220> FEATURE:
<223> OTHER INFORMATION: Chemically synthesized sequence

<400> SEQUENCE: 216
aacucaagua uaccuuuuau acaaccguuc uacacucaac gcgauguaaa uaucgcaauc    60
ccuuuuauaa caaccauucu gccucugaac cauugaaacc uu                     102

<210> SEQ ID NO 217
<211> LENGTH: 102
<212> TYPE: RNA
<213> ORGANISM: Artificial Sequence
<220> FEATURE:
<223> OTHER INFORMATION: Chemically synthesized sequence

<400> SEQUENCE: 217
aacucaagua uaccuuuuau acaaccguuc uugugagaac gcgauguaaa uaucgcaauc    60
ccuuuuauaa caaccauuga cggacugaac cauugaaacc uu                     102

<210> SEQ ID NO 218
<211> LENGTH: 101
<212> TYPE: RNA
<213> ORGANISM: Artificial Sequence
<220> FEATURE:
<223> OTHER INFORMATION: Chemically synthesized sequence

<400> SEQUENCE: 218
aacucaagua uaccuuuuau acaaccguuc uacacuuaac gcgauguaaa uaucgcaauc    60
ccuuuuauac aaccauucug ccuuugaacc auugaaaccu u                      101

<210> SEQ ID NO 219
<211> LENGTH: 101
<212> TYPE: RNA
<213> ORGANISM: Artificial Sequence
<220> FEATURE:
<223> OTHER INFORMATION: Chemically synthesized sequence -continued

<400> SEQUENCE: 219
aacucaagua uaccuuuuau acaaccguuc uacacugaac gcgauguaaa uaucgcaauc    60
ccuuuuauac aaccauucug ccugugaacc auugaaaccu u                       101

<210> SEQ ID NO 220
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 220
ugagguagua gguuguauag uuuggaauau uaccaccggu gaacuaugca auuuucuacc    60
uuacc                                                                65

<210> SEQ ID NO 221
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 221
ugagguagua gguuguauag uuuccaauau uaccaccggu gaacuaugca auuuucuacc    60
uuacc                                                                65

<210> SEQ ID NO 222
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 222
ugagguagua gguuguauag uuuccaauau uaccaggccu gaacuaugca auuuucuacc    60
uuacc                                                                65

<210> SEQ ID NO 223
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 223
ugagguagua gguuguauag uuuggaauau uaccaggccu gaacuaugca auuuucuacc    60
uuacc                                                                65

<210> SEQ ID NO 224
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 224
ugagguagua gguuguauag uuuccaauau uaccaccccu gaacuaugca auuuucuacc    60
uuacc                                                                65

<210> SEQ ID NO 225

```
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 225
aacuauacaa ccuacuaccu ca                                              22

<210> SEQ ID NO 226
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 226
aacuauacaa ccuacuguga ga                                              22

<210> SEQ ID NO 227
<211> LENGTH: 22
<212> TYPE: RNA
<213> ORGANISM: Artificial Sequence
<220> FEATURE:
<223> OTHER INFORMATION: Chemically synthesized sequence

<400> SEQUENCE: 227
aacuauacaa ccuagacgga ca                                              22

<210> SEQ ID NO 228
<211> LENGTH: 187
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (103)..(122)
<223> OTHER INFORMATION: n is a, c, g, or u

<400> SEQUENCE: 228
aacucaagua uaccuuuuau acaaccguuc uacacucaac gcgauguaaa uaucgcaauc      60
ccuuuuuaua caaccauucu gccucugaac cauugaaacc uunnnnnnnn nnnnnnnnnn     120
nnugagguag uagguuguau aguuuggaau auuaccaccg gugaacuaug caauuuucua     180
ccuuacc                                                              187

<210> SEQ ID NO 229
<211> LENGTH: 187
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (103)..(122)
<223> OTHER INFORMATION: n is a, c, g, or u

<400> SEQUENCE: 229
aacucaagua uaccuuuuau acaaccguuc uacacucaac gcgauguaaa uaucgcaauc      60
ccuuuuuaua caaccauucu gccucugaac cauugaaacc uunnnnnnnn nnnnnnnnnn     120
nnugagguag uagguuguau aguuuccaau auuaccaccg gugaacuaug caauuuucua     180
ccuuacc                                                              187
```

```
<210> SEQ ID NO 230
<211> LENGTH: 187
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (103)..(122)
<223> OTHER INFORMATION: n is a, c, g, or u

<400> SEQUENCE: 230
aacucaagua uaccuuuuau acaaccguuc uacacucaac gcgauguaaa uaucgcaauc    60
ccuuuuuaua caaccauucu gccucugaac cauugaaacc uunnnnnnnn nnnnnnnnnn   120
nnugagguag uagguuguau aguuuccaau auuaccaggc cugaacuaug caauuuucua   180
ccuuacc                                                            187

<210> SEQ ID NO 231
<211> LENGTH: 187
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (103)..(122)
<223> OTHER INFORMATION: n is a, c, g, or u

<400> SEQUENCE: 231
aacucaagua uaccuuuuau acaaccguuc uacacucaac gcgauguaaa uaucgcaauc    60
ccuuuuuaua caaccauucu gccucugaac cauugaaacc uunnnnnnnn nnnnnnnnnn   120
nnugagguag uagguuguau aguuuggaau auuaccaccc cugaacuaug caauuuucua   180
ccuuacc                                                            187

<210> SEQ ID NO 232
<211> LENGTH: 187
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (103)..(122)
<223> OTHER INFORMATION: n is a, c, g, or u

<400> SEQUENCE: 232
aacucaagua uaccuuuuau acaaccguuc uacacucaac gcgauguaaa uaucgcaauc    60
ccuuuuuaua caaccauucu gccucugaac cauugaaacc uunnnnnnnn nnnnnnnnnn   120
nnugagguag uagguuguau aguuuccaau auuaccaccc cugaacuaug caauuuucua   180
ccuuacc                                                            187

<210> SEQ ID NO 233
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 233
acucguagua gguuguauag uuuggaauau uaccaccggu gaacuaugca auuuucuacg    60
agucc                                                               65
```

```
<210> SEQ ID NO 234
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 234
ugagcaucua gguuguauag uuuggaauau uaccaccggu gaacuaugca auuuugaugc      60
uuacc                                                                 65

<210> SEQ ID NO 235
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 235
ugagguagau ccaacuauag uuuggaauau uaccaccggu gaacuauggu uggaacuacc      60
uuacc                                                                 65

<210> SEQ ID NO 236
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 236
ugagguagua gguugauauc aauggaauau uaccaccggu guugauauca auuucuacc      60 uuacc                                                                 65

<210> SEQ ID NO 237
<211> LENGTH: 65
<212> TYPE: RNA
<213> ORGANISM: Artificial Sequence
<220> FEATURE:
<223> OTHER INFORMATION: Chemically synthesized sequence

<400> SEQUENCE: 237
ugagguagua gguuguauag uuuggaauau uaccaccggu gaacuauaca accuacuacc      60
ucacc                                                                 65

<210> SEQ ID NO 238
<211> LENGTH: 45
<212> TYPE: RNA
<213> ORGANISM: Artificial Sequence
<220> FEATURE:
<223> OTHER INFORMATION: Chemically synthesized sequence

<400> SEQUENCE: 238
accgaccaga aucaugcaag ugcgguaaga uaguccgcgg ccggg                     45

<210> SEQ ID NO 239
<211> LENGTH: 68
<212> TYPE: RNA
<213> ORGANISM: Artificial Sequence
<220> FEATURE:
<223> OTHER INFORMATION: Chemically synthesized sequence
```

```
<400> SEQUENCE: 239
ugagguagua gguuguauag uuuggggcuc ugcccugcua ugggauaacu auacaaucua     60
cugucuuu                                                             68
```

PRECURSOR MIRNA LOOP-MODULATED TARGET REGULATION

CROSS-REFERENCE TO RELATED APPLICATIONS

This application claims benefit under 35 U.S.C. §119(e)(1) of U.S. Provisional Application No. 61/271,615, filed Jul. 23, 2009, and is a continuation in-part of U.S. application Ser. No. 12/214,793, filed Jun. 20, 2008, each of which are hereby incorporated by reference in their entireties.

FEDERALLY-SPONSORED RESEARCH OR DEVELOPMENT

This invention was made with Government support under contracts HL081612 and OD006435 awarded by the National Institutes of Health. The Government has certain rights in this invention.

TECHNICAL FIELD

The field of this invention is the preparation and use of precursor molecules to mature miRNA with modifications of pri- and pre-miRNA, including loop nucleotides, for quantitative and selective control of the expression of mRNA targets.

BACKGROUND

One of the most important developments in the 21$^{st}$ century is the use of RNAi to modulate expression in cells. Use of RNAi avoids the tedious use of knockout protocols, while allowing for the determination of the effect of reduced or eliminated expression of a protein on the phenotype of a cell. The major variations of RNAi are referred to as miRNA (microRNA), siRNA (short interfering RNA), shRNA (short hairpin RNA) and piRNA (piwi RNA).

For miRNA the conventional wisdom is that a gene encodes the miRNA in a form referred to as the primary-miRNA (pri-miRNA). The gene may be in any portion of the genome, frequently being found in regions that do not code for proteins and in introns. Not infrequently, a number of pri-miRNA genes are found in proximity, where the mature miRNAs will differ by only a few nucleotides, providing a group of isoforms that appear to have similar binding specificities and affinities. The expressed pri-miRNA will generally contain from a few hundred to a few thousand nucleotides. The pri-miRNA is then processed in the nucleus by the proteins Drosha and Pasha to the pre-miRNA that has a stem and loop structure with flanking sequences. The pre-miRNA will generally have about 60 to 70 bases. The pre-miRNA is then actively transported into the cytoplasm by exportin 5 and Ran-GTP. In the cytoplasm, the pre-miRNA is then further processed into small RNA duplexes of approximately 22 nucleotides by the proteins Dicer and Loquacious. The functional or guiding strand of the miRNA duplex is then loaded into the RNA-induced silencing complex (RISC). Finally, the miRNA guiding strand guides the RISC to the cognate messenger RNA (mRNA) target for translational repression or degradation of the mRNA. Mature miRNAs are thought to be the only functional species of miRNA genes that have direct role in target recognition. Pri- and pre-miRNAs are merely transitory intermediates during mature miRNA biogenesis and have no direct role in target recognition and repression.

The miRNA is frequently found to lack perfect complementarity with the target mRNA. Frequently, there are bulges, e.g. mismatches, deletions and insertions, not only between the target mRNA and the mature miRNA, but also between the two chains of the stem of the pre-miRNA. Also, it has frequently been found that more than one mRNA may be regulated by the same mature miRNA. A sequence of the miRNA from 5'-nucleotides 2-8. usually 2-7, is called the "seed" sequence. A sequence of from 7-8 nucleotides is found sufficient to recognize and bind to the target mRNA and provide translational repression or mRNA destabilization, while fewer nucleotides may still provide repression where there is substantial complementarity between the 3' miRNA sequence and a target mRNA sequence in proximity to the sequence binding to the 5' miRNA sequence.

There have been extensive efforts to define the sequences in the target mRNAs and the mature miRNAs that define effective binding between the two RNA species. It is frequently found that there are numerous mRNAs complementary to the same seed sequences, so that the miRNA has a potentially large repertoire for regulation. It remains a conundrum how the miRNA provides for specific regulation in light of the frequency of seed sequences and the substantial redundancy of seed sequences among miRNAs.

Because of the evident importance of miRNA in cell regulation—miRNAs have been found to be associated with cancers, cardiac and other diseases—there is great interest in understanding the mechanism whereby the miRNA regulates expression. In addition, the repertoire of miRNAs being expressed in a cell has been found to be associated with various indications and may indicate the severity of the indication and potentially a particular therapeutic protocol. Also, there is a great effort to develop miRNAs that may have therapeutic activity for the treatment of various diseases, such as cancer, where down regulation of one or more genes may inhibit tumor growth, control autoimmune diseases, correct genetic deficiencies associated with the expression of miRNAs and the like. In order to prepare arrays for screening miRNA profiles of cells it will be necessary to better understand the binding requirements between the miRNA and the target(s) mRNAs. To prepare drugs that have specificity for one or a few mRNAs, it will be essential to be able to design miRNAs that are specific for the desired targets and/or have substantially attenuated activity toward mRNAs other than the target mRNA. It will also be critical to be able to design antisense oligonuclotides (RNA and DNA) that can specifically silence miRNA genes that encode identical or nearly identical mature miRNAs. It is therefore of great interest to find additional components of the miRNA regulation that will allow improved identification of miRNAs and their targets, enhanced specificity for the miRNA toward the desired target and discrimination between the activities of miRNAs sharing substantial homology in the seed region.

Having the ability to specifically bind to one target mRNA provides a powerful tool for functional genomic screening. By being able to reduce expression of a specific protein one can determine the role the protein plays in the physiological processes of the cell. By employing RNAi using combinations of miRNA or its precursors, the interactions of the proteins and the effect on the physiology of the cell can be determined. The role of various proteins and combinations of proteins in native cells, cell lines, cancer cells, and the like can be investigated toward an understanding of the pathways of cells under various conditions.

LITERATURE

Reviews of miRNA may be found in Ying, et al 2006 Methods Mol Biol 342, 1-18 and Dykxhorn (2006) Gene Therapy, 1-12. References concerned with miRNA including applications for miRNA with translation suppression include: Qi-Jing Li, et al 2007 Cell 129, 147-61 (hematopoiesis regulation); Chang-Zheng 2005 NEJM 353, 1768-71 (oncogene and tumor suppression); Beuvink, et al 2007 Nucl Acids Res 35:e52 (miRNA array); Lin, et al 2006 Methods Mol Biol 342, 313-29 (intronic miRNA); Nilsen 2007 Trends in Genetics 23:243-9; Gaidatzis, et al 2007 8, 69 (predicting targets); Schmittgen 2004 Nucleic Acids Res 32:e43 (PCR amplification of genomic miRNA); Krutzfeldt, et al 2007 Nucleic Acids Res 35, 2885-92; and Li, et al 2007 Cell 129, 147-61 ("antagomirs" modified miRNA). Patent references of interest, particularly for the preparation of arrays and selection of probes include: U.S. patent applications 2007/0099196 (probes using LNA); 2007/0100563 (probe selection methods); 2007/0099193 (modified probes); 2007/0009915 (miRNA identification with DNA and nuclease); 2006/0130176 (modifies miRNA to enhance complementarity); 2005/0277139 (miRNA array); 2005/0075492 (preparation and use of miRNA) and 2004/0053411 (miRNA genomic precursor construct for translation suppression). See also, U.S. Pat. Nos. 7,056,704 and 7,078,196 (preparation of miRNA molecules). Synthetic miRNAs are described in Vatolin, et al 2006 J Mol Biol 358, 983-6 and Tsuda, et al 2005 Int J Oncol 27, 1299-306. These references are incorporated herein in their entirety as if completely set forth herein.

SUMMARY OF THE INVENTION

In accordance with the subject invention precursors for mature miRNAs (Hereinafter, precursor miRNA, which includes both the pri- and pre-miRNA and mimetic compositions thereof, shall be referred to as "ta-RNA" for their nature as trans-acting long non-coding RNAs and to differentiate them from the small ~22-nt siRNA and mature miRNAs), are employed to provide a different activity from the wild-type mature miRNA and a more selective range of mRNA targets and more efficient and selective inhibition than are normally obtained with mature miRNAs. The ta-RNAs provide multiple levels of regulatory controls for target recognition and interaction that are absent in the small ~22-nt miRNAs. Both the primary nucleotides as well as the elements of secondary and tertiary structures of ta-RNAs may provide controls to ta-RNA and target RNA interaction. ta-RNAs provide target recognition information in the primary nucleotide sequence and secondary or tertiary structural levels. At the level of primary nucleotide sequences, the mature ~22-nt (include the 6-8 nt seeds), loop nucleotides, and even the complementary strand of mature miRNA all contribute to target recognition and interaction. At the level of secondary and tertiary structure, structural constrained loop and stem nucleotides and the stability of these structure elements also control the ta-RNA and target interaction. Moreover, interaction between ta-RNA and target interaction can be modulated by proteins and small molecules that can influence the interaction. Collectively, ta-RNAs provide more regulatory elements than the linear ~22-nt mature miRNAs that can be used to control target expression.

It has now been found that pri-miRNA has activity independent of the mature miRNA, so that modifications of ta-RNAs can be made for improved modulation of target mRNA. The naturally occurring ta-RNA molecules may be modified for enhancing the complexing of the ta-RNAs to increase the efficiency of binding and selectivity in binding to target mRNA. In addition, the modifications can provide improved properties of the ta-RNAs, such as enhanced transcription and stability, or synthetic ta-RNAs are prepared differing from the wild-type ta-RNA portion in their flanking region, stem and/or loop, and in the substitution of naturally occurring nucleotides with synthetic nucleotides. Either the flanking, stem or loop regions may be modified, where the loop regions are identified as enhancing the activity for target mRNAs, whereby target mRNAs are determined based on complementarity to both the guiding sequence of the stem and at least 3 nt of the loop. Alternatively, synthetic ta-RNAs are prepared where the seed sequence and at least 2 nt of the loop are complementary to the target mRNA, desirably without bulges or interruptions between binding nucleotides.

Because it has been discovered that the pri-miRNA has activity independent of the mature miRNA, by referring to precursors it is intended that the precursor (ta-RNA) includes the miRNA or mutated miRNA sequences as described herein and has the general structure of the wild-type precursors, but may be processed into functional mature miRNAs. Therefore, the ta-RNA-mimetics of the subject invention may have shorter flanking regions or no flanking regions, generally having at least about 10, usually at least 25, number percent and up to 100% of the nucleotides in the wild-type flanking regions.

The ta-RNAs may be modified to change the thermodynamics between the ta-RNAs and the target mRNA. By varying nucleotides in the guiding strand, the passenger strand and/or the loop, one can improve the binding efficiency of the precursor miRNA with the target miRNA. (As is known, the guiding strand binds to the mRNA and includes the seed sequence, the passenger strand is the other strand of the stem and the two strands terminate in a loop in the 5'-3' direction beginning with the guiding strand.) By employing Mfold and UNAFold, the relative binding energies of the ta-RNAs and the target mRNA can be determined allowing for the determination of the effect of nucleotide replacement on complex formation between the ta-RNAs and the target mRNA. Using such software and comparable software, one can define the sites of the ta-RNAs that significantly affect the ability of the ta-RNAs to modulate the expression of the mRNA.

In developing algorithms for determining target mRNAs from ta-RNAs, or designing synthetic ta-RNAs for target mRNA, the algorithms are modified to include complementarity to at least a sequence of 2 nts of the loop sequence, desirably in a portion of the loop in proximity to the seed sequence. ta-RNAs are screened for their binding profile of mRNAs in a mixture of mRNAs in vitro and in vivo and specific targets are identified by stem and loop complementarity. ta-RNAs may be produced based on known pre-miRNAs and pri-miRNAs or on mRNA sequences, where specificity is enhanced by increasing complementarity of at least some of the nucleotides in the loop. Also, mimetic ta-RNAs may be produced where the seed sequence and the loop are directly joined or joined by other than a natural linker. ta-RNAs with improved target gene selectivity and/or modified activity may be selected from a library of ta-RNA molecules with randomized loop sequences through in vitro and in vivo screening assays. Enhanced specificity in translational suppression is achieved with the subject ta-RNAs and mimetics thereof, which may be provided by introduction into cells as a composition or introduced into cells as DNA for transcription of the ta-RNAs. The subject ta-RNAs may be used in arrays, where at least two ta-RNAs, as may be modified, will have similar sequences, but stems and/or loops differing by at least one nucleotide.

ta-RNAs with unique loop nucleotides are screened for antisense oligonucleotides that complement to the loop region of the ta-RNAs that can selectively silence miRNA genes which encode identical or nearly identical mature miR-NAs.

The ta-RNA molecules may be redesigned to recognize novel sequences for repression. Either or both the stem or loop regions may be designed, where the loop regions are identified as enhancing selectivity for target mRNAs, whereby target mRNAs are determined based on complementarity to both the guiding sequence, particularly the seed sequence, of the stem and at least 3 nt of the loop. Target mRNAs may be perfectly matched or be partly complementary to the guiding sequence of the stem and at least 3 nt of the loop. Synthetic or DNA encoded re-designed ta-RNAs are prepared where the seed sequence and at least 2 nt of the loop are complementary to the target mRNA, desirably without bulges or interruptions between binding nucleotides.

By assaying for the binding affinity of a designed ta-RNA or mimetic with a target mRNA sequence, high binding affinity correlates with effectiveness in modulating the translation of the mRNA.

BRIEF DESCRIPTION OF THE DRAWINGS

FIGS. 2A, 2B, and 2C. The pre-miR-181a-1 loop nucleotides control the distinct activities of the mir-181a-1 and mir-181c genes in DP cell development. (A) Nucleotide sequences of mature miR-181a (SEQ ID NO:60) and miR-181c (SEQ ID NO:61). (B) Schematics and nucleotide sequences depicting the wild-type mir-181a-1 and mir-181c genes (SEQ ID NOS:62 and 63) and corresponding precursors. Also shown are the chimeric miRNA genes, with the mature miRNAs (SEQ ID NOS:64-67), pre-miRNAs (SEQ ID NOS:63 and 62, respectively), and pre-miRNA loops (SEQ ID NOS:65 and 64, respectively) swapped between mir-181a-1 and mir-181c and termed "mature-chimeric", "pre-chimeric", and "loop-chimeric", respectively. These mutant genes are designated as mir-181a (c stem), mir-181c (a stem), mir-181a (pre-181c), mir-181c (pre-181a), mir-181a (c-loop), and mir-181c (a-loop). (C) The effects of the chimeric mir-181a-1/c genes on DP cell development. Normalized data from 3-7 independent T cell assays (each with 12 independent replicates for a total of 36-84 replicates) are pooled and graphed in the distribution box plots. Mann-Whitney Rank Sum Tests were performed to determine whether the activities of the chimeric miRNA genes are statistically different from those of the negative control vector (*, $p<0.0001$) and/or mir-181a-1 positive control (*, $p<0.0001$). A representative OP9-DL1 stromal co-culture assay without normalization is also shown (FIG. 13).

FIGS. 7A, 7B and 7C. Effects of the mutations in the stem region on mir-181a-1 activity in promoting DP cell development. (A) Scanning mutations in the stem region of the mir-181a-1 gene (SEQ ID NO:74). The mutations are shown in the sequences listed below the mir-181a-1 gene and correspond to SEQ ID NOS:76-90, respectively. Two nucleotides (2-nt mutants, light shading) or a stretch of nucleotides (segment mutants, light shading) in the mature miRNA region are altered. Nucleotides are altered to disrupt their potential base pairing to target genes. Compensatory mutations are also generated on the miR* strand to maintain the secondary structure of the pre-miRNAs (See FIG. 8.) (B) Expression and processing of wild-type mir-181a-1 and stem mutants. A gel is depicted where specific probes that perfectly match the mature miR-181a and each of its mutant forms were used in hybridization to determine the expression of mature miR-181a and its stem mutant forms. (C) The effects of mir-181a-1 and its stem mutants on DP cell development. Normalized data from 3-5 independent T cell assays (each with 12 independent replicates, total 36-60 replicates) are pooled and graphed in the distribution box plots to summarize the distribution of the relative activities of mir-181a-1, the 2-nt mutants, and the segment mutants in DP cell development. Mann-Whitney Rank Sum Tests were performed to determine whether the activities of individual 2-nt mutants were statistically different from those of the control vector (*, p<0.0001, or specific p value indicated) and the mir-181a-1 vector. A representative OP9-DL1 stromal co-culture assay without normalization (12 independent replicates for each constructs) is also shown (FIG. 12).

FIG. 8. Schematic and nucleotide sequences depict mature mir-181a-1 mutants. Compensatory mutations are introduced to maintain the integrity of the pre-miRNA secondary structure. (Indicated by shading and lower case.) These sequences correspond to SEQ ID NO:62 and SEQ ID NOS:91-105, respectively.

FIGS. 10A and 10B. Members of the mir-181 gene family. (A) Alignment of the mature miR-181 miRNAs (SEQ ID NOS:106-109). (B) Schematics and nucleotide sequences depicting the pre-miRNAs of the mouse (SEQ ID NOS:110-115) and human (SEQ ID NOS:116-121) mir-181 gene family members. (Variations indicated by shading.)

FIGS. 13A and 13B. The effects of the chimeric mir-181a-1 and mir-181c genes on DP cell development (See FIG. 2). (A) Box-plots summarize the percent of DP cells generated from DN progenitor cells infected with mir-181a-1, mir-181c, or their chimeric mutants (GFP positive). A representative OP9-DL1 stromal co-culture assay (12 independent replicates for each construct) is shown. The ends of the boxes define the $25^{th}$ and $75^{th}$ percentiles, a line indicates the median, and bars define the $5^{th}$ and $95^{th}$ percentiles. (B) Statistical summary. Mann-Whitney Rank Sum Tests were performed on this representative data set to determine whether the activity of mir-181a-1, mir-181c, or their chimeric mutants is statistically different from the control vector or the mir-181a-1 vector.

FIG. 17. Phylogenetic comparison of pre-miR-181a-1 and pre-mIR-181c loop sequences (SEQ ID NOS:122-143). The full genus and species names and their abbreviations are as follows: *Danio rerio*, dre; *Fugu rubripes*, fru; *Homo sapiens*, hsa; *Gallus gallus*, gga; *Gorilla gorilla*, ggo; *Lagothrix lagotricha*, lla; *Macaca mulatta*, mml; *Mus musculus*, mmu; *Macaca nemestrina*, mne; *Pan paniscus*, ppa; *Pongoi pygmaeus*, ppy; *Pan troglodytes*, ptr; *Rattus norvegicus*, rno; *Sus scrofa*, ssc; *Tetraodon nigroviridis*, tni.

FIGS. 20A, 20B, 20C, 20D, 20E and 20F. The first seed nucleotide (SD1) is missing from the pre- and mature let-7 RNAs, but is essential for the activity of *C. elegans* let-7 gene (c-let-7) in target repression in BOSC 23 cells. (A) Northern-blot showing the expression of c-let-7 and SD1 mutant genes. Bands representing endogenous human pre-let-7 RNAs (hsa-pre) and *C. elegans* pre-let-7 (cel-pre) are indicated. (B and C) Mapping the 5' ends of mature let-7 (B) and pre-let-7 (C) made from the c-let-7 and SD1 mutants by primer extension analyses. Bands represent primer extension products derived from let-7 RNAs (22 and 20-nt bands) and spiked miR-181 (26-nt band) are indicated. The relative levels of 22 and 20-nt bands were quantified as described in the Experimental Procedures. A representative blot from four independent repeats is shown (A-C). Note that in (C) the products of LNA primers migrate at a rate ~1 nt slower than corresponding DNA primers, such that the DNA ladder of 17 nt corresponds to the unreacted 16 nt LNA primer. (D) Schematic diagrams indicate base-parings between the mature let-7 and the two let-7 complementary sites (designated as T1 and T2) within the 102-nt fragment of the lin-41 3' UTR. Nucleotide changes are indicated (Bold). (E, F) Repression of wild-type (E) or mutant (F) lin-41_LCS *Renilla* luciferase reporters by c-let-7 and SD1 mutants. Reporter activity was normalized to show seed-dependent repression as described in Experimental Procedures. Representative results of at least six independent trials (±S.D.) are shown (*, p<0.0001).

FIGS. 22A, 22B, 22C, 22D and 22E. Biogenesis of c-let-7 RNAs from wild-type c-let-7 and SD1 mutants. (A) The biogenesis of c-let-7 RNAs from the wild-type c-let-7 and SD1 mutants determined by northern blot analyses. Values shown represent the average of three independent trials ±S.D. (B) Primer extension analyses of total RNA fractions from BOSC 23 cells transfected with wild-type c-let-7 and SD1 mutant genes. Primer extension analyses were carried out to determine the 5' ends and the relative levels these species in (C) total RNA, (D) purified mature miRNA fractions, and (E) purified pre-let-7 RNA fractions made from the wild-type and mutant c-let-7 genes. The relative levels of 22 and 20-nt bands were quantified and normalized to the miR-181 loading controls and then to the levels of corresponding RNAs made from the wild-type c-let-7. Average results of more than three independent trials ±S.D. are shown. Expression of pri-let-7 indicated by northern blot analyses.

FIG. 26. Effects on loop mutations on lin-41_LCS and pre-let-7 interactions based on mfold prediction. Schematic diagrams depict the potential pairing of the mature miRNA sequences in the pre-miRNAs of c-let-7 and loop mutants with the passenger strand sequence (sel f), or the target site 1 (T1), or target site 2 (T2) of the lin-41_LCS RNA. Sequences were input as shown, consisting of the lin-41_LCS, a 20-nt neutral linker, and the pre-miRNA sequence of c-let-7 or loop mutants.

FIGS. 27A, 27B, 27C and 27D. Pri-let-7 loop mutations may affect the activity of c-let-7 by modulating the potential complex formation between lin-41_LCS and let-7 precursor RNAs. (A and B) Electrophoretic mobility shift assay (EMSA) was used to determine the complex formation between a synthetic precursor let-7 RNA (syn-pre-let-7) and the lin-41_LCS-wt RNA (A) or the lin-41_LCS-sm RNA (B). Major syn-pre-let-7 and lin-41_LCS target complexes 1 (C1) and 2 (C2) are indicated. (C) Dose-dependent binding of the syn-pre-let-7 RNAs with the lin-41_LCS-wt or lin-41_LCS-sm RNAs (n≥3). (D) Dose-dependent binding of the lin-41_LCS-wt and syn-pre-let-7_wt (dashed lines) or syn-pre-let-7 loop mutants (solid lines) (n≥2). Concentrations of syn-pre-let-7 RNAs required for sequestering 40% of the lin-41_LCS-wt RNA (the half-maximal binding concentration for the syn-pre-let-7_wt) are indicated with dotted lines.

FIGS. 29A, 29B and 29C. Characterization of complexes formed by synthetic precursor let-7 (syn-pre-let-7) and the lin-41_LCS-wt RNAs. (A) Radiolabeled LCS-wt (1 μM) and syn-pre-let-7 (4 μM) RNAs were mixed, incubated for 45 minutes at 37° C., and resolved on 6% native polyacrylamide gel. Major syn-pre-let-7 and target complexes 1 (C1) and 2 (C2) are indicated. (B) Complexes C1 and C2 were then excised and eluted from the gel fragments. The composition of the C1 and C2 complexes were determined by resolving purified complexes on denaturing PAGE. A sample of the original 1:4 mixture of radiolabeled LCS-wt and syn-pre-let-7 was also resolved on denaturing PAGE as a loading control. (C) The molar ratio of lin-41_LCS-wt and syn-pre-let-7 RNAs with the C1 and C2 complexes was determined by normalizing the input fractions to the loading control. Average results of nine independent trials ±S.D. were shown.

DESCRIPTION OF THE SPECIFIC EMBODIMENTS

Figure 1A:
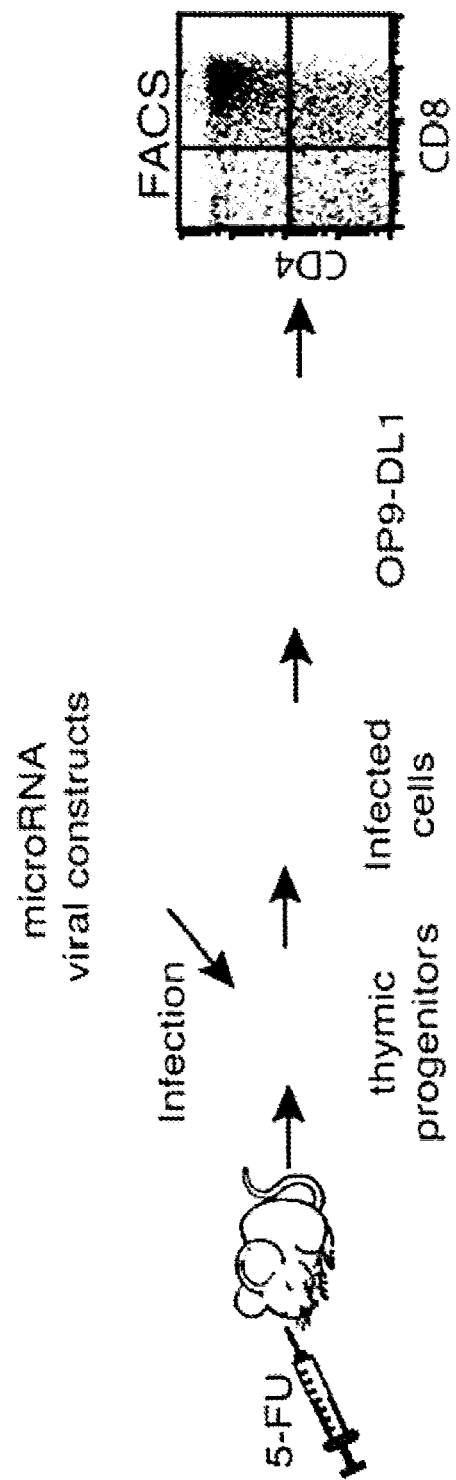
FIGS. 1A, 1B, 1C and 1D. The OP9-DL1 co-culture assay for measuring the effects of miRNA ectopic expression on T cell differentiation. (A) Schematics depicting the OP9-DL1 stromal co-culture assay for T cell differentiation. (B) Box-plots to summarize the effects of mir-181a-1 on the percentage of DP cells differentiated from DN progenitor cells. The results of a representative OP9-DL1 stromal co-culture assay (12 independent replicates for each construct) are shown. (C) Normalized box-plots. (D) Representative FACS plots showing the effects of mir-181a-1 on DP cell development (gated on infected GFP cells).

Modulation of mRNA activity is achieved with precursor miRNAs (ta-RNAs). ta-RNAs, primarily pre-miRNAs and pri-miRNAs, including truncated and mutated ta-RNAs, are employed for modulation of mRNA expression where it is found that pri- and pre-miRNA have activity independently of the presence of functional mature miRNAs. Modification of at least one of the stem and loop of the ta-RNAs to enhance binding of the ta-RNA to the target mRNA is employed. The modification may be enhanced complementarity between the ta-RNA and the target mRNA and/or improved thermodynamic efficiency in binding of the ta-RNA to the target.

In referring to the parts of the pre-miRNA contained in the pri-miRNA, the pre-miRNA has a stem and loop, the 5'-strand of the stem being the guide sequence and comprising the seed sequence, the 3'-sequence being the passenger sequence, with the flanking sequences extending from the ends of the stem. The complete flanking sequences results in the pri-miRNA. For the purposes of this invention, in referring to miRNA precursors, it is intended ta-RNA and mimetics thereof.

The portion of the precursors that is concerned with modification is identified with both the stem and loop of the pre-miRNA portion of about 65 nt±10 nt, usually about 60 nt, having a stem that may lack perfect complementarity between the two strands and the target and a loop of at least about 8 nt. With the discovery that the pri-miRNA has activity independent of subsequent processing, both natural and unnatural bases may be used, for synthetic ta-RNAs or smaller fragments, thereof comprising at least the guiding sequence of the stem with or without the loop and the passenger sequence of the stem. The stem and/or relevant members of the loop will have enhanced complementarity to the target mRNA, either partial (seed sequence or guide stem sequence), for example, where the seed sequence of the stem and the relevant nucleotides of the loop are complementary to the mRNA, but are separated by a sequence which need not have perfect complementarity to the target, or perfect complementarity to the target, for example, complementarity for the guiding stem, and optionally at least one-half of the contiguous loop.

One part of this invention deals with ta-RNA as a precursor to mature miRNA and processing of a limited number, preferably 1, target mRNA, although in some instances there will be an interest in the modified ta-RNA providing for processing of a plurality of mRNAs, usually not more than 10, more usually not more than 5. Also, for expression in cells of sequences comprising natural nucleotides, the ta-RNAs may include a gene encoding RNA from which the pri-RNA is transcribed, or encoding the pri-RNA or pre-RNA, or extended sequences thereof, where the extended sequences do not interfere or may be processed in a cell to a pre-miRNA.

With the subject discovery that the pri-miRNA is effective in modulating mRNA expression and it is not only the guide sequence of the pre-miRNA but also the loop sequence that should be included for enhanced specificity, new opportunities are provided for using RNAi for modulating protein expression and phenotype of cells. By providing for sequences in the stem and loop that enhance or diminish affinity for one or more target mRNAs, the use of RNAi is made more precise in selecting targets and affecting cellular pathways. Affinity with one or more mRNAs can be modified by substitution of nucleotides, use of unnatural sequences as the backbone, replacing the natural sugar phosphate backbone, deletions and insertions, changing the number of loop members and changing the secondary structure of the loop. In this manner one can run the gamut of no or little activity toward a particular mRNA to high specificity for a particular mRNA, as compared to mRNAs with which a naturally occurring mature miRNA would act.

In addition, one can select flanking regions—regions attached to the 5'- and 3'-termini of the pre-miRNA where such flanking regions are known to provide increased transcription, enhanced stability, less interference with binding of the pri-miRNA with the target or with other DNA or RNA in the cell, etc. As an increasing number of ta-RNAs are discovered and their properties evaluated, advantageous properties of these flanking regions can be recruited for joining to the functional sequences, primarily the stem and loop, of the pre-miRNA.

mRNAs are identified as targets of the ta-RNAs by hybridizing the ta-RNAs with at least a portion of mRNA, usually the 3'-UTR of the mRNA, although introns may be employed, or DNA encoding such sequence and identifying the sequence that hybridizes with both the guiding sequence of the stem and at least 2 nt of the loop, where such sequences and loop nucleotides need not be contiguous, nor need the complementary sequences in the mRNA be contiguous. Identification may be achieved with individual ta-RNAs employing protocols that permit detection of the hybridization of the pre-miRNA with one or more mRNAs and identifying the mRNA(s) with the closest complementarity to both the stem and loop, by using arrays of ta-RNAs, where the ta-RNAs may have the same or similar stems, but will differ in at least one nucleotide in the loop, by comparison of the sequences of mRNAs and the ta-RNAs or by using algorithms designed to identify related ta-RNAs and mRNA(s), or by the direct measuring of the repression of a target gene in a functional assay and library screen.

Libraries of modifications, e.g. random modifications, of wild-type ta-RNAs can be prepared. Alternatively, the libraries may be prepared using mFold or UNAfold to compare the affinity of a mutated ta-RNA to a target mRNA. By employing these programs or similar programs, one can devise specific sequences that have a high probability of binding to a target mRNA. The probability of active repression of an mRNA can be verified using binding assays for complex formation between the ta-RNA and a target mRNA. Using a labeled member, labeling either or both the ta-RNA and the mRNA, or portion thereof, one can measure the level of complexation between the ta-RNA and the mRNA. By combining under complexing conditions the two sources of RNA, the ta-RNA and mRNA, where the latter may only be a portion of the target mRNA, and either one or both are labeled, one can determine the formation of any complex. One can analyze for total complex formation, as compared to the amount of wild-type complex formation or determine the amount of the ta-RNA required to achieve the same level of complexation as the wild-type pair. The labels can be any convenient labels, where numerous assays for detecting complexation are known. One can use a radioactive label and analyze by EMSA, use a fluorescent label and analyze by gel electrophoresis or particle capture, using antibodies or complementary nucleic acid sequences to a single stranded portion of the complex, or use two labels as are employed in FRET and BRET. The libraries or individual members can be used in assays to detect changes in phenotype of cells, as arrays to identify mRNAs that bind, or identification of genomic sequences having the same sequence as the library member.

These libraries will generally be limited to modifications in the loop sequence, the stem sequence or both. In addition to the random modifications, changes are made in the sequence to maintain the complementarity or lack of complementarity in the wild-type sequence. For example, where the modification in the loop results in there being complementarity between pairs of nucleotides on opposite sides of the loop, which complementarity did not previously exist, then the wild-type sequence would be further changed to remove the complementarity. In the stem, one will usually maintain the same level of complementarity between the 5'-seed sequence and complementary 3'-sequence, although maintaining the same complementarity or varying the complementarity is permissible. In the stem, one may enhance the level of complementarity between the seed sequence and/or the guiding sequence and the mRNA target. Based on the analysis using mFOLD and UNAFold, one may change the stem and/or loop sequences to enhance the reduction in enthalpy between the ta-RNA and mRNA when not complexed and when complexed.

The subject invention allows for improved prediction of the modulation of mRNA expression with ta-RNA. By including complementarity between the stem and a portion of the loop with the candidate mRNA, one will be able to better predict whether the ta-RNA will affect the expression of the mRNA. One may include the sequence of the loop as a modification of the algorithm or use the presently available or future algorithms and then compare the adjacent nucleotides of the mRNA with the nucleotides of the loop sequence. See, for example, U.S. Patent application nos. 2007/0100563 and 2007/0099196, for methods of designing miRNA molecules and predicting mRNA targets, the disclosure of which is specifically incorporated herein by reference. Greater homology between indicated portions of the loop sequence and the nucleotides in the mRNA proximal to the sequence complementary to the seed sequence will indicate the greater likelihood of regulation of the mRNA by the pri- or pre-miRNA.

One can define a particular RNA sequence based on algorithm predictions, where both the stem and the loop sequences are included in the analysis. By introducing such subject ta-RNA into cells as the precursor or the gene, one can determine the effect on the phenotype of the cell. A change in phenotype indicates that the subject ta-RNAs have an effect in the degradation or storage of the target mRNA(s). In addition, one may search the sequence database for mRNA sequences, particularly 3'-UTR sequences, that have substantial complementarity to the seed sequence and at least 2, preferably at least 3, nt of the loop sequence to identify mRNAs that are likely to be regulated by the subject ta-RNA. Most of the loop sequence need not be complementary, desirably up to 6 nt, where bulges of 1 to 3 nt and mismatches are permitted. Where the function of the mRNAs is known, the regulatory effect of the ta-RNA will then also be known. Thus, one determines the sequence of an mRNA complementary to at least the seed sequence of a stem sequence of a ta-RNA, where the seed sequence will generally be of from about 6 to 10, usually 6-8, nucleotides of the 5' strand. One would also include in the analysis a sequence of at least 2, preferably 8, nucleotides of the loop sequence for complementation of the first two and last two of the 8 nt to a sequence of at least a comparable number of nucleotides of said mRNA sequence that is proximal to said mRNA seed complementarity sequence. Desirably, the complementary nucleotides in the loop and the mRNA will be equally spaced apart, so that there will be no bulges, although there may be mismatches.

While not being bound to any theory, it would appear that the loop of the ta-RNA is involved in binding to the mRNA and may initiate the binding of the ta-RNA to the target mRNA, followed by the mRNA invading the stem and displacing the 3'-strand while binding to the 5'-strand.

The number of permutations is not great and is readily achieved as shown in the Experimental section. Where one has a phenotype associated with a family of isoforms, by screening cells from which the wild-type mi-RNA or ta-RNA has been identified, the ability to modify the phenotype of the cells can be evaluated. In one application, one modifies the seed sequence to have identical complementarity with the mRNA and randomly modifies the loop, using single or double replacements.

Figure 6:
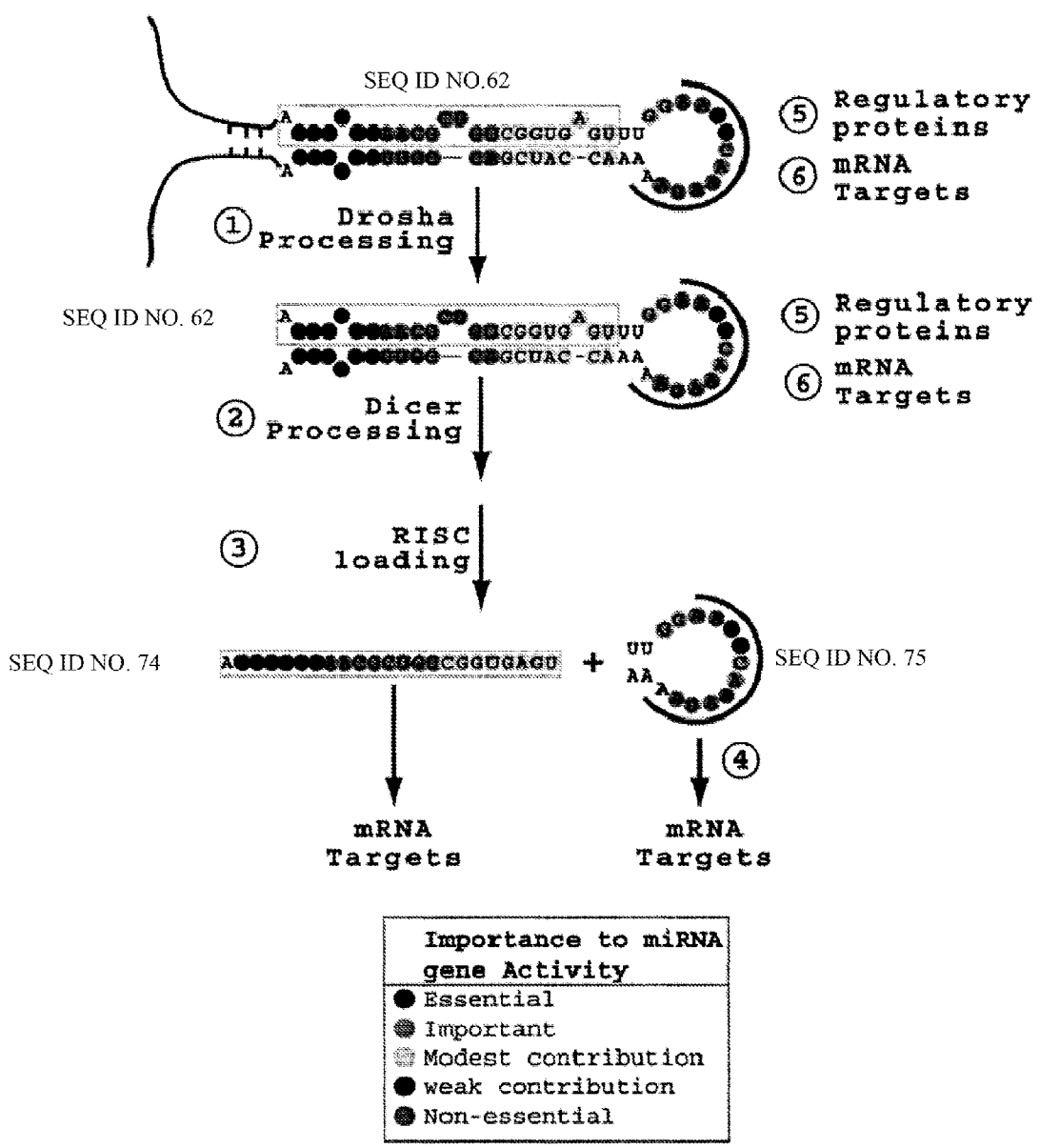
FIG. 6. A "heat map" of the functionally important nucleotides in the pre-miR-181a-1 region according to mutagenesis analyses. Shading was used to illustrate the importance of the pre-miRNA nucleotides to the activity of the miR-181a-1 gene (SEQ ID NO:62), the more darkly shaded the greater the contribution to selectivity. Possible mechanisms by which pre-miRNA loop nucleotides control the activities of miRNA genes are also listed. The mRNA target stem and loop sequences are also shown as SEQ ID NOS:74 and 75, respectively.
Figure 7B:
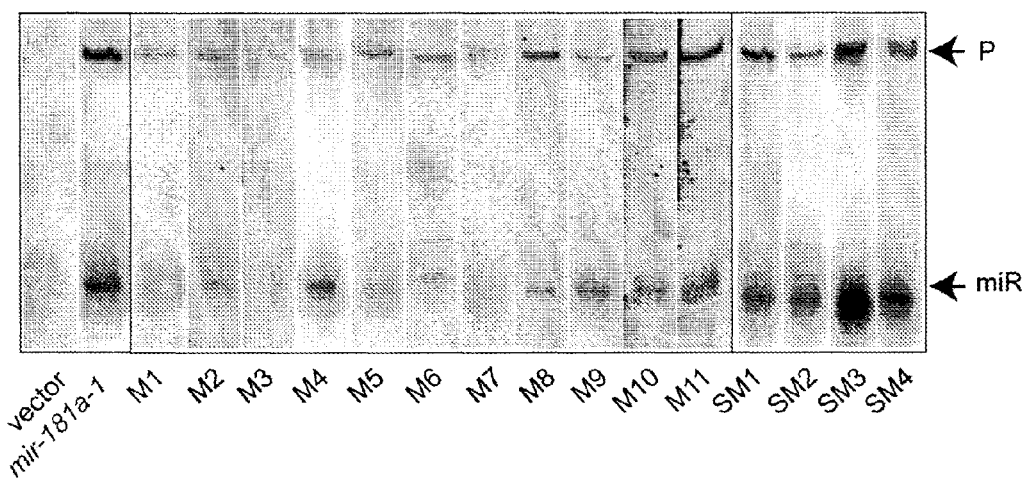
Figure 7C:
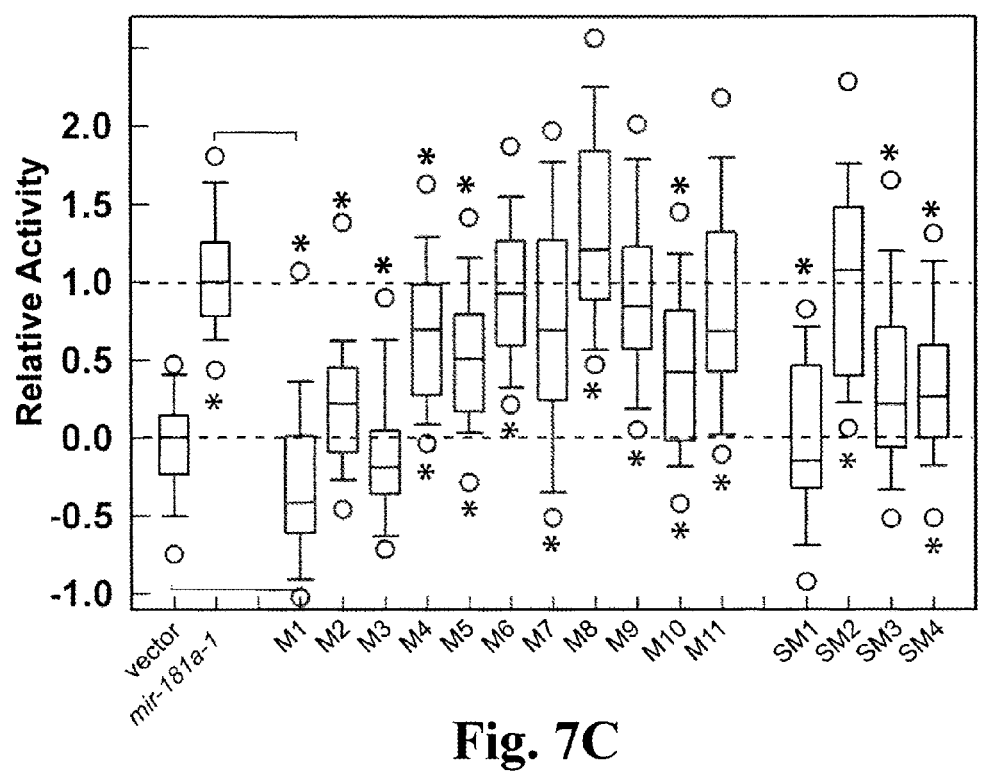
Figures 9A, 9B:
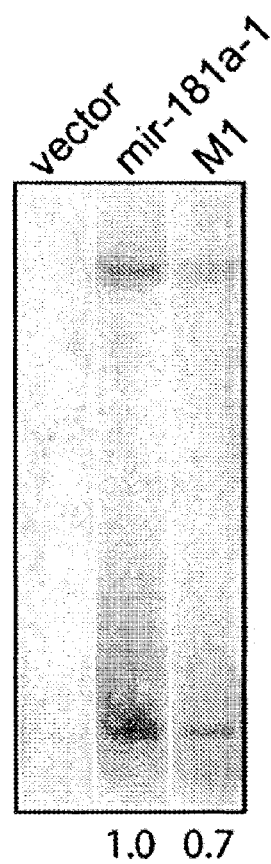
FIGS. 9A and 9B. Expression and processing of wild-type mir-181a-1 and the M1 stem mutant gene. (A) Nucleotide sequences of the wild-type miR-181a (SEQ ID NO:74) and the M1 mutant (SEQ ID NO:76). (B) Northern blot analyses of mature miRNA expression from the wild-type miR-181a and the M1 mutant. Total RNA was prepared from BOSC cells transfected with constructs expressing mir-181a-1, or the M1 mutant genes. Relative transfection efficiencies were determined by qPCR analyses of GFP mRNA levels produced from the transfected miRNA constructs, then used to normalize RNA loadings in Northern blot analyses. A shorter probe that perfectly matches to both mature miR-181a and the M1 mutant forms is used in hybridization to determine the expression of mature miR-181a and its mutant forms. Relative expression levels of the mature miRNAs determined by phosphoimager quantification is indicated.

As partially shown in FIG. 6, starting with the 5' terminus and counting from the first nucleotide that initiates the stem, at least the first 6 nucleotides are essential for binding to the target. The next 8 nucleotides may have varying degrees of complementarity to the target, from 0 to 8 being complementary, where there may be 0 to 3 bulges of 1 to 2 nucleotides in either sequence (ta-RNA and target sequences). (By bulge is intended that complementarity is enhanced by removing the nucleotides in the bulge.) The next 8 to 10, particularly 8, nucleotides include at least some degree of complementarity, generally there being at least 2, usually at least 4, complementary nucleotides with the target and there may be up to 10 complementary nucleotides, including from 0 to 3 bulges in either sequence to provide the complementarity. The first 2 members of the loop are important in matching the target and the 7th and 8th nucleotides in the loop can affect the specificity, with lesser effect from the 5th and 6th nucleotides. The other nucleotides in the loop are generally less significant in determining specificity.

For synthesized ta-RNA, where complementarity to the target mRNA is enhanced, the ta-RNA will have the following formula:

$$5'\text{-}X_{n1}\text{-}S_{n2}\text{-}Y_{n3}\text{-}Z_{n4}\text{-}L_{n5}\text{-}Z'_{n6}\text{-}Y_{n7}\text{-}S'_{n8}\text{-}X'_{n9} \quad \text{(SEQ ID NO:1)},$$

where the pri-miRNA will include at least one of 5' and 3' flanking sequences.

The subscript n intends the number of nucleotides in the particular portion of the pre-miRNA. X and X' will substantially be removed during processing of the pre-miRNA, where processing occurs, leaving fewer than about 10 nt attached to the stem sequences, where $n^1$ and $n^9$ may be the same or different and will generally be from about 0 to the number of nucleotides present in the pri-miRNA, which may be as many as one thousand nucleotides or more. S is the seed sequence and S' is the complementary sequence where $n^2$ and $n^8$ may be same or different, preferably the same, and will generally be in the range of about 6 to 10, preferably 6 to 8, and more preferably 6, where there may or may not be perfect complementarity between S and S', there generally not being more than 2 mismatches, usually not more than 1 mismatch. Y and Y' are spacers and the relevance of their sequence will depend on the desired complementarity desired between the guiding sequence and the target mRNA, and desirably they should be chosen to avoid secondary structure with the other portions of the pre-miRNA. $n^3$ and $n^7$ will generally be from about 6 to 10, more usually about 7 to 9, preferably about 8. Z and Z' are sequences where at least 2, preferably at least 3, and generally not more than all (10), if desired, not more than 8, are complementary to the mRNA target, including from 0 to 3 bulges in either sequence to provide the complementarity and not more than 3, usually not more than 2, and preferably not more than 1, mismatch. L is the loop sequence where the nucleotides are substantially mismatched to avoid secondary structure in the loop. $n^5$ will be about 10 to 15, more usually 11 to 14, preferably 13. At least one of the first two nucleotides, preferably both will bind to the mRNA, while it is desirable that the 7th and 8th nucleotides also bind to the mRNA downstream from the mRNA sequence complementary to the seed sequence, as well as the 5th and 6th nucleotides of lesser relevance, where the intervening sequence between the seed sequence and the loop may have a plurality of bulges and mismatches, so that the complementary loop nucleotides need not be separated from the seed sequence by the same number of nucleotides that the complementary sequences of the target are separated.

In the 5' direction from the seed complementary sequence of the mRNA, the nucleotides of the mRNA complementary to nucleotides in the loop will be within 40, usually within 30, nucleotides of the 5' terminal nucleotide of the mRNA sequence complementary to the seed sequence. Frequently, mRNA nucleotides complementary to the loop nucleotides will be within 26 nucleotides of the 5' terminal nucleotide of the mRNA sequence complementary to the seed sequence.

The subject invention finds employment with any source of ta-RNA, both prokaryotes and eukaryotes, animals, including vertebrates, insects, fish, etc., more particularly mammals, e.g. primates, rodents, domestic animals, etc., unicellular eukaryotes, plants, and the like. Cells, tissues and whole mammals, including human, may be modified by introducing a gene encoding a mutated ta-RNA according to the subject invention in such cells, whereby the transcriptional regulatory region is selected to be functional in the host cells. The transcriptional construct will have a transcriptional initiation region, e.g. promoter region, which may include an enhancer, and a termination region, and a gene, where the gene is under the regulation of the transcriptional regulatory regions, being flanked at the 5'-terminus with the initiation region and the 3'-terminus with the termination region.

Known miRNAs may be found in the following references, which references are incorporated herein by reference. The sequences of several hundred miRNAs from a variety of different species, including humans, may be found at the microRNA registry (Griffiths-Jones, Nucl. Acids Res. 2004 32:D109-D111), as found at the world-wide website of the Sanger Institute (Cambridge, UK) (which may be accessed by typing "www" followed by ".sanger.ac.uk/cgi-bin/Rfam/mirna/browse.pl" into the address bar of a typical interne browser). The sequences of all of the microRNAs deposited at the microRNA registry, including more than 300 microRNA sequences from humans (see Lagos-Quintana et al, Science 294:853-858 (2001); Grad et al, Mol Cell 11:1253-1263 (2003); Mourelatos et al, Genes Dev 16:720-728 (2002); Lagos-Quintana et al, Curr Biol 12:735-739 (2002); Lagos-Quintana et al, *RNA* 9:175-179 (2003); Dostie et al, *RNA* 9:180-186 (2003); Lim et al, Science 299:1540 (2003); Houbaviy et al, Dev Cell 5:351-358 (2003); Michael et al, Mol Cancer Res 1:882-891 (2003); Kim et al, Proc Natl Acad Sci USA 101:360-365 (2004); Suh et al, Dev Biol 270:488-498 (2004); Kasashima et al, Biochem Biophys Res Commun 322:403-410 (2004); and Xie et al, Nature 434:338-345 (2005)).

Of particular interest is the use of modified precursor miRNAs. The modifications may be as to sequence, backbone, chemical conjugation, use of unnatural bases, deletions, insertions, etc. The purpose(s) of the modifications may be to enhance affinity, reduce degradation by nucleases, prevent or enhance cross-reactivity, permit ready identification of hybridization, etc. Where the precursor miRNA is naturally cellularly expressed, then the modifications will usually be limited to sequence modifications, rather than modifications involving substitution of bases with entities that bind to the same complementary base.

The ta-RNAs of this invention may be modified using unnatural nucleotides, so as to be less degradable, enhance binding affinity, allow for isolation, and the like. The ta-RNA may be all or in part peptide NA having an amide backbone, LNA, 2'O-modified ribose, e.g. methyl, 2-methoxyethyl, etc. Exemplary ta-RNA molecules having modified backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'.

Exemplary modified ta-RNA backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholinio linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and CH.sub.2 component parts.

The literature provides ample direction for synthesis of the various modified RNAs. See, for example, U.S. Patent application nos. 2005/0032068; 2008/0255065; 0268441; 2009/0143319; 2009/0143326; and references cited therein.

The ta-RNAs of this invention may be used in the modulation of numerous cellular pathways. Pathways of interest include cellular division, immune response, stress response, injury response, hormone secretion, synthesis of non-proteins, glucose response, organ development, differentiation, etc. Diseased pathways can also be studied, associated with cancer, heart disease, diabetes, blood diseases, neurological diseases, skin diseases, lung diseases, etc.

The phenotype of a cell can be modified with greater specificity by employing a particular ta-RNA that acts on a single target in a pathway, of interest, acts on a plurality of targets while excluding other targets, or acts with greater efficiency on one or more targets, particularly where the targets may be in single or related pathways. Using loop sequences that bind to selected target(s), particular a single target, the modulation of the cellular pathway can be more precisely controlled. The ta-RNA can be matched with a particular mRNA or small number of mRNAs, usually not more than 5, more usually, not more than 3, mRNAs.

As indicated above, the sequence modifications may take many forms. Where the pre-miRNA is produced by cellular expression, then differences will be as to the sequence, which will involve deletions, insertions and substitutions. Modifications can be selected to allow for greater or lesser complementarity between the two sequences of the stem. With 6 to 8 or more nucleotides of the guide sequence complementary to the target mRNA, the binding of a second portion of the same strand (guide sequence) of the ta-RNA to the mRNA while not required for repression, can be desirable to enhance affinity and/or specificity. However, for fewer nucleotides than 6 complementary to the mRNA, then the second portion will usually be involved. Once the mRNA sequence that binds the miRNA guide sequence is known, one can enhance affinity by providing for greater complementarity between the guide sequence and the mRNA sequence, up to perfect complementarity. As already indicated, where the ta-RNA is synthesized, one may use modified nucleotides that provide for higher affinity between the guide sequence and the mRNA sequence. Various unnatural bases may be used, such as phosphorothioates, phosphorodithioates, polyamido (peptide) or polyamino backbones, modified sugars, e.g. LNA, modified bases, etc.

The mimetic molecules may be varied in different manners. The seed sequence and the complementary sequence in the loop will usually have a linking group of up to 20 nucleotide units, more usually not more than about 18 nucleotide units, and at least about 16 nucleotide units. Usually the number of nucleotides between the termini of the seed sequence and its complementary mRNA sequence and the loop sequence and its complementary mRNA sequence will not differ by more than 4 nt, usually not more than 2 nt, for the ta-RNA and the mRNA. In some instances other than nucleotides or nucleotide mimetics may be employed as the linker, where there will generally be from about 54 to 120 atoms in the chain, usually from about 60 to about 108 atoms in the chain, where a ribose phosphate is counted as 6 atoms, an amide as 3 atoms, etc. The particular spacer will be selected to provide the optimum activity of the ta-RNA in repressing translation. The linking group may be a naturally occurring linking group from a naturally occurring ta-RNA binding to the target mRNA, a truncated naturally occurring linking group, truncated by from 1 to 6 nucleotides, may be a poly-U or -A or combination thereof, random, alternating or block, abasic nucleotides, or portions of one with another. The linker may be varied widely providing for minimal interference with the binding of the ta-RNA with the target mRNA, minimizing cross-reactivity with non-target mRNA, avoiding false positives and negatives, and providing for optimum binding of the seed sequence and the loop sequence with the target mRNA.

The loop sequence beginning with unpaired nucleotides at the end of the stem will generally be from about 3 to 18 nucleotides, more usually from about 4 to 15 nucleotides, frequently at least 8 nucleotides and up to the upper limits indicated above, where the loop sequence will include at least the sequence of nucleotides binding to the target mRNA. The loop sequence that binds will have at least 2 contiguous nucleotides that are complementary to the target mRNA, and may have at least 4 or more, usually not more than about 10, more usually not more than about 8, and conveniently not more than about 6, that are complementary to the target mRNA, where beyond 2 nt, the nucleotides of the loop and the target that are complementary need not be contiguous. The binding loop sequence may have from 0 to 12 mismatches with the target mRNA sequence. There may be deletions or bulges of 1 to 2 nt in the target mRNA to provide for complementarity. The nucleotides of the loop of primary interest counting from the 5' end are 1, 2, 7, and 8, with 5, and 6 being of secondary interest.

The spacing between the seed sequence and the loop sequence, can be varied as to the number of nucleotides, in view of mismatches, bulges, spacings, etc., so that the spacing between the complementary sequences of the seed sequence with the mRNA and the complementary sequences of the loop sequence and the mRNA need not be the same, but will usually be within about 4 nt, more usually within about 2 nt.

However, in the pri- and pre-miRNAs, where the guiding sequence is modified from the 3' seed terminus to increase the number of nucleotides that are complementary to the target mRNA, there will be a sequence of at least about 8 nucleotides, more usually at least about 9 nucleotides, frequently at least about 12 to 16 nucleotides, and may be 22 or more, that is the entire mature miRNA which is linked to the loop, that provides a contiguous sequence including the seed sequence that is complementary to the target mRNA. In this event, where there is enhanced complementarity between the sequence of the mature miRNA and the target mRNA, one may leave the loop as the wild-type sequence. The passenger sequence, that is, the sequence complementary to the guiding sequence need not and preferably is not perfectly complementary to the guiding sequence of the stem. One may leave the passenger sequence as the wild-type or enhance the complementarity to less than perfect complementarity, there usually being at least one mismatch or bulge, usually 2 or more mismatches or bulges between the guiding sequence and the passenger sequence.

The ta-RNAs may be prepared by transcription of mutated genes, using transcription constructs having an appropriate transcription regulatory region as described in the references cited above. The genes may be for ta-RNA or other precursor to pre-miRNA. The ta-RNA gene may be a separate gene or intronic. The gene may be introduced into a cellular host as bare DNA, plasmid, viral vector or the like. For preparation of the miRNA precursor, either prokaryotic or eukaryotic hosts can be employed. Alternatively, the pre-miRNA can be synthesized using commercially available synthesizers in known ways. Since in some cases, the subject ta-RNAs will have fewer than the naturally occurring pri-miRNAs, the synthesis will be easier and provide for a purer product. Of course, one can isolate a wild-type gene and by appropriate manipulation modify the nucleotides to obtain the desired sequence. Truncated pre-miRNAs will generally have at least about 80 nts, more usually at least about 100 nts and up to the number of wild-type pri-miRNA nucleotides.

The subject ta-RNAs may be divided into linear strands or stem and loop strands. The linear strands would comprise at least the seed sequence and at least the binding portion of the loop and a linker between the seed sequence and the portion of the loop or would have a stem and loop, where the 3' strand of the stem would be at least partially complementary to the 5' strand, usually having fewer than 8 mismatches total between the two strands, e.g. bulges, mismatches and spacers, where the 3' strand may also be at least partially complementary to a sequence in the mRNA target sequence.

Instead of having a single nucleic acid complementary to putative mRNAs, one may have two different complementary nucleic acids: one comprising at least the complementary seed sequence and preferably at least about 80% of the guide stem; and a second complementary nucleic acid of at least the binding portion of the loop sequence up to the entire loop sequence. One could add both of these sequences together for hybridization to mRNA or preferably separately. By using the two components of the ta-RNA one can screen for active ta-RNAs as to hybridization for the seed sequence followed by hybridization for one or more loop sequences or vice-versa, screen for the hybridizing loop sequences, followed by screening for the seed sequence. This offers many opportunities for unraveling the presence of similar ta-RNAs, where one is interested in the role of the loop in regulating expression and/or the role of the stem in regulating expression. The loop sequence used for capturing the mRNA will be at least about 6 nt, more usually at least about 8 nt and up to the entire loop. In some instances it may also include up to 3, usually not more than about 2 nt, of the nucleotides in one or each of the strands adjacent to the loop.

Depending upon the application for the subject ta-RNAs, the subject ta-RNAs may take many forms. For example, there are the uses of the ta-RNAs in arrays. The arrays may be used for research purposes, where one is attempting to identify ta-RNAs or target mRNAs from a host. In this case one might take a known stem and vary the loop one or two nucleotides at a time, where the entire possible population of nucleotides would be presented. In this manner one would identify numerous mRNAs that would bind to the seed sequence, which mRNAs might have a variety of different sequences, varying as to the sequence that ta-RNAs bind, so that the sequences employed in the array would be complementary to known ta-RNAs or ta-RNAs of known stems, but possibly unknown loops. By providing for hybridization between the bound sequences and ta-RNAs binding to such sequences in the array, one could determine both qualitatively and quantitatively, the ta-RNAs that are present in cells, tissue or the like. By having sequences where the sequences have a higher binding affinity to target mRNAs than the natural ta-RNAs by virtue of sequence modifications, one obtains a more accurate transcriptome as a result of lower levels of cross-reactivity.

As described in the references cited herein and many other articles in the literature, there are numerous methods for detecting binding between two nucleic acid strands. By having a stem, a fluorescer and a quencher can be bound at proximal sites on opposite strands, so that binding opens the stem and allows for fluorescence. One can use DNA fixed strands that are labeled at the unbound terminus, where by treating DNA-RNA hybrids with a DNA-RNA nuclease, the label is released into the supernatant and can be measured. One can bind the sample mRNAs or ta-RNAs to a surface and interrogate the bound RNA with labeled subject ta-RNAs or mimetic sequences and measure the label that is bound. The particular method of determining binding is not crucial to this invention and any convenient method providing for the appropriate specificity and sensitivity can be employed.

The terms "specific binding", "specifically bind", or other like terms, refer to the ability of a capture agent to preferentially bind to a particular target that is present in a mixture of different molecules, normally including one or more target molecules. Desirably, there will be discrimination between target molecules and non-target molecules of about 10 to 100-fold or more. Frequently, the binding constant between the capture ta-RNA and target mRNA or capture mRNA and target ta-RNA is greater than $10^6 M^{-1}$, and usually not more than about $10^{10} M^{-1}$. "Specific binding conditions" are conditions sufficient to allow a capture agent to preferentially bind to a particular analyte, e.g. stringent assay conditions. Stringent assay conditions are the summation or combination (totality) of both hybridization and wash conditions.

A "stringent hybridization" and "stringent hybridization wash conditions" in the context of nucleic acid hybridization (e.g., as in Southern or Northern hybridizations, or hybridization of molecules in solution, or in array assays) are sequence dependent, and are different under different experimental conditions. Hybridization conditions are well known to those of skill in the art. Illustrative stringent hybridization conditions, in solution or with the nucleic acid bound to a surface, that can be used to identify nucleic acids within the scope of the invention may include, e.g., hybridization in a buffer comprising 50% formamide, 5×.SSC, and 1% SDS at 42° C., or hybridization in a buffer comprising 5×SSC and 1% SDS at 65° C., both with a wash of 0.1×SSC and 0.1% SDS at 37° C. a buffer of 40% formamide, 1 M NaCl, and 1% SDS at 37° C., and a wash in 1×SSC at 45° C. 0.5 M $NaHPO_4$, 7% sodium dodecyl sulfate (SDS), 1 mM EDTA at 65° C., and washing in 0.1×SSC/0.1% SDS at 68° C., 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5.

The particular protocols will vary depending upon the source of the RNA, the agents involved in the assay, the specificity and required sensitivity, the employed label, the available equipment and the like. Usually, one of the members of the binding pair will be associated with a surface, either covalently or non-covalently bound. For covalent binding the subject ta-RNAs or mimetics thereof may be prepared bound to a surface by a convenient linking group, particularly a particle surface, and the particles used in the assay. Alternatively, the subject ta-RNAs may be functionalized, usually at a terminus and with a short linker, generally not more than 30 atoms in the chain, so as to be able to react with a functionalized solid surface that may be planar or spherical. Arrays can be prepared on microparticles, planar plastic and metal surfaces, etc. Conveniently, ink jet printing can be employed to ensure the spatial integrity of the different nucleic acid entities. Various functional groups can be used that are compatible with the nucleic acids, such as thiols, disulfides, activated olefins, amines, oxo- and non-oxo-carbonyl, etc.

Depending on the source of the sample, the sample may be pretreated before being assayed. From a cellular source, the RNA is isolated, purified and separated by size, e.g. gel electrophoresis. (Yi, et al. 2002 RNA 8, 180-7; Yi, et al. 2003

Genes Dev 17, 3011-6). The band having the desired molecular weight is then extracted from the gel and may be used for further studies.

The subject invention can be used in substantially all of the ways that have been taught for ta-RNA and miRNA with the added advantage that there will be fewer target mRNAs that are affected by employing a ta-RNA that has a higher affinity for a narrower range of mRNAs, particularly as a result of a defined loop sequence that defines a particular target mRNA. Thus, the subject ta-RNAs, mimetics or fragments thereof, can be used in investigations of cellular pathways, the effect of modulation on cellular phenotype, modulation of cellular properties, both healthy and diseased cells, screening of ta-RNA profiles, with greater specificity as to targets and their relationship to cellular states, e.g. diseased, propensity for particular diseases or mutations, evaluate particular proteins and pathways as to the state of cells, e.g. level of development, response to external stimuli, such as drugs, effect of protein expression modulation on the response of cells to drugs, and the like.

Toward this purpose cells may be prepared that are transiently or permanently modified with a genetic construct having a gene encoding only the ta-RNA and having transcriptional regulatory sequences functional in the host cell, so as to provide either inducibly or constitutively, the encoded ta-RNA. These cells may be used in culture to study the effect of external agents in the presence and absence of the ta-RNA on the pathway in which the protein modulated by the ta-RNA is active.

The subject invention also allows for the determination of the effect of changes in the loop sequence, such as isoforms of ta-RNA families. Methods such as exchanging all or part of loop sequences between the isoforms, substituting one or two nucleotides in a nucleotide walk using the different combinations of nucleotides, while avoiding pairing that results in new secondary structure within the loop, provides information about what the regulatory role of the subject ta-RNA is and can provide new regulatory ta-RNAs.

One can also identify the role of a loop sequence of a ta-RNA among a plurality of isoforms differing at least in their loop sequences. One can substitute a portion of one loop from one isoform with a comparable portion of a loop from a different isoform. The first isoform and the modified isoform may then be introduced in separate cells of the same type and the phenotype of each of the cells determined. Where the effect on the phenotype of the ta-RNAs is the same, one can conclude that the loop does not affect the phenotype, while if the phenotypes are different, then the loop isoform affects the phenotype for the two isoforms.

The subject ta-RNAs, that is, modified ta-RNAs, can be used in investigating more accurately the development of an embryo, stem cell or differentiated cell. By introducing a gene that expresses the ta-RNA constitutively or inducibly, one can observe the effect on the cells and their development when the expression of a particular protein is modulated. One can introduce the gene into an intron, so as to have concomitant expression of the protein and the ta-RNA. One can coordinate expression of the ta-RNA with the expression of one or more proteins, where the same transcription factors for the expression of the ta-RNA and protein(s) are the same, that is, the transcriptional regulatory regions respond to the same transcription factors.

One can define targets for treating diseased states by introducing the ta-RNA directed to a specific protein to see the effect of the modulation of the expression of the protein has on the diseased state and the cells response to drugs.

One can use various delivery systems for delivering the subject ta-RNAs to cells and to tissue, in vitro and in vivo. Delivery of drug to cells or tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). Other methods of delivery may be found in U.S. Patent application nos. 2008/0241198; 2009/0124534; 2009/0124777; 2005/0008617; and references cited therein.

Instead of having binding to mRNA, antisense ta-RNAs may be used to investigate the role of the ta-RNA in a cell or the role of the protein(s) that is suppressed by the ta-RNA. The antisense sequence will bind to at least the seed sequence and a portion of the loop, preferably the 3'-stem and at least half of the loop proximal to the 5'-terminus of the stem. One compares cells that express the ta-RNA by itself or together with the antisense with differences being associated with the presence and absence of ta-RNA activity.

The following examples are offered by way of illustration and not by way of limitation.

EXPERIMENTAL

Experimental for Pre-miRNA

Nucleotide Sequences of miRNA Genes Used in this Study:
(1) The nucleotide sequences of wild-type mir-181a-1 gene

```
                                               (SEQ ID NO: 2)
CTCGAGtgtgacaggtttggttaaaggattgggctttcctctgcctccc tcctgctccagactcccacagatactgtttaaatcagcacatctctgcc tcacaggttgcttcagtgAACATTCAACGCTGTCGGTGAGTttggaatt caaataaaaACCATCGACCGTTGATTGTAccctatagctaaccatcatc tactccatggccctctgcgtttgctgaagacagaaccgcaaagcaggac ccgacaggattcttttttaattaagaattcctagGaattcTTGCCAAAC

CTACAGGTGGGGTCTTTCATTCCCCCCTTTTTCTGGAGACTAAATAAAA

TCTTTTATTTTATCGATaagcttGGCTGCAGGTCGACgcggccgc
```

(2) Pre-miRNA nucleotide sequences of the mir-181a-1 mature and loop mutants

I. Wild-Type Pre-miR-181a-1 Precursor

```
                                               (SEQ ID NO: 3)
AACATTCAACGCTGTCGGTGagtttggaattcaaataaaaACCATCGAC

CGTTGATTGTA
```

II. 2-nt Mature miR-181a-1 Mutants

```
M1:
                                               (SEQ ID NO: 4)
AtaATTCAACGCTGTCGGTGAGTttggaattcaaataaaaACCATCGAC
CGTTGATTtaA M2:
                                               (SEQ ID NO: 5)
AACtaTCAACGCTGTCGGTGAGTttggaattcaaataaaaACCATCGAC
CGTTGAaaGTA
```

M3:
(SEQ ID NO: 6)
AACATaaAACGCTGTCGGTGAGTtttggaattcaaataaaaACCATCGAC
CGTTttTTGTA M4:
(SEQ ID NO: 7)
AACATTCttCGCTGTCGGTGAGTtttggaattcaaataaaaACCATCGAC
CGaaGATTGTA M5:
(SEQ ID NO: 8)
AACATTCAAacCTGTCGGTGAGTtttggaattcaaataaaaACCATCGAC
gtTTGATTGTA M6:
(SEQ ID NO: 9)
AACATTCAACGaaGTCGGTGAGTtttggaattcaaataaaaACCATCGAC
CGTTGATTGTA M7:
(SEQ ID NO: 10)
AACATTCAACGCTcaCGGTGAGTtttggaattcaaataaaaACCATCGtg
CGTTGATTGTA M8:
(SEQ ID NO: 11)
AACATTCAACGCTGTacGTGAGTtttggaattcaaataaaaACCATgtAC
CGTTGATTGTA M9:
(SEQ ID NO: 12)
AACATTCAACGCTGTCGcaGAGTtttggaattcaaataaaaACCtgCGAC
CGTTGATTGTA M10:
(SEQ ID NO: 13)
AACATTCAACGCTGTCGGTctGTtttggaattcaaataaaaACgATCGAC
CGTTGATTGTA M11:
(SEQ ID NO: 14)
AACATTCAACGCTGTCGGTGAcattggaattcaaataaaatgCATCGAC
CGTTGATTGTA III. Segment Mature miR-181a-1 Mutants SM1:
(SEQ ID NO: 15)
AtataaaAACGCTGTCGGTGAGTtttggaattcaaataaaaACCATCGAC
CGTTtttataA SM2:
(SEQ ID NO: 16)
AACATTCttacaacaCGGTGAGTtttggaattcaaataaaaACCATCGtg
gtaaGATTGTA SM3:
(SEQ ID NO: 17)
AACATTCAACGCTGTaccactcattggaattcaaataaaatggtggtAC
CGTTGATTGTA SM4:
(SEQ ID NO: 18)
AACATTCttacaacaaccactcattggaattcaaataaaatggtggttg
gtaaGATTGTA IV. miR-181a-1 Loop Mutant LP1:
(SEQ ID NO: 19)
AACATTCAACGCTGTCGGTGAGTttCCaattcaaataaaaACCATCGAC
CGTTGATTGTA LP2:
(SEQ ID NO: 20)
AACATTCAACGCTGTCGGTGAGTttggTTttcaaataaaaACCATCGAC
CGTTGATTGTA LP3:
(SEQ ID NO: 21)
AACATTCAACGCTGTCGGTGAGTtttggaaAAcaaataaaaACCATCGAC
CGTTGATTGTA LP4:
(SEQ ID NO: 22)
AACATTCAACGCTGTCGGTGAGTtttggaattGTaataaaaACCATCGAC
CGTTGATTGTA LP5:
(SEQ ID NO: 23)
AACATTCAACGCTGTCGGTGAGTtttggaattcaCGtaaaaACCATCGAC
CGTTGATTGTA LP6:
(SEQ ID NO: 24)
AACATTCAACGCTGTCGGTGAGTtttggaattcaaaATaaaACCATCGAC
CGTTGATTGTA (3) The nucleotide sequences of the wild-type mir-181c gene (SEQ ID NO: 25)
GATCCTCGAGgtgagtcaaaggggaccctggtttctctctcgtcccac atgctctctgccttgctggcctactctcccaactccagttatccaaga acttgccaaggggtttggggAACATTCAACCTGTCGGTGAGTttgggc agctcagacaaaCCATCGACCGTTGAGTGGAccccgaggcctggaact gccacccgtctacccatccccaccctgtagacccgggagagcccag gcagcatccctgcctcaggccacagcaaaggtcacaattGAATTCGA

TC

Figures 1B, 1C:
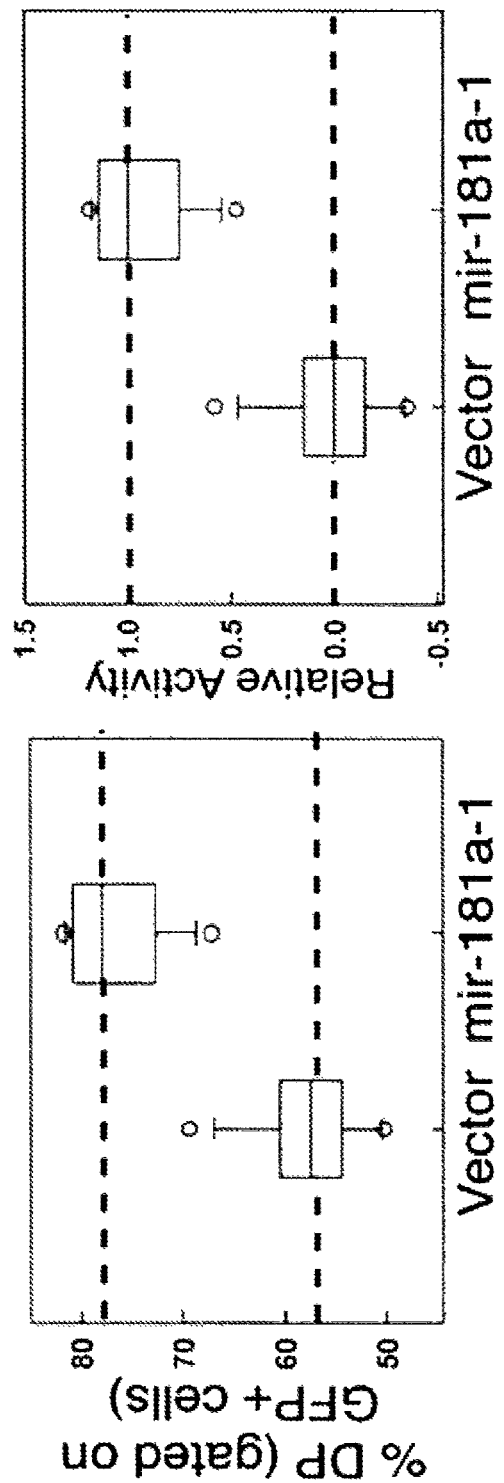
Figure 1D:
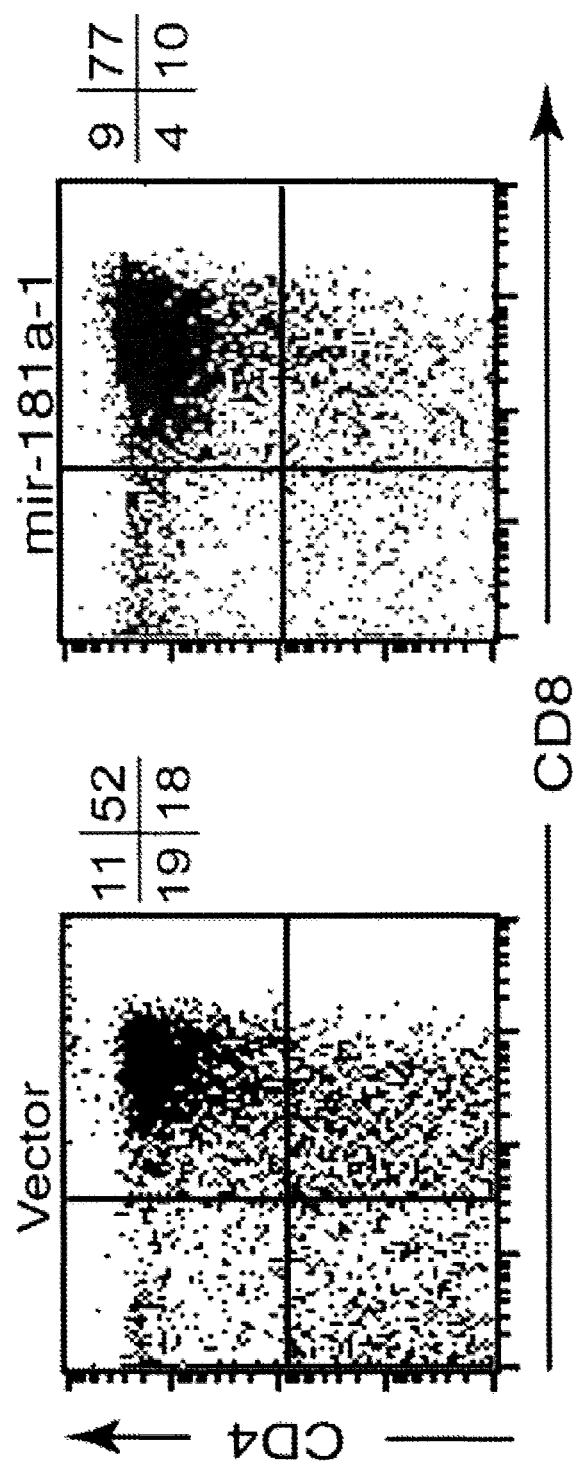

An In Vitro Assay for Measuring the Effects of mir-181 Genes on DP Cell Development We used T cell development as a functional readout to determine the nucleotides and structural domains that are required for the function of mir-181 genes. mir-181a-1 plays important roles in T and B lymphocyte development (10-12), and can function as a rheostat to modulate the strength and threshold of T cell receptor (TCR) signaling (11). Moreover, mature miR-181a is developmentally regulated during early T cell differentiation, in the transition from CD4 and CD8 double-negative (DN) to CD4 and CD8 double-positive (DP) cells, in the thymus (11-13). Using the OP9-DL1 co-culture assay, which can recapitulate the differentiation of DN progenitors into DP cells in vitro (14), we showed that ectopic expression of mir-181a-1 in DN thymic progenitor cells lead to a significant increase in the percentage of DP cells, from a median level of ~57% in the control group to a median level of ~77% in the mir-181a-1 expressing group (FIG. 1). We have found that mir-181a-1 potentiates DN to DP cell development by targeting negative regulators in the Notch and pre-TCR signaling pathways. This assay allowed us to quantitatively measure the contribution of nucleotide sequences and structural domains to miRNA gene function via mutagenesis analyses.

We generated "stem mutants" by systematically mutate the nucleotides in the mature miRNA region and then tested the activities of mir-181a-1 "stem mutants" in the OP9-DL1 co-culture assay. (FIGS. 7-10) We found that nucleotides in the 5' seed region are critical for mir-181a-1's activity in promoting DP cell development, whereas the nucleotides in the 3' end of the mature miR-181a region make only minor contributions and the nucleotides in the center are not at all important to mir-181a-1 activity (FIGS. 7-10). These findings confirmed the importance of the seed nucleotides, shown previously by computational and biochemical analyses (6-8), thus validating the use of this assay to dissect the structural and functional relationships of mir-181 genes by mutagenesis.

mir-181a-1, but not mir-181c, can Promote DP Cell Development

The members of mir-181 family of genes produce four mature miRNAs, miR-181a, miR-181b, miR-181c, and miR-181d, from three putative polycistronic transcripts, mir-181a-1/b-1, mir-181a-2/b-2, and mir-181c/d, respectively (FIG. 10). The mature miRNAs of the miR-181 family, all with identical 5' seed nucleotides, differ from one another by no more than 3-nt in either the center or the 3' end of the mature miRNAs. Particularly, mature miR-181a differs from miR-181c by only one nucleotide in the center of the mature miRNA (FIGS. 2A, 2B). Thus, according to the results of "stem mutant" analyses (FIGS. 7-10), it would be expected that mir-181a-1 and mir-181c should have similar activities in this co-culture assay.

Figure 2C:
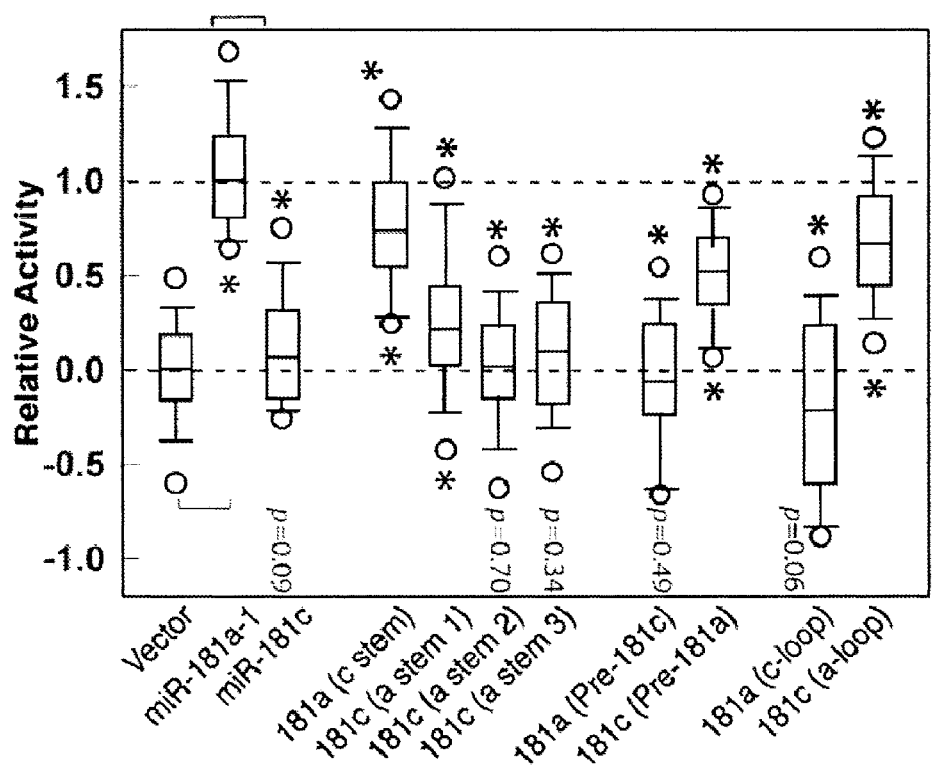
Figure 11:
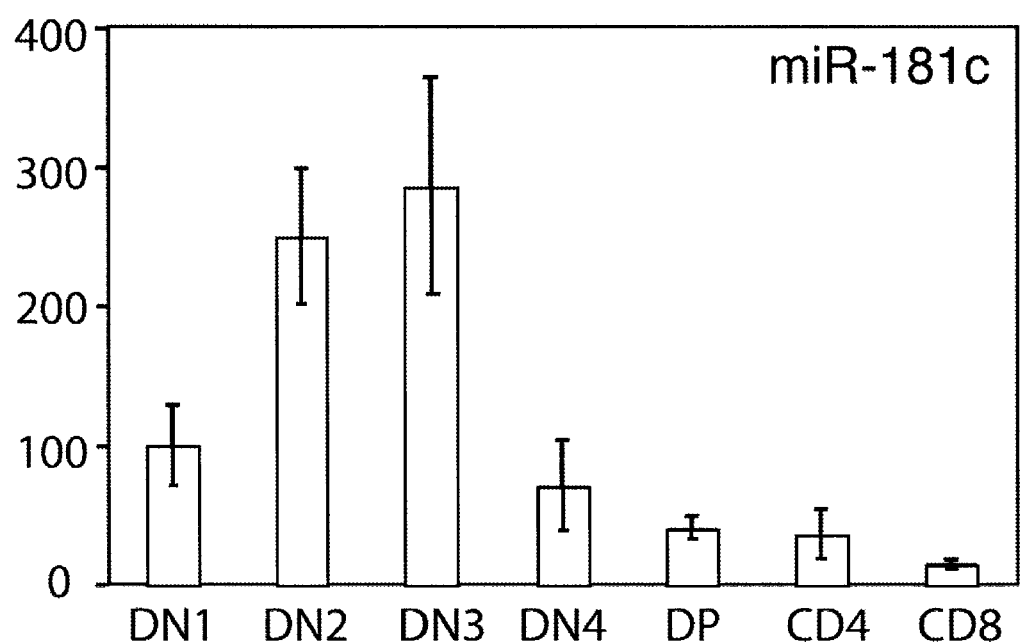
FIG. 11. Developmental regulation of miR-181c expression in various purified thymocyte populations determined by miRNA qPCR.
Figure 12:
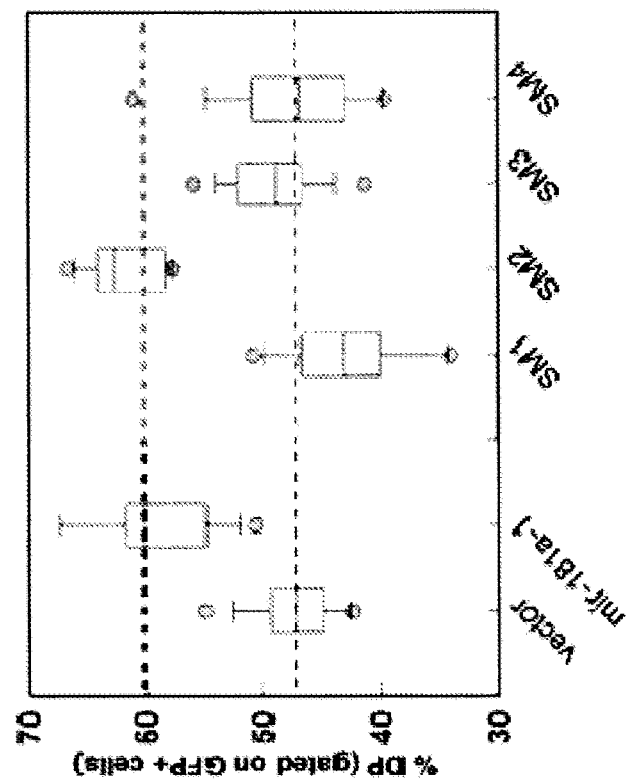
FIGS. 12A, 12B and 12C. The effects of mutations in the mature miRNA region of the mir-181a-1 genes on DP cell development (See FIG. 7). (A,B) Box-plots summarize the percent of DP cells generated from DN progenitor cells infected with mir-181a-1, or mature miRNA mutant genes (gated on GFP positive). A representative OP9-DL1 stromal co-culture assay (12 independent replicates for each construct) is shown. The ends of the boxes define the $25^{th}$ and $75^{th}$ percentiles, a line indicates the median, and bars define the $5^{th}$ and $95^{th}$ percentiles. (C) Statistical summary. Mann-Whitney Rank Sum Tests were performed on this representative data set to determine whether the activity of mir-181a-1, mir-181c, or their chimeric mutants is statistically different from the control vector or the mir-181a-1 vector.
Figure 12A:
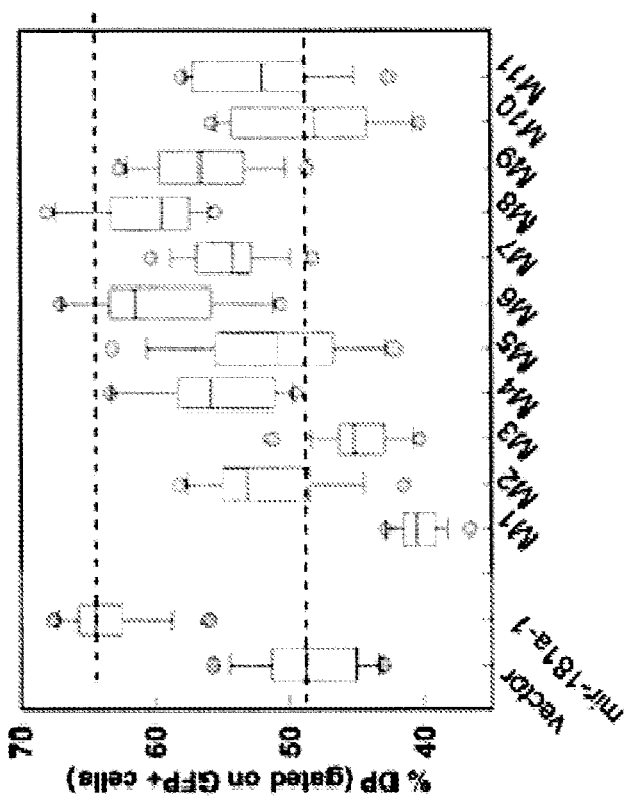
Figure 13A:
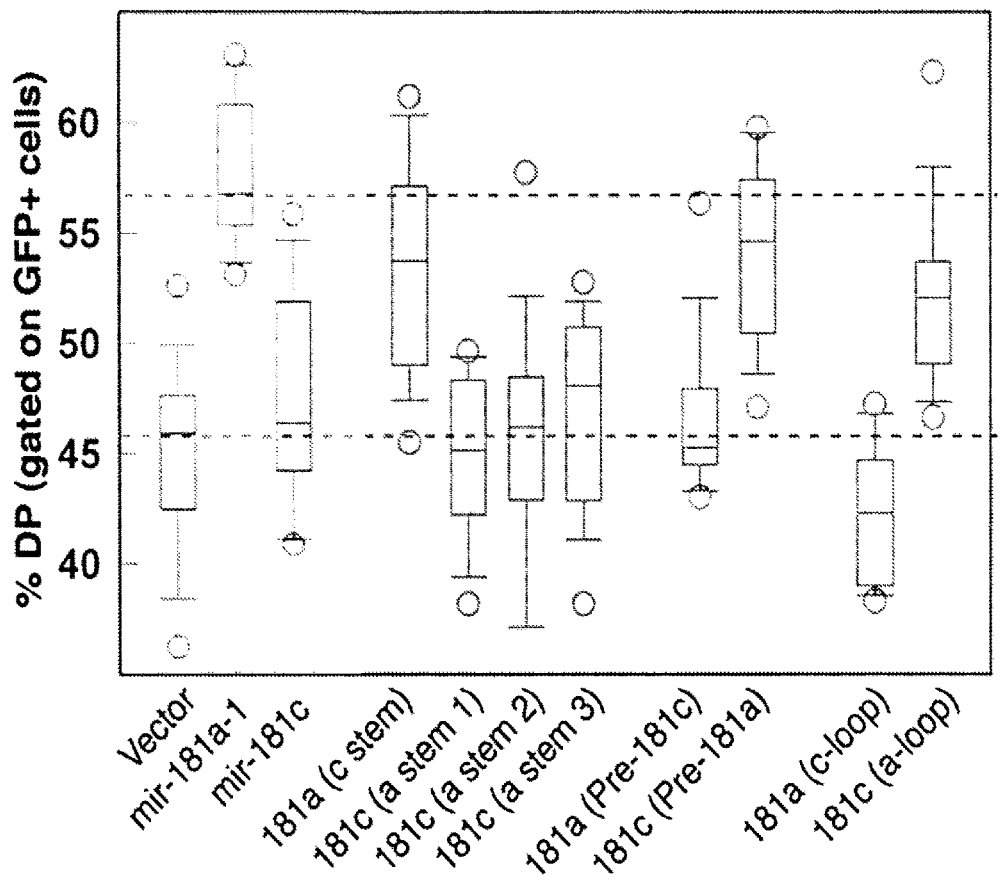

To test this idea, we examined the abilities of mir-181a-1 and mir-181c in promoting DP cell development. Of note, mature miR-181a and miR-181c are differentially expressed during T cell development in the thymus (11, 12) (FIG. 11), indicating that both miRNA genes are processed in thymocytes and may have roles in normal thymocyte development. Thus, by perturbing mir-181a-1 and mir-181c expression in thymocytes we can interrogate their functions in an RNA milieu that consists of physiologically relevant miRNAs and target mRNAs. Interestingly, while the ectopic expression of mir-181a-1 results in a substantial increase in the generation of DP cells, the expression of mir-181c does not (FIG. 2C, grey), demonstrating that mir-181a-1 but not mir-181c can promote DP cell development.

miRNA Genes Encoding Identical Mature miRNAs can Have Distinct Biological Activities To examine whether the single nucleotide variation in the mature miRNA regions may contribute to their differences in activity, we swapped the stem regions (miR and miR* duplexes) between mir-181a-1 and mir-181c (FIG. 2B, yellow). The resulting "mature chimeric" miRNA genes, termed mir-181a (c stem) and mir-181c (a stem 1), express mature miR-181c and mature miR-181a, respectively. Two additional "mature chimeric" miRNA genes, mir-181c (a stem 2) and mir-181c (a stem 3), were also generated by replacing mature miR-181c with mature miR-181a while maintaining the miR-181c* strand. Even though mir-181a (c-stem) produces mature miR-181c, we observed that this "mature chimeric" miRNA gene was still functionally active in promoting DP cell development, albeit with a median activity of 73% that of the wild-type mir-181a-1 (FIG. 2C, yellow). In contrast, the mir-181c (a stem 1, 2, 3) genes, which encode mature miR-181a, have a median activity of ~21%, 1.7, 9.6% that of the wild-type mir-181a-1, respectively (FIG. 2C, yellow). These results demonstrate that the distinct activities of mir-181a-1 and mir-181c are not caused by the single nucleotide difference between their mature miRNA forms. Most notably, we have proven that miRNA genes encoding identical mature miRNAs, such as mir-181c and mir-181a (c-stem) that encode miR-181c, or mir-181c and mir-181a (c-stem) that encode miR-181a, can have distinct biological activities.

Pre-miRNAs and Their Loops Determine the Activities and Specificities of the mir-181 Genes Since mir-181a-1 and mir-181c have divergent pre-miRNA flanking and loop sequences, we then tested whether their differences in activity are determined by their unique pre-miRNAs or pre-miRNA flanking sequences (FIG. 2B). We generated "pre-miRNA chimeric" genes by swapping the pre-miRNA regions between mir-181a-1 and mir-181c (FIG. 2B, orange). The resulting "pre-miRNA chimeric" genes, termed mir-181a (pre-181c) and mir-181c (pre-181a), encode mature miR-181c and miR-181a, respectively (FIG. 2B). When tested in the OP9-DPL1 co-culture assay, the miRNA gene with pre-miR-181a, mir-181c (pre-181a), can promote DP cell development, albeit with a median activity of ~52% that of the wild-type mir-181a-1, whereas the miRNA gene with pre-miR-181a, mir-181a (pre-181c), has no activity (FIG. 2C, SI Table 2). These results demonstrate that pre-miRNAs have a key role in determining the distinct biological activities of the mir-181a-1 and mir-181c genes. However, pre-miRNA flanking sequences may also contribute to the functions of the mir-181a-1 and mir-181c genes, since mir-181c (pre-181a) has a reduced activity when compared to the wild-type mir-181a-1.

Since pre-miR-181a-1 and pre-miR-181c differ mainly in their pre-miRNA loop nucleotides (FIG. 2B), we next asked whether pre-miRNA loop sequences are involved in the distinct functions of these two miRNA genes. "Chimeric loop" miRNA genes, mir-181a (c-loop) and mir-181c (a-loop), were generated by swapping the pre-miRNA loops between mir-181a-1 and mir-181c (FIG. 2B). When tested in the OP9-DPL1 co-culture assay, mir-181c (a-loop) can promote DP cell development with a median activity of ~67% that of wild-type mir-181a-1, while mir-181a (c-loop) is inactive in promoting DP cell development (FIG. 2C, demonstrating that the distinct biological activities of the mir-181a-1 and mir-181c genes are largely determined by the differences in their pre-miRNA loops.

Figure 3A:
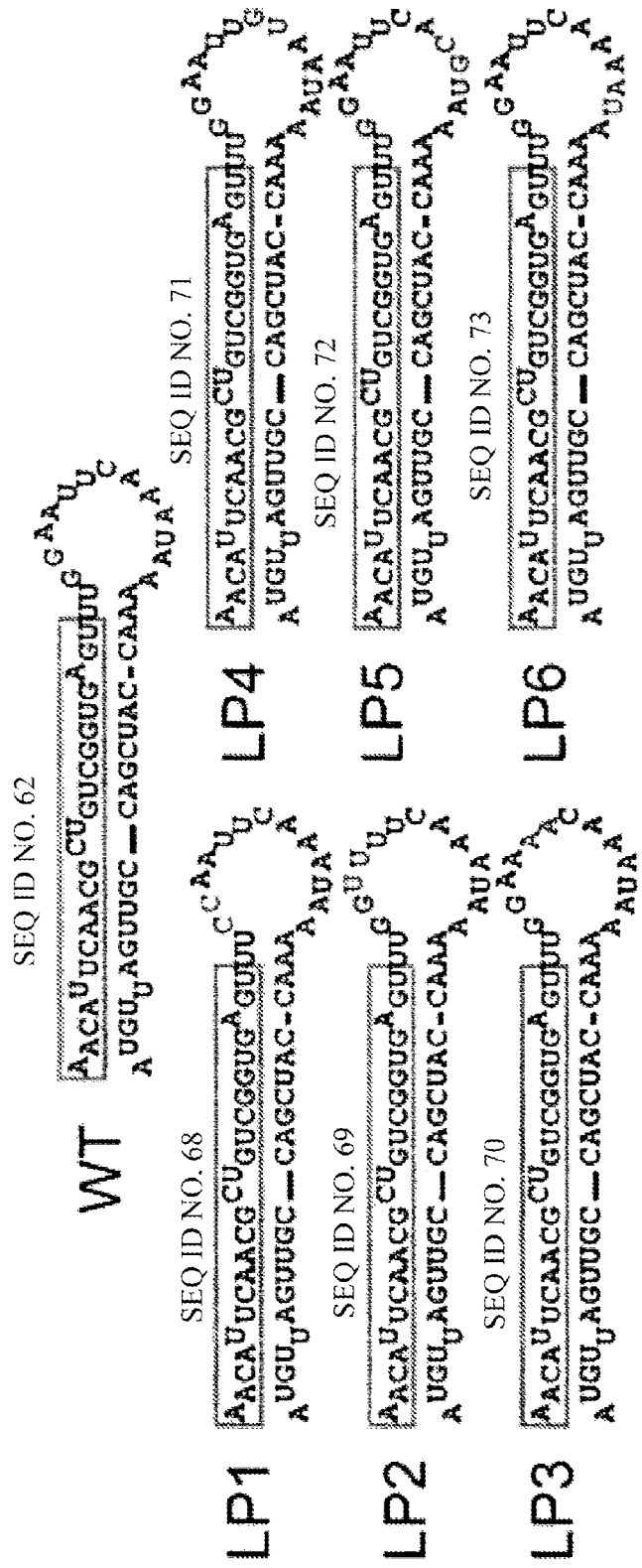
FIGS. 3A and 3B. The activity of the mir-181a-1 gene in DP cell development is highly sensitive to nucleotide changes in the pre-miR-181a-1 loop region. (A) Schematics of the pre-miR-181a-1 loop mutants (SEQ ID NOS:68-73), with the wild-type sequence shown on top (SEQ ID NO:62). Two nucleotides at a time around the pre-miR-181a-1 loop were mutated (gray nucleotides), while the mature miR-181a nucleotides remained constant (boxed nucleotides). (B) The effects of pre-miR-181a-1 loop mutants on DP cell development. Normalized data from at least six independent T cell assays (each with 12 independent replicates for a total of 72 replicates) are pooled and graphed in the distribution box plots to summarize the relative activities of mir-181a-1 and its loop mutants in DP cell development. Mann-Whitney Rank Sum Tests were performed to determine whether the activities of the loop mutants are statistically different from those of the negative control vector (*, $p<0.0001$) and/or the mir-181a-1 positive control vector (*, $p<0.0001$). A representative OP9-DL1 stromal co-culture assay without normalization (12 independent replicates for each construct) is also shown (FIG. 14).
Figure 3B:
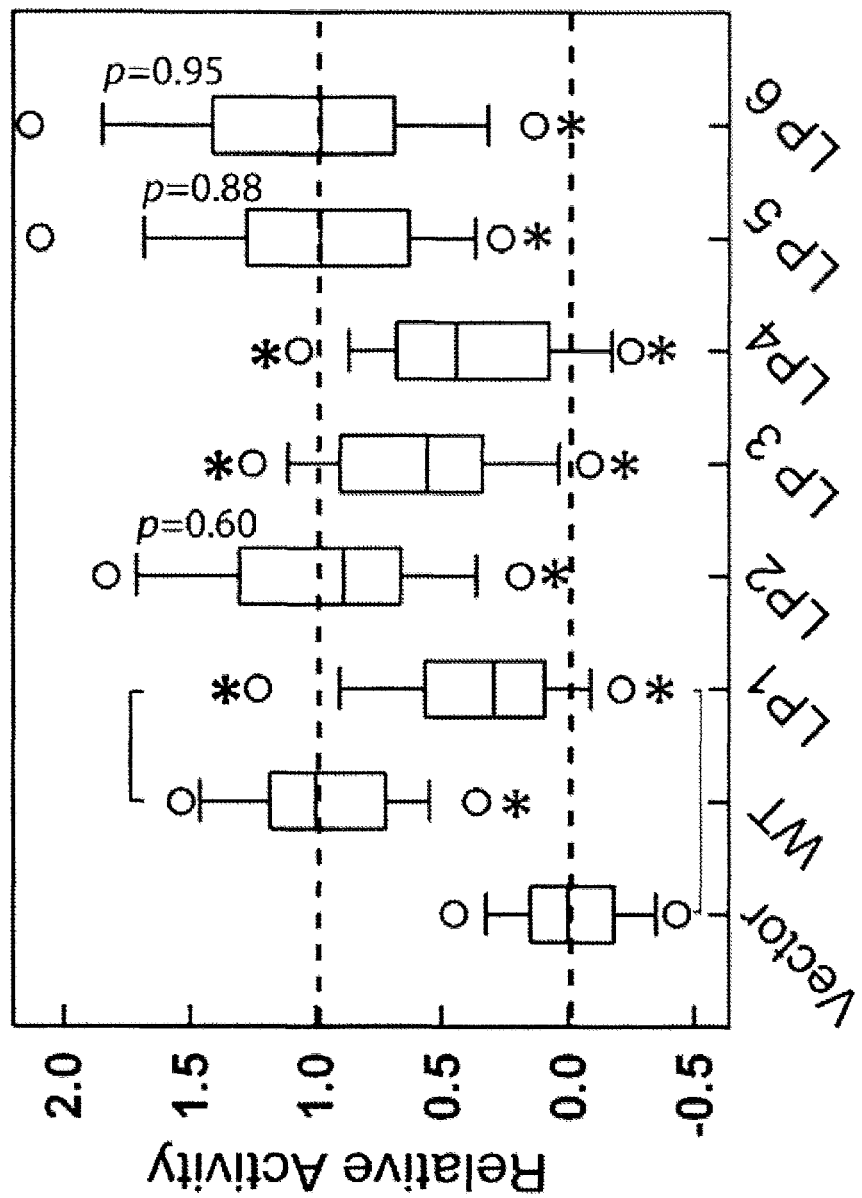

The mir-181a-1 Activity is Sensitive to Nucleotide Changes in its Pre-miRNA Loop To further investigate the role of pre-miRNA loop nucleotides, we carried out scanning mutagenesis around the pre-miR-181a-1 loop (FIG. 3A). When tested in the OP9-DPL1 co-culture assay, we found that the dinucleotide mutations in the pre-miR-181a-1 loop had varied effects on mir-181a-1 activity (FIG. 3B). The LP1, LP3, and LP4 mutants have median activities of ~29%, 55%, and 46% that of the wild-type mir-181a-1, respectively (FIG. 3B). In contrast, the LP2, LP5 and LP6 mutations did not significantly affect mir-181a-1 activity. The LP1 nucleotides are conserved between the pre-miR-181a and pre-miR-181c loops, but the LP3 and LP4 nucleotides are not, suggesting that LP 1 mutations may not contribute to the functional differences between the mir-181a-1 and mir-181c genes. This loop mutagenesis analyses further demonstrate that pre-miRNA loop nucleotides can quantitatively influence the activity of the mir-181a-1 gene.

The Effects of mir-181a-1/c Mutations on Mature miRNA Biogenesis

Figures 4A, 4B:
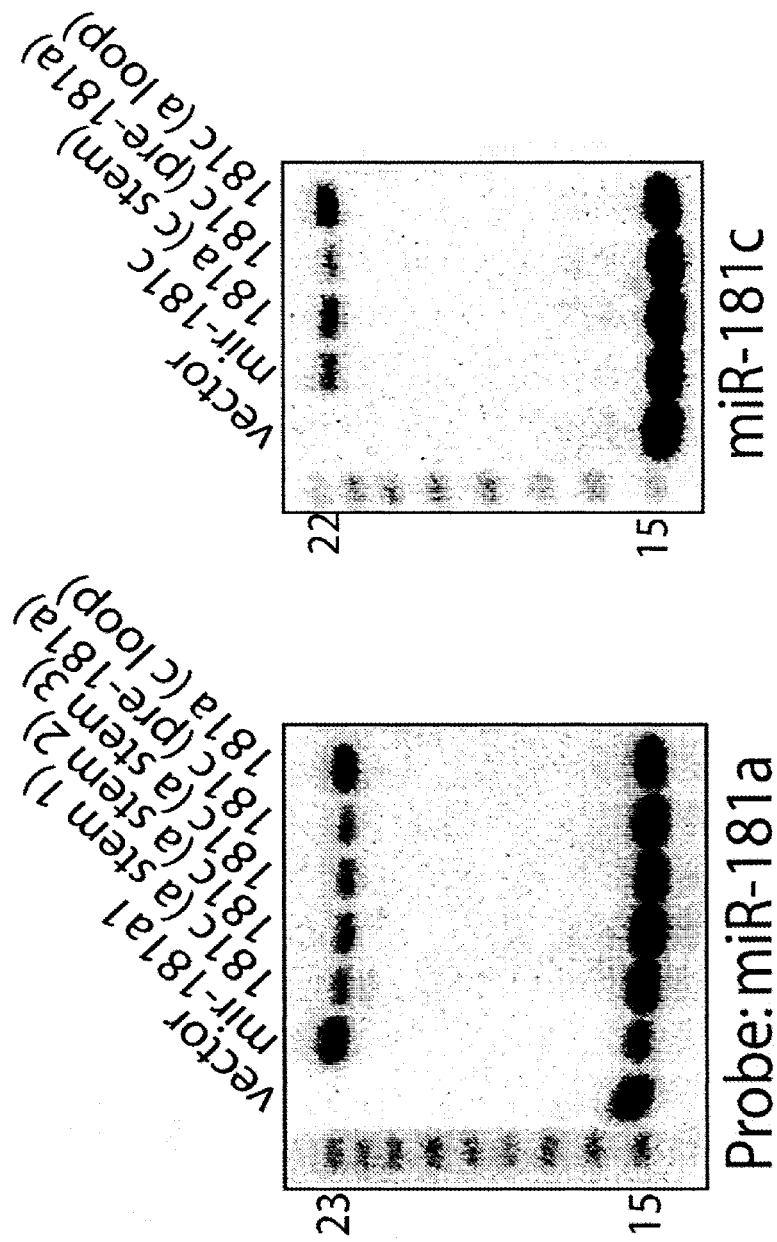
FIGS. 4A, 4B and 4C. Mature miRNAs produced from the mir-181a-1/c mutants have the same 5' ends, as indicated by primer extension analyses. Gel separations are shown for the different modified miR-181s using miR-181a as a probe in FIGS. 4A and 4C, and miR-181c as a probe in FIG. 4B.
Figure 4C:
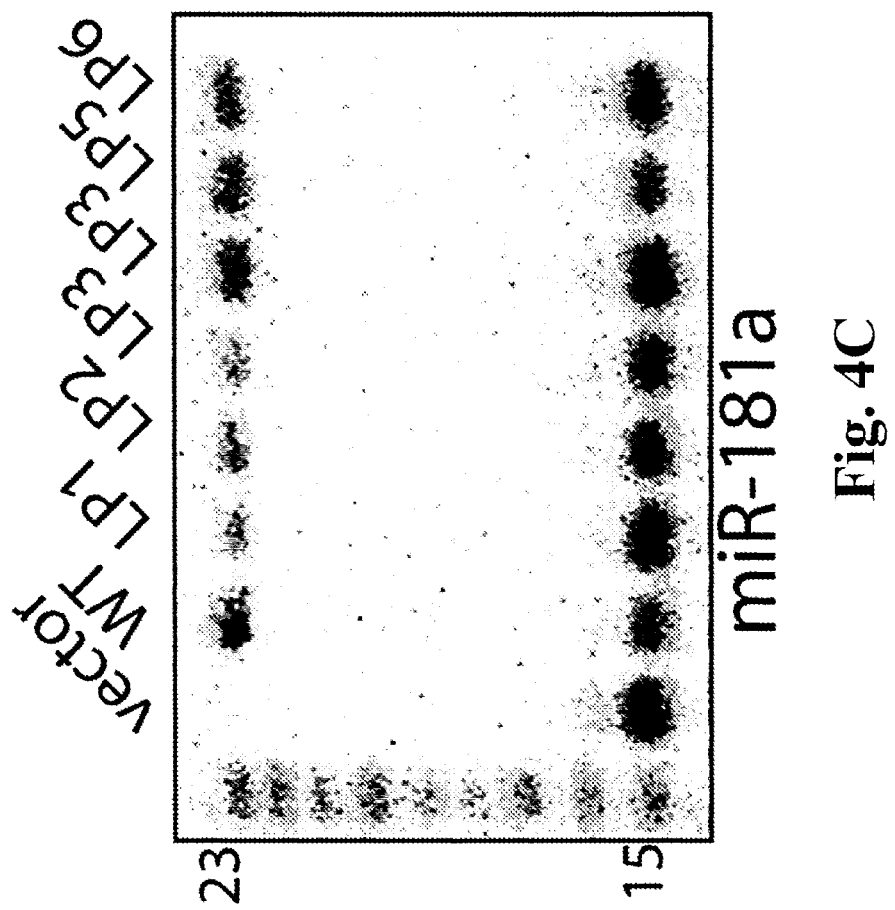

To understand how pre-miRNA loop nucleotides control the activities and specificities of miRNA genes, we characterized the 5' ends of mature miR-181a and miR-181c produced from various mir-181a-1/c mutants. It is likely that shifts in the 5' end of mature miRNAs may change the seed nucleotides and affect the activities of the corresponding miRNA genes. To this end we carried out primer extension analyses and showed that mature miRNAs produced from various mir-181a-1/c mutants have the same 5' end as those produced from the corresponding wild-type mir-181a-1/c genes (FIGS. 4A-C). These results demonstrate that 181a-1/c mutants do not cause changes in 5' end of the mature miRNA sequences, eliminating the possibility that mir-181a-1/c mutants affect the activities of the mir-181a-1 or mir-181c genes by controlling the fidelity of the 5' ends of the mature miRNAs produced.

Figure 5B:
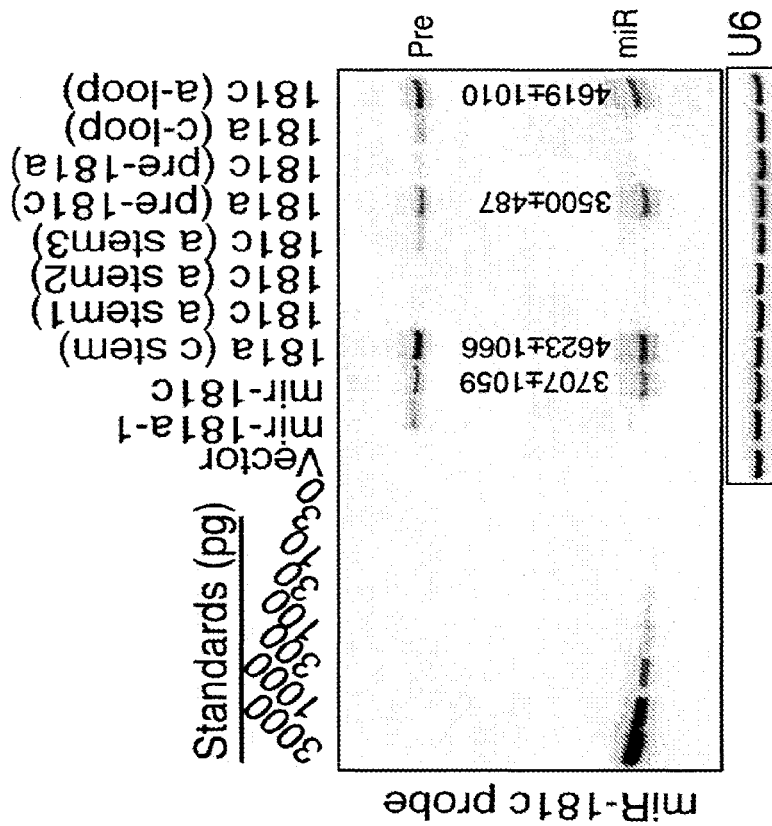
FIGS. 5A, 5B, 5C, 5D, 5E and 5F. The effects of mir-181a-1/c mutants on mature miRNA expression in BOSC23 and DP cells. (A, B) Gels providing the copy numbers of mature miR-181a (A) and miR-181c (B) expressed in BOSC23 cells transfected with the same amounts of various viral vectors expressing different mir-181a-1/c mutants, determined by quantitative Northern blot analyses (See also FIG. 15.) (C, D) The copy numbers of mature miR-181a (C) and miR-181c (D) expressed in DP thymocytes transduced with viral vectors expressing various mir-181a-1/c mutants, determined by miRNA qPCR analyses. (E) A gel providing the copy numbers of mature miR-181a expressed in BOSC23 cells transfected with the same amounts of various viral vectors expressing unique mir-181a-1 loop mutants, determined by quantitative Northern blot analyses (See also FIG. 16). (F). The copy numbers of mature miR-181a expressed in DP thymocytes transduced with viral vectors expressing various mir-181a-1 loop mutants, determined by miRNA qPCR analyses. Statistical significance was determined by an unpaired two-tailed student's t test (compared to the control vector, *, $p<0.05$). Representative blots of four or more independent quantitative Northern blot analyses are shown (A, B, E).
Figure 5A:
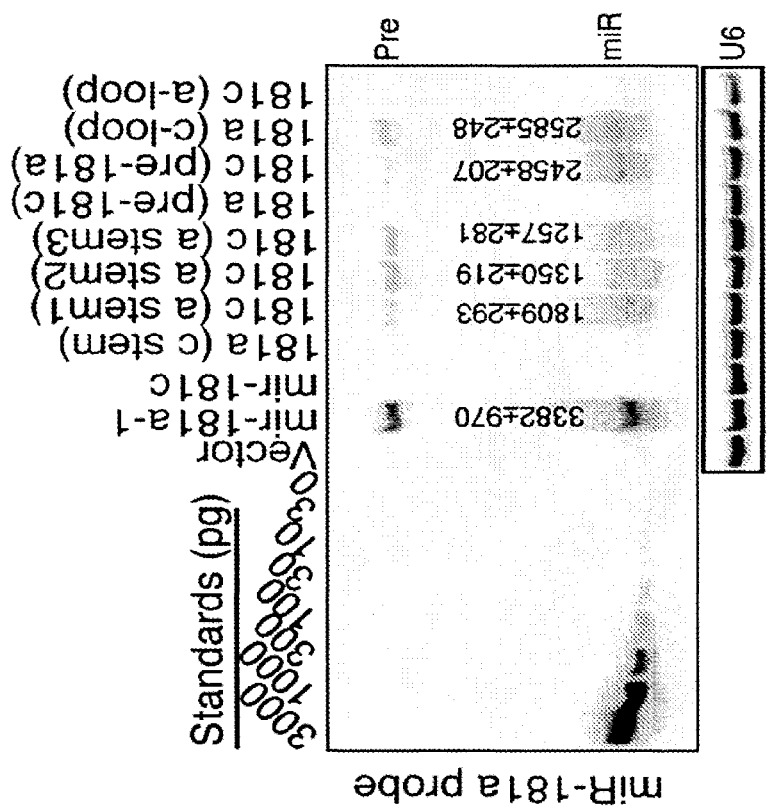
Figures 5C, 5D:
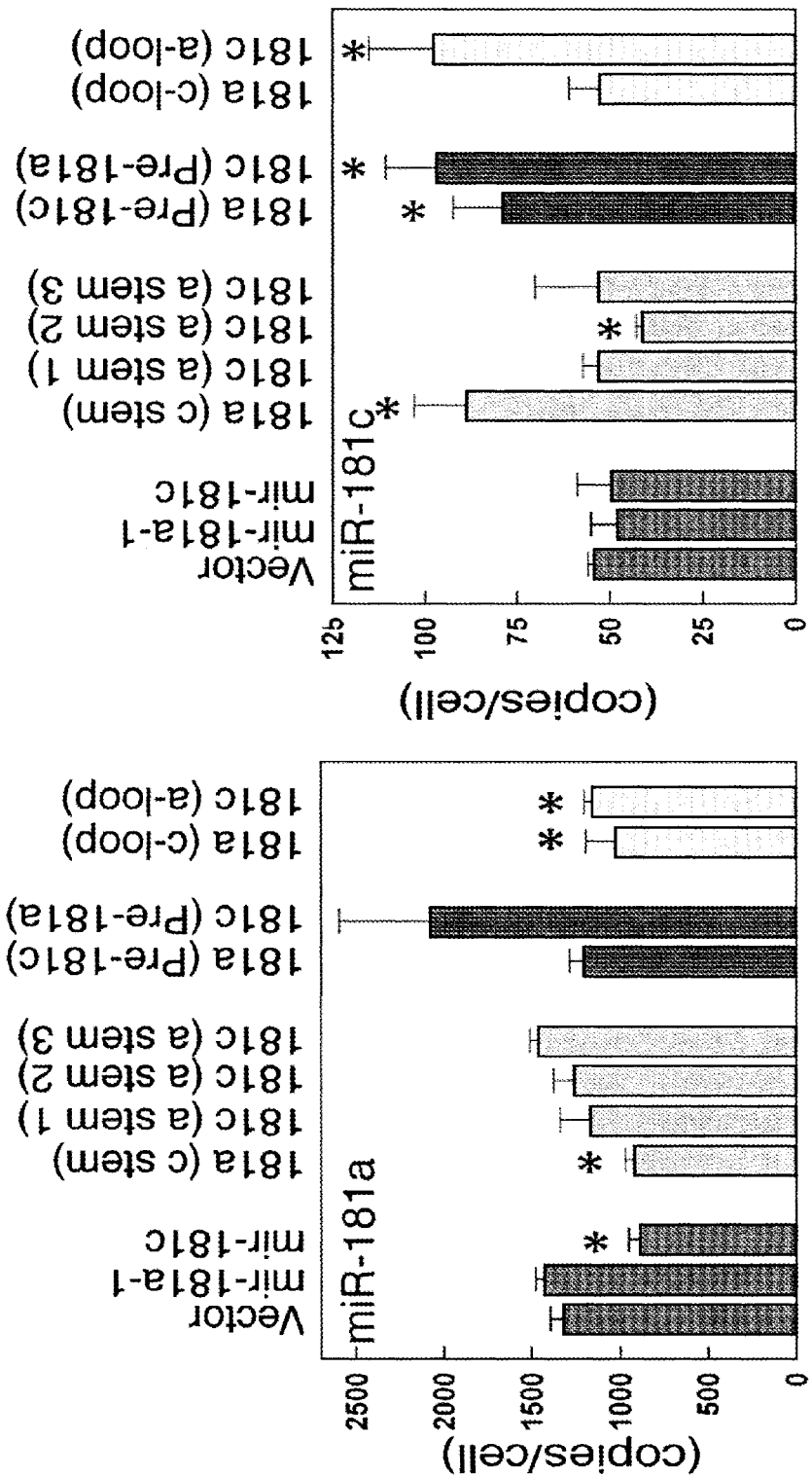

We then investigated whether mir-181a-1/c mutants cause changes in the levels of mature miRNAs made, and if so whether these changes correlate with the activities of corresponding miRNA genes. Quantitative Northern blot analyses were used to define the levels of mature miR-181a and miR-181c, as well as the sizes of the mature miRNAs and the levels of the pre-miRNAs, produced from various mir-181a-1/c mutant constructs. Since it is difficult to obtain sufficient numbers of infected DP thymocytes for Northern blot analyses, we first examined miRNA expression of various mir-181a-1/c mutants in BOSC 23 cells using quantitative Northern blot analyses (FIGS. 5A, B, and 15). In addition, BOSC 23 cells do not express endogenous mature miR-181a or miR-181c, thus allowing for accurate measurement of the levels of mature miRNAs produced. In parallel, we also carried out miRNA qPCR analyses to determine the number of copies of mature miR-181a and miR-181c in DP cells transduced with mir-181a-1/c mutant viruses (FIGS. 5C, 5D). Reasonable quantity of DP cells can be isolated from OP9-DL1 culture by FACS-sorting for miRNA qPCR analysis.

Figures 5E, 5F:
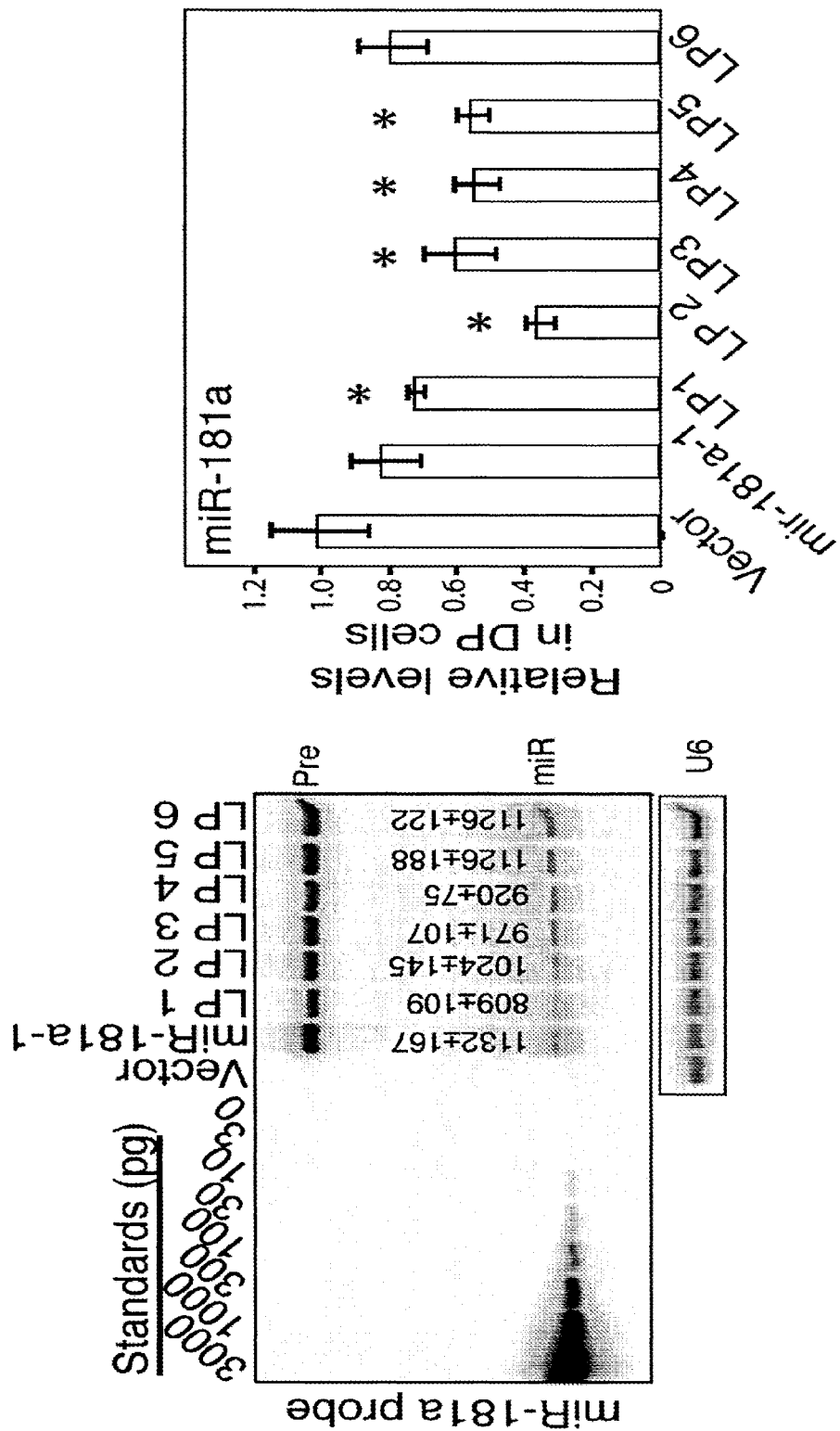

The levels of mature miR-181a in DP cells expressing mir-181a-1/c mutants seem to vary irregularly and have no apparent correlation with the gene activity (FIG. 5C). mir-181a-1 and mir-181c produce comparable levels of mature miR-181a and miR-181c in BOSC 23 cells (FIGS. 5A, B, and 15). However, the ectopic expression of mir-181a-1 or mir-181c does not result in a significant increase in mature miR-181a or miR-181c expression in the infected DP cells (FIGS. 5C, 5D). Ectopic expression of the mir-181c gene actually caused a decrease in the level of mature miR-181a (FIG. 5C), although no decrease in the percentage of DP cells was observed (FIG. 2C, grey). Further, the LP2 mutant exhibits the same activity as wild-type mir-181a-1, but DP cells infected with this mutant expresses ~50% less mature miR-181a (FIGS. 3B, 5E, 5F). Finally, mature miR-181a levels in DP and BOSC 23 cells expressing the mir-181a-1 loop mutants have no apparent correlation with the activities of mutant genes (FIGS. 3, 5E, 5F, 16). For example, LP3, LP4, and LP5 produced similar levels of mature miR-181a in DP cells and BOSC 23 cells (FIGS. 5E, 5F, 16), but these mutants had different activities in promoting DP cell development (FIG. 3B). LP5 mutations had no effect on mir-181a-1 activity, while LP3 and LP4 mutations caused ~45% and 56% reduction in median activity, respectively. Thus, the levels of mature miR-181a in DP cells have little correlation with their activities in DP cell development (FIGS. 2, 5C).

In comparison, the levels of mature miR-181c in DP cells expressing mir-181a-1/c mutants had a partial correlation with their activities in DP cell development, (FIGS. 2, 5D). Ectopic expression of mir-181a (c-stem), mir-181a (pre-181c), and mir-181c (a-loop) resulted in significant increases in the levels of mature miR-181c in DP cells (FIG. 5D). However, while mir-181a (c-stem) and mir-181c (a-loop) can promote DP cells development, mir-181a (pre-181c) cannot (FIG. 2C), further showing that increases of mature miR-181c in DP cells do not always correlate with the activities of corresponding miRNA genes. Intriguingly, we noted that mature miRNA expression from some miRNA genes might be differentially regulated in DP and BOSC 23 cells. For example, while mir-181c, mir-181a (c-stem), mir-181a (pre-181c), and mir-181c (a-loop) all produce similar levels of mature miR-181c in BOSC 23 cells (FIGS. 5B and 15), ectopic expression of mir-181a (c-stem), mir-181a (pre-181c), and mir-181c (a-loop), but not mir-181c, resulted in significant increases, in the levels of mature miR-181c in DP cells (FIG. 5D). Moreover, among the ones that caused increases in mature miR-181c levels, mir-181a (c-stem) and mir-181c (a-loop) can promote DP cell development, mir-181a (pre-181c) cannot. Overall, mature miR-181a and miR-181c levels in DP cells or BOSC 23 cells expressing the mir-181a-1/c mutants do not consistently correlate with the activities of corresponding miRNA genes (FIGS. 2, 3, 5).

Here have been examined the nucleotide sequences and structural domains that are required for the function of mir-181a-1 and mir-181c through mutagenesis and domain-swapping analyses. We found that both the specificities and activities of mir-181a-1 and mir-181c are controlled by their pre-miRNA loops (FIGS. 2 and 3), and miRNA genes encoding identical or nearly identical mature miRNAs can exert different biological activities determined by their unique loop nucleotides. Interestingly, the pre-miRNA loop sequences of mir-181a-1 and mir-181c are divergent but each is evolutionarily conserved in multiple animal species (FIG. 17), indicating that members of the same miRNA gene families have evolved to achieve distinct specificities or degrees of activity via alterations in their pre-miRNA loop sequences. Intriguingly, mir-181a-1/c mutants do not change the 5' ends of mature miRNAs produced (FIG. 4) and the levels of mature miRNAs produced from these genes do not always correlate with the activities of corresponding miRNA genes (FIG. 5). These findings together with the fact that pre-miRNA loop nucleotides can control the activities and specificities of mir-181a-1/c genes, demonstrate that mature miRNAs are not the sole determinant for miRNA gene function (FIGS. 2, 3).

Also, pre-miRNA loop nucleotides were thought to have little or no role in either pri-miRNA processing by Drosha or pre-miRNA transport by exportin-5 according to previous biochemical analyses (15-18). However, we have found that mir-181a-1/c mutants affect both mature miRNA and pre-miRNA processing (FIGS. 5A, 5B, 5E, 15 and 16), indicating that pre- and mature miRNA biogenesis is sensitive to pre-miRNA loop nucleotide changes. These findings have revealed a previously unrecognized regulatory complexity of miRNA biogenesis in vivo, suggesting that earlier in vitro analyses on pre- and mature miRNA biogenesis may only in part recapitulate the processing and function of miRNA genes in vivo. When interpreting the above findings, it is critical to draw a distinction between the activity of a miRNA gene and the activity of a mature miRNA. Since long RNA transcripts of the wild-type or mutant miRNA genes were expressed in thymic progenitor cells via retroviral transduction, we have measured the activities of miRNA genes in this study. In contrast, many previous studies probably measured the activities of mature miRNAs by using siRNA duplexes as miRNA surrogates, therefore, did not address the roles of pre-miRNA loop and flanking sequences in miRNA gene function (8, 19).

We were unable to test whether transfected mature miR-181a and miR-181c might be functionally equivalent to full-length mir-181a-1 and mir-181c in the OP9-DL1 co-culture assays. Transfected miRNAs are diluted quickly during cell expansion in a long-term culture assay. Further, complex small RNA sorting pathways may limit efficient and specific incorporation of transfected miRNAs into the pathways used by mir-181a-1/c mutants (20, 21). Also important to note, since multiple small RNAs are made from the primary miRNA transcripts, mutations and deletions in miRNA genes invariably affected the pri-, pre-, and mature miRNA species. Thus, phenotypes observed for mir-181a-1/c mutant genes cannot be attributed to one particular small RNA species in these analyses. Such limitations would also apply to genetic analyses on specific miRNA genes in worms, in which loss-of-function of miRNA genes was only rescued with genomic fragments encoding their pri-miRNAs but not with mature miRNAs (2, 22, 23). In fact, it was recognized that precursor lin-4 RNA contain the mature lin-4 sequence, and genetic analyses were unable to definitively rule out the possible involvement of precursor lin-4 RNA in target gene binding and recognition (2).

Despite that we did not observe consistent correlations between mature miRNA levels and the activities of miRNA genes (FIGS. 2, 3, 5), we could not rule out the possibility that mutations in mir-181a-1/c genes might have affected the activities of mature miRNAs produced from these genes. Likewise, we could not rule out the possibility that pri-miR-NAs and pre-miRNAs might have functions independent of the mature miRNAs. Nevertheless, our findings revealed unexpected regulatory complexities encoded in the pre-miRNA loops, suggesting that many scenarios exist by which pre-miRNA loop nucleotides may control the activities of miRNA genes. (FIG. 6). Given that pre-miRNAs contain not only the mature miRNA sequences that can pair with cognate target sites but also the loop nucleotides that are important for the activities and specificities of mir-181a-1 and mir-181c, it would appear that pre-miRNA loops may actually have a functional role in target gene binding and recognition. This model would readily explain why pre-miRNA loops are important for the function of miRNA genes. Supporting this model, pre-miRNA-like stem-loop structures have been shown to be a common module for intermolecular RNA:RNA interactions (24-26).

Methods

Retroviral Constructs for miRNA Gene Expression

A double-copy retroviral vector with a human H1 polymerase III expression cassette was used to express mir-181a-1, mir-181c, and their mutant genes (10, 11). A GFP reporter driven by an independent murine 3-phosphoglycerate kinase promoter ($P_{PGK}$) was used as a marker for infection.

OP9-DL1 Stromal Co-Culture Assay for In Vitro T Cell Differentiation

An OP9-DL1 stromal co-culture assay was used for measuring the effects of the mir-181a genes on DP cell development in vitro (see below for details). We use box-plots to summarize the distribution of relative miRNA activity in DP cell development. The ends of the boxes define the $25^{th}$ and $75^{th}$ percentiles, a line indicates the median, and bars define the $5^{th}$ and $95^{th}$ percentiles. Individual outliers are also shown. The activities of mir-181a-1, mir-181c, and mutant genes in DP cell development were normalized so that the empty vector (negative control) had a median activity of "0" and the mir-181a-1 expressing vector (positive control) had a median activity of "1." Since limited progenitor cells can be isolated from each mouse, it is often not possible to analyze all miRNA mutant constructs in a single T cell assay; thus, such normalization allows comparison between different experimental data sets. Mann-Whitney Rank Sum Tests were performed to determine whether the activities of mutants were statistically different from the negative control or mir-181a-1 positive control vectors.

miRNA Expression And Processing Analyses

Primer extension, quantitative Northern blot, and TaqMan miRNA qPCR analyses were all used to determine the expression and processing of pre-miRNAs and mature miRNAs from various miRNA genes (see below for details).

Retroviral Constructs for miRNA Gene Expression

A double-copy retroviral vector with a human H1 polymerase III expression cassette was used to express mir-181a-1, mir-181c, and their mutant genes. Briefly, a ~270-nt gene segment containing a ~22-nt mature miRNA and ~125 nt of genomic sequences flanking both sides of the miRNA was amplified from genomic DNA and placed in the U3 region of the 3' LTR under the control of the human H1 pol III promoter (a, b). A GFP reporter driven by an independent murine 3-phosphoglycerate kinase promoter ($P_{PGK}$) was used as a marker for infection. mir-181a-1 and mir-181c mutant constructs were generated using an overlapping PCR strategy to introduce mutations in the stem and loop regions of the miRNA genes. All mutant constructs were validated by DNA sequencing. For mutations in the miRNA stem regions, compensatory mutations were also introduced to the miR* strands to preserve the integrity of the stem and loop structures (FIG. 8). High titer retroviral supernatant was generated by co-transfecting the miRNA expression vector and pCLeco packaging construct into BOSC23 cells (293T based viral packaging cell line).

OP9-DL1 Stromal Co-Culture Assay for In Vitro T Cell Differentiation.

Six-week old male C57BL/6J mice were obtained from the Jackson Laboratory (Bar Harbor, Me.). Mice were administered a single intravenous dose of 5-fluorouracil (5-FU; 150 mg/kg body weight; SIGMA, St. Louis, Mo.) 4 days before culture initiation. Animals were treated in accordance with Stanford University and Administrative Panels on Laboratory Animal Care guidelines. Thymocytes were isolated from the 5-FU (Fluorouracil) primed-mice, infected with miRNA expression vectors by spinoculation, and seeded at $1 \times 10^5$ infected cells/well into 24-well tissue culture plates containing a monolayer of OP9-DL1 stromal cells. For each viral construct, 12 independent culture replicates were seeded. The cells were cultured in Minimum Essential Medium (MEM) Alpha Medium supplemented with 20% FCS, 10 mM Hepes, 1 mM Sodium pyruvate, 5 ng/ml IL-7, and 27.5 ng/ml Flk2/Flt3L for 24 hours and then medium was changed to remove non-adherent thymocytes. The cultures were fed with fresh medium on day 6. After about 8-10 days of culturing, cells were harvested and stained for surface marker CD4, CD8, and CD45. Percentage of DP cells yielded from culture was quantified by flow cytometry. Both adherent and non-adherent cells were collected. Adherent cells were removed by treatment with collagenase type VI (0.8 mg/ml; Worthington, Lakewood, N.J.) followed by forceful pipetting. Cells were then immunolabeled with PE-conjugated anti-CD4 antibody (clone RM4-5; BD Pharmingen, San Diego, Calif.) and PE-Cy5-conjugated anti-CD8a antibody (clone 53-6.7; BD Pharmingen) and analyzed on a FACSCalibur (BD Biosciences, San Jose, Calif.) for the expression of CD4 and CD8 cell surface antigens. GFP positive thymocytes were distinguishable from GFP positive stromal cells by FSC/SSC gate and the intensity of green fluorescence. When the infect-rate was low, anti-CD45 antibody staining was used to gate out contaminating GFP+OP9-DL1 cells. The appropriate dilution for each antibody was determined prior to use.

Box-plots summarize the distribution of relative miRNA activity in DP cell development. The ends of the boxes define the $25^{th}$ and $75^{th}$ percentiles, a line indicates the median, and bars define the $5^{th}$ and $95^{th}$ percentiles. Individual outliers are also shown. The activities of mir-181a-1, mir-181c, and mutant genes in DP cell development were normalized so that the empty vector (negative control) has a median activity of "0" and mir-181a-1 expressing vector (positive control) had a median activity of "1." The percentage of DP cells yielded from the co-culture assay varies between experiments possibly due to heterogeneous nature of the thymic progenitor cells and intrinsic variation between the batches of mice used. Therefore, such normalization is necessary to reset the base-line and allows for comparison among the independent repeats. Mann-Whitney Rank Sum Tests were performed to determine whether the activities of individual 2-nt mutants were statistically different from the control vector or the mir-181a-1 vector.

Quantitative Northern Blot Analyses

Figures 14A, 14B:
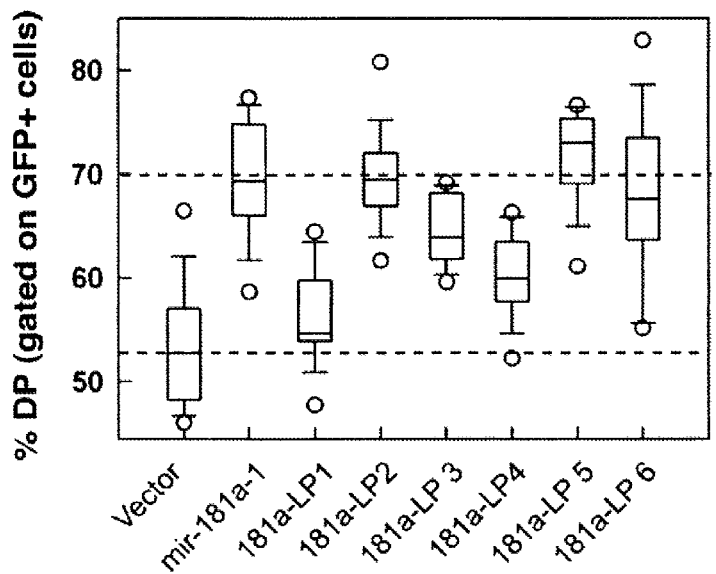
FIGS. 14A and 14B. The effects of the pre-miR-181a-1 loop mutants on DP cell development (See FIG. 3). (A) Box-plots summarize the percent of DP cells generated from DN progenitor cells infected with mir-181a-1, or pre-miR-181a-1 loop mutant genes (GFP positive). A representative OP9-DL1 stromal co-culture assay (12 independent replicates for each construct) is shown. The ends of the boxes define the $25^{th}$ and $75^{th}$ percentiles, a line indicates the median, and bars define the $5^{th}$ and $95^{th}$ percentiles. (B) Statistical summary. Mann-Whitney Rank Sum Tests are performed on this representative data set to determine whether the activity of mir-181a-1 and pre-miRNA loop mutant genes is statistically different from the empty vector (negative control) or the mir-181a-1 expressing vector (positive control).
Figure 15A:
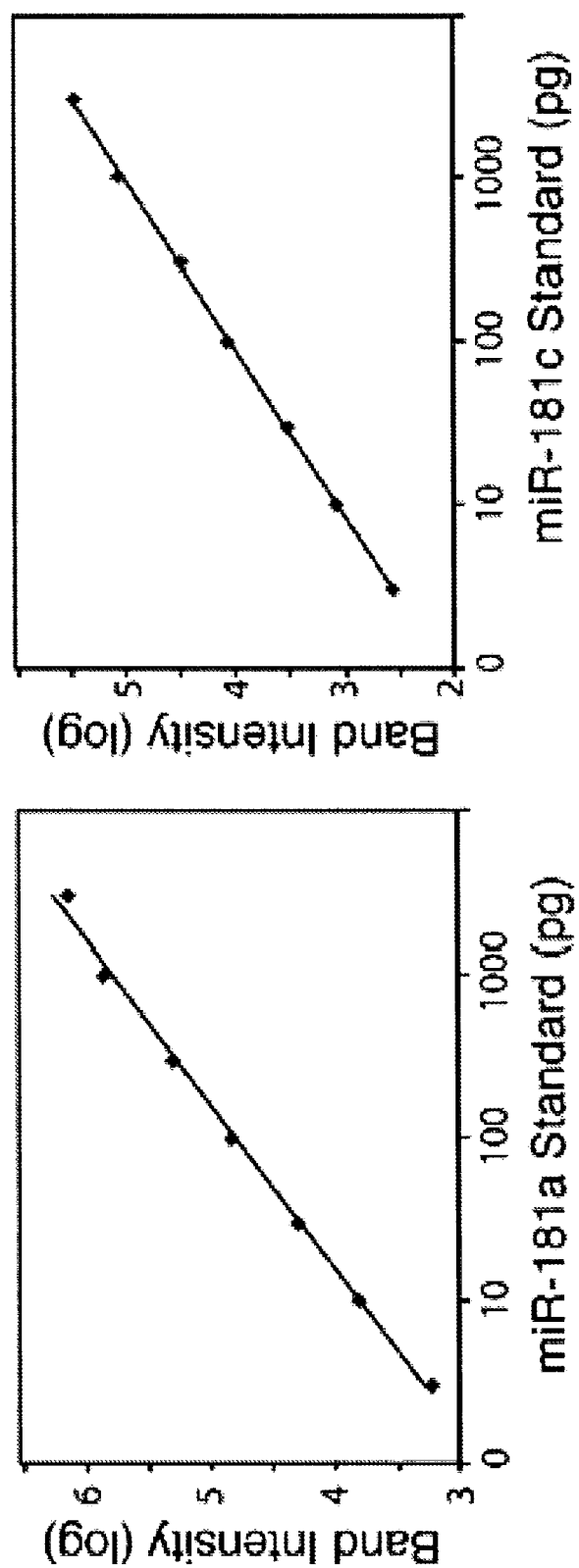
FIGS. 15A, 15B and 15C. Mature and pre-miRNA expression levels from the chimeric mir-181a-1 and mir-181c genes (See FIGS. 5A and 5B). Total RNA was prepared from BOSC cells transfected with constructs expressing mir-181a-1, mir-181c, and the chimeric mir-181a-1 and mir-181c genes. Since all miRNA vectors contain an independent GFP reporter, percentage cells that are GFP positive were determined by FACS analyses and used to control for variations in transfection efficiency. Quantitative Northern blot analyses were carried out to determine the expression of mir-181a-1, mir-181c, and the chimeric mir-181a-1 and mir-181c genes. Specific probes that perfectly match to mature miR-181a or miR-181c were used in hybridization to determine the expression of mature and pre-miRNA forms. Band intensities were determined by phosphoimager quantification and normalized to the levels of wild-type controls accordingly. (A) Standard Curves for miR-181a and miR-181c. (B) The copies of mature miR-181a and miR-181c in BOSC 23 cells transfected with mir-181a-1/c mutants determined by quantitative Northern blot analyses. Average results of four independent experiments were plotted. (C) Relative levels of pre-miR-181a and pre-miR-181c in BOSC 23 cells transfected with mir-181a-1/c mutants determined by Northern blot analyses. Average results of four independent experiments were plotted.
Figure 15B:
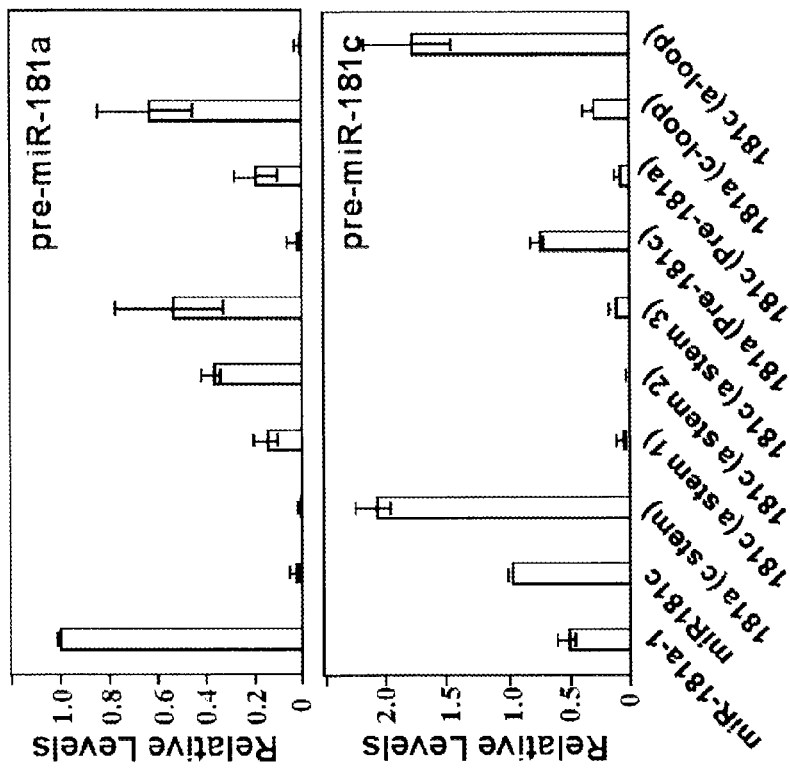
Figure 15C:
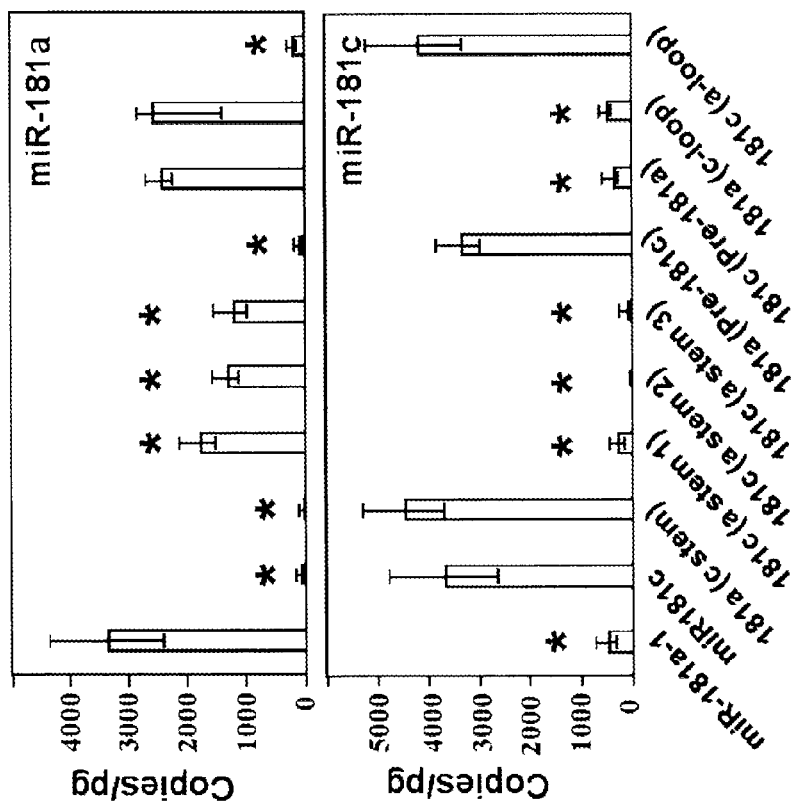
Figure 16A:
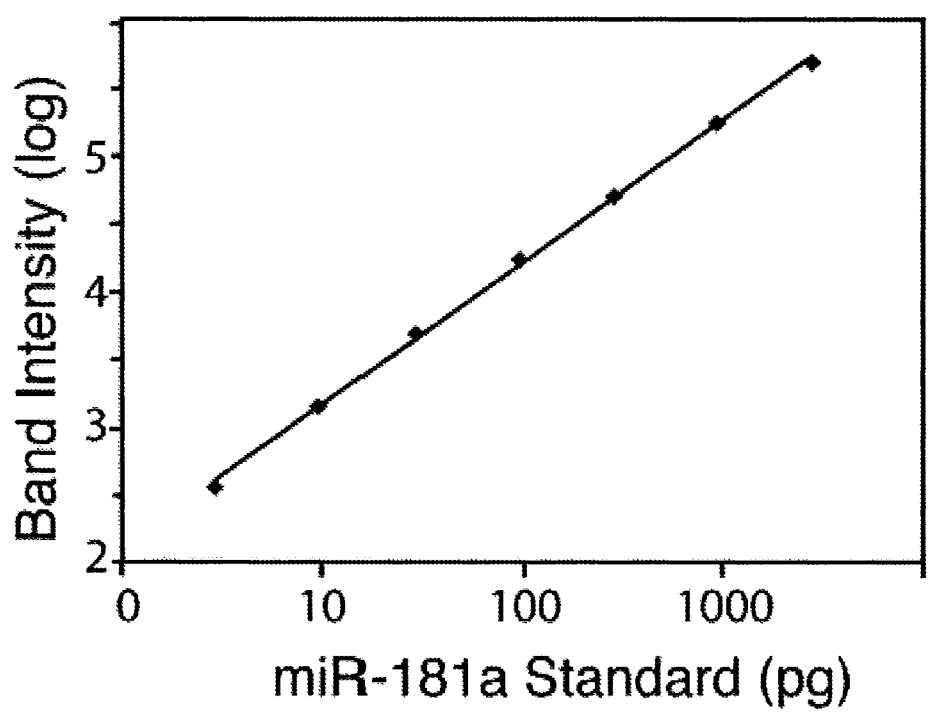
FIGS. 16A, 16B and 16C. Mature and pre-miRNA expression levels from the pre miR-181a-1 loop mutant genes (See FIG. 5E). Total RNA was prepared from BOSC cells transfected with constructs expressing the mir-181a-1 loop mutant genes. Since all miRNA vectors contain an independent GFP reporter, percentage cells that are GFP positive were determined by FACS analyses and used to control for variations in transfection efficiency. Quantitative Northern blot analyses were carried out to determine the expression of the pre-mir-181a-1 loop mutant genes. A probe that perfectly matches to the mature miR-181a was used in hybridization to determine the expression of mature and pre-miRNA forms. Band intensity was determined by phosphoimager quantification and normalized to the levels of wild-type controls accordingly. (A) Standard Curves for miR-181a. (B) The copies, of mature miR-181a in BOSC 23 cells transfected with mir-181a-1 loop mutants determined by quantitative Northern blot analyses. Average results of four independent experiments were plotted. (C) Relative levels of pre-miR-181a in BOSC 23 cells transfected with mir-181a-1 loop mutants determined by Northern blot analyses. Average results of four independent experiments were plotted.
Figure 16C:
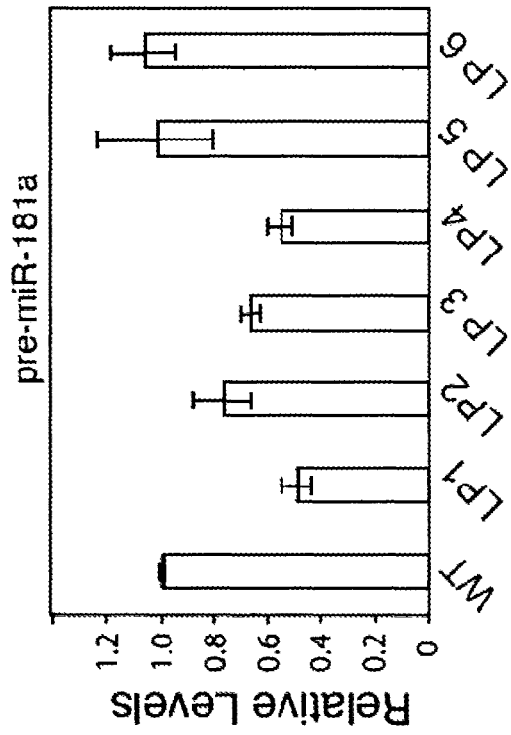
Figure 16B:
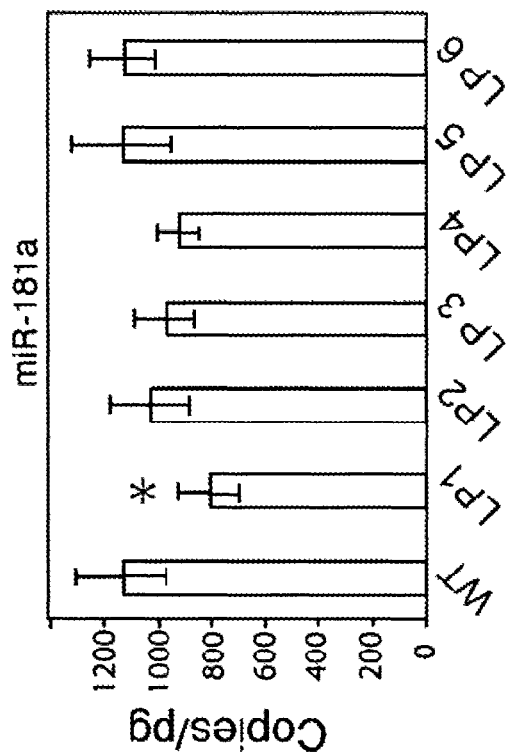

Quantitative Northern blot analyses were used to determine the level of mature miRNA expression and processing of the pre-miRNA and mature miRNA. Total RNA was prepared from BOSC 23 cells transfected with constructs expressing mir-181a-1, or mir-181c, or their mutant genes and loaded onto 15% PAGE gel (10 µg/sample). Since all of the miRNA expressing vectors contain an independent GFP reporter, percentage cells that are GFP positive were determined by FACS analyses and used to control for variations in transfection efficiency. Various amounts of synthetic mature miRNA were loaded onto the same gel to generate standard curves. Specific probes that perfectly match to mature miRNAs were used in hybridization to determine the expression of both mature and pre-miRNA species. Band intensity was determined by phosphoimager quantification. Blots were also probed with U6 probes for normalizing loading. Exact copies/pg of total RNA were determined by comparing to the corresponding standard curve. Representative blots of four or more independent quantitative Northern blot analyses were shown in FIG. 5. Standard Curves and average results of four independent quantitative Northern blot analyses were summarized and plotted (FIGS. 14 and 15).

DNA Oligos were Used as Northern Blot Probes.

Following are the Northern Probe sequences for miR-181a, miR-181c, and stem mutants.

```
miR-181a
ACTCACCGACAGCGTTGAATGTT         (SEQ ID NO: 26)

miR-181c
ACTCACCGACAG GTTGAATGTT         (SEQ ID NO: 27)

M1 (613, #831)
TCACCGACAGCGTTGAATTAT           (SEQ ID NO: 28)

M2 (612, #830)
TCACCGACAGCGTTGATAGTT           (SEQ ID NO: 29)

M3 (611, #829)
TCACCGACAGCGTTTTATGTT           (SEQ ID NO: 30)

M4 (610, #828)
TCACCGACAGCGAAGAATGTT           (SEQ ID NO: 31)

M5 (638, #898)
ACTCACCGACAGGTTTGAATGTT         (SEQ ID NO: 32)

M6 (608, #826)
TCACCGACTTCGTTGAATGTT           (SEQ ID NO: 33)

M7 (637, #897)
ACTCACCGTGAGCGTTGAATGTT         (SEQ ID NO: 34)

M8 (636, #896)
ACTCACGTACAGCGTTGAATGTT         (SEQ ID NO: 35)

M9 (635, #895)
ACTCTGCGACAGCGTTGAATGTT         (SEQ ID NO: 36)

M10 (639, #899)
ACAGACCGACAGCGTTGAATGTT         (SEQ ID NO: 37)

M11 (640, #900)
TGTCACCGACAGCGTTGAATGTT         (SEQ ID NO: 38)

SM1 (644, #904)
ACTCACCGACAGCGTTTTTATAT         (SEQ ID NO: 39)

SM2 (641, #901)
TGAGTGGTACAGCGTTGAATGTT         (SEQ ID NO: 40)

SM3 (642, #902)
ACTCACCGTGTTGTAAGAATGTT         (SEQ ID NO: 41)

SM4 (643, #903)
TGAGTGGTTGTTGTAAGAATGTT         (SEQ ID NO: 42)
```

Primer Extension Analyses

Primer extension was used to map the 5' ends of the mature miRNAs produced from the mir-181a-1/c mutant genes. Total RNA was prepared from BOSC23 cells 48 hours after transfection with constructs expressing mir-181a-1, or mir-181c, or their mutant genes. $P^{32}$ labeled primer was mixed with appropriate RNA samples (10 ug total RNA) in the reaction buffer (1×RT reaction buffer with 0.25 mM of each dNTP), heated at 55° C. for 20 minutes, and slowly cooled to 16° C. to allow for annealing. The primer extension reaction was initiated by adding reverse transcriptase at 16° C. for 20 minutes, 42° C. for 2 hours, 85° C. for 5 minutes. Samples were loaded onto a 15% denaturing PAGE gel. Synthetic miR-181a or miR-181c oligos in single nucleotide increments (15 nt-22/23 nt) were labeled and loaded onto the gel as size ladder. The primer extension results were visualized by overnight exposure to phosphoimager screen.

The extension primers:

```
15-nt miR-181a primer:
5' ACTCACCGACAGCGT 3'            (SEQ ID NO: 43)

15 nt miR-181c primer:
5' ACTCACCGACAGCGT 3'            (SEQ ID NO: 44)
``` miR-181a Ladder Oligos:

```
16 nt:    ACTCACCGACAGCGtT        (SEQ ID NO: 45)

17 nt:    ACTCACCGACAGCGtTG       (SEQ ID NO: 46)

18 nt:    ACTCACCGACAGCGtTGA      (SEQ ID NO: 47)

19 nt:    ACTCACCGACAGCGtTGAA     (SEQ ID NO: 48)

20 nt:    ACTCACCGACAGCGtTGAAT    (SEQ ID NO: 49)

21 nt:    ACTCACCGACAGCGtTGAATG   (SEQ ID NO: 50)

22 nt:    ACTCACCGACAGCGtTGAATGT  (SEQ ID NO: 51)

23 nt:    ACTCACCGACAGCGtTGAATGTT (SEQ ID NO: 52)
``` miR-181c Ladder Oligos:

```
16 nt:    ACTCACCGACAGGTTG        (SEQ ID NO: 53)

17 nt:    ACTCACCGACAGGTTGA       (SEQ ID NO: 54)

18 nt:    ACTCACCGACAGGTTGAA      (SEQ ID NO: 55)

19 nt:    ACTCACCGACAGGTTGAAT     (SEQ ID NO: 56)

20 nt:    ACTCACCGACAGGTTGAATG    (SEQ ID NO: 57)

21 nt:    ACTCACCGACAGGTTGAATGT   (SEQ ID NO: 58)

22 nt:    ACTCACCGACAGGTTGAATGTT  (SEQ ID NO: 59)
``` miRNA qPCR Analyses

GFP positive DP T cells from OP9-DL1 co-culture assay were isolated by FACS-sorting (>94% pure). Synthetic miR- 223 was spiked into sorted cells at the ratio of 100 pmol of miR-223 per 100,000 cells before RNA purification. Total RNA was isolated using Trizol reagent (Invitrogen, Carlsbad, Calif.). We assumed that the ratio of spiked miR-223 to a miRNA of interest would not change during RNA purification. cDNA was then synthesized using miRNA-specific looped primers (Applied Biosystems, Foster city, CA) and amplified with miRNA specific forward primers, TaqMan probe, and reverse primers (Applied Biosystems). PCR amplification was performed in triplicate in an ABI-7000 sequence detection system (Applied Biosystems) at 95° C. for 10 min followed by 40 cycles at 95° C. for 15 sec and 60° C. for 1 min. To determine exact copy number of a miRNA in sorted DP cells, we carried out absolute miRNA quantification with miRNA qPCR assay. Exact copies of test and spiked miRNAs in defined amount of total RNA input were determined by using standard curves for mature miR-181a, miR-181c, and spiked miR-223. miR-181a or miR-181c expression was normalized using miR-15b as internal loading control. Representative results of three miRNA qPCR analyses of independently sorted virally infected DP cells were shown. All reactions were carried out according to the manufacturer's instructions.

a. Chen, C. Z., L. Li, H. F. Lodish, and D. P. Bartel. 2004. MicroRNAs modulate hematopoietic lineage differentiation. *Science* 303:83.
b. Li, Q. J., J. Chau, P. J. Ebert, G. Sylvester, H. Min, G. Liu, R. Braich, M. Manoharan, J. Soutschek, P. Skare, L. O. Klein, M. M. Davis, and C. Z. Chen. 2007. miR-181a is an Intrinsic Modulator of T Cell Sensitivity and Selection. *Cell* 129:147.

Experimental for Pri-miRNA

Aberrant Biogenesis of *C. elegans* Pre- and Mature let-7 in Human Cells

Figure 19:
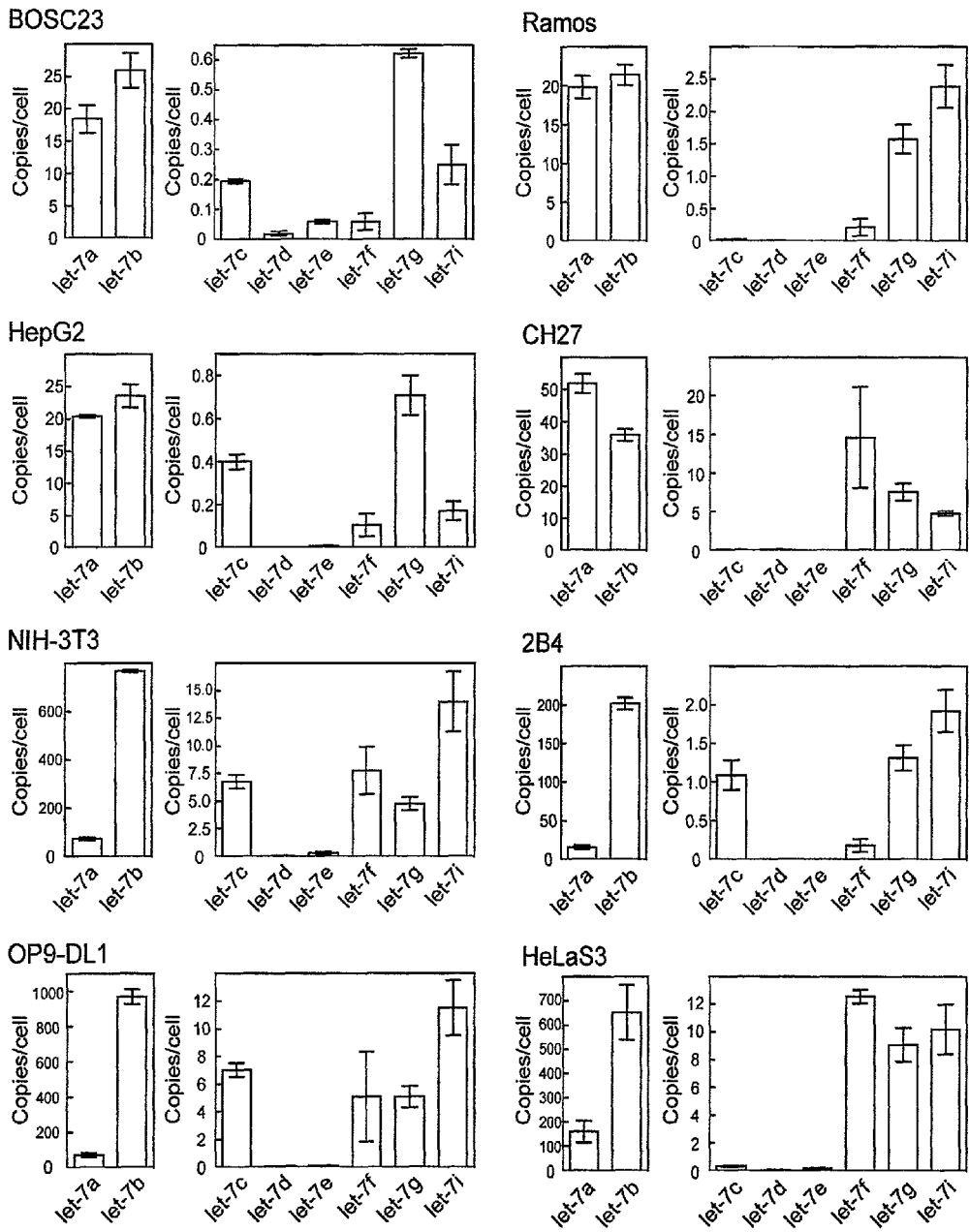
FIG. 19. Mature Let-7 expression in various cultured cell lines. miRNA qPCR analyses were carried out to determine the exact copy number of the mature let-7 family members in variety of cultured cell lines as indicated. Total RNA samples were prepared from cultured cells ($1\times10^6$ cells) spiked with 22.5 fmol synthetic miR-223. Mature let-7 RNAs were determined by using standard curve method miRNA pRCR analyses.

To dissect the molecular mechanisms by which miRNA genes control target expression, we recapitulated target repression by the *C. elegans* miRNA gene let-7 (c-let-7) through the lin-41 3' UTR in BOSC 23 cells—a derivative of 293T cells[27]. BOSC 23 cells express only ~18 and 25 copies/cell of let-7a and let-7b, respectively, and no detectable other let-7 family members (FIG. 19). Ectopic expression of c-let-7 in BOSC 23 cells results in two mature miRNA species: a predominant 20-nt mature let-7 species and a minor 22-nt species that is expressed at a level slightly increased over that of the 22-nt endogenous human mature let-7 (FIG. 20a). Primer extension analyses of both total RNAs (data not shown) and gel-purified 15- to 30-nt small RNA fractions (FIG. 20b) show that c-let-7 produces no detectable mature let-7 with the expected 5' end. Rather, all mature let-7 RNAs produced from c-let-7—both 20 nt and 22 nt species seen in the Northern blot—are two nucleotides shorter at the 5' end than the endogenous human and *C. elegans* let-7 (FIG. 20b)[28,29]. This aberrant mature let-7 biogenesis is the result of erroneous processing of pri-let-7 by Drosha since pre-let-7 made from c-let-7 is also truncated by 2-nt (FIG. 20c). These findings demonstrate that c-let-7 expression in BOSC 23 cells results in pre- and mature let-7 that lack two nucleotides at their 5' ends, notably including the first canonical seed nucleotide (denoted "SD1" here) that is thought to be essential for the activity of mature miRNAs[30,31].

Pri-let-7 has a Direct Role in Target Repression

Figure 20D:
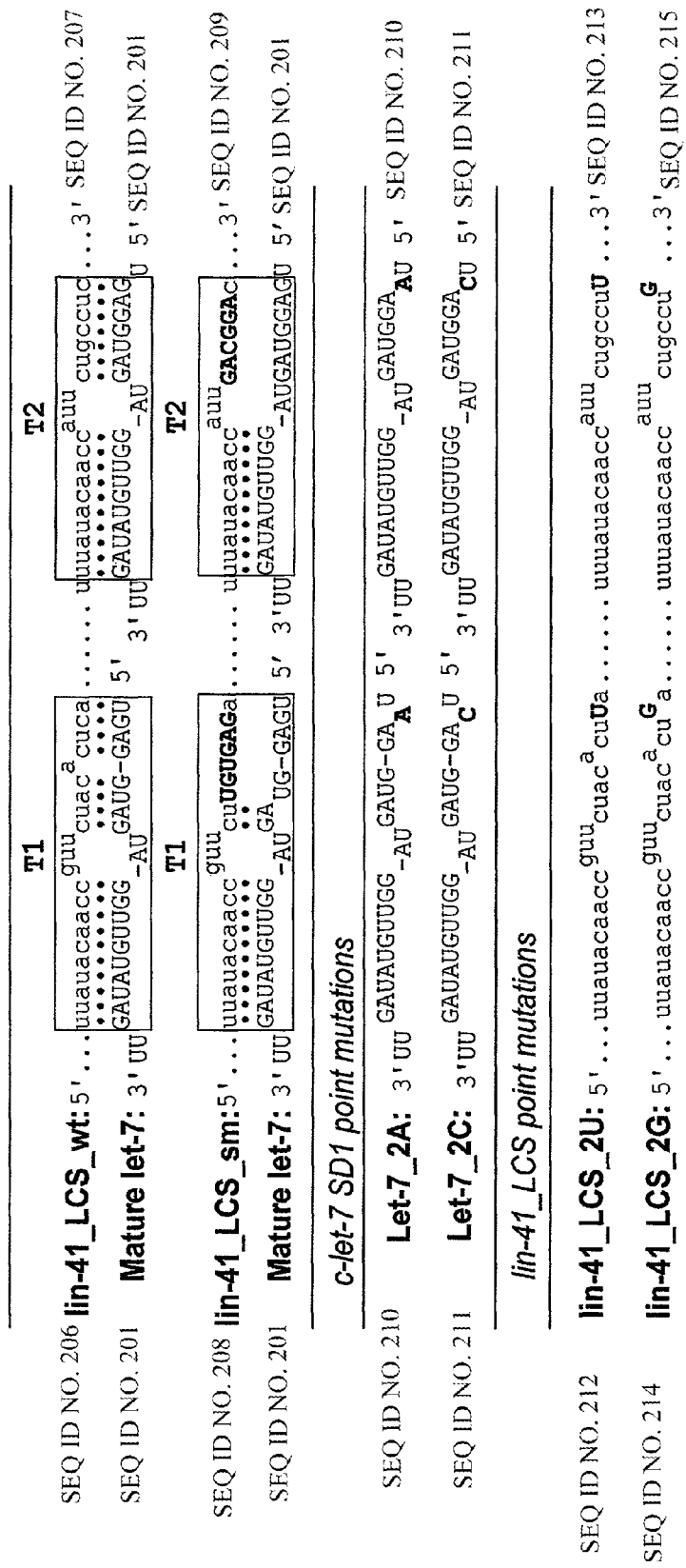
Figure 20E:
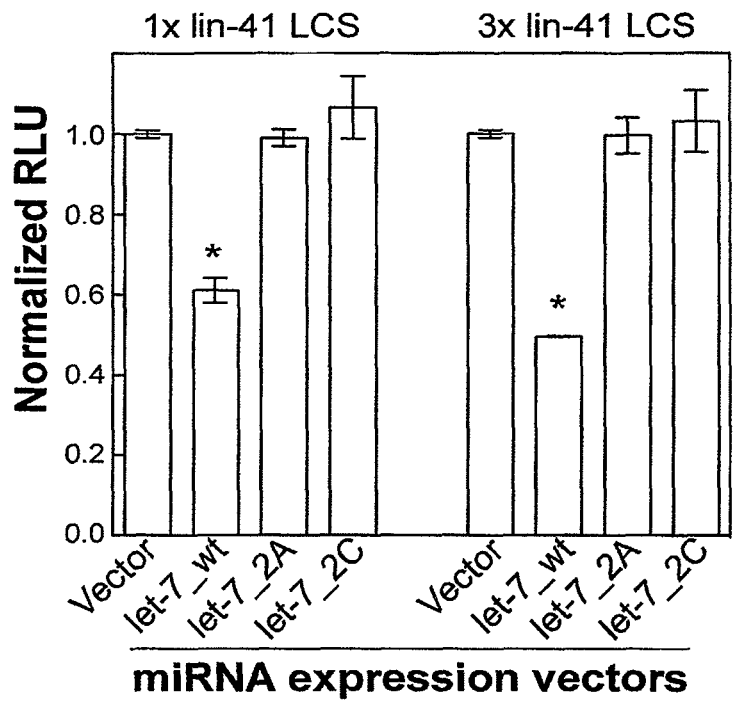
Figure 21:
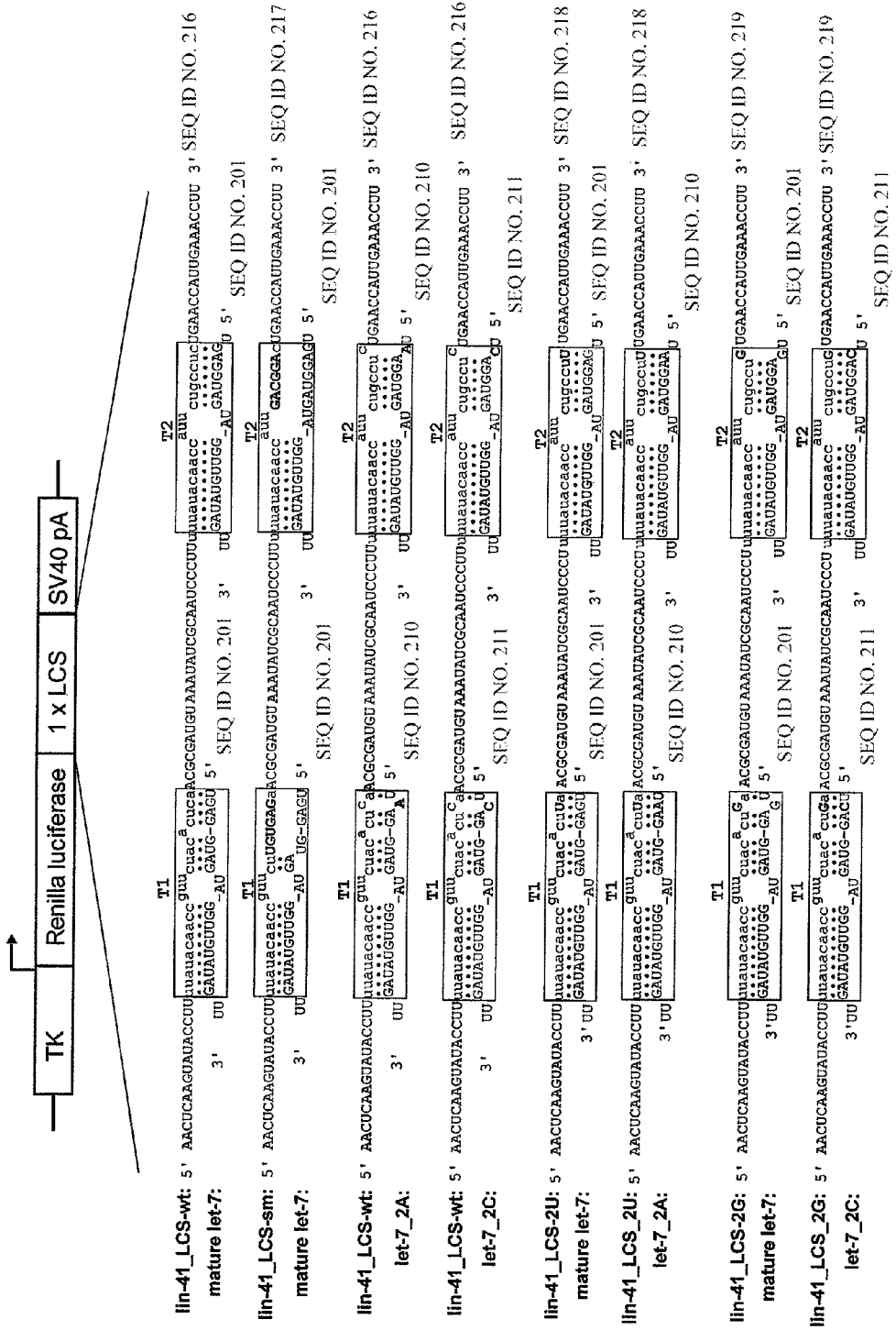
FIG. 21: Schematics of luciferase reporter constructs used to evaluate target gene repression by the c-let-7 genes. The wild-type construct has a 102-nt fragment of the lin-41 3' UTR containing two let-7 complementary sites (lin-41_LCS-wt) inserted within the *Renilla* luciferase 3'UTR. The seed-mutant construct was identical to the wild-type construct except that mutations were introduced to disrupt pairings to the mature let-7 seed nucleotides (lin-41_LCS-sm). The compensatory mutants for SD1-mutant cel-let-7 had only the SD1-paired nucleotide mutated. Diagrams also indicate the base-parings between the mature let-7 RNA and the two let-7 complementary sites (designated as T1 and T2) within lin-41_LCS. Nucleotide changes (bold) were introduced into T1 and T2 sites of the lin-41_LCS or the SD1 nucleotide of c-let-7 to disrupt the base pairings between let-7 and lin-41 UTR. All mutations in the mature let-7 sequence contain complementary mutations on the passenger strand to maintain pre-miRNA stem structure.
Figure 22D:
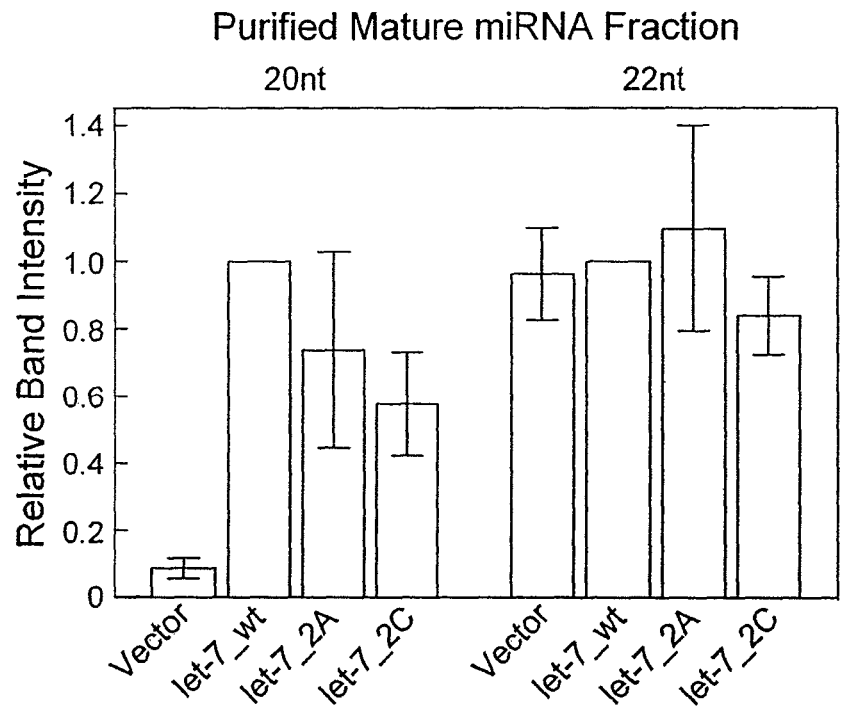
Figure 22E:
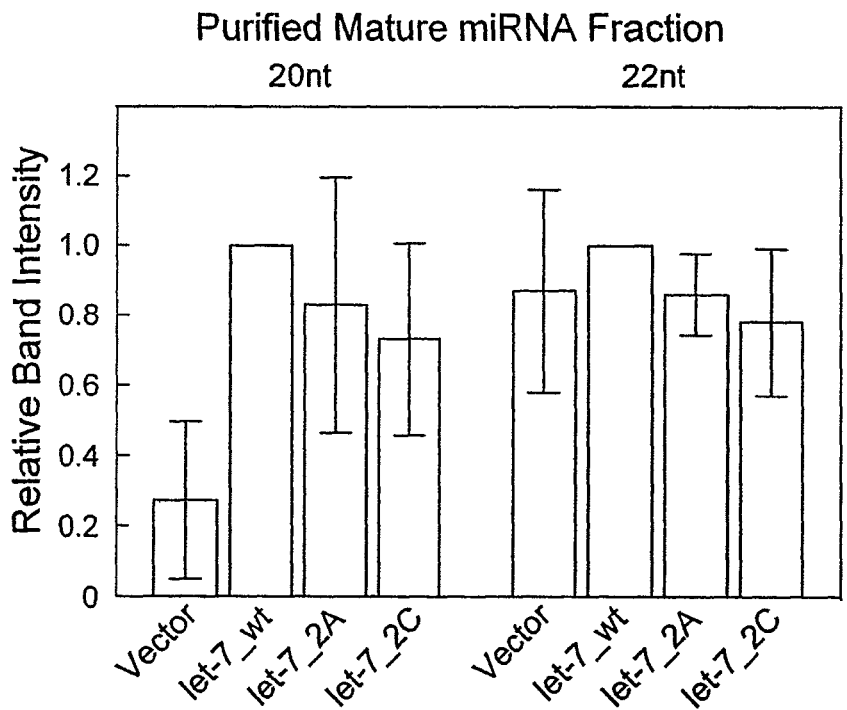

We then measured the activity of c-let-7 in target repression using a luciferase reporter assay. We generated luciferase reporter constructs bearing one or three copies of a 102-nt segment of the lin-41 3' UTR[27] containing two let-7 target sites (1×lin-41_LCS or 3×lin-41_LCS). Mutant reporters abrogating LCS pairings to the let-7 seed nucleotides (1×lin-41_LCS-sm, 3×lin-41_LCS-sm) were designed as controls for determining seed-specific repression (FIG. 20d, FIG. 21). The lin-41_LCS-sm reporters were repressed by c-let-7 at the same level as the reporters with no lin-41_LCS in the UTRs, indicating that mutations disrupting seed binding would completely eliminate target repression mediated by the lin-41_LCS in the reporter UTR. Therefore, throughout this study, seed-dependent repression activities of various miRNA constructs were measured and normalized as described in Experimental Procedures. c-let-7 expression results in approximately 40% and 49% seed-specific repression of the 1×lin-41_LCS and 3×lin-41_LCS luciferase reporters, respectively (FIG. 20e). The degree of repression observed in these analyses is largely consistent with the activity of c-let-7 in other heterologous reporter systems[32] and large-scale proteomic analyses of miRNA-mediated repression[33,34]. These results demonstrate that c-let-7 can specifically repress target gene expression despite the fact that it produces truncated pre- and mature let-7 (FIG. 20a-e).

These findings raised the question of whether truncated mature let-7 functions in target repression despite lacking the first seed nucleotide. To address this question, we generated c-let-7 mutants, let-7__2A and let-7__2C (FIG. 20d, FIG. 21), by altering the SD1 nucleotide. As indicated by Northern blot and primer extension analyses (FIGS. 20a-c), both pre- and mature let-7 RNAs made from these mutants are expressed at comparable levels and have the same 5' ends as those made from the wild-type (wt) c-let-7. However, the SD1 mutations completely abolish seed-dependent repression of both 1×lin-41_LCS and 3×lin-41_LCS reporters (FIG. 20e). Furthermore, corresponding mutations in the lin-41_LCS of reporter constructs that abolish base-pairing to the SD1 nucleotide, lin-41_LCS-2U and lin-41_LCS-2G (FIG. 20d, FIG. 21), also abrogate the activity of wild-type c-let-7 (FIG. 20l). The loss of repression of the lin-41_LCS-2U reporter can be partly restored by the compensatory SD1 mutant let-7__2A (FIG. 20l).

Importantly, the c-let-7 activity in target repression is mediated through its RNA products but not the DNA since transfection of c-let-7 DNAs (either the 2.5 kb fragment used to rescue let-7 null phenotype in worms[28] or the 600 by fragment used in our expression vectors) in the absence of mammalian promoters has no effect on target repression. Further, c-let-7 expression in BOSC 23 cells yields probably less than 4 copies/cell of let-7 with the correct 5' end (Calculated based on the assumption that it should account for less than 10% of endogenous human let-7 in BOSC 23 cells, FIG. 19). Finally, as the SD1 nucleotide is present only in pri-let-7 but not in the truncated pre- and mature let-7, altogether these results indicate that pri-let-7 has activity in target recognition and repression.

Loop Nucleotides can Control the Activity of Pri-let-7

Figures 23A, 23B:
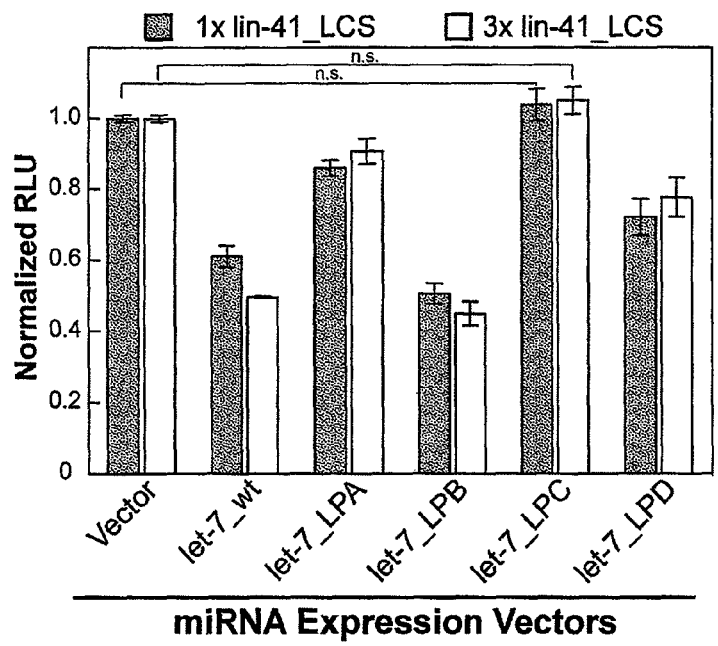
FIGS. 23A and 23B. Effects of pri-let-7 loop mutations on the activity of c-let-7. (A) Schematic diagrams depict the pre-miRNA sequences and structures of c-let-7_wt and corresponding pri-let-7 loop mutants. (B) Repression of luciferase reporter expression by c-let-7_wt and loop mutants. Representative results of at least six independent trials (±S.D.) are shown (p<0.0001 except as indicated).
Figure 24A:
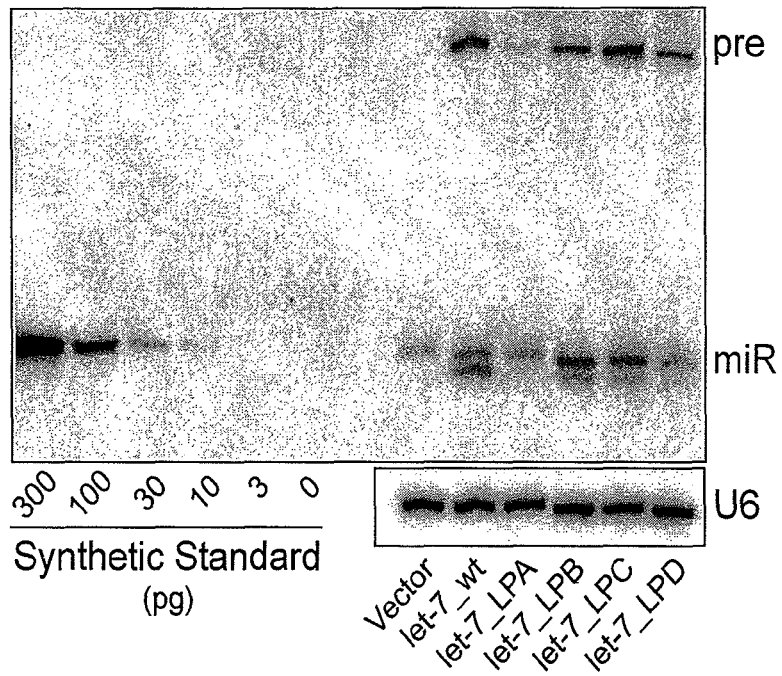
FIGS. 24A, 24B, 24C and 24D. Effects of pre-let-7 loop mutations on pre- and mature let-7 biogenesis. (A) Northern blot shows the expression of c-let-7 and pri-let-7 loop mutants (a representative of five independent repeats). (B) Relative levels of 22-nt, 20-nt, and total small RNA (22+20 nt) mature let-7 in BOSC 23 cells transfected with the wild-type c-let-7 and pri-let-7 loop mutants (n=5, ±S.D.). (C and D) Mapping the 5' ends of mature let-7 (B) and pre-let-7 (C) RNAs made from the type c-let-7 and pri-let-7 loop mutants by primer extension analyses (a representative of five independent repeats).
Figure 24B:
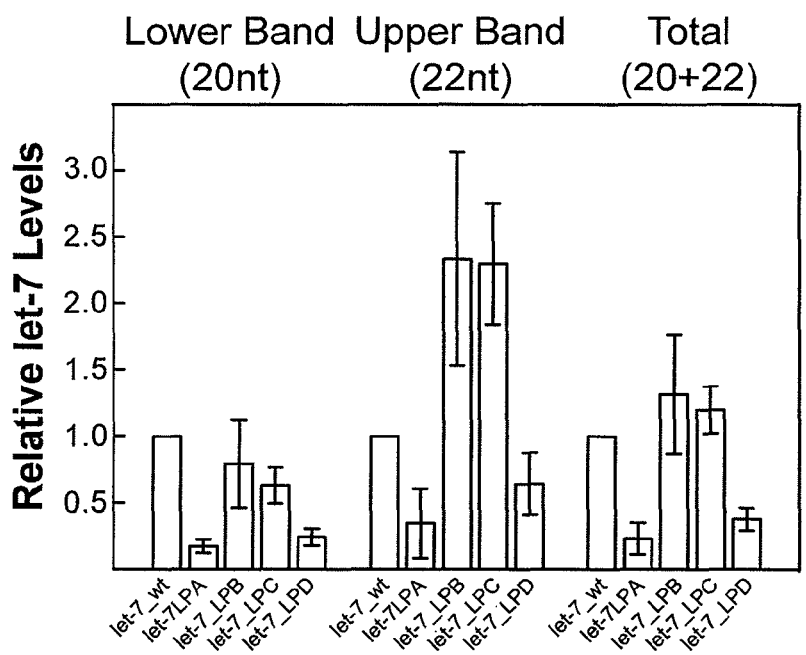
Figure 24C:
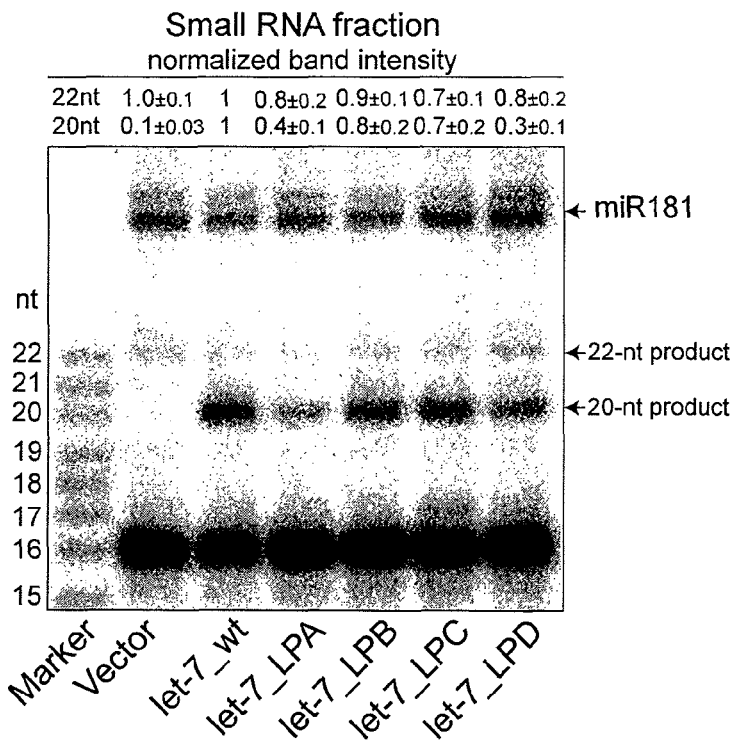
Figure 24D:
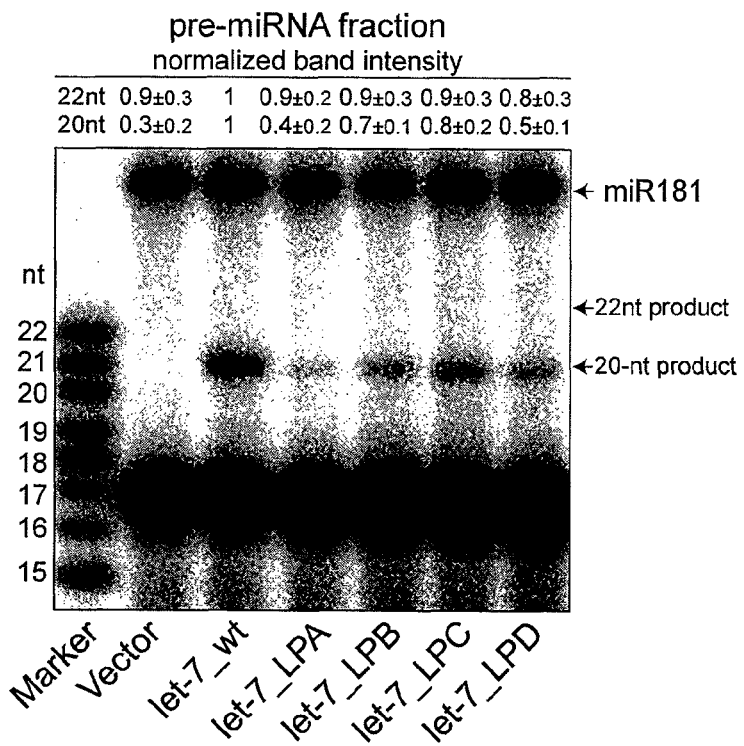

The observed activity of pri-let-7 in target recognition and repression could be directly influenced by both structure and sequence elements outside of the mature miRNA region. Loops of structured stem-loop RNAs have been shown to play key roles in controlling the specificity and degrees of activity of bacterial antisense RNAs[35] and miRNA genes[36]. Drawing analogies from these examples, we hypothesized that the pri-let-7 loop may also play a role in controlling the activity of c-let-7 in target gene repression. Since both pri-miR-181a-1 and *C. elegans* pri-let-7 contain a GG dinucleotide at the 5' end of their loops and mutation of these nucleotides in mir-181a-1 impairs its function[36], we first generated a c-let-7 mutant (let-7_LPA) with these nucleotides mutated (FIG. 23a). Strikingly, the let-7_LPA mutations result in significant reduction in c-let-7 activity from 40% and 49% to about 15 or 10% seed-specific repression of the 1× and 3×lin-41_LCS reporters, respectively (FIG. 23b).

Since the GG to CC mutations alter the predicted pri-let-7 loop secondary structure, we generated three additional pri-let-7 loop mutants, let-7_LPB, let-7_LPC, and let-7_LPD to determine whether the deleterious effect on c-let-7 activity is caused by alterations of loop sequence or structure (FIG. 23a). The let-7_LPB mutant contained compensatory mutations to restore the wild-type loop structure and resulted in a slight increase of repression activity compared to that of let-7_wt (FIG. 23b). The let-7_LPC mutant, which has the same predicted loop structure as let-7_LPA while maintaining the wild-type 5' GG dinucleotide, had no activity in target gene repression for either reporter (FIG. 23b). The let-7_LPD mutant, which was altered to remove all intra-loop base pairing, resulted in an intermediate phenotype of ~24% and 21% specific repression of 1× and 3×lin-41_LCS reporters, respectively (FIG. 23b). Since loop mutations only affect pri-let-7, not the truncated pre- and mature let-7, these findings further support the idea that pri-let-7 has a direct role in target repression and indicates that its activity can be controlled by its loop nucleotides.

Pri-let-7 Loop Mutants Produce Defective Pre- and Mature let-7

Figure 20F:
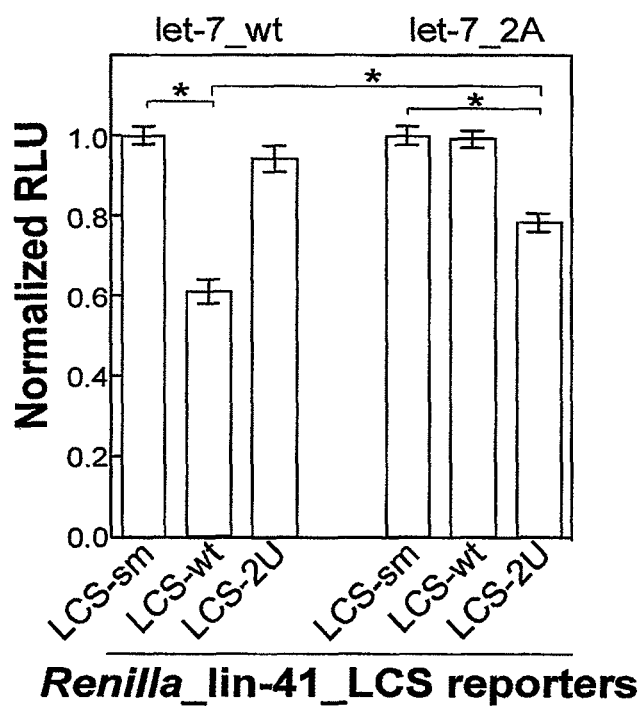

Quantitative Northern blot analyses reveal that pri-let-7 loop mutants produce widely varying amounts of mature 20 and 22-nt let-7 and pre-let-7 (FIGS. 24a, 24b), but have no consistent correlation with the activity of these mutant genes in target repression (FIGS. 21 & 24). Further primer extension analyses of total RNA (data not shown), mature miRNA (FIG. 24c) and pre-miRNA (FIG. 24d) fractions show that, as seen for the SD1 mutants (FIG. 20), both pre- and mature let-7 made from these loop mutants lack the first two 5' nucleotides, thus missing the essential SD1 nucleotide. It is apparent that size variations of mature let-7 made from pre-let-7 loop mutants are due to alterations at the 3' end of these small RNAs (FIGS. 24a, 24c) as both 20 and 22-nt species have the same 5' ends. Pri-let-7 loop mutations can cause a significant decrease in the levels of pre- and mature let-7 with the truncated 5' ends (20 nt primer extension product) relative to c-let-7_wt, but none results in the expression of pre- and mature let-7 with the correct 5' ends (22 nt primer extension product) (FIGS. 24c, 24d). Since pri-let-7 is the only RNA species made from c-let-7 that contains both the SD1 nucleotide and the loop region, these findings further demonstrate that pri-let-7 has a direct role in target repression and that its activity can be controlled by its loop nucleotides (FIGS. 23, 24).

Figure 25A:
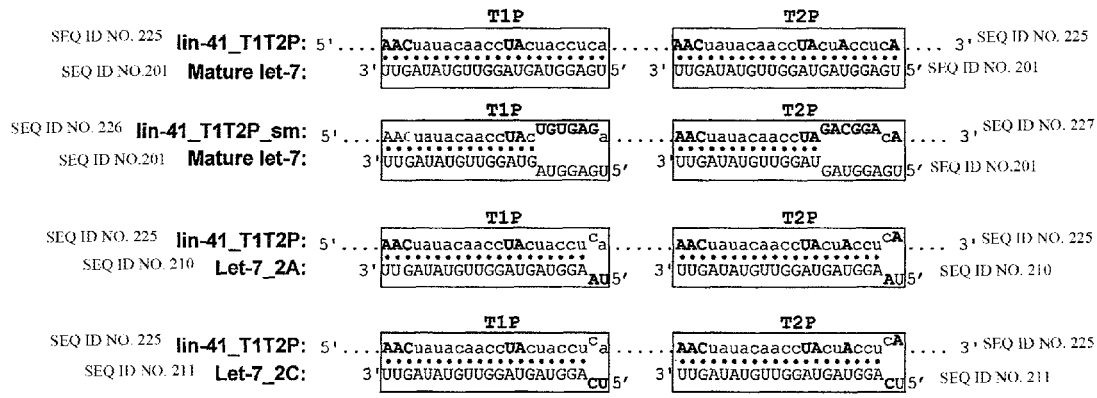
FIGS. 25A, 25B and 25C. SD1 and pri-let-7 loop mutants have little effects on the repression of a perfect let-7 target reporter. (A) Schematic diagrams show the base-parings between let-7 and a modified lin-41_LCS with perfect let-7 target sites (lin-41_T1T2P). Nucleotide changes (bold) were introduced into the seed-pairing region of the lin-41_T1T2P or the SD1 nucleotide of c-let-7. (B and C) Repression of the lin-41_T1T2P *Renilla* luciferase reporter by c-let-7 SD1 mutants (B) and loop mutants (C). Representative results of at least six independent trials (±S.D.) are shown (p<0.0001 except as indicated).
Figure 25B:
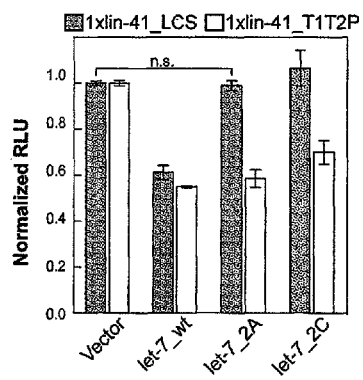
Figure 25C:
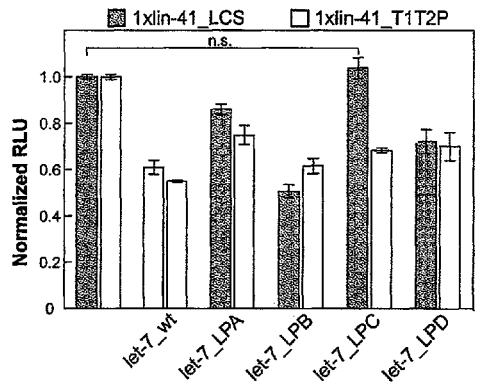

The SD1 and Loop Mutations have Minimal Effects on the Repression of Perfect Target The above analyses demonstrate that mature let-7 produced from c-let-7 in BOSC 23 cells is not functional in repressing reporters containing one or multiple copies of lin-41_LCS in the UTR (FIGS. 20, 23, 24), raising the question of whether these aberrantly produced mature miRNAs are functional in gene silencing. To this end we examined whether the SD1 and pri-let-7 loop mutations affect the repression of luciferase reporters bearing perfect let-7 complementary sites in its UTR (FIG. 25). We modified the LCS sites of the 102-nt lin-41_LCS so that both target sites are perfectly matched to the 22-nt mature let-7 (lin-41_T1T2P) (FIG. 25a). An analogous reporter (lin-41_T1T2P_sm) with mutations abrogating all pairings to the let-7 seed nucleotides was used as the negative control to determine seed-dependent target repression (FIG. 25a). Intriguingly, the SD1 and pri-let-7 loop mutations, which have strong effects on the repression of the lin-41_LCS-wt reporters (FIGS. 20, 23), have little or no effect on seed-dependent repression of the lin-41_T1T2P reporter (FIGS. 25b, 25c). Thus, increasing degree of pairings between targets and mature miRNAs can largely abrogate the role of the SD1 and pri-let-7 loop nucleotides in target repression. One of the possible explanations for these observations is that aberrantly processed mature let-7 can be incorporated into RISC and suppress reporters with perfect target sites.

Loop Nucleotides may Modulate Pri-let-7 and Target RNA Interaction

Figure 26:
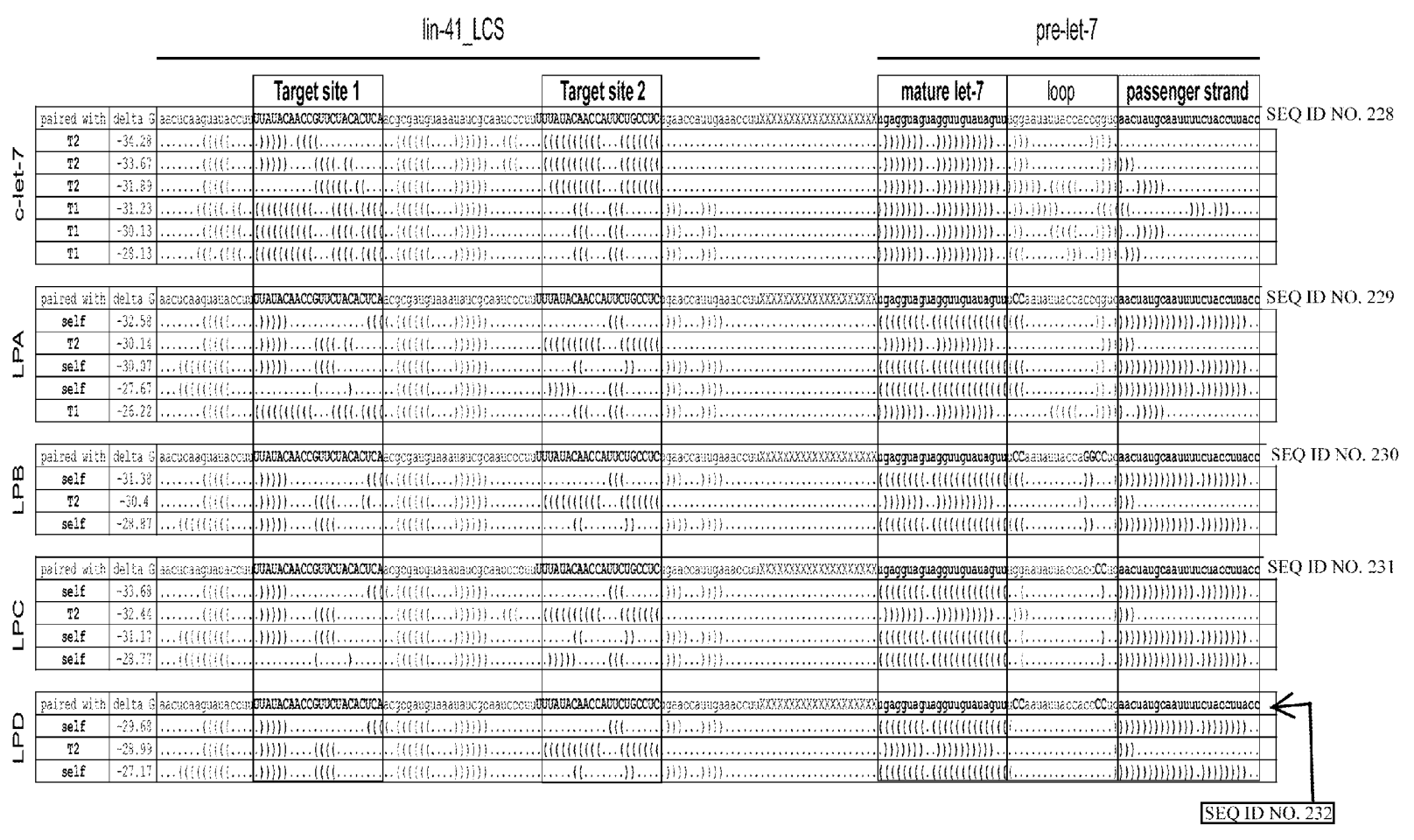

Since mfold simulations indicate that the pri-let-7 hairpin may be able to interact with lin-41_LCS RNA, and that loop mutants with low activity in target reporter repression are less likely to form these complexes (FIG. 26), we developed a surrogate in vitro assay to further test this possibility. We found that radioactively labeled lin-41_LCS RNA forms complexes with a synthetic pri-let-7 hairpin (with 15 extra nucleotides and designated as syn-pri-let-7 to differentiate from pre- or pri-let-7 made from c-let-7) in an electrophoretic mobility shift assay (EMSA). Two strong bands with reduced mobility can be resolved on the gel (FIG. 27a), and their intensity changes asynchronously with the increased concentration of syn-pri-let-7 in the binding reaction. Similar shifted bands were also observed for reciprocal conditions, in which a constant amount of radioactively labeled syn-pre-let-7 RNA was paired with unlabeled lin-41_LCS RNA (FIG. 28), demonstrating that the shifted bands are complexes containing both syn-pri-let-7 and lin-41_LCS and are not random aggregates resulting from increasing RNA concentration. The more predominant lower complex (C1) contains a 1:1 ratio of syn-pri-let-7 to lin-41_LCS RNAs, while the larger complex (C2) may consist of a 2:1 ratio (FIG. 29). The fraction of lin-41_LCS in complex with syn-pri-let-7 was determined by quantifying the reduction in the intensity of the unpaired lin-41_LCS band relative to the control sample lacking any syn-pri-let-7 RNA. The bound fraction is plotted against the concentration of syn-pre-let-7 (FIG. 27c), showing that syn-pre-let-7 interacts with lin-41_LCS-wt with half-maximal binding (approximately 40% of the lin-41_LCS-wt) at approximately equimolar concentration (1.1 µM syn-pri-let-7 to 0.97 µM lin-41_LCS). In contrast, complex formation is completely blocked by mutations in the lin-41_LCS RNA that abrogate base pairing to the let-7 seed nucleotides (FIG. 27b), demonstrating that parings to these nucleotides are essential for the interaction, just as they are necessary for target repression in vivo. Although it does not serve as direct evidence for such complexes in vivo, EMSA analysis can be used as a surrogate assay to evaluate the relative physical effects of loop mutations on the potential interaction between syn-pre-let-7 and lin-41_LCS and whether such effects would correlate with the function of pri-miRNA in target repression.

Figure 27D:
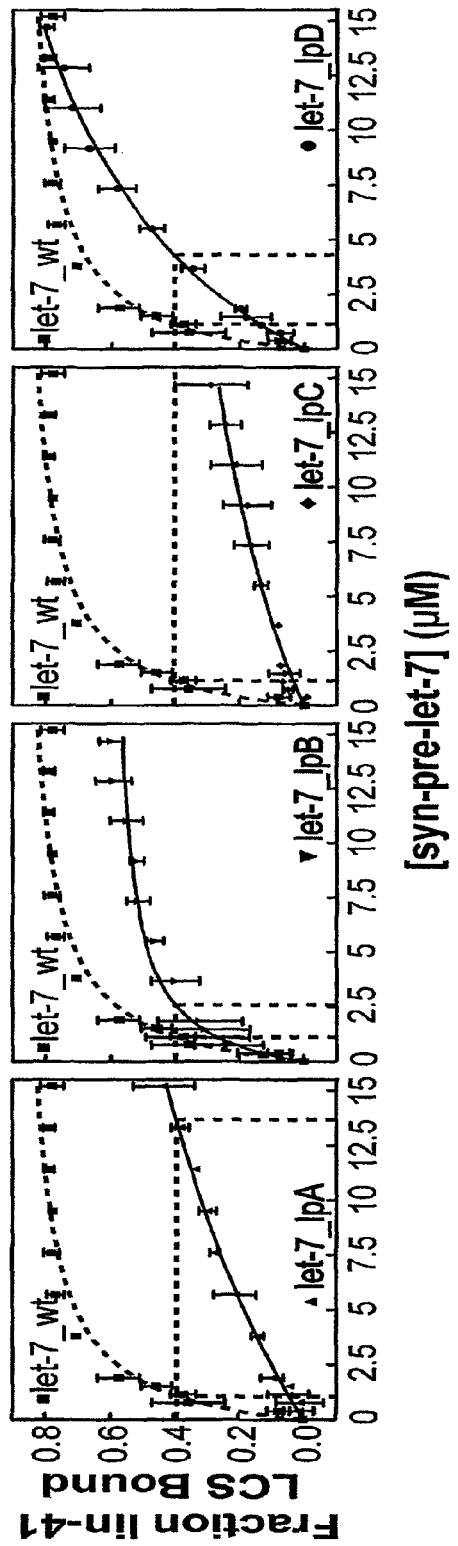
Figure 28A:
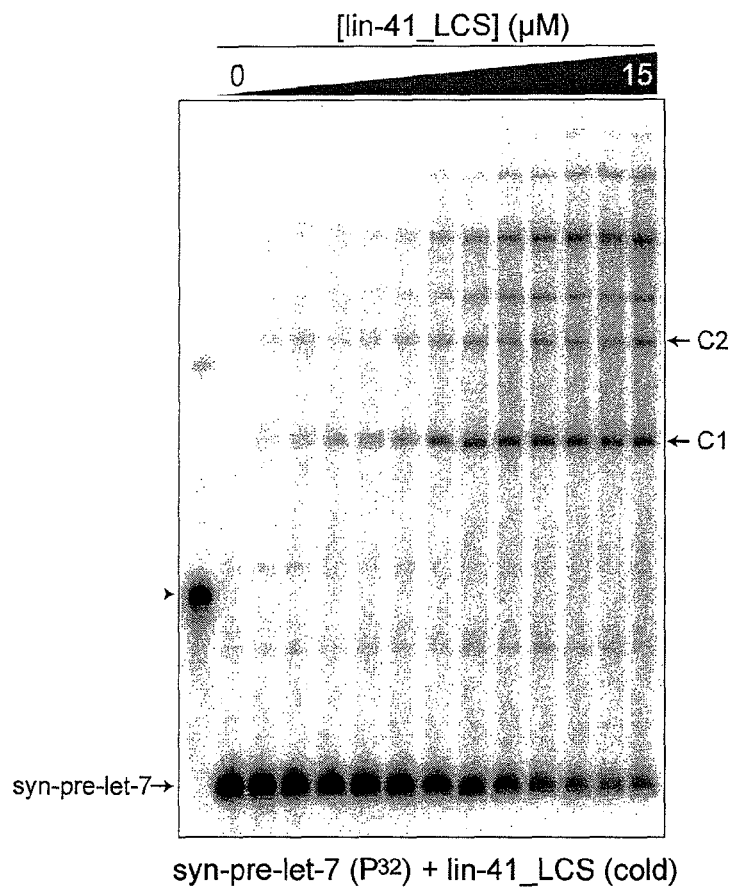
FIGS. 28A and 28B. In vitro complex formation between synthetic precursor let-7 (syn-pre-let-7) and lin-41_LCS target RNA. (A) EMSA was used to determine complex formation between radiolabeled syn-pre-let-7 (1.9 mM) and unlabeled lin-41-LCS (varying concentration), as the converse of the experiment seen in FIG. 5. (B) Dose-dependent binding of syn-pre-let-7 by increasing concentrations of lin-41_LCS.
Figure 28B:
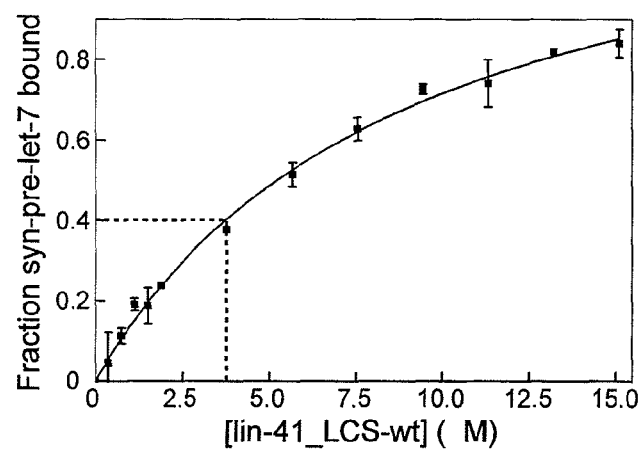
Figure 30:
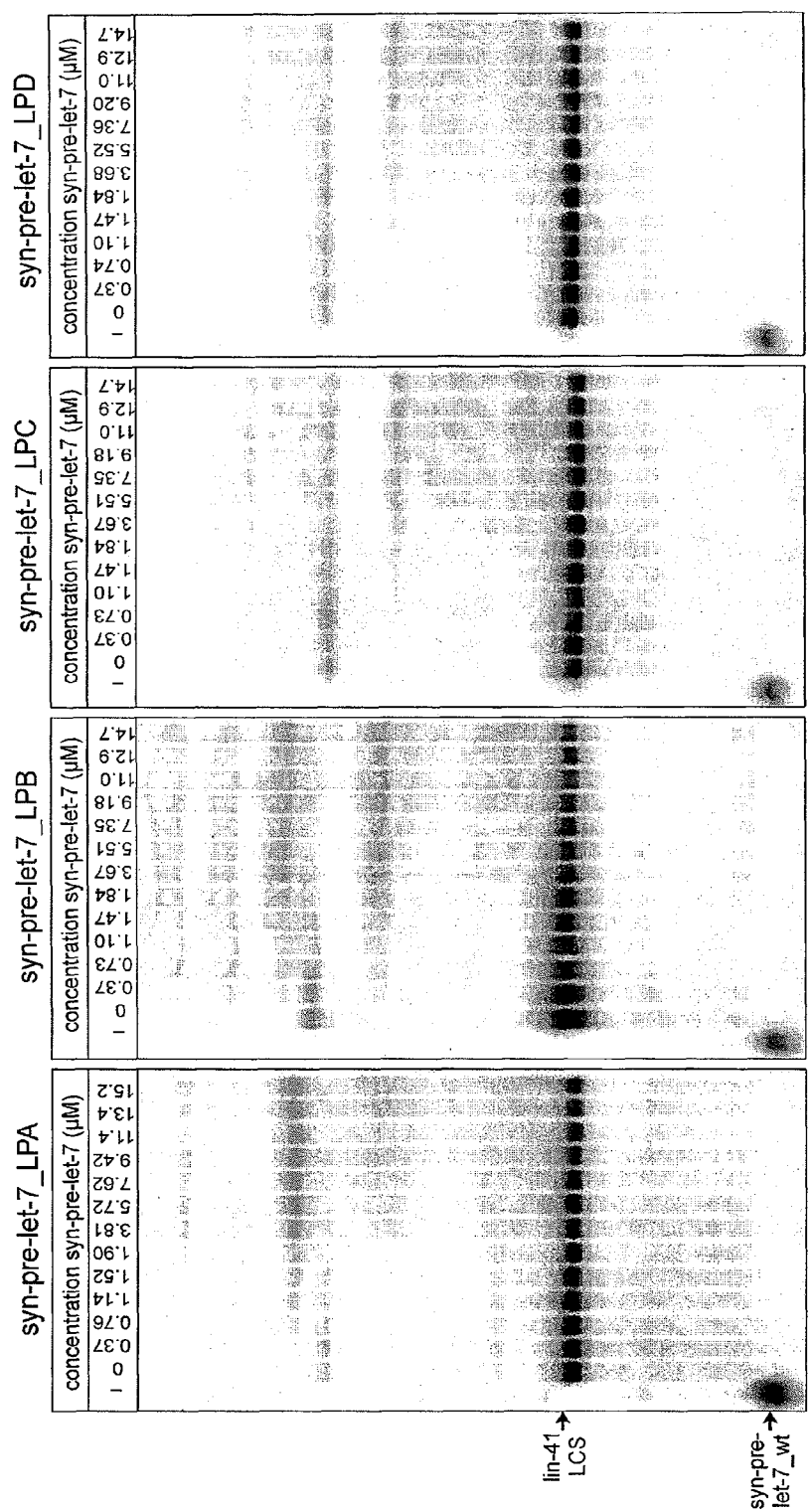
FIG. 30. Pre-miRNA loop mutations affect the complex formation between lin-41_LCS and synthetic precursor let-7 RNAs. EMSA was used to determine the complex formation between the lin-41_LCS-wt and syn-pre-let-7-wt or syn-pre-let-7 loop mutants. Concentrations of syn-pre-let-7 used in each reaction are indicated.

We found that loop mutations have profound effects on in vitro binding between syn-pri-let-7 and lin-41_LCS. As indicated by EMSA analyses, both the fraction of lin-41_LCS RNA shifted and mobility of complexes formed were affected by loop mutations (FIGS. 27d, 30). Compared to syn-pri-let-7_wt, which binds 40% of the lin-41_LCS at equimolar ratio, molar ratios of approximately 14, 2.6, 33.6, and 4.3 of corresponding mutant syn-pre-let-7 RNAs are required for binding to the same fraction of target RNA by the let-7_LPA, let-7_LPB, let-7_LPC, and let-7_LPD loop mutants, respectively. The dramatic differences of in vitro binding activity between the lin-41_LCS and syn-pre-let-7 derived from loop mutants correlate well with the activity of these mutants in target repression (FIGS. 21, 27d, Table 3b, Pearson's r=−0.90, two-tailed p=0.036). These results demonstrate that loop nucleotides can modulate the ability of stem-loop RNAs to form complexes with the same binding sites on target RNA, indicating that pri-let-7 nucleotides may affect the activity of pri-miRNA in target repression by modulating its ability to physically interact with target RNA.

Figure 31A:
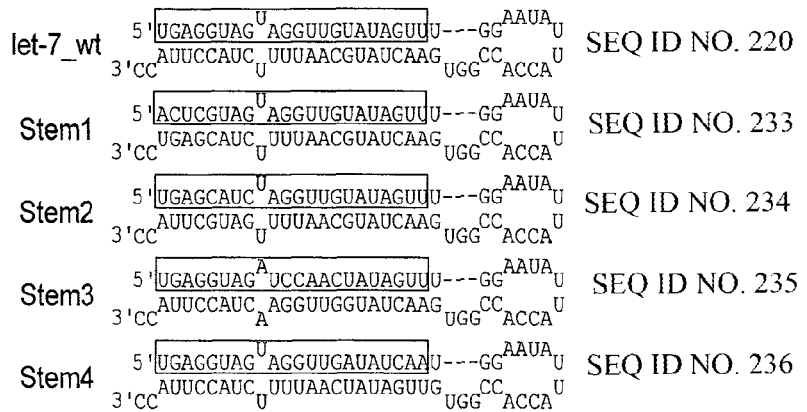
FIGS. 31A, 31B, 31C, 31D and 31E. Mutations in the stem region of pri-let-7 may affect the activity of c-let-7 by modulating the complex formation between lin-41_LCS and let-7 precursor RNAs. (A) Schematic diagrams depict the pre-miRNA sequences and structures of the c-let-7 stem mutants. (B) Repression of the lin-41_LCS reporter by the c-let-7 stem mutants. Representative results of at least six independent trials (±S.D.) are shown (*, p<0.0001). (C) Expression of let-7 RNAs from the c-let-7 stem mutants was determined by quantitative Northern-blot analyses (n=3). (D) The absolute levels of mature let-7 miRNAs in BOSC 23 cells transfected with the c-let-7 stem mutant genes (n=3, ±S.D.). (E) Dose-dependent binding of the lin-41_LCS and syn-pre-let-7_wt (black) or syn-pre-let-7 stem mutants (n=3).
Figure 31B:
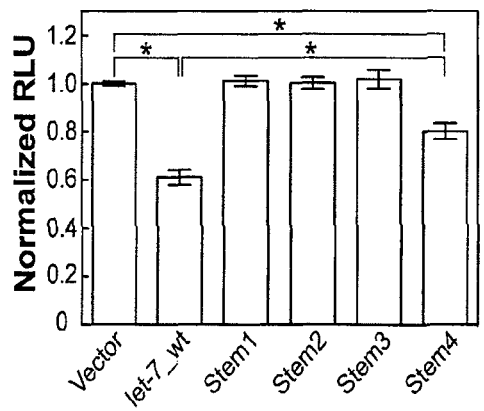
Figure 31C:
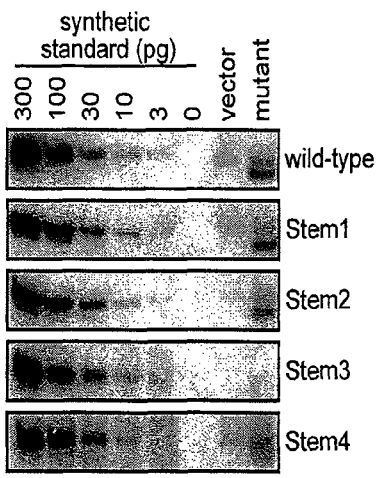
Figure 31D:
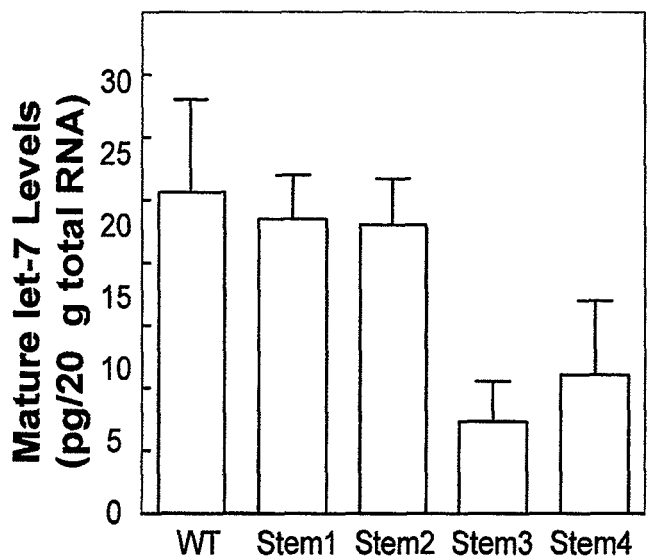

Pri-let-7 Stem Nucleotides Influence Target Repression by Modulating Pri-miRNA and Target Complex Formation Since nucleotide SD1 and other mature miRNA nucleotides in the stem region of pri-let-7 are integral components of this structured RNA, these nucleotides also control the function of pri-let-7 by influencing the formation of target and miRNA precursor complexes. To test this idea, we generated a set of c-let-7 stem mutants with stretches of nucleotides in the mature let-7 region altered (FIG. 31). Mutations in the 5' seed region (Stem1 and Stem2) and the center of mature let-7 (Stem3) all completely abolish the activity of c-let-7 in target gene repression, while mutations in the 3' end of the mature region (Stem4) have modest negative effects (FIGS. 31a, 31b). The Stem4 mutant resulted in an intermediate phenotype of ~20% repression of 1×lin-41_LCS reporters. Quantitative Northern blot analyses show that the levels of mature let-7 from these stem mutations have no consistent correlation with their target repression activities (FIGS. 31b, 31d).

Figure 31E:
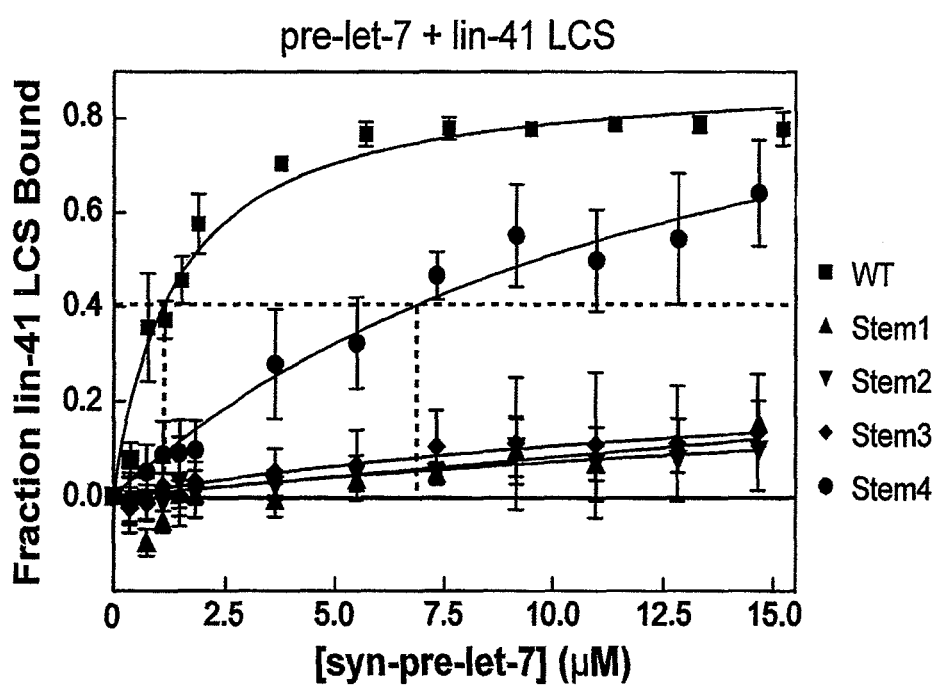
Figure 32:
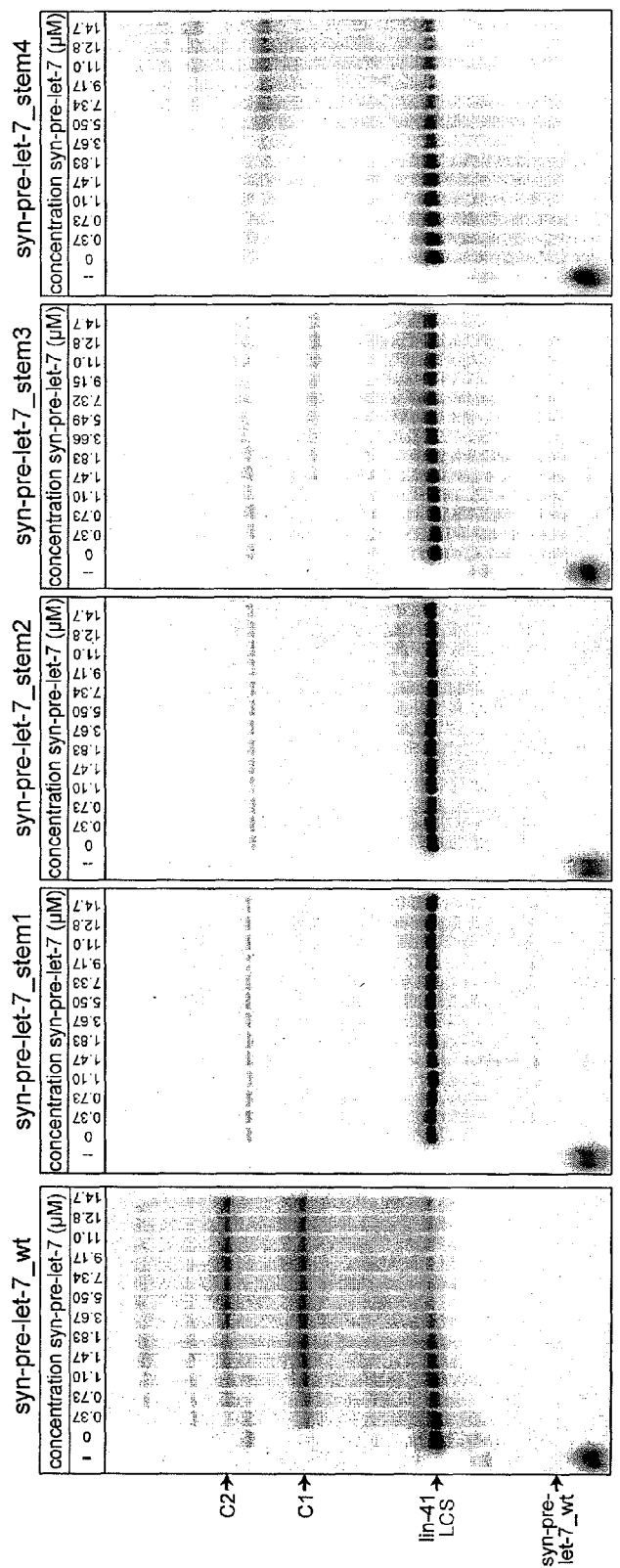
FIG. 32. Mutations in the stem region of c-let-7 affect complex formation between lin-41_LCS-wt and the synthetic precursor let-7 RNAs. EMSA was used to determine the complex formation between lin-41_LCS-wt and syn-pre-let-7 stem mutants. Concentrations of syn-pre-let-7 used in each reaction are indicated.
Figures 33A, 33B:
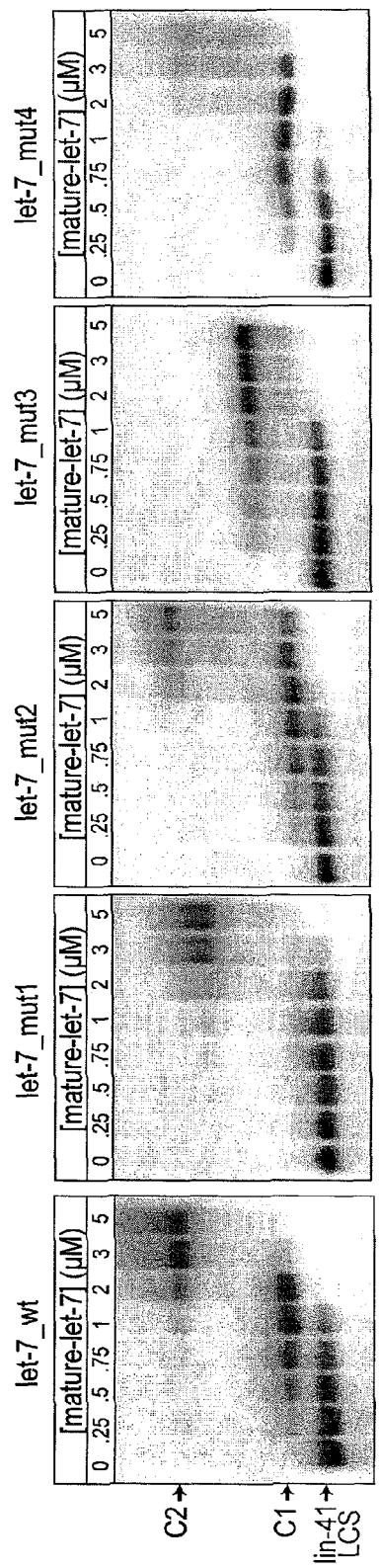
FIGS. 33A, 33B and 33C. Mutations in mature miRNAs have minimal effects on complex formation between the lin-41_LCS-wt and synthetic mature let-7 RNAs. (A) Schematics depict mature miRNA sequences corresponding to the pri-let-7 stem mutants (FIG. 7). (B) EMSA was used to determine the complex formation between lin-41_LCS-wt and synthetic mature let-7 mutant RNAs (n≥2). Each reaction contained 1 mM lin-41_LCS, and concentrations of mature let-7 used in each reaction are indicated. (C) Quantification of dose-dependent binding of lin-41_LCS-wt and synthetic mature let-7 mutant RNAs (n≥2).
Figure 33C:
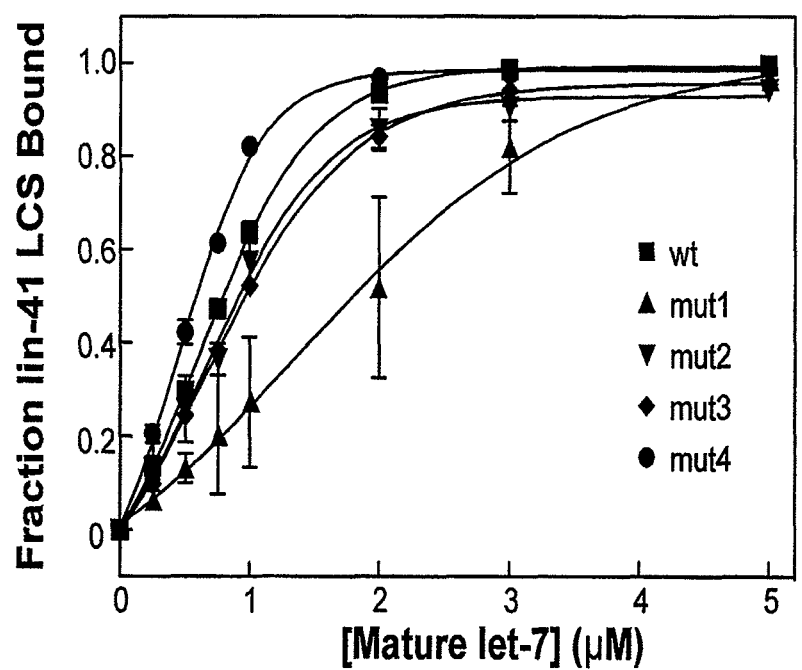

We then generated syn-pre-let-7 RNA corresponding to the stem mutants and tested their ability to form complexes with lin-41_LCS in EMSA (FIG. 31e, FIG. 32). Interestingly, syn-pre-let-7 of the Stem4 mutant can bind to the lin-41_LCS, while others cannot. Again, compared to syn-pre-let-7_wt, which binds 40% of the lin-41_LCS RNA at approximately equimolar ratio, 7-fold more Stem4 mutant syn-pre-let-7 is required for binding to the same fraction of target RNA (FIG. 31e). Interestingly, the affinity of complex formation in vitro and the activity in target repression by the Stem4 and let-7_LPD mutants are comparable (FIGS. 27, 31), indicating that the activities of c-let-7 stem mutants in target repression, like those of loop mutants, correlate with the potential for formation of target and precursor let-7 complexes (Table 4, Pearson's r=−0.8536, two-tailed p=0.0306). Further supporting the hypothesis that structured pri-miRNA may provide more extensive and possibly more stringent regulatory controls for target recognition as compared to mature miRNAs, we find that unlike their precursor forms, Stems 2-4 synthetic 22-nt let-7 RNAs can bind lin-41_LCS with equally high efficiency (FIG. 33). Thus the target regulation activity of c-let-7 stem mutants has no correlation with the ability of the corresponding mutant mature let-7 to form complexes with lin-41_LCS in vitro. Collectively, the above findings demonstrate that both loop and mature miRNA sequences of the structured pri-let-7 can provide regulatory controls for target recognition and repression (FIGS. 27, 31).

Figure 18A:
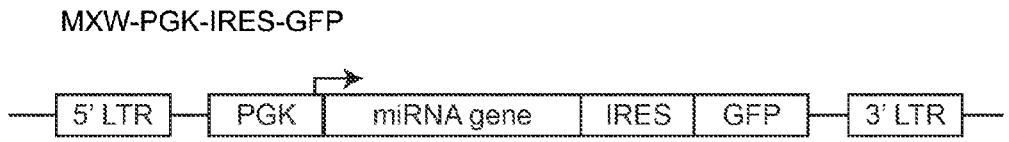
FIGS. 18A, 18B and 18C. Expression constructs. (A) Schematic diagram of a pol II vector used for expressing pre-let-7_wt and pre-let-7_PS RNAs in the context of the c-let-7 gene. The PGK promoter was used to drive the expression of the wild-type and modified c-let-7 genes. The pol II bicistronic expression cassette allows for the constitutive coexpression of miRNA(s) and GFP. (B) Schematic diagram of a pol III vector used for expressing pre-let-7_wt and pre-let-7_PS RNAs as hairpins alone. The human H1 promoter was used to drive expression of genes encoding the hairpin RNAs. The vector also contains an independent PGK promoter that controls the expression of GFP, which can serve as a transfection marker. (C) Relative levels of mature let-7 made from constructs expressing c-let-7_wt and c-let-7_PS. The intensities of the 22-nt, 20-nt, and total small RNA (22+20 nt) bands were determined by phosphoimager quantification. The relative levels of the 22-nt, 20-nt, and total small RNA (22+20 nt) bands were normalized to the RNA levels from BOSC 23 transfected with the c-let-7 gene. Average results of three independent trials ±S.D. are shown.
Figure 18B:
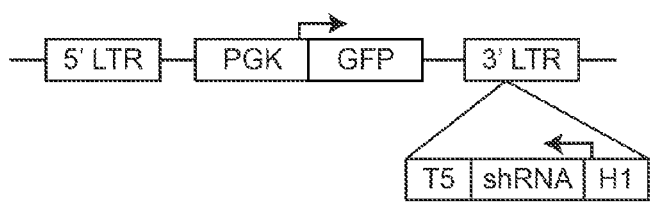
Figure 18C:
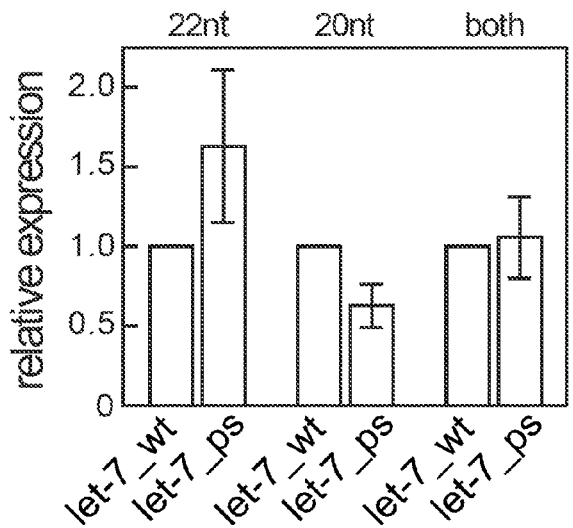
Figure 34A:
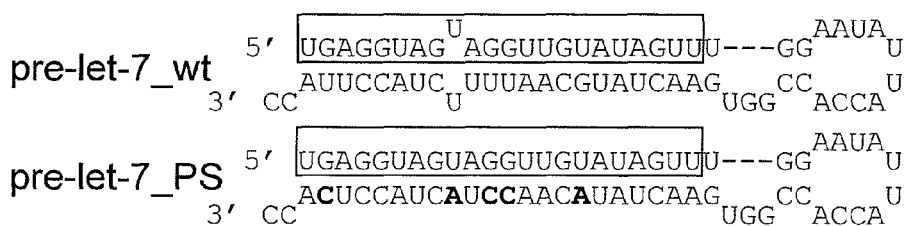
FIGS. 34A, 34B, 34C, 34D and 34E. Differential effects of stem stability on target gene repression. (A) Schematics show mutations that convert the imperfect pre-let-7 stem-loop (pre-let-7_wt) into a perfect pre-let-7 stem-loop (pre-let-7_PS). (B) Diagrams depict the expression of wild-type and perfect-stem hairpin in the context of c-let-7 (designated as c-let-7_wt and c-let-7_PS) or as hairpins alone (designated as pre-let-7 and sh-let-7). (C) Northern blot analyses of mature let-7 biogenesis from constructs expressing c-let-7_wt, c-let-7_PS, pre-let-7, and sh-let-7 (a representative of three repeats is shown). (D and E) Repression of the lin-41_T1T2P (D) the lin-41_LCS-wt (E) reporters by constructs expressing pre-let-7_wt and pre-let-7_PS in the context of c-let-7 or as hairpins alone. Representative results of at least six independent trials (±S.D.) are shown.
Figure 34B:
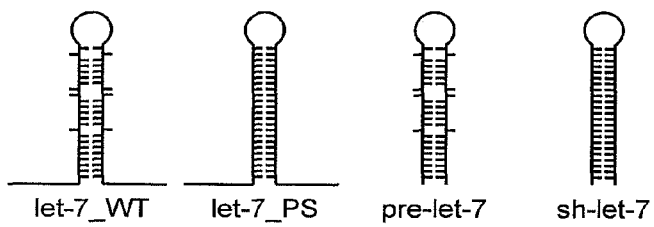
Figure 34C:
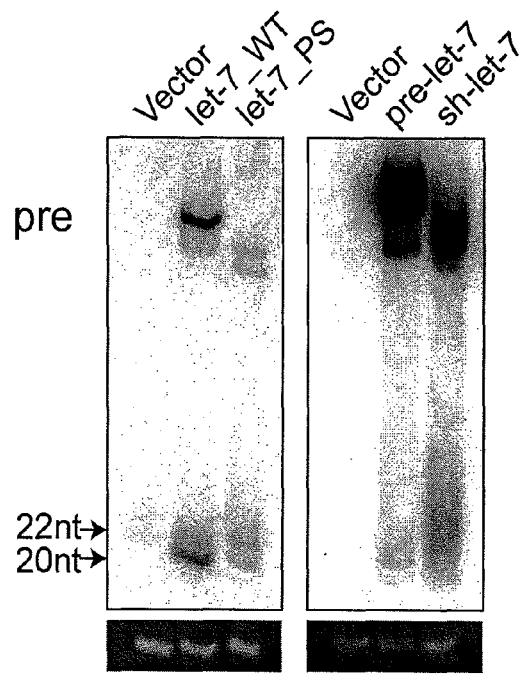
Figure 34E:
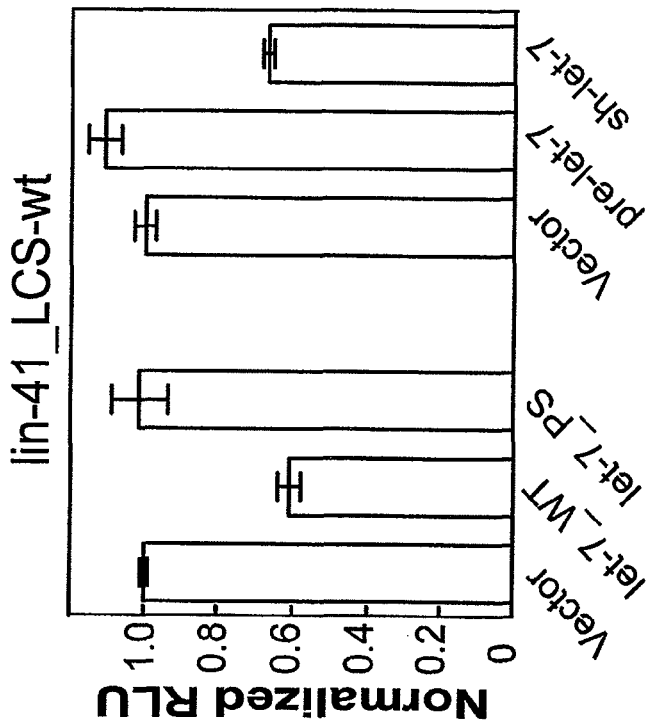
Figure 34D:
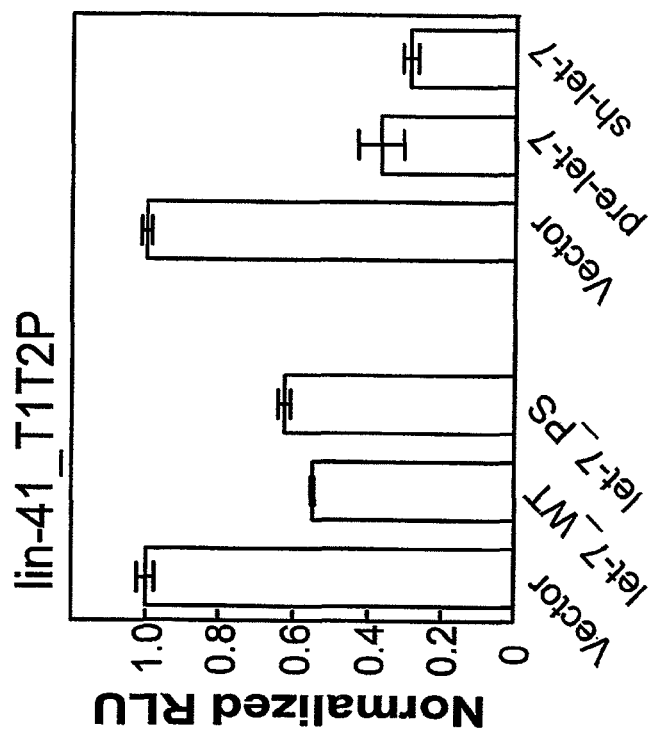

Distinct Effects of Stem Stability on Target Repression by Pri-miRNA and Short-Hairpin RNAs In addition to the loop structure and mature miRNA sequences of miRNA precursors, complex formation with their targets may also be influenced by the degree of base-pairing of the stem region. Interestingly, miRNA genes generally encode precursor miRNAs with imperfectly paired stem(s), suggesting that evolution favors imperfectly paired stem-loop structures for pri-miRNAs. In fact, it has been shown that stem stability can determine whether miRNA genes function through the miRNA or siRNA pathways in worms[37]. Here we further examine how stem-loop stability may affect target gene repression. We designed a mutant pre-let-7 with a perfectly paired stem by modifying the passenger strand to eliminate the bulge and wobble pairings in the wild type pre-let-7 hairpin (FIG. 34a). We then expressed this hairpin in the context of c-let-7 flanking sequence (designated c-let-7_PS) in the same Pol II-based vector that was used for c-let-7_wt expression (FIGS. 34b, 18a). Alternatively, both wild-type and perfect-stem hairpins were expressed as stand-alone-short-hairpin RNAs, designated pre-let-7 and sh-let-7, respectively, using a pol III-based expression vector (FIGS. 34b, 18b). Northern blot analyses reveal that pre- and mature miRNAs are made from all of these constructs, although the processing of short-hairpin constructs into mature miRNAs is inefficient (FIG. 34c). All four constructs are capable of repressing perfectly matched target lin-41_T1T2P (FIG. 34d), demonstrating that they may produce functional small RNAs. However, converting the imperfectly paired stem-loop of cel-let-7_wt to perfect complementarity abolishes the repression of the lin-41_LCS reporter (FIG. 34e). In contrast, perfect-stem (sh-let-7) but not imperfectly paired (pre-let-7) short-hairpin RNA can repress the lin-41_LCS reporter. Clearly, the imperfect stem-loop is required for the function of pri-let-7 but is detrimental for that of pre-let-7, whereas perfect pairing in the stem region is required for the function of sh-let-7 but is unfavorable for that of pri-let-7. Although we cannot establish whether c-let-7_wt and sh-let-7 have quantitatively the same efficiency in target repression due to differences in expression systems, these results demonstrate that both pri-let-7 and sh-let-7 RNAs can repress lin-41_LCS reporters. Nevertheless, stem stability has differential effects on the activities of these two classes of regulatory RNAs, indicating that pri-let-7 and sh-let-7 may function through distinct pathways.

Plasmid Constructs

A bicistronic vector driven by murine 3-phosphoglycerate kinase (PGK) promoter (Mao and Chen, 2007)[27] was used to co-express c-let-7 and a GFP reporter. DNA fragments containing the pre-let-7 hairpin and ~250 nt sequence flanking sequences on each side were amplified from *C. elegans* genomic DNA and placed under the control of the PGK promoter. A double-copy retroviral vector with a human H1 polymerase III expression cassette[28] was used to express shRNA constructs. A ~102-nt lin-41 3' UTR containing the let-7 complementary sites (LCS) was cloned into the UTR of *Renilla* luciferase reporter vector phRL-TK (Promega).

Luciferase Reporter Assay

BOSC 23 cells in 96-well plates were co-transfected with 0.25 ng of firefly luciferase control reporter, 0.05 ng of *Renilla* luciferase target reporter, and 40 ng miRNA expression vector. Firefly and *Renilla* luciferase activities were measured 48 hours after transfection using the Dual-Luciferase assay kit (Promega). Triplicate transfections and assays were carried out for each sample, and at least six repeats were carried out for each experiment using independent DNA preparations by more than two researchers. No discernable difference was noted in miRNA-mediated reporter repression activity when different transfection reagents (Fugene, Roche; Turbofection, Fermentas) or different DNA preparation Kits (Qiagen or Sigma) were used. DNA concentrations were determined using NanoDrop™ spectrophotometer and verified in some cases by semi-quantitative Ethidium Bromide gel electrophoresis assay. *Renilla* luciferase activity of a specific reporter was first normalized to that of firefly luciferase transfection control, then to the *Renilla*/firefly value of the empty control vector to determine the relative luciferase unit (RLU) activity of c-let-7 or mutants, and finally to the RLU of the corresponding seed mutant reporter (lin-41_LCS-sm) to determine the seed-dependent repression activity. Statistical significance was determined by an unpaired two-tailed students' t test.

Northern Blot Analyses

Northern blot analyses were carried out as described (Liu et al., 2008). Total RNA was prepared from BOSC 23 cells transfected with equal masses of miRNA expression vector. Data was normalized by either FACS analysis of GFP transfection marker signal, reprobing blots for U6 RNA, or ethidium bromide gel staining. For quantitative Northern blot analyses, serial dilutions of synthetic mature miRNA were resolved alongside total RNA samples to generate standard curves. DNA or LNA (locked nucleic acid) (Varallyay et al., 2008) probes complementary to the mature miRNA were used to detect both mature and pre-miRNA. U6 or 5S ribosomal RNAs were used for normalizing loading. Band intensity was determined by phosphoimaging, and copies/pg total RNA were determined by comparison to the corresponding standard curve. Representative blots and averaged data of three or more repetitions from cells transfected with independent DNA preparations are shown.

Primer Extension Analyses

Primer extension was used to map the 5' ends of the pre- and mature miRNAs produced from c-let-7_wt and its mutant genes. A 16-nt DNA oligo was used to probe the total RNA and mature miRNA fractions and a LNA version of the same oligo was used to probe pre-miRNA fractions. Expected primer extension products for mature let-7 or pre-let-7 RNAs should be of 22-nt in length. Of note, the products from LNA probes migrate ~1-nt slower than the corresponding products of DNA primers and DNA ladders. Primer extension reactions were simultaneously carried out for the let-7 RNAs and spiked synthetic miR-181a, which serve as an internal control for loading normalization. 16-nt DNA or LNA primers were used to probe the spiked synthetic miR-181a and pre-miR-181a, which result in extended products of 26-nt in length. Linear range of the assay was calibrated with synthetic standards. Relative levels of each RNA species were determined by normalizing to the internal control and then to the c-let-7_wt controls. At least repeats were performed using RNA samples from cells transfected with independent plasmid preparations.

Electrophoretic Mobility Shift Assay (EMSA)

In vitro transcribed pre-let-7 or synthetic mature let-7 RNA oligos were paired with 0.97 μM $P^{32}$-labeled target RNA in 1×TMN buffer (20 mM Tris pH 7.5, 10 mM $MgCl_2$, 0.1M NaCl). Samples were incubated at 37° C. (45 min), separated on 6% TBE-acrylamide native gels at 4° C., and then quantified. As noted, a 5' leader sequence of the syn-pre-let-7 RNAs stabilizes the complexes on PAGE gel. Since this sequence is present in all in vitro transcribed syn-pre-let-7 RNAs, EMSA allows us to compare the relative effects of loop nucleotides on the complex formation. A hyperbolic function was fitted to the data using the nonlinear fitting method of GraphPad Prism. Amounts of the wild-type and mutant syn-pre-let-7 RNAs required to sequester 40% of the lin-41_LCS-wt RNA' were determined using the fitted curves. The correlation between the suppression activity of wild-type and mutant c-let-7 genes and mature miRNA expression levels or in vitro binding affinity were determined by Pearson's correlation analyses (GraphPad Prism).

Methods

Vectors and Sequences

A bicistronic vector driven by murine 3-phosphoglycerate kinase (PGK) promoter[39] was used to co-express c-let-7 and a GFP reporter. DNA fragments containing the pre-let-7 hairpin and ~250 nt sequence flanking sequences on each side were amplified from *C. elegans* genomic DNA and placed under the control of the PGK promoter. A double-copy retroviral vector with a human H1 polymerase III expression cassette[40] was used to express shRNA constructs. A ~102-nt lin-41 3' UTR containing the let-7 complementary sites (LCS) was cloned into the UTR of *Renilla* luciferase reporter vector phRL-TK (Promega).

c-let-7 and mutant expression vectors: A bicistronic vector driven by murine 3-phosphoglycerate kinase (PGK) promoter[39] was used for the co-expression of c-let-7 and GFP reporter. DNA fragments containing the pre-let-7 hairpin and ~250 nt genomic sequence flanking sequences on each side were amplified from *C. elegans* genomic DNA and placed under the control of the murine 3-phosphoglycerate kinase promoter.

Wild-Type and Mutant c-let-7 Sequences (Pre-let-7 Region)

```
Wild-type    5'-TGA GGT AGT AGG TTG TAT AGT TTG GAA
             TAT TAC CAC CGG TGA ACT ATG CAA TTT
             TCT ACC TTA CC-3'
             (SEQ ID NO: 144)

Let-7_2G->A  5'-TAA GGT AGT AGG TTG TAT AGT TTG GAA
             TAT TAC CAC CGG TGA ACT ATG CAA TTT
             TCT ACC TTA CC-3'
             (SEQ ID NO: 145)

Let-7_2G->C  5'-TCA GGT AGT AGG TTG TAT AGT TTG GAA
             TAT TAC CAC CGG TGA ACT ATG CAA TTT
             TCT ACC TTA CC-3'
             (SEQ ID NO: 146)

Let-7_LPA    5'-TGA GGT AGT AGG TTG TAT AGT TTC CAA
             TAT TAC CAC CGG TGA ACT ATG CAA TTT
             TCT ACC TTA CC-3'
             (SEQ ID NO: 147)

Let-7_LPB    5'-TGA GGT AGT AGG TTG TAT AGT TTC CAA
             TAT TAC CAG GCC TGA ACT ATG CAA TTT
             TCT ACC TTA CC-3'
             (SEQ ID NO: 148)

Let-7_LPC    5'-TGA GGT AGT AGG TTG TAT AGT TTG GAA
             TAT TAC CAC CCC TGA ACT ATG CAA TTT
             TCT ACC TTA CC-3'
             (SEQ ID NO: 149)

Let-7_LPD    5'-TGA GGT AGT AGG TTG TAT AGT TTC CAA
             TAT TAC CAC CCC TGA ACT ATG CAA TTT
             TCT ACC TTA CC-3'
             (SEQ ID NO: 150)

Let-7_stem1  5'-ACT CGT AGT AGG TTG TAT AGT TTG GAA
             TAT TAC CAC CGG TGA ACT ATG CAA TTT
             TCT ACG AGT CC-3'
             (SEQ ID NO: 151)

Let-7_stem2  5'-TGA GCA TCT AGG TTG TAT AGT TTG GAA
             TAT TAC CAC CGG TGA ACT ATG CAA TTT
             TGA TGC TTA CC-3'
             (SEQ ID NO: 152)

Let-7_stem3  5'-TGA GGT AGA TCC AAC TAT AGT TTG GAA
             TAT TAC CAC CGG TGA ACT ATG GTT GGA
             ACT ACC TTA CC-3'
             (SEQ ID NO: 153)

Let-7_stem4  5'-TGA GGT AGT AGG TTG ATA TCA ATG GAA
             TAT TAC CAC CGG TGT TGA TAT CAA TTT
             TCT ACC TTA CC-3'
             (SEQ ID NO: 154)

Let-7_PS     5'-TGA GGT AGT AGG TTG TAT AGT TTG GAA
             TAT TAC CAC CGG TGA ACT ATA CAA CCT
             ACT ACC TCA CC-3'
             (SEQ ID NO: 155)
``` shRNA expression vectors: A double-copy retroviral vector with a human H1 polymerase III expression cassette[40] was used to express shRNA constructs. Oligos encoding sense and antisense DNA for pre-let-7 and sh-let-7 were synthesized, annealed, and cloned into the H1 expression vector.

Pre-let-7 and sh-let-7 Sequences pre-let-7:
(SEQ ID NO: 156)
5'-TCGAGCCCtgaggtagtaggttgtatagtttggaatattaccacc
ggtgaactatgcaattttctaccttaccTTTTTAATTAAG-3' sh-let-7:
(SEQ ID NO: 157)
5'-TCGAGCCCtgaggtagtaggttgtatagtttggaatattaccacc
ggtgaactatAcaaCCtActacctCaccTTTTTAATTAAG-3'

*Renilla* luciferase reporter vectors with lin-41_LCS in the 3' UTRs: *Renilla* luciferase reporter vectors (phRL-TK, Promega) containing one or multiple copies of wild-type or mutant lin-41_LCS in the 3' UTR were generated.

Wild-Type and Mutant Lin-41-LCS Sequences

Lin-41_LCS-wt:
(SEQ ID NO: 158)
5'-AACTCAAGTATACCTTtttatacaaccgttctacactcaACGCGAT
GTAAATATCGCAATCCCTTtttatacaaccattctgcctcTGAACCAT
TGAAACCTT-3'

Lin-41_LCS-sm:
(SEQ ID NO: 159)
5'-AACTCAAGTATACCTTtttatacaaccgttctTGTGAGaACGCGAT
GTAAATATCGCAATCCCTTtttatacaaccattGACGGAcTGAACCAT
TGAAACCTT-3'

Lin-41_LCS-2U:
(SEQ ID NO: 160)
5'-AACTCAAGTATACCTTtttatacaaccgttctacactTaACGCGAT
GTAAATATCGCAATCCCTTtttatacaaccattctgcctTTGAACCAT
TGAAACCTT-3'

Lin-41_LCS-2G:
(SEQ ID NO: 161)
5'-AACTCAAGTATACCTTtttatacaaccgttctacactGaACGCGAT
GTAAATATCGCAATCCCTTtttatacaaccattctgcctGTGAACCAT
TGAAACCTT-3'

Wild-Type or Mutant Lin-41_T1 T2P Sequences

Lin-41_T1T2P-wt:
(SEQ ID NO: 162)
5'-AACTCAAGTATACCTTAACtatacaacctActacctcaACGCGAT
GTAAATATCGCAATCCCTTAACtatacaacctActAcctcATGAACCA
TTGAAACCTT-3'

Lin-41_T1T2P-sm:
(SEQ ID NO: 163)
5'-AACTCAAGTATACCTTAACtatacaacctAcTGTGAGaACGCGAT
GTAAATATCGCAATCCCTTAACtatacaacctAcGACGGAATGAACCA
TTGAAACCTT-3'

Luciferase Reporter Assay

BOSC 23 cells were plated at a density of 1.2-1.5×10$^4$ cells/well in 96-well plates 18 hours before transfection, and co-transfected with 0.25 ng of firefly luciferase control reporter plasmid, 0.05 ng of *Renilla* luciferase target reporter, and 40 ng miRNA expression vector. Wells around the edge of the plate were not used for transfection. Fugene (Roche) and TurboFect (Fermentas) transfection reagents were used according to manufacturers' instructions, and no difference in target suppression was observed for the two reagents. 24 hours post-transfection, 100 ml culture medium was added to all wells. Cells were harvested 48 hours post-transfection and assayed using the Dual-Luciferase system (Promega).

Figure 35:
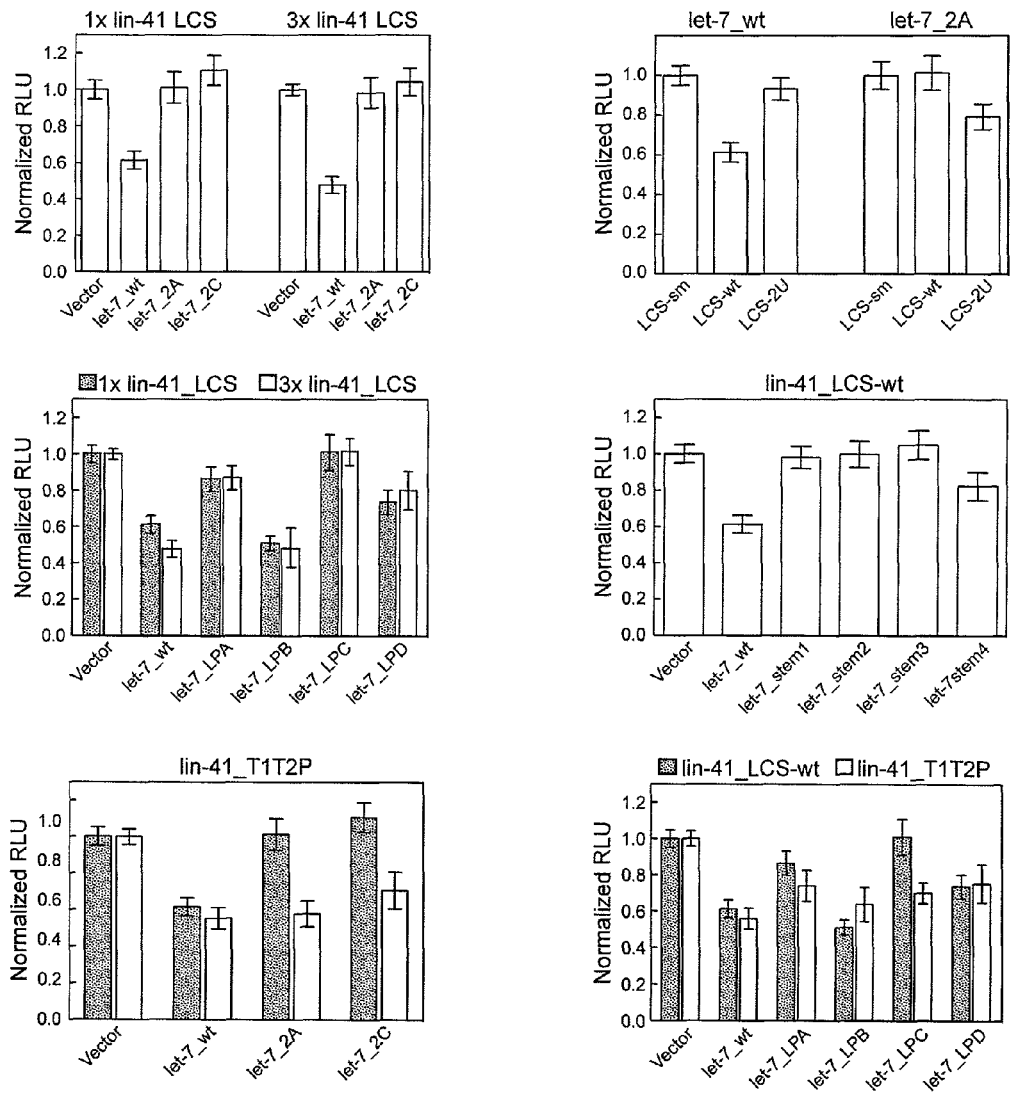
FIG. 35. Compiled results of luciferase reporter assays. Results of independent luciferase reporter assays of each sample group (n≥6, samples in each experiment are in triplicates) were compiled. Mean and S.D. of complied analyses are shown. Representative plots shown in the previous figures were selected to represent the corresponding mean values of the complied analyses.

Relative luciferase units (RLU) were calculated by normalizing *Renilla* luciferase intensity to firefly luciferase intensity for each individual well as a transfection control. RLU values for each miRNA construct were then normalized to that of the vector control to determine the relative activity of c-let-7 mutant genes in repression of each particular target. Finally, seed-dependent repression was determined by normalizing the miRNA-mediated repression of wild-type reporter to that of corresponding seed-mutant reporter. Combinational conditions were transfected and assayed in triplicate wells in each individual experiment, and each experiment was repeated at least three times with independent DNA preparations using Qiagen or Fermentas DNA mini-prep or Sigma DNA Maxi-prep kits by more than two researchers. No discernable difference was noted in miRNA-mediated reporter repression activity when different transfection reagents (Fugene, Roche; Turbofection, Fermentas) or different DNA preparation Kits (Qiagen or Sigma) were used. DNA concentrations were determined using NanoDrop™ spectrophotometer and verified in some cases by semi-quantitative Ethidium Bromide gel electrophoresis assay. Representative data sets are present in the Figures, while compiled results of all independent analyses (n≥6, samples in each experiment are in triplicates) for corresponding experiments are summarized in FIG. 35. Statistical significance was determined by an unpaired two-tailed students' t test.

Northern Blot Analyses

Northern blot analyses were carried out as described[41]. Northern blot analyses were used to determine the level of mature miRNA expression as well as processing of both pre- and mature miRNA. BOSC 23 cells were plated at a density of 7×10$^5$ cells per well in E-well plates 18-24 hours prior to transfection. Cells were transfected with 2 mg miRNA expression vector using Fugene (Roche) or TurboFect (Fermentas) transfection reagents and harvested at 48 hours post-transfection. Total RNA was prepared using Trizol reagents. RNA concentrations were determined by NanoDrop™ spectrophotometer. Briefly, 20 mg of total RNA for each sample was fractionated on 15% PAGE gels. Gels were stained with ethidium bromide and UV-visualized, then transferred to nylon membranes (Perkin Elmer). For quantitative analyses, serial dilutions of synthetic mature miRNAs were run alongside total RNA samples to generate a standard curve. DNA or LNA (locked nucleic acid)[42] probes complementary to the mature miRNA were used to detect both mature and pre-miRNA. U6 or 5S ribosomal RNAs were used for normalizing loading. Blots were probed overnight with a P$^{32}$ labeled DNA or LNA probe complementary to mature let-7 at 50° C. After washing, blots were dried and exposed to phosphorimager screens (GE Healthcare) overnight. Band intensity was determined using the Storm system (GE Healthcare). Blots were subsequently re-probed for U6 RNA with the same protocol, and U6 band intensity for each well was used as a loading control. For relative quantification, let-7 band intensities were divided by corresponding U6 band intensities and then normalized to wild-type c-let-7. For quantitative analysis, miRNA concentration was then calculated by extrapolating band intensity to the corresponding standard curve.

Northern Probe Sequences:

(SEQ ID NO: 164)
Let-7 (DNA):   5'-AACTATACAACCTACTACCTCA-3'

(SEQ ID NO: 165)
Let-7 (LNA):   5'-AACTATACAACCTACTACCTCA-3'

(SEQ ID NO: 166)
Stem1:         5'-AACTATACAACCTACTACGAGT-3'

(SEQ ID NO: 167)
Stem2:         5'-AACTATACAACCTAGATGCTCA-3'

```
                                (SEQ ID NO: 168)
Stem3:       5'-AACTATAGTTGGATCTACCTCA-3'

(SEQ ID NO: 169)
Stem4:       5'-TTGATATCAACCTACTACCTCA-3'
```

Primer Extension Analyses

Primer extension was used to map the 5' ends of the pre- and mature miRNAs produced from c-let-7_wt and its mutant genes. A 16-nt DNA oligo was used to probe the total RNA and mature miRNA fractions and a LNA version of the same oligo was used to probe pre-miRNA fractions. Expected primer extension products for mature let-7 or pre-let-7 RNAs should be of 22-nt in length. Of note, the products from LNA probes migrate ~1-nt slower than the corresponding products of DNA primers and DNA ladders. Primer extension reactions were simultaneously carried out for the let-7 RNAs and spiked synthetic miR-181a, which serve as an internal control for loading normalization. 16-nt DNA or LNA primers were used to probe the spiked synthetic miR-181a and pre-miR-181a, which result in extended products of 26-nt in length. Linear range of the assay was calibrated with synthetic standards. Relative levels of each RNA species were determined by normalizing to the internal control and then to the c-let-7_wt controls. At least repeats were performed using RNA samples from cells transfected with independent plasmid preparations.

Gel Purification of Pre- and Mature miRNA Fractions:

Total RNA samples (100 mg) from BOSC 23 cells transfected with miRNA expression constructs were spiked with synthetic pre-miR-181a-1 (800 pg) and synthetic mature miR-181a (150 pg) and then resolved on 15% PAGE gels. $P^{32}$ labeled mature let-7, cel-pre-let-7, and hsa-pre-let-7a-3 were mixed and run alongside total RNA samples to serve as markers for pre- and mature let-7 RNAs. Using the positions of these markers, gel slices containing mature let-7 RNA or pre-let-7 RNA were excised, subjected to three freeze-thaw cycles, and eluted in 0.3M NaCl for 30 minutes or overnight. Pre-let-7 and mature let-7 RNA fractions were subsequently obtained by ethanol precipitation. Replicate experiments were performed using RNA samples from cells transfected with independent plasmid preparations.

Primer Extension Reaction and Analysis:

Pre-let-7 or mature let-7 RNA fractions were analyzed by primer extension analyses to determine the 5' ends of pre-let-7 and mature let-7 RNAs. Briefly, total RNA or pre- or mature let-7 RNA fractions isolated from 100 mg of total RNA were mixed with $P^{32}$-labeled primers in 1×RT buffer. LNA primers were used to prime pre-let-7 and pre-miR-181a-1. For mature miRNA analyses, the mixture was heated to 70° for 10 minutes in a PCR thermocycler, then transferred to ice for 5 minutes to allow for annealing. For pri-miRNA analyses, more stringent conditions were used for annealing—the primer/RNA mixture was denatured in a beaker of boiling water for 10 minutes and then cooled slowly to room temperature over 30 minutes. Primer extension reaction was initiated by the addition of dNTP and reverse transcriptase (Applied Biosystems), carried out for 1 hour at 42° C., and terminated at 85° C. for 10 minutes. Products were resolved on 15% denaturing PAGE gels. $P^{32}$-labeled synthetic let-7 oligonucleotides in single nucleotide increments (16 to 22-nt) were used as size ladders. Note that products of reactions with LNA primers migrate at a rate ~1 nt longer than corresponding DNA primer reactions. Gels were exposed to a phosphorimager screen for two hours and analyzed with the Storm system. Quantitative analyses were performed by normalizing the intensities of pre- or mature let-7 products to that of pre- or mature miR-181 internal controls, respectively.

Oligo Sequences for Primer Extension Analyses:

Mature let-7 Primer (DNA): 16-nt, MW: 4793.2

```
                                (SEQ ID NO: 173)
Sequence:       5'-AACTATACAACCTACT-3'
```

Predicted Pairing:

```
                                (SEQ ID NO: 170)
Primer:         3'-TCATCCAACATATCAA-5'

(SEQ ID NO: 171)
Mature let-7:   5'-UGAGGUAGUAGGUUGUAUAGUU-3'

(SEQ ID NO: 186)
Expected product: 5'-AACTATACAACCTACTACCTCA-3'

(SEQ ID NO: 172)
Truncated product 5'-AACTATACAACCTACTACCT-3'
detected:         (20-nt)
```

Pre-let-7 Primer (LNA): 16-nt, MW: 4975.3

```
                                     (SEQ ID NO: 173)
Sequence: 5'-AACTATACAACCTACT-3'
(underlined nt are LNA)
```

Base pairing to pre-let-7 and expected primer extension products for pre-let-7 RNAs are the same as those for the mature let-7 RNAs.

Mature miR-181 Primer (DNA): 16-nt, MW: 4835.2

```
                                (SEQ ID NO: 174)
Sequence:       5'-AGTACTCACCGACAGC-3'
```

Predicted Pairing:

```
                                (SEQ ID NO: 175)
Primer:         3'-CGACAGCCACTCATGA-5'

(SEQ ID NO: 176)
miR-181a:       5'-AACAUUCAACGCUGUCGGUGAGU-3'

(SEQ ID NO: 177)
Expected product: 5'-AGTACTCACCGACAGCGTTGAATGTT-3'
                  (26-nt)
```

Pre-miR-181a-1 Primer (LNA): 16-nt, MW: 4989.3

```
                                (SEQ ID NO: 178)
Sequence:       5'-AGTACTCACCGACAGC-3'
```

Base pairing to pre-miR-181a-1 and expected primer extension products for pre-miR-181a-1 RNAs are the same as those for the mature miR-181a RNA.

Size Ladder for Mature let-7:

```
16 nt: 5'-AAC TAT ACA ACC TAC T-3'        MW: 4793.3
       (SEQ ID NO: 179)

17 nt: 5'-AAC TAT ACA ACC TAC TA-3'       MW: 5106.52
       (SEQ ID NO: 180)

18 nt: 5'-AAC TAT ACA ACC TAC TAC-3'      MW: 5395.7
       (SEQ ID NO: 181)
```

-continued

```
19 nt: 5'-AAC TAT ACA ACC TAC TAC C-3'     MW: 5684.88
        (SEQ ID NO: 182)

20 nt: 5'-AAC TAT ACA ACC TAC TAC CT-3'    MW: 5989.09
        (SEQ ID NO: 183)

21 nt: 5'-AAC TAT ACA ACC TAC TAC CTC-3'   MW: 6278.27
        (SEQ ID NO: 184)

22 nt: 5'-AAC TAT ACA ACC TAC TAC CTC      MW: 6591.4
        A-3'
        (SEQ ID NO: 185)
```

Electrophoretic Mobility Shift Assay (EMSA)

In vitro transcribed pre-let-7 or synthetic mature let-7 RNA oligos were paired with 0.97 µM $P^{32}$-labeled target RNA in 1×TMN buffer (20 mM Tris pH 7.5, 10 mM $MgCl_2$, 0.1M NaCl). Samples were incubated at 37° C. (45 min), separated on 6% TBE-acrylamide native gels at 4° C., and then quantified. As noted, a 5' leader sequence of the syn-pre-let-7 RNAs stabilizes the complexes on PAGE gel. Since this sequence is present in all in vitro transcribed syn-pre-let-7 RNAs, EMSA allows us to compare the relative effects of loop nucleotides on the complex formation. A hyperbolic function was fitted to the data using the nonlinear fitting method of GraphPad Prism. Amounts of the wild-type and mutant syn-pre-let-7 RNAs required to sequester 40% of the lin-41_LCS-wt RNA were determined using the fitted curves. The correlation between the suppression activity of wild-type and mutant c-let-7 genes and mature miRNA expression levels or in vitro binding affinity were determined by Pearson's correlation analyses (GraphPad Prism).

In Vitro Transcription (IVT) Templates:

DNAs encoding wild-type or mutant pre-let-7 and lin-41-LCS were cloned into the CU Minus™ IVT vector pDP19 (Ambion). IVT pre-lei-7 and lin-41-LCS RNAs contain 5' extra 15 nucleotides GGG AGA AGA GAA UUC (SEQ ID NO:190) and GGG AGA AGA GAA UUC CUC GAG (SEQ ID NO:191), respectively, derived from the vector multiple cloning sites. These extra nucleotides do not affect predicted secondary structure based on mfold prediction.

Sequences of the Syn-Pre-let-7 RNAs:

```
WT:
                                           (SEQ ID NO: 192)
5'-GGGAGAAGAGAAUUCugagguaguagguuguauaguuuggaauau
uaccaccggugaacuaugcaauuuucuaccuuaccA-3'

LPA:
                                           (SEQ ID NO: 193)
5'-GGGAGAAGAGAAUUCugagguaguagguuguauaguuuCCaauau
uaccaccggugaacuaugcaauuuucuaccuuaccA-3'

LPB:
                                           (SEQ ID NO: 194)
5'-GGGAGAAGAGAAUUCugagguaguagguuguauaguuuCCaauau
uaccaGGCCugaacuaugcaauuuucuaccuuaccA-3'

LPC:
                                           (SEQ ID NO: 195)
5'-GGGAGAAGAGAAUUCugagguaguagguuguauaguuuggaauau
uaccaccCCugaacuaugcaauuuucuaccuuaccA-3'

LPD:
                                           (SEQ ID NO: 196)
5'-GGGAGAAGAGAAUUCugagguaguagguuguauaguuuCCaauau
uaccaccCCugaacuaugcaauuuucuaccuuaccA-3'
```

```
Stem1:
                                           (SEQ ID NO: 197)
5'-GGGAGAAGAGAAUUCACUCguaguagguuguauaguuuggaauau
uaccaccggugaacuaugcaauuuucuacGAGUccA-3'

Stem2:
                                           (SEQ ID NO: 198)
5'-GGGAGAAGAGAAUUCugagCAUCuagguuguauaguuuggaauau
uaccaccggugaacuaugcaauuuuGAGUcuuaccA-3'

Stem3:
                                           (SEQ ID NO: 199)
5'-GGGAGAAGAGAAUUCugagguagAUCCAACuauaguuuggaauau
uaccaccggugaacuaugGUUGGAAcuaccuuaccA-3'

Stem4:
                                           (SEQ ID NO: 200)
5'-GGGAGAAGAGAAUUCugagguaguagguugAUAUCAAuggaauau
uaccaccgugUUGAUAUcaauuuucuaccuuaccA-3'
```

Sequences of Synthesized Mature let-7 RNA Oligos

```
                                           (SEQ ID NO: 201)
    Let-7 wt:     5'-UGAGGUAGUAGGUUGUAUAGUU-3'

(SEQ ID NO: 202)
    Let-7 mut1:   5'-ACUCGUAGUAGGUUGUAUAGUU-3'

(SEQ ID NO: 203)
    Let-7 mut2:   5'-UGAGCAUCUAGGUUGUAUAGUU-3'

(SEQ ID NO: 204)
    Let-7 mut3:   5'-UGAGGUAGAUCCAACUAUAGUU-3'

(SEQ ID NO: 205)
    Let-7 mut4:   5'-UGAGGUAGUAGGUUGAUAUCAA-3'
```

Preparation of IVT RNAs:

IVT vectors were linearized and then transcribed using the MEGAshortscript™ kit according to manufacturer's instruction (Ambion). To produce radiolabeled RNAs, 1 ml of $P^{32}$-g-UTP (Perkin Elmer, 3000 mCi/mmol) was added to 20 ml IVT reactions. IVT RNA samples were fractionated on 15% denaturing PAGE gels. Specific RNA bands indicated by radioactive signal or SYBR gold staining were excised from the gel, crushed and suspended in 4 ml 0.3M NaCl, and then subjected to three freeze-thaw cycles (freezing in a dry ice/ethanol bath ~10 minutes, thawing in a 37° C. water bath ~10 minutes). After 30 minutes elution at room temperature, samples were spun briefly and then supernatants were filtered into new tubes through 0.22 micron filters and precipitated in 8 ml 100% ethanol overnight at −80° C. with 2 mg glycogen as a carrier. Gel pieces were then subjected to a second elution overnight. Non-radioactive RNA samples were quantified by NanoDrop™ spectrophotometer. Radioactive samples were quantified by scintillation counting (see equation below).

Electrophoretic Mobility Shift Assay (EMSA):

IVT syn-pre-let-7 or synthetic mature let-7 RNA oligos were paired with radioactively labeled lin-41 target RNA (final target concentration 0.97 µM) in 1×TMN buffer (20 mM Tris-HCl pH 7.5, 10 mM $MgCl_2$, 0.1M NaCl) in 10 µl total volume at 37° C. for 45 minutes. The concentrations of internally radiolabeled RNAs were quantified based the incorporation of $P^{32}$ UTP. Reactions were then terminated by adding 2 µl native loading dye (40% sucrose, 0.25% xylene cyanol, 0.25% bromphenol blue) and resolved on 6% TBE-acrylamide native gels at 4° C. Gels were dried for 1 hour under vacuum and then exposed to phosphorimager screens (GE Healthcare) overnight. Band intensities were quantified by the Storm system (GE Healthcare). Background signals were subtracted from all values, and fractions of lin-41_LCS bound to syn-pre-let-7 were determined by the reduction of unbound radioactively labeled targets comparing to the total target input.

miRNA Quantitative PCR Analyses 1 million cells were collected, spiked with 22.5 fmol synthetic miR-223, and lysed with Trizol reagent (Invitrogen) for total RNA preparation. miRNA qPCR analyses were carried out for each of the human let-7 family members and miR-223 according to the manufacturer's instructions. Briefly, cDNA was synthesized from 5 ng purified total RNA in a 7.5 ml reaction using miRNA-specific looped primers (Applied Biosystems) and amplified with miRNA-specific forward primers, TaqMan probes and reverse primers (Applied Biosystems). PCR amplification was performed in triplicate at 95° C. for 10 minutes followed by 40 cycles of 95° C. for 15 seconds and 60° C. for 1 minute in an ABI-7000 sequence detection system. Exact copies of test and spiked miRNAs in the defined amount of total RNA input were determined by using standard curves for let-7 and spiked miR-223. Representative results of two repeats are shown.

TABLE 3

Pearson Correlation Analyses.

a. The activity of c-let-7 loop mutants in target repression has no correlation with the levels of mature miRNA expression. Observed values for target repression and mature miRNA expression

| Sample | Suppression of lin-41_LCS luciferase reporter (%) | Relative expression (Northern blot) | | |
|---|---|---|---|---|
| | | 20nt band | 22nt band | Both bands |
| Wild type | 38.7 ± 4.8 | 1 | 1 | 1 |
| LPA | 13.6 ± 6.7 | 0.18 ± 0.05 | 0.44 ± 0.20 | 0.23 ± 0.12 |
| LPB | 48.9 ± 4.1 | 0.79 ± 0.33 | 2.34 ± 0.80 | 1.32 ± 0.45 |
| LPC | −1.1 ± 9.9 | 0.63 ± 0.14 | 2.30 ± 0.46 | 1.20 ± 0.18 |
| LPD | 26.4 ± 6.6 | 0.24 ± 0.06 | 0.64 ± 0.23 | 0.38 ± 0.09 |

Statistical correlation analysis

| Quantification | Pearson r | $R^2$ | Two-tailed p value | Significant? |
|---|---|---|---|---|
| 20nt band | 0.4890 | 0.2392 | 0.4031 | No |
| 22nt band | 0.04887 | 0.002389 | 0.9378 | No |
| Both bands | 0.2713 | 0.07360 | 0.6589 | No | b. The activity of c-let-7 mutants in target repression correlates with the potential of complex formation between syn-pre-let-7 loop mutants and lin-41_LCS RNAs. Observed values for target repression and in vitro complex formation

| Sample | Suppression of lin-41_LCS luciferase reporter (%) | [syn-pre-let-7] required to bind 40% of target RNA (μM) |
|---|---|---|
| Wild type | 38.7 ± 4.8 | 1.10 |
| LPA | 13.6 ± 6.7 | 13.96 |
| LPB | 48.9 ± 4.1 | 2.64 |
| LPC | −1.1 ± 9.9 | 33.57 |
| LPD | 26.4 ± 6.6 | 4.26 |

Statistical correlation analysis

| Pearson r | $R^2$ | Two-tailed p value | Significant? |
|---|---|---|---|
| −0.9025 | 0.8146 | 0.0360 | Yes |

TABLE 4

Pearson Correlation Analyses.
The activity of c-let-7 mutants in target repression correlates with the potential of complex formation between syn-pre-let-7 and lin-41_LCS RNAs.
Observed values for target repression and in vitro complex formation

| Sample | Suppression of lin-41_LCS luciferase reporter (%) | [syn-pre-let-7] required to bind 40% of target RNA (μM) |
|---|---|---|
| Wild type | 38.7 ± 4.8 | 1.10 |
| LPA | 13.6 ± 6.7 | 13.96 |
| LPB | 48.9 ± 4.1 | 2.64 |
| LPC | −1.1 ± 9.9 | 33.57 |
| LPD | 26.4 ± 6.6 | 4.26 |
| Stem4 | 17.5 ± 7.7 | 6.78 |

Experimental for Lin-41 and Let-7 Sequences

Results

Pri-let-7 RNA Forms Complexes with Target mRNAs In Vivo

To test whether pri-let-7 RNAs can form complexes with target mRNA in cells, we tagged the *Renilla* reporters with the S1 aptamer (Vasudevan et al, 2007); the aptamer binds to streptavidin beads to enable selective enrichment tagged RNAs (FIG. 40A). Reporter constructs with the wild-type lin-41_LCS UTR, seed mutant lin-41_LCS UTRs, or no UTR were tagged with the S1 aptamer. Tagged reporters were co-transfected with cel-let-7 expression vectors into BOSC 23 cells under the same conditions that were used for the luciferase assays. Introducing the 51 aptamer into these *Renilla* reporter constructs did not alter their potential to be repressed by cel-let-7 (data not shown). S1-tagged reporter mRNAs can be specifically recovered using streptavidin beads. Over 50% of tagged reporter mRNAs in the cell lysates was bound onto streptavidin beads and selective elution with biotin resulted in over 250-fold enrichment of S1-tagged reporter mRNAs.

Figure 36:
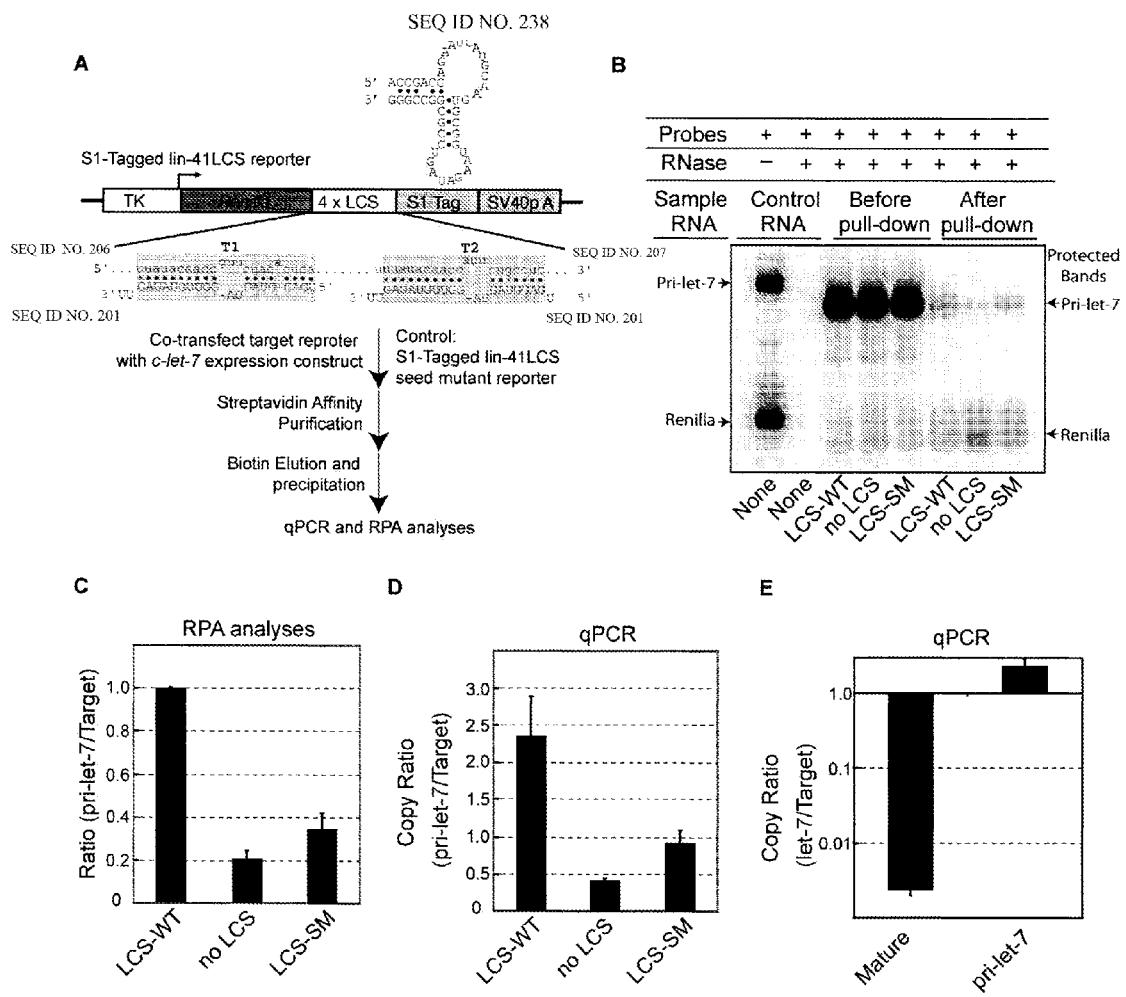
FIGS. 36A, 36B, 36C, 36D and 36E. Complex formation between lin-41_LCS and pri-let-7 RNAs in vivo. (A) Schematic diagram depicting the selective pull-down of S1 aptamer tagged lin-41_LCS reporter mRNAs and its associated pri-let-7 RNA. S1-tagged reporter mRNAs either with the Lin41-LCS_sm UTR or without the Lin41-LCS UTR were used as negative controls. (B) RPA demonstrates specific enrichment of the pri-let-7 RNA by the S1-tagged lin-41_LCS reporter mRNA but not by the control S1-tagged reporter mRNAs. Input total RNAs and streptavidin beads bound RNAs were subjected to the RPA analyses (radiolabeled pri-let-7 and RLuc probes before and after RNase treatments are indicated). (C) The ratios between pri-let-7 and corresponding target RNAs with lin-41_LCS_WT and control UTRs were determined by quantifying the intensity of protected pri-let-7 and target RNA bands; data were normalized first to the loading controls and then to lin-41_LCS_WT reporter RNA. (D & E) Copies of pri-let-7 (D) and mature let-7 (E) per target RNA in RNA samples pulled-down with streptavidin beads. Standard curve-based qPCR was carried out to determine the copy numbers of pri-let-7 and target RNAs in the pull-down RNA samples.

We purified tagged reporter mRNAs from transfected BOSC 23 cells and then determined the levels of pri-let-7 and reporter RNAs in the purified RNA samples using an RNase protection assay (RPA) and qPCR. Protection of radiolabeled RPA probes by the *Renilla* luciferase reporters and pri-let-7 RNAs resulted in a 163-nt and 88-nt bands, respectively (FIG. 36B). Pri-let-7 RNA was selectively enriched when the reporter carried the wild-type lin-41_LCS UTR, but not in reactions containing reporters without the UTR or with the seed mutant UTR (FIG. 36B). After normalizing to the input levels of reporter mRNA, relative levels of pri-let-7 RNA associated with the wild-type lin-41_LCS UTR were 5 and 3-fold higher than that associated with the control mRNAs with no UTR or the seed mutant UTR, respectively (FIG. 36C). Again, we noted no significant degradation of S1-tagged reporter mRNA upon cel-let-7 expression (FIG. 5B, before pull-down).

There were about 2.4 copies of pri-let-7 RNA on each reporter mRNA with the wild-type lin-41_LCS UTR (FIG. 36D) based on standard curve qPCR analyses (in vitro transcribed standards for pri-let-7 and *Renilla* reporter RNAs were used as standards). Both RPA and qPCR analyses revealed about 20% of background association between pri-let-7 and control mRNAs without the lin-41_LCS UTR; this may reflect non-specific binding or contamination. After subtracting the non-specific binding, both RPA and qPCR showed that pri-let-7 RNA specifically associated only with target mRNAs with the wild-type lin-41_LCS UTR in vivo. Under the same condition, we only detected about 0.002 copy of mature let-7 RNA per S1-target mRNA (FIG. 36E). However, we cannot preclude that mature let-7 RNA binds to target mRNA based on these results. First, cel-let-7 does not make functional full-length mature let-7 RNA and BOSC 23 cells make low levels of endogenous full-length mature let-7 RNA. Second, the endogenous mature full-length mature let-7 RNA bound to the S1-tagged reporter mRNA might have fallen off during the purification. Finally, it is possible that any endogenous mature let-7 interacting with the target would subsequently lead to target degradation, thereby precluding pull-down of bound targets. Nevertheless, these results demonstrate that pri-let-7 can directly interact with target reporter miRNA in vivo, further supporting that pri-let-7 has a direct role in target recognition and repression.

Loop Nucleotides Control Target and Pri-let-7 RNA Complex Formation In Vivo

Figure 37:
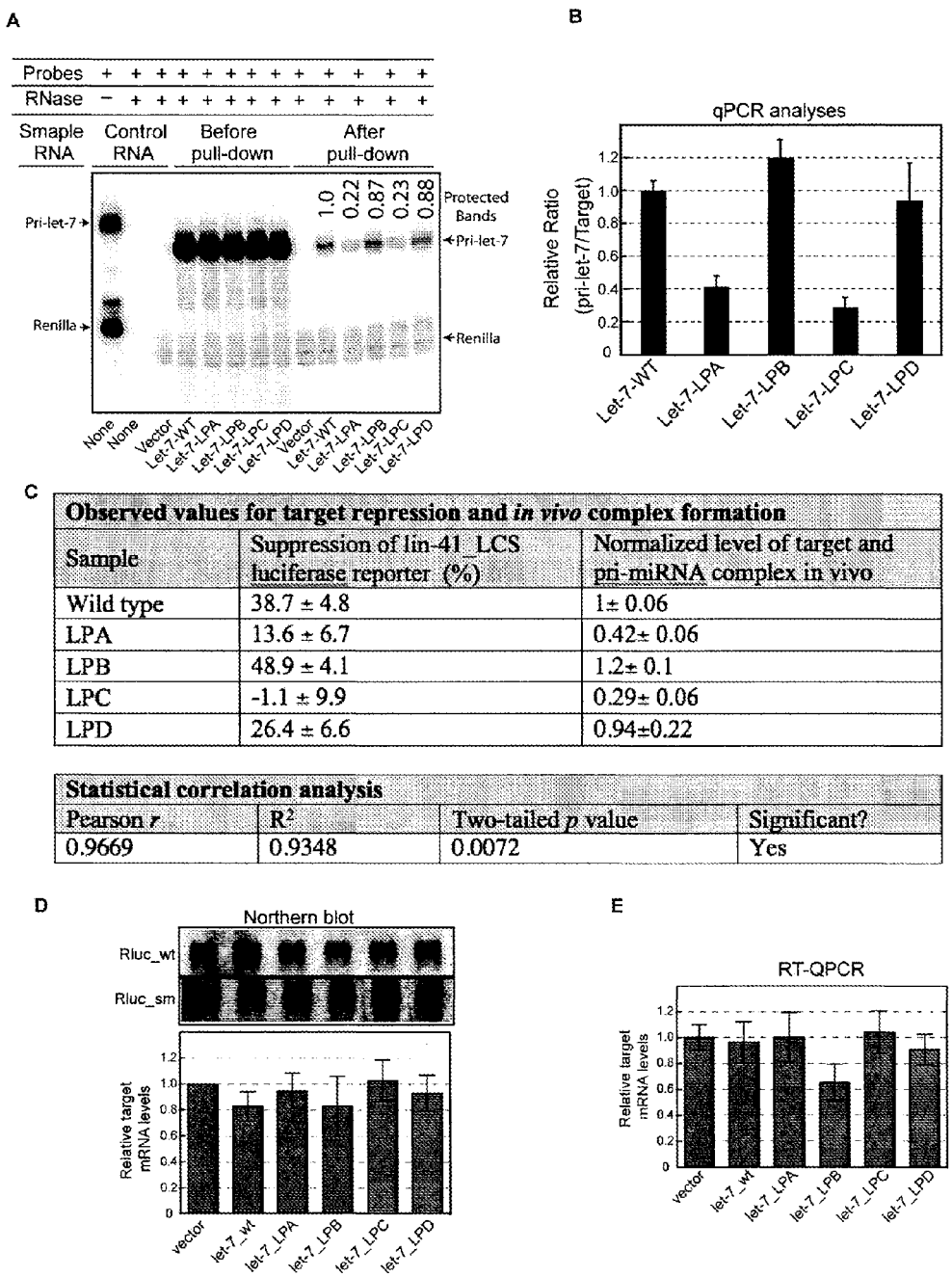
FIGS. 37A, 37B, 37C, 37D and 37E. Pri-let-7 loop mutations modulate complex formation between pri-let-7 and lin-41_LCS reporter RNAs in vivo. (A) RPA showing the effects of loop mutations on the complex formation between S1-tagged lin-41_LCS reporter mRNA and pri-let-7 loop mutants. The ratios between pri-let-7 and corresponding target RNAs in the pull-down samples that were determined and are indicated. (B) Normalized ratios between lin- 41_LCS_WT reporter RNA and pri-let-7 loop mutant RNAs were determined by standard curve-based qPCR quantification of the levels of pri-let-7 and target RNAs in the pull-down RNA samples. (C) The correlation between the activity of c-let-7 mutants in target repression and the potential of complex formation between pri-let-7 and lin-41_LCS RNAs in vivo was determined by Pearson correlation analyses. (D &E) The effects of wild-type and mutant cel-let-7 expression on the levels of target mRNAs determined by Northern blot (D) and qPCR analyses (E). (D) Northern-blot showing the levels of wild-type and seed mutant *Renilla* reporter mRNAs in BOSC 23 cells expressing wild-type and mutant cel-let-7 constructs. Representative results of four independent analyses (blots) and average of normalized all four experiments (Bar graph) were shown. (E) RNA samples used in Northern blot analyses were also independently quantified with qPCR analyses to determine the relative expression of wild-type and seed mutant *Renilla* reporter mRNAs in these cells. Expression of β-actin mRNA was also quantified and used to normalize RNA input.

Based on the result of in vitro EMSA analyses, we then examined the effects of loop mutations on complex formation between target and pri-let-7 RNAs in vivo. Consistent with in vitro analyses, we found that loop mutations had profound effects on in vivo binding between pri-let-7 and lin-41_LCS RNAs (FIG. 37). As indicated by RPA, the let-7_LPA, let-7_LPB, let-7_LPC, and let-7_LPD loop mutants decreased the relative levels of pri-miRNA associated with target mRNAs to about 22%, 87%, 23%, and 88% of the wild-type levels, respectively (FIG. 37A). Similar results were obtained using qPCR analyses (FIG. 37B). The dramatic decreases of the in vivo binding between the lin-41_LCS and pri-let-7 RNAs derived from let-7_LPB or let-7_LPC mutants were correlated with the reduction in activity of these mutants in target repression (FIG. 37C and, Pearson's r=−0.9669, two-tailed p=0.0072). These correlations demonstrate that the activity of pri-let-7 and loop mutants in target repression may be modulated by the ability of pri-let-7 to physically interact with target mRNA. Intriguingly, we noted expression of cel-let-7 and loop mutants did not cause significant changes in the levels of reporter mRNA as indicated by Northern blot (FIG. 37D) and qPCR analyses (FIG. 37E), demonstrating that pri-let-7 does not significantly degrade the targets.

Human Pri-let-7a-3 can Form Specific Complexes with Target mRNAs In Vivo

Figure 38:
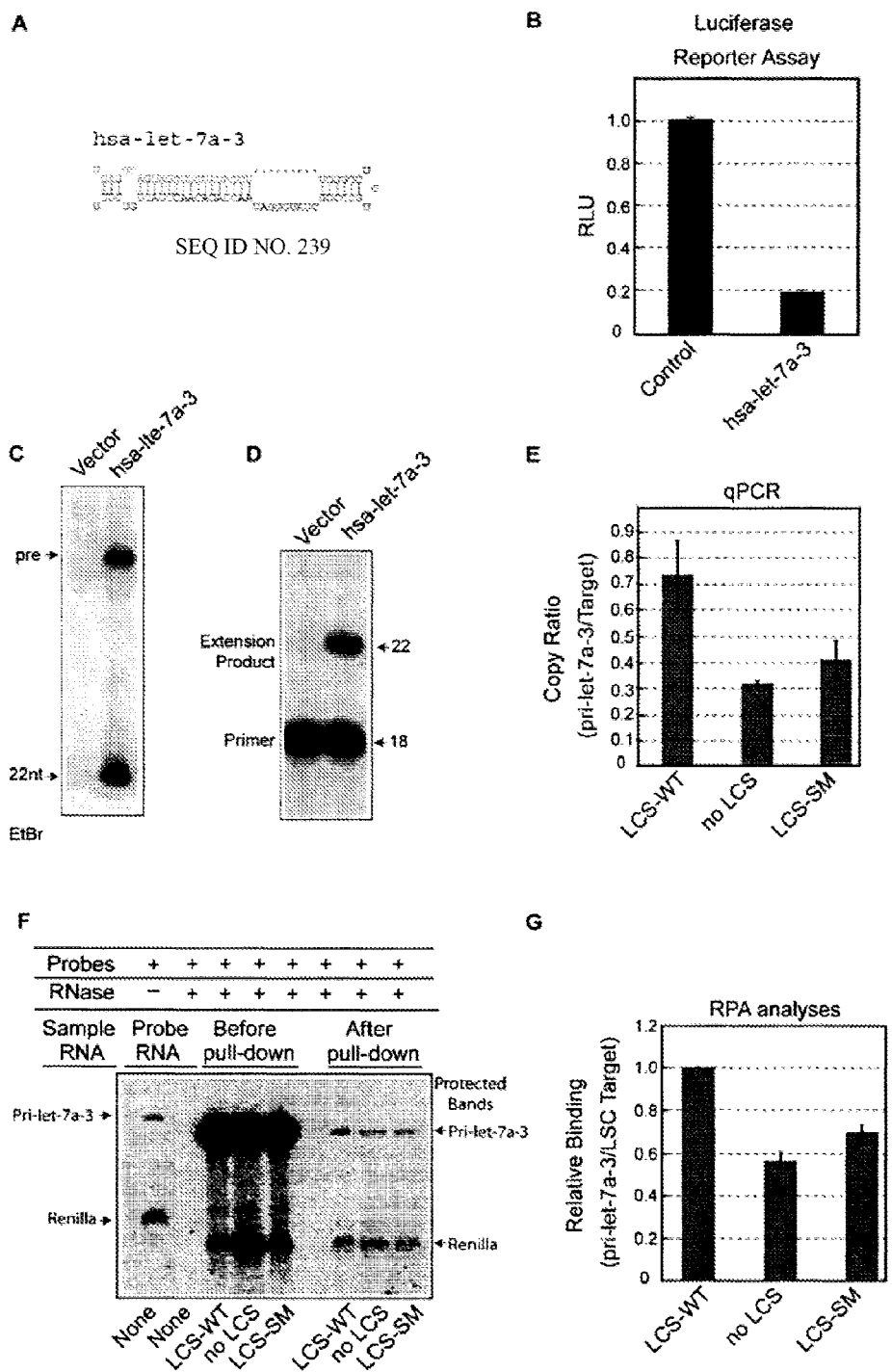
FIGS. 38A, 38B, 38C, 38D, 38E, 38F and 38G. In vivo complex formation between target mRNA and human let-7a-3 (hsa-let-7a-3) pri-miRNA (pri-let-7a-3). (A) Schematics depicting the pre-miRNA structure and nucleotide sequence of let-7a-3. (B) Seed-dependent repression of lin-41_LCS *Renilla* luciferase reporters by hsa-let-7a-3. Representative results of at least four independent trials (±S.D.) are shown (*, p<0.0001). (C) Northern-blot showing the expression and processing of hsa-let-7a-3 (n=3). (D) Mapping the 5' ends of mature let-7 made from hsa-let-7a-3 by primer extension analyses (n=3). (E) Number of copies of pri-let-7a-3 per target RNA in S1-tag pulled-down samples. Standard curve-based qPCR was carried out to determine the copy numbers of pri-let-7a-3 and target lin-41_LCS reporter RNAs in the pull-down RNA samples. (F & G) RPA demonstrates specific enrichment of the pri-let-7a-3 RNA by the S1-tagged lin-41_LCS reporter mRNA but not by the S1-tagged control mRNAs (n=3). Radiolabeled pri-let-7a-3 and RLuc probes before and after RNase treatments are indicated (F). The ratios between pri-let-7 and corresponding target RNAs with lin-41_LCS_WT and control UTRs were determined by quantifying the intensity of protected pri-let-7a-3 and target RNA bands; data were normalized first to the loading controls and then to lin-41_LCS_WT reporter RNA (G).

The above analyses demonstrate that pri-let-7 RNAs may play a direct role in recognizing and repressing the expression of target reporters in the absence of functional pre-let-7 and mature let-7. However, it is not know whether pri-miRNAs form complexes with their cognate target RNAs when miRNA biogenesis results in pre- and mature miRNAs with the correct 5' ends. To answer this question, we tested whether human pri-let-7a-3 formed specific target complexes with target miRNAs in vivo. Human let-7a-3 (hsa-let-7a-3) was selected among the human let-7 genes because it encodes the same mature let-7 as cel-let-7 (FIG. 38A) and it is expressed at a low level in BOSC 23 cells. When co-transfected into BOSC 23 cells with the lin-41_LCS Renilla luciferase reporter, hsa-let-7a-3 effectively repressed the expression (80%) of the reporter (FIG. 38B). Moreover, ectopic expression of hsa-let-7a-3 resulted in properly processed mature let-7a as indicated by Northern blot and primer extension analyses (FIGS. 38C, 38D).

We then tested whether pri-let-7a-3 RNA might be specifically associated with the wild-type Lin-41_LCS UTR using these S1-tagged reporters. We purified reporter mRNAs from BOSC 23 cells co-transfected with the S1-tagged reporter constructs and hsa-let-7a-3 expression vectors and determined the levels of pri-let-7 and reporter RNAs in the purified RNA samples by qPCR and RPA. qPCR analyses showed that there were about 0.7 copies of pri-let-7a-3 RNA on each reporter mRNA containing the wild-type lin-41_LCS UTR (FIG. 38E). Similarly, as indicated by RPA analyses of RNA pull-down samples, relative levels of pri-let-7 RNA associated with the wild-type lin-41_LCS UTR are nearly 2-fold higher than that associated with the control mRNAs with no UTR or the seed mutant, respectively (FIGS. 38F, 38G). Intriguingly, we noted significant degradation of S1-tagged reporter mRNA upon hsa-let-7a-3 expression (FIG. 38F, before pull-down). Significantly reduced target mRNA levels, likely due to target degradation by hsa-let-7a-3, may have compromised pull-down efficiency and contributed to the relatively higher background binding we observed. After subtraction of signal due to the non-specific binding to the reporter mRNAs with the seed mutant UTR, both RPA and qPCR clearly showed that pri-let-7a-3 RNA specifically associated with target mRNAs with the wild-type lin-41_LCS UTR. Since pri-, pre-, and mature let-7a-3 all contain the same mature miRNA sequence, it was not possible in these experiments to distinguish the functional contribution of the each RNA species to target repression. Nevertheless, pri-let-7a-3 RNA forms complexes with their cognate target RNAs in the presence of pre- and mature miRNAs with the correct 5' ends, supporting the proposition that this type of interaction may contribute to target recognition.

Materials and Methods

Luciferase Reporter Assay

BOSC 23 cells in 96-well plates were co-transfected with 0.25 ng of firefly luciferase control reporter, 0.05 ng of Renilla luciferase target reporter and 40 ng miRNA expression vector. Firefly and Renilla luciferase activities were measured 48 hours after transfection using the Dual-Luciferase assay kit (Promega). Triplicate transfections and assays were carried out for each sample and at least six repeats were carried out for each experiment using independent DNA preparations by more than two researchers. No discernable difference was noted in miRNA-mediated reporter repression activity when different transfection reagents (Fugene, Roche; Turbofection, Fermentas) or different DNA preparation Kits (Qiagen or Sigma) were used. DNA concentrations were determined using a NanoDrop™ spectrophotometer and verified in some cases by a semi-quantitative ethidium bromide gel electrophoresis assay. Renilla luciferase activity from a specific reporter was first normalized to that of firefly luciferase transfection control, then to the Renilla/firefly value of the empty control vector to determine the relative luciferase unit (RLU) activity of cel-let-7 or mutants, and finally to the RLU of the corresponding seed mutant reporter (lin-41_LCS-sm) to determine the seed-dependent repression activity. Representative data sets are presented in the figures. Statistical significance was determined by an unpaired two-tailed Student's t test.

Purification of Target and Pri-let-7 Complex from Cultured Cells

The lin-41_LCS Renilla luciferase reporters, Rluc-lin-41_LCS-wt or Rluc-lin-41_LCS-sm, were tagged with an S1 aptamer. The S1-tagged Renilla luciferase reporters were co-transfected with various c-let-7 expression constructs into 7×10$^5$ BOSC23 cells. Fugene (Roche) and TurboFect (Fermentas) transfection reagents were used according to manufacturers' instructions. Consistent transfection efficiencies (70-80%) were achieved as indicated by FACS analyses of GFP expression. At 48 hours after transfection, cells were washed twice with cold PBS and then resuspended in lysis buffer (150 mM KCl, 10 mM Hepes 7.4, 3 mM MgCl$_2$, 2 mM DTT, 10% glycerol, 0.5% NP-40). Cell suspensions were incubated on ice for 10 minutes and subjected to repeated pipeting to mix. Lysates were cleared by centrifugation at 2000 g for 5 minutes. The extracts were incubated with avidin beads for 1 hour in cold room to remove endogenous biotin and then bound to magnetic streptavidin beads in the presence 100 µg/ml tRNA and glycogen for 4 hours. Bound beads were then subjected to ten washes using binding buffer (50 mM HEPES, pH 7.4, 10 mM $MgCl_2$, 100 mM NaCl, 100 µg/ml tRNA, XX glycogen, and 2% NP-40). S1-tagged reporter was eluted by incubating beads with binding buffer containing 5 mM biotin for 1 hour. RNAs were then precipitated and analyzed by qPCR and RPA.

1. Bushati N, Cohen S M (2007) microRNA Functions. *Annu Rev Cell Dev Biol* 23:175-205
2. Lee R C, Feinbaum R L, Ambros V (1993) The *C. elegans* heterochronic gene lin-4 encodes small RNAs with antisense complementarity to lin-14. *Cell* 75:843-854.
3. Wightman B, Ha I, Ruvkun G (1993) Posttranscriptional regulation of the heterochronic gene lin-14 by lin-4 mediates temporal pattern formation in *C. elegans*. *Cell* 75:855-862.
4. Bartel D P (2004) MicroRNAs: genomics, biogenesis, mechanism, and function. *Cell* 116:281-97.
5. Kim V N (2005) MicroRNA biogenesis: coordinated cropping and dicing. *Nat Rev Mol Cell Biol* 6:376-85
6. Stark A, Brennecke J, Russell R B, Cohen S M (2003) Identification of *Drosophila* MicroRNA Targets. *PLoS Biol* 1:E60.
7. Lewis B P, Shih I H, Jones-Rhoades, M W, Bartel D P, Burge C B (2003) Prediction of mammalian microRNA targets. *Cell* 115:787-98.
8. Doench J G, Sharp P A (2004) Specificity of microRNA target selection in translational repression. *Genes Dev* 18:504-11.
9. Altuvia Y, et al. (2005) Clustering and conservation patterns of human microRNAs. *Nucleic Acids Res* 33:2697-706.
10. Chen C Z, Li L, Lodish H F, Bartel D P (2004) MicroRNAs modulate hematopoietic lineage differentiation. *Science* 303:83-6.
11. Li Q J, et al. (2007) miR-181a Is an Intrinsic Modulator of T Cell Sensitivity and Selection. *Cell* 129:147-61.
12. Neilson J R, Zheng G X, Burge C B, Sharp P A (2007) Dynamic regulation of miRNA expression in ordered stages of cellular development. *Genes Dev* 21:578-89.
13. Zhou B, Wang S, Mayr C, Bartel D P, Lodish, H. F. (2007) miR-150, a microRNA expressed in mature B and T cells, blocks early B cell development when expressed prematurely. *Proc Natl Acad Sci USA* 104:7080-5.
14. Ciofani M, Knowles G C, Wiest D L, von Boehmer H, Zuniga-Pflucker J C (2006) Stage-specific and differential notch dependency at the alphabeta and gammadelta T lineage bifurcation. *Immunity* 25:105-16.
15. Lee Y, et al. (2003) The nuclear RNase III Drosha initiates microRNA processing. *Nature* 425:415-9.
16. Denli, A. M., Tops, B. B., Plasterk, R. H., Ketting, R. F. & Hannon, G. J. (2004) Processing of primary microRNAs by the Microprocessor complex. *Nature* 432:231-5.
17. Han J, et al. (2006) Molecular basis for the recognition of primary microRNAs by the Drosha-DGCR8 complex. *Cell* 125:887-901.
18. Yi R, Qin Y, Macara I G, Cullen B R (2003) Exportin-5 mediates the nuclear export of pre-microRNAs and short hairpin RNAs. *Genes Dev* 17:3011-6.
19. Lim L P et al. (2005) Microarray analysis shows that some microRNAs downregulate large numbers of target mRNAs. *Nature* 433:769-73.
20. Steiner, F A, et al. (2007) Structural features of small RNA precursors determine Argonaute loading in *Caenorhabditis elegans*. *Nat Struct Mol Biol* 14:927-33.
21. Forstemann K, Horwich M D, Wee L, Tomari Y, Zamore P D (2007) *Drosophila* microRNAs Are Sorted into Functionally Distinct Argonaute Complexes after Production by Dicer-1. *Cell* 130:287-97.
22. Reinhart B J et al. (2000) The 21 nucleotide let-7 RNA regulates developmental timing in *Caenorhabditis elegans*. *Nature* 403:901-906.
23. Johnston R J, Hobert O (2003) A microRNA controlling left/right neuronal asymmetry in *Caenorhabditis elegans*. *Nature* 426:845-9.
24. Eisinger J, Gross N (1974) The anticodon-anticodon complex. *J Mol Biol* 88:165-74.
25. Tomizawa J (1984) Control of ColE1 plasmid replication: the process of binding of RNA I to the primer transcript. *Cell* 38:861-70.
26. Eguchi Y, Itoh T, Tomizawa J (1991) Antisense RNA. *Annu Rev Biochem* 60:631-52.
27. Vella, M. C., Reinert, K. & Slack, F. J. Architecture of a validated microRNA::target interaction. *Chem Biol* 11, 1619-23 (2004).
28. Reinhart, B. J. et al. The 21 nucleotide let-7 RNA regulates developmental timing in *Caenorhabditis elegans*. *Nature* 403, 901-906 (2000).
29. Ruby, J. G. et al. Large-scale sequencing reveals 21U-RNAs and additional microRNAs and endogenous siRNAs in *C. elegans*. *Cell* 127, 1193-207 (2006).
30. Doench, J. G. & Sharp, P. A. Specificity of microRNA target selection in translational repression. *Genes Dev* 18, 504-11 (2004).
31. Rajewsky, N. microRNA target predictions in animals. *Nat Genet*. 38 Suppl, S8-13 (2006).
32. Lewis, B. P., Shih, I. H., Jones-Rhoades, M. W., Bartel, D. P. & Burge, C. B. Prediction of mammalian microRNA targets. *Cell* 115, 787-98 (2003).
33. Baek, D. et al. The impact of microRNAs on protein output. *Nature* 455, 64-71 (2008).
34. Selbach, M. et al. Widespread changes in protein synthesis induced by microRNAs. *Nature* 455, 58-63 (2008).
35. Eguchi, Y., Itoh, T. & Tomizawa, J. Antisense RNA. *Annu Rev Biochem* 60, 631-52 (1991).
36. Liu, G., Min, H., Yue, S. & Chen, C. Z. Pre-miRNA loop nucleotides control the distinct activities of mir-181a-1 and mir-181c in early T cell development. *PLoS ONE* 3, e3592 (2008).
37. Steiner, F. A. et al. Structural features of small RNA precursors determine Argonaute loading in *Caenorhabditis elegans*. *Nat Struct Mol Biol* 14, 927-33 (2007).
38. Mao, T. K. & Chen, C. Z. Dissecting microRNA-mediated gene regulation and function in T-cell development. *Methods Enzymol* 427, 171-89 (2007).
39. Vasudevan S, Tong Y, Steitz J A Switching from repression to activation: microRNAs can up-regulate translation. *Science* 318(5858): 1931-1934 (2007).
40. Wagner E G, Simons R W Antisense RNA control in bacteria, phages, and plasmids. *Annu Rev Microbiol* 48: 713-742 (1994).

It is evident from the above results that the subject invention provides for novel opportunities to regulate mRNA expression. One can employ ta-RNA when no functional mature miRNA is generated, can employ optimal flanking sequences and can be prepared synthetically to have enhanced stability. For the ta-RNAs one can provide better and more specific use of RNAi using ta-RNA where both the seed sequence and the essential nucleotides of the loop sequence provide for specificity in giving unique results not available from the mature stem sequence. Different isoforms of ta-RNA provide for different phenotypic outcomes, so that by defining both the stem seed sequence, the sequence 3' of the stem sequence, and the essential nucleotides of the loop sequence one can specifically control the protein whose activity is being modulated, usually suppressed. Particularly, by enhancing complementarity between the guiding sequence and the target mRNA, so that extended contiguous nucleotides are complementary, enhanced specificity and/or suppression can be achieved. By employing both the seed sequence and loop sequence for screening, one can identify mRNAs for which the particular ta-RNA is specific and modulate its expression in host cells. The subject ta-RNAs and constructs employing the sequences can be used to express the RNA product in cells under various conditions allowing for investigating cell properties, cell pathways, response of cells and tissue to an external environment, and the like. In addition, one can prepare novel ta-RNAs with enhanced specificity for a target mRNA, so as to reduce the variations in activity and phenotype due to the multiplicity of mRNAs that are targeted. By controlling the seed sequence, the sequence 3' to the seed sequence and the relevant nucleotides in the loop, ta-RNAs are produced that are complementary to wild-type ta-RNAs and miRNAs and can be used in screening of cells for the wild-type ta-RNAs and miRNAs. The non-wild-type ta-RNAs can be used to identify target genes, elucidate cellular pathways, determine whether single or multiple mRNAs are modulated and lead to therapeutic ta-RNAs.

To identify ta-RNAs as to their capability to regulate expression of one or more genes, one can randomly or algorithm directed mutate by one or two nucleotides at least the loop region of wild-type ta-RNA of precursor genes to produce a family of isoforms of ta-RNA genes. One can then introduce into cells individual modified family members under the transcriptional control of a regulatory region functional in the cells under conditions providing for induced or constitutive transcription. One can then evaluate any changes in the phenotype of the cell. Phenotype can be measured as to the expression of proteins, differentiation, growth, change in cell type, etc. By using different cell types, one can screen for the effect on phenotype. In those cells that demonstrate a change in phenotype, one can then screen for the mRNAs that bind the active isoforms.

One can enhance specificity and/or suppression of expression of mRNA by increasing complementarity between the guiding sequence and the target mRNA, particularly making the seed sequence perfectly complementary to the mRNA and the sequence 3' of the seed sequence perfectly complementary to the mRNA, where the guiding sequence of the stem is perfectly complementary to the target mRNA to which it complexes.

One can also use the random isoform set to screen for complementary sequences in mRNAs. As discussed previously, one can determine the binding of members of a mixture of mRNAs, e.g. a transcriptome. Where a plurality of mRNAs bind, one can determine the affinity of individual mRNAs for individual ta-RNAs by measuring the level of binding by conventional assays for double stranded RNA, replacement and isolation of the bound mRNAs using sequences complementary to the ta-RNAs and measuring the mRNA by conventional procedures, e.g. mass spectrometry.

All references referred to in the text are incorporated herein by reference as if fully set forth herein. All procedures disclosed in the references are incorporated as demonstrating the level of skill in the art to perform the procedures indicated in this application. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

---

What is claimed is:

1. A composition comprising:

a mutated precursor miRNA that hybridizes to a separate target mRNA, wherein said mutated precursor miRNA is from a wild-type precursor miRNA that hybridizes with said separate target mRNA sequence and which has an wild-type terminal loop comprising a wild-type terminal loop sequence, and wherein said mutated precursor miRNA comprises a stem sequence and a terminal loop, wherein said terminal loop comprises a mutated terminal loop sequence with the same length as said wild-type terminal loop sequence, wherein at least the first and second nucleotides, and/or the seventh and eighth nucleotides, counting from the 5' end of said mutated terminal loop sequence, are substituted to enhance or reduce activity of said mutated precursor miRNA in binding and repressing said target mRNA sequence as compared to said wild-type precursor miRNA.

2. The composition of claim 1, further comprising said separate target mRNA sequence.

3. The composition of claim 1, wherein said mutated terminal loop sequence comprises at least 8 nucleotides, and wherein said at least 8 nucleotides are numbered from the 5' end of said loop sequence as follows: position 1, position 2, position 3, position 4, position 5, position 6, position 7, and position 8.

4. The composition of claim 3, wherein at least said positions 1 and 2 of said mutated terminal loop are substituted compared to said wild-type terminal loop.

5. The composition of claim 3, wherein at least positions 7 and 8 of said mutated terminal loop are substituted compared to said wild-type terminal loop.

* * * * *